United States Patent
Kato et al.

(10) Patent No.: US 11,895,917 B2
(45) Date of Patent: Feb. 6, 2024

(54) MATERIAL FOR ORGANIC ELECTROLUMINESCENCE DEVICE AND ORGANIC ELECTROLUMINESCENCE DEVICE USING THE SAME

(71) Applicant: IDEMITSU KOSAN CO., LTD., Tokyo (JP)

(72) Inventors: Tomoki Kato, Sodegaura (JP); Masaki Numata, Sodegaura (JP); Kazuki Nishimura, Sodegaura (JP); Toshihiro Iwakuma, Sodegaura (JP); Chishio Hosokawa, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 189 days.

(21) Appl. No.: 17/345,838

(22) Filed: Jun. 11, 2021

(65) Prior Publication Data

US 2022/0407018 A1 Dec. 22, 2022

Related U.S. Application Data

(63) Continuation of application No. 15/785,896, filed on Oct. 17, 2017, now Pat. No. 11,069,862, which is a continuation of application No. 15/379,130, filed on Dec. 14, 2016, now Pat. No. 9,847,493, which is a continuation of application No. 14/987,249, filed on
(Continued)

(30) Foreign Application Priority Data

Jun. 5, 2008 (JP) .................................. 2008-148514

(51) Int. Cl.
| | | |
|---|---|---|
| H01L 51/00 | (2006.01) |
| C07D 487/04 | (2006.01) |
| C07D 519/00 | (2006.01) |
| C09K 11/06 | (2006.01) |
| H05B 33/14 | (2006.01) |
| C07D 493/04 | (2006.01) |
| C07D 495/04 | (2006.01) |
| C09K 11/02 | (2006.01) |
| C07D 307/91 | (2006.01) |
| H10K 85/60 | (2023.01) |
| H10K 85/30 | (2023.01) |
| H10K 30/80 | (2023.01) |
| H10K 50/11 | (2023.01) |
| H10K 50/12 | (2023.01) |
| H10K 50/13 | (2023.01) |
| H10K 50/14 | (2023.01) |
| H10K 50/15 | (2023.01) |
| H10K 50/16 | (2023.01) |
| H10K 50/81 | (2023.01) |
| H10K 50/82 | (2023.01) |

(Continued)

(52) U.S. Cl.
CPC ....... *H10K 85/6574* (2023.02); *C07D 307/91* (2013.01); *C07D 487/04* (2013.01); *C07D 493/04* (2013.01); *C07D 495/04* (2013.01); *C07D 519/00* (2013.01); *C09K 11/025* (2013.01); *C09K 11/06* (2013.01); *H05B 33/14* (2013.01); *H10K 85/324* (2023.02); *H10K 85/342* (2023.02); *H10K 85/623* (2023.02); *H10K 85/654* (2023.02); *H10K 85/6572* (2023.02); *H10K 85/6576* (2023.02); *C09K 2211/1007* (2013.01); *C09K 2211/1029* (2013.01); *C09K 2211/1088* (2013.01); *C09K 2211/185* (2013.01); *H10K 30/865* (2023.02); *H10K 50/11* (2023.02); *H10K 50/12* (2023.02); *H10K 50/13* (2023.02); *H10K 50/14* (2023.02); *H10K 50/15* (2023.02); *H10K 50/16* (2023.02); *H10K 50/171* (2023.02); *H10K 50/81* (2023.02); *H10K 50/82* (2023.02); *H10K 2101/10* (2023.02)

(58) Field of Classification Search
None
See application file for complete search history.

(56) References Cited

U.S. PATENT DOCUMENTS

| 5,843,607 A | 12/1998 | Hu et al. |
| 5,942,340 A | 8/1999 | Hu et al. |

(Continued)

FOREIGN PATENT DOCUMENTS

| DE | WO 2006/122630 | 11/2006 |
| EP | 0 906 947 A1 | 4/1999 |

(Continued)

OTHER PUBLICATIONS

Non-Final Office Action dated Nov. 17, 2016 issued in U.S. Appl. No. 14/987,249.
(Continued)

*Primary Examiner* — Jay Yang
(74) *Attorney, Agent, or Firm* — Oblon, McClelland, Maier & Neustadt, L.L.P.

(57) ABSTRACT

Provided are an organic electroluminescence device, which shows high luminous efficiency, is free of any pixel defect, and has a long lifetime, and a material for an organic electroluminescence device for realizing the device. The material for an organic electroluminescence device is a compound having a π-conjugated heteroacene skeleton crosslinked with a carbon atom, nitrogen atom, oxygen atom, or sulfur atom. The organic electroluminescence device has one or more organic thin film layers including a light emitting layer between a cathode and an anode, and at least one layer of the organic thin film layers contains the material for an organic electroluminescence device.

24 Claims, No Drawings

Related U.S. Application Data

Jan. 4, 2016, now Pat. No. 9,660,203, which is a continuation of application No. 14/634,069, filed on Feb. 27, 2015, now Pat. No. 10,020,454, which is a continuation of application No. 13/173,486, filed on Jun. 30, 2011, now Pat. No. 9,056,870, which is a continuation of application No. 12/253,586, filed on Oct. 17, 2008, now Pat. No. 8,049,411.

(51) Int. Cl.
  *H10K 50/17* (2023.01)
  *H10K 101/10* (2023.01)

(56) References Cited

U.S. PATENT DOCUMENTS

| | | |
|---|---|---|
| 5,952,115 A | 9/1999 | Hu et al. |
| 6,479,172 B2 | 11/2002 | Hu et al. |
| 6,562,485 B2 | 5/2003 | Hu et al. |
| 8,138,355 B2 | 3/2012 | Watanabe |
| 8,372,529 B2 | 2/2013 | Kato et al. |
| 8,748,010 B2 | 6/2014 | Heil et al. |
| 9,056,870 B2 | 6/2015 | Kato et al. |
| 2005/0040757 A1 | 2/2005 | Chen et al. |
| 2005/0112406 A1 | 5/2005 | Han et al. |
| 2005/0127823 A1 | 6/2005 | Iwakuma et al. |
| 2006/0051612 A1 | 3/2006 | Ikeda et al. |
| 2006/0214155 A1 | 9/2006 | Ong et al. |
| 2007/0112172 A1 | 5/2007 | Li et al. |
| 2007/0120466 A1 | 5/2007 | Arakane et al. |
| 2007/0237982 A1 | 10/2007 | Inoue et al. |
| 2007/0252139 A1 | 11/2007 | McKiernan et al. |
| 2008/0145708 A1 | 6/2008 | Heil et al. |
| 2008/0193797 A1 | 8/2008 | Heil |
| 2008/0220285 A1* | 9/2008 | Vestweber ............... C07C 13/72 564/426 |
| 2008/0284322 A1 | 11/2008 | Hosokawa et al. |
| 2009/0066225 A1 | 3/2009 | Kimura et al. |
| 2009/0096356 A1 | 4/2009 | Murase et al. |
| 2009/0184313 A1 | 7/2009 | Buesing et al. |
| 2009/0253883 A1 | 10/2009 | McKiernan et al. |
| 2009/0261717 A1 | 10/2009 | Buesing et al. |
| 2009/0295276 A1 | 12/2009 | Asari et al. |
| 2009/0302742 A1 | 12/2009 | Komori et al. |
| 2009/0302743 A1 | 12/2009 | Kato et al. |
| 2010/0148161 A1 | 6/2010 | Kai et al. |
| 2010/0148162 A1 | 6/2010 | Komori et al. |
| 2010/0187520 A1 | 7/2010 | Sugimoto et al. |
| 2010/0187977 A1 | 7/2010 | Kai et al. |
| 2011/0037027 A1 | 2/2011 | Stoessel et al. |
| 2011/0062429 A1 | 3/2011 | Kai et al. |
| 2011/0065895 A1 | 3/2011 | Miura et al. |
| 2012/0104943 A1 | 5/2012 | Kato et al. |
| 2012/0112629 A1 | 5/2012 | Kato et al. |
| 2013/0020563 A1 | 1/2013 | Kato et al. |
| 2013/0153874 A1 | 6/2013 | Kato et al. |

FOREIGN PATENT DOCUMENTS

| | | |
|---|---|---|
| EP | 0909787 | 4/1999 |
| EP | 1 672 713 A1 | 6/2006 |
| EP | 1 860 097 A1 | 11/2007 |
| EP | 1 956 022 A1 | 8/2008 |
| EP | 1 956 666 A1 | 8/2008 |
| EP | 1 962 354 | 8/2008 |
| EP | 2 080 762 A1 | 7/2009 |
| EP | 2 166 011 A1 | 3/2010 |
| EP | 2 169 029 A1 | 3/2010 |
| EP | 2 172 534 A1 | 4/2010 |
| EP | 2 251 342 A1 | 11/2010 |
| EP | 2 284 920 A1 | 2/2011 |
| EP | 2 298 774 A1 | 3/2011 |
| EP | 2 301 921 A1 | 3/2011 |
| JP | 11-167215 A | 6/1999 |
| JP | 11-176578 A | 7/1999 |
| JP | 2004071500 | 3/2004 |
| JP | 2004-253298 A | 9/2004 |
| JP | 2005-289914 A | 10/2005 |
| JP | 2006-193729 A | 7/2006 |
| JP | 2006-199679 A | 8/2006 |
| JP | 2006-339577 A | 12/2006 |
| JP | 2007-88222 A | 4/2007 |
| JP | WO 2007/063796 A1 | 6/2007 |
| JP | 2008-509266 A | 3/2008 |
| JP | 2008-81494 | 4/2008 |
| JP | 2008-148514 | 6/2008 |
| KR | 10-2011-0058246 | 6/2011 |
| KR | 10-2011-0066766 | 6/2011 |
| WO | WO 2005/023894 A2 | 3/2005 |
| WO | WO 2005/023894 A3 | 3/2005 |
| WO | 2006/001333 | 1/2006 |
| WO | WO 2006/015862 A1 | 2/2006 |
| WO | WO 2006/100896 A1 | 9/2006 |
| WO | WO 2006/108497 A1 | 10/2006 |
| WO | 2006/122630 | 11/2006 |
| WO | WO-2006122630 A1 * | 11/2006 |
| WO | WO 2007/018007 A1 | 2/2007 |
| WO | 2007/022845 | 3/2007 |
| WO | 2007/029798 | 3/2007 |
| WO | 2007/063796 | 6/2007 |
| WO | 2007/069569 | 6/2007 |
| WO | WO 2007/063754 A1 | 6/2007 |
| WO | WO 2007/140847 A1 | 12/2007 |
| WO | WO 2008/006449 A1 | 1/2008 |
| WO | WO 2008/009343 A1 | 1/2008 |
| WO | WO 2008/056746 A1 | 5/2008 |
| WO | WO 2008/132103 A1 | 11/2008 |
| WO | WO 2008/146839 A1 | 12/2008 |
| WO | WO 2008/149691 A1 | 12/2008 |
| WO | WO 2009/016964 A1 | 2/2009 |
| WO | WO 2009/044615 A1 | 4/2009 |
| WO | WO 2009/124627 A1 | 10/2009 |
| WO | WO 2009/136595 A1 | 11/2009 |
| WO | 2010/107244 | 9/2010 |
| WO | WO 2010/131855 | 11/2010 |

OTHER PUBLICATIONS

Japanese Office Action issued in connection with corresponding Japanese Patent Appiication No. 2015-025867, filed Feb. 12, 2015.
Observation of a third party against ERA-2301926 issued Apr. 14, 2016 in connection with European Patent Application No. 09758282.9, filed Jun. 1, 2009.
K-T. Wong, et al. "Synthesis and Structures of Novel Heteroarene-Fused Coplanar π-Conjugated Chromophores", Organic Letters 2006 8(22), pp. 5033-5036.
Petition for Inter Partes review of U.S. Pat. No. 9,056,870 filed on Nov. 2, 2016.
Petition for Inter Partes Review of U.S. Pat. No. 9,056,870 filed Nov. 4, 2015.
Excerpts from Prosecution File History of the '870 patent.
Declaration of Benjamin J. Schwartz, Ph.D.
Curriculum Vitae of Benjamin J. Schwartz, Ph.D.
U.S. Appl. No. 12/253,586 ("The '586 parent application").
Transmittal Letter to U.S. Designated/Elected Office Concerning Submission Under 35 U.S.C. 371 for International Application PCT/EP2006/007386.
Kawaguchi et al., "Synthesis, Structures, and Properties of Asymmetrical Heteroacenes Containing Both Pyrrole and Furan Rings," Organic Letters 2008 vol. 10, No. 6, pp. 1199-1202 (Online published Feb. 16, 2008) ("Kawaguchi").
Transmittal Letter to U.S. Designated/Elected Office Concerning Submission Under 35 U.S.C. 371 for International Application PCT/JP2007/071728.
Transmittal Letter to U.S. Designated/Elected Office Concerning Submission Under 35 U.S.C. 371 for International Application PCT/EP2006/003670.
English Translation of PCT/EP2006/007386.
Machine English translation of Matsuura et al. (JP 2004-071500 A). Feb. 2, 2017.

(56) References Cited

OTHER PUBLICATIONS

International Search Report and Written Opinion dated Sep. 1, 2009 in corresponding international Application No. PCT/JP2009/059980 filed on Jun. 1, 2009.
Chuanjun Xia et al., "Ladder-Type Oligo(p-phenylene)s Tethered to a Poly(atkylene) Main Chain: The Orthogonal Approach to Functional Light-Emitting Polymers", Macromolecules, vol. 34, No. 20, 2001, pp. 6922-6928.
Josemon Jacob et al., "Ladder-Type Pentaphenytenes and Their Polymers: Efficient Blue-Light Emitters and Electron-Accepting Materials via a Common Intermediate", J. Am. Chem. Soc., vol. 126, No. 22, 2004, pp. 6987-6995.
Josemon Jacob et al., "A Fully Aryl-Substituted Poly(ladder-type pentaphenylene): A Remarkably Stable Blue-Light-Emitting Polymer", Macromolecules, vol. 38, No. 24, 2005, pp. 9933-9938.
Herbert Wiesenhofer et al., "Molecular Origin of the Temperature-Dependent Energy Migration in a Rigid-Rod Ladder-Phenyfene Molecutar Host", Advanced Materials, vol. 18, 2006, pp. 310-314.
Ashok K. Meshra et al., "Blue-Emitting Carbon- and Nitrogen-Bridged Poly(ladder-type tetraphenylene)s", Chem. Mater., vol. 18, No. 12, 2006, pp. 2879-2885.
Frédéric Laquai et al., "Photophysical Properties of a Series of Poly(ladder-type phenytene)s", Advanced Functional Materials, vol. 17, 2007, pp. 3231-3240.
Henning Serringhaus et al., "Dibenzothienobisbenzothiophene—A Novel Fused-Ring Oligomer with High Field-Effect Mobility", J. Mater. Chem., vol. 9, 1999, pp. 2095-2101.
Martin Sonntag et al., "Synthesis and Characterization of Novei Conjugated Bisindenocarbazoles", Tetrahedron, vol. 62, 2006, pp. 8103-8108.
Martin Sonntag et al., "Novel Bisindenocarbazole Derivative Exhibiting a Nematic Mesophase", Tetrahedron Letters, vol. 47, 2006, pp. 8313-8317.
Toby D. M. Bell et al., "Charge Transfer Enhanced Annihilation Leading to Deterministic Single Photon Emission in Rigid Perylene End-Capped Polyphenylenes", Chem. Commun., No. 39, 2005, pp. 4973-4975.
Ming Zhang et al., "Conjugated Atternating Copolymers Containing Both Donor and Acceptor Moieties in the Main Chain", Chem. Commun., No. 17, 2007, pp. 1704-1706.
Martin Sonntag et al., "Synthesis of a Novel Liquid Crystalline Bisindenocarbazole Derivative", Liquid Crystals, vol. 34, No. 1, Jan. 2007, pp. 49-57.
Eduard Fron et al., "Singlet-Singlet Annihitation Leading to a Charge-Transfer Intermediate in Chromophore-End-Capped Pentaphenylenes", Chem. Phys. Chem., vol. 8, 2007, 1386-1393.
M. Angeles Izquierdo et al., "Switching of the Fluorescence Emission of Single Molecules Between the Locally Excited and Charge Transfer States", Chemical Physics Letters, vol. 401, 2005, pp. 503-508.
Wen-Ya Lee et al., "Synthesis of New Fluorene-Indolocarbazole Alternating Copolymers for Light-Emitting Diodes and Field Effect Transistors", Polymer Journal, vol. 40, No. 3, 2008, pp. 249-255.
John P. Amara et al., "Conjugated Polymers with Geminal Trifluoromethyl Substituents Derived from Hexafluoroacetone", Macromolecules, vol. 39, 2006, pp. 5753-5759.
Nan-Xing Hu et al., "5,11-Dihydro-5,11-di-1-naphthylindolo[3.2-b]carbazole: Atropisomerism in a Novel Hole-Transport Molecule for Organic Light-Emitting Diodes", J. Am. Chem. Soc., vol. 121, No. 21, 1999, pp. 5097-5098.
Extended European Search Report dated Dec. 6, 2011, in Patent Application No. 09758282.9.
Yuncheol Na, et al., "Formation of Pyro-products by the Pyrolysis of Monobromophenols", Bulletin Korean Chemical Society, vol. 24, No. 9, XP 2664291, 2003, pp. 1276-1280.
Holger Erdtman, et al., "Studies on Humic Acids", Acta Chemica Scandinavica, vol. 13, No. 4, XP 2664292, 1959, pp. 653-658.
Masaki Shimizu, et al., "Palladium-Catalyzed Annulation of vic-Bis(pinacolatoboryl)alkenes and -phenanthrenes with 2,2'-Dibromobiaryls: Facile Synthesis of Functionalized Phenanthrenes and Dibenzo[g,p]chrysenes", Angewandte Chemie, International Edition, vol. 47, No. 42, XP 2664293, 2008, pp. 8096-8099.
Teruhisa Tsuchimoto, et al., "Indium-Catalyzed Annulation of 2-Aryl- and 2-Heteroarylindoles with Propargyl Ethers: Concise Synthesis and Photophysical Properties of Diverse Aryl- and Heteroaryl-Annulated[a]carbazoles", Journal of Amerecan Chemical Society, vol. 130, XP 2664294, 2008, pp. 15823-15835.
Korean Office Action dated May 12, 2014, in Korea Patent Application No. 10-2010-7027215.
Teruhisa Tsuchimoto, et al., "Easy Access to Aryl-and Heteroaryl-Annulated[a]carbazoles by the Indium-Catalyzed Reaction of 2-Arylindoles with Propargyl Ethers", Angew. Chem Int. Ed. 2005, vol. 44, (Jan. 21, 2005), pp. 1336-1340.
Office Action dated Jul. 15, 2014 in Japanese Patent Application No. 2013-178412.
Li et al., "Novel Starburst Molecule as a Hole Injecting and Transporting Material for Organic Light-Emitting Devices" Chem. of Materials 17, 615-619 (2005).
Taft et al., "A Survey of Hammett Substituent Constants and Resonance and Field Parameters," 91 Chem. Rev. 165-195 (1991).
Guisado et al., "The Facile Preparation of Primary and Secondary Amines via an Improved Fukuyama-Mitsunobu Procedure. Application to the Synthesis of a Lung-Targeted Gene Delivery Agent" 3 Organic and Biomolecular Chem., 3 1049-1057 (2005).
Curriculum Vitae of John E. Anthony, Ph.D.
Patent Owner Preliminary Response submitted in IPR 2016-00148.
PTAB Decision to Institute Trial submitted in IPR2016-00148.
Patent Owner Response submitted in IPR2016-00148.
Petitioner's Reply submitted in IPR2016-00148.
Petition for Inter Partes review (IPR2017-00197) of U.S. Pat. No. 9,056,870 filed on Nov. 2, 2016.
Deposition of John Anthony, Ph. D. Atexandria, VA (Sep. 29, 2016), including Errata Sheet.
Anthony, Functionalized Acenes and Heteroacenes for Organic Electronics, Chem. Rev. 2006, 108,p. 5028.
Declaration of Benjamin J. Schwartz Ph. D. in Support of Petitioner's Reply.
Moorthy et al., *Steric Inhibition of π-Stacking: 1,3,6,8-Tetraarylpyrenes as Efficient Blue Emitters in Organic Light Emitting Diodes (OLEDs)*, 9 Organic Letters (25) 5215-5218 (2007).
Park et al., *High mobility solution processed 6,13-bis(triisopropyl-silylethynyl) pentacene organic thin film transistors*, 91 Applied Physics Letters, 063514-01-03 (2007).
Wolak et al., *Photophysical Properties of Dioxolane-Substituted Pentacene Derivatives Dispersed in Tris(quinolin-8-olato)aluminum(III)*, 110 J. Phys. Chem. B.; 7928-37 (2006).
Shih et al., *A Novel Fluorene-Triphenylamine Hybrid That is a Highly Efficient Host Material for Blue-, Green-, and Red-Light-Emitting Electrophosphorescent Devices*, 17 Advanced Functional Materials, 3514-3520 (2007).
Deposition of Benjamin J. Schwartz, Ph. D. Los Angeles, CA (Jun. 28, 2016), including Errata Sheet.
Declaration of John E. Anthony, Ph.D.
Garnier et al., "Molecular Engineering of Organic Semiconductors: Design of Self-Assembly Properties in Conjugated Thiophene Oligomers" 115 J. Am. Chem. Soc'y., 8716-8721 (1993).
Wang et al., "Graphene-Assisted Solution Growth of Vertically Oriented Organic Semiconducting Single Crystals" 9 ACS Nano 9486-9496 (2015).
Murphy et al., "Organic Semiconducting Oligomers for Use in Thin Film Transistors" 107 Chem. Rev., 1066-1096 (2007).
Vehoff et al.. "Charge Transport in Organic Crystals: Role of Disorder and Topological Connectivity" 132 J. Am. Chem. Soc'y., 11702-11708 (2010).
Meng et al., "High Field-Effect Mobility Oligofluorene Derivatives with High Environmental Stability" 123 J. Am. Chem. Soc'y., 9214-9215 (2001).
May et al., "Design rules for charge-transport efficient host materials for phosphorescent organic light-emitting diodes" 134 J. Am. Chem. Soc'y. 13818-13822 (2012).
Li et al., "Maximizing $Alq_3$ OLED Internal and External Efficiencies: Charge Balanced Device Structure and Color Conversion Outcoupling Lenses" 2 J. Display Tech., 143-152 (2006).

(56) References Cited

OTHER PUBLICATIONS

Yang et al., "Porous Shape Persistent Fluorescent Polymer Films: An Approach to TNT Sensory Materials" 120 J. Am. Chem. Soc'y., 5321-5322 (1998).
Landis et al., "Silylethynylated Anthracene Derivatives for Use in Organic Light-Emitting Diodes" 44 Japanese J. of Applied Physics, 3921-3922 (2005).
Picciolo et al., "RGB Emission Using a Dimesitylboryl-bithiophene as a Universal Host and Pentacene Derivatives as the Red Emitters" Proceedings of the SPIE—The Int'l Soc'y for Optical Engineering, 4464 (2002).
Wolak et al., "High Performance Organic Light-Emitting Diodes Based on Dioxolane-Substituted Pentacene Derivatives" 16 Advanced Functional Materials, 1943-1947 (2006).
Sapochak et al., "Inductive Effects of Diphenylphosphoryl Moieties on Carbazole Host Materials: Design Rules for Blue Electrophosphorescent Organic Light-Emitting Devices" J. of Physical Chem. C 112, 7989-7996 (2008).
David St. C. Black et al.; "Modified Vilsmeier Reactions of Activated Benzofurans with Indolines: Synthesis of Benzofuran-fused Benzocarbazoles"; Tetrahedron Letters 40, pp. 4251-4254, 1999.
Oct. 13, 2014 fetter from Mr. Hyejin Kang.
Oct. 22, 2014 tetter from Mr. Hyejin Kang.
Japanese Office Action dated Apr. 23, 2013 in connection with Japanese Patent Application No. 2010-515858.

\* cited by examiner

MATERIAL FOR ORGANIC ELECTROLUMINESCENCE DEVICE AND ORGANIC ELECTROLUMINESCENCE DEVICE USING THE SAME

TECHNICAL FIELD

The present invention relates to a material for an organic electroluminescence device and an organic electroluminescence device using the material, in particular, an organic electroluminescence device, which shows high luminous efficiency, is free of any pixel defect, and has a long lifetime, and a material for an organic electroluminescence device for realizing the device.

BACKGROUND ART

An organic electroluminescence device (hereinafter, "electroluminescence" may be abbreviated as "EL") is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported, many studies have been conducted on organic EL devices using organic materials as the constituent materials. The devices of the laminate type use tris(8-quinolinolato) aluminum for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato) aluminum complexes, coumarine derivatives, tetraphenylbutadiene derivatives, distyrylarylene derivatives, and oxadiazole derivatives are known. It is reported that light in the visible region ranging from blue light to red light can be obtained by using these light emitting materials, and development of a device exhibiting color images is expected.

In addition, it has been recently proposed that a phosphorescent material as well as a fluorescent material be utilized in the light emitting layer of an organic EL device. High luminous efficiency is achieved by utilizing the singlet and triplet states of an excited state of an organic phosphorescent material in the light emitting layer of an organic EL device. Upon recombination of an electron and a hole in an organic EL device, singlet excitons and triplet excitons may be produced at a ratio of 1:3 owing to a difference in spin multiplicity between the singlet and triplet excitons, so the use of a phosphorescent material may achieve luminous efficiency three to four times as high as that of a device using fluorescence alone.

Patent Documents 1 to 7 are exemplary inventions each describing such materials for an organic EL device.

Patent Document 1 describes a compound using, as a mother skeleton, a structure obtained by crosslinking a terphenylene skeleton with, for example, a carbon atom, nitrogen atom, or oxygen atom. The document, which mainly discloses data indicative of the potential of the compound to serve as a hole transporting material, describes that the compound is used as a host material for a phosphorescent material in a light emitting layer. However, the description is limited to a red phosphorescent device, and the luminous efficiency of the device is not high enough for the device to be put into practical use.

Patent Document 2 describes an indolocarbazole compound having a substituent on a nitrogen atom or on an aromatic ring. The document recommends that the compound be used as a hole transporting material, and describes that a thermally and morphologically stable, thin hole transporting layer can be prepared from the compound. However, the document does not describe data indicative of the usefulness of the compound as a host material or electron transporting material to be used together with a phosphorescent material.

Patent Document 3 describes indolocarbazole compounds each having a substituent on a nitrogen atom or on an aromatic ring. The document discloses data on a green light emitting device using any one of those compounds as a host material for a phosphorescent material in its light emitting layer. However, a high voltage must be applied to the device to drive the device, and the device shows low luminous efficiency, so the device cannot be sufficiently put into practical use.

Patent Document 4 describes indolocarbazole compounds each having a substituent. The document describes that each of the compounds functions as a host material for a phosphorescent material in a light emitting layer. However, each of those compounds is characterized in that the compound has a dimer or trimer structure through a linking group, and each of the compounds tends to have a large molecular weight. The document discloses data on a green phosphorescent device using any one of those compounds, but all the compounds used each have a large molecular weight of 800 or more. The efficiency with which a material having a large molecular weight is deposited in a vacuum is poor, and the material may decompose owing to heating for a long time period, so the material may be insufficient in terms of practical use.

Patent Documents 5 and 6 describe indenofluorene compounds each having a substituent on an aromatic ring, and describe that each of the compounds functions as a fluorescent material in a light emitting layer. However, none of the documents describes data indicative of the usefulness of each of the compounds as a host material or electron transporting material to be used together with a phosphorescent material.

Patent Document 7 describes compounds each using, as a mother skeleton, a structure obtained by crosslinking a terphenylene skeleton with a sulfur atom, boron atom, or phosphorus atom. The document describes that each of those compounds has excellent oxidation resistance, and allows the formation of an organic semiconductor active layer by an application method. However, the document does not describe data indicative of the usefulness of each of the compounds as a host material or electron transporting material to be used together with a fluorescent material or phosphorescent material.

Patent Document 1: WO 2006/122630
Patent Document 2: EP 0909787
Patent Document 3: WO 2007/063796

Patent Document 4: WO 2007/063754
Patent Document 5: US 2002/0132134
Patent Document 6: US 2003/0044646
Patent Document 7: JP 2008-81494

DISCLOSURE OF THE INVENTION

Problems to be Solved by the Invention

The present invention has been made with a view to solving the above problems, and an object of the present invention is to provide an organic EL device which shows high luminous efficiency, is free of any pixel defect, and has a long lifetime, and a material for an organic EL device for realizing the device.

Means for Solving the Problems

The inventors of the present invention have made extensive studies with a view to achieving the above object. As a result, the inventors have found that the above object can be achieved by using a compound having a π-conjugated heteroacene skeleton crosslinked with a carbon atom, nitrogen atom, oxygen atom, or sulfur atom as a material for an organic EL device. Thus, the inventors have completed the present invention.

That is, the present invention provides a material for an organic EL device represented by the following formulae (1) or (2).

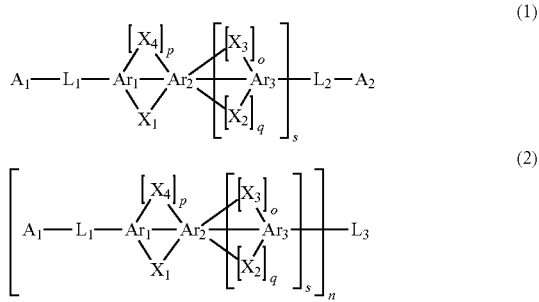

[In the formulae (1) and (2), $Ar_1$, $Ar_2$, and $Ar_3$ each independently represent a substituted or unsubstituted aromatic hydrocarbon group having a ring formed of 6 to 24 carbon atoms or a substituted or unsubstituted aromatic heterocyclic group having a ring formed of 3 to 24 atoms, provided that, $Ar_1$, $Ar_2$, and $Ar_3$ each may have one substituent Y or multiple substituents Ys, in the case of multiple substituents Ys, the substituent Ys may be different from each other, Y represents an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $Ar_1$, $Ar_2$, or $Ar_3$ through a carbon-carbon bond.

In the formulae (1) and (2), $X_1$, $X_2$, $X_3$, and $X_4$ each independently represent O, S, N—$R_1$ or $CR_2R_3$ (N atom of N—R, or C atom of $CR_2R_3$ binds to $Ar_1$, $Ar_2$, or $Ar_3$).

In the formulae (1) and (2), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_1$ and $X_2$ represent N—$R_3$, o and p each represent 0, and q represents 1, or when both $X_1$ and $X_3$ represent N—$R_1$, p and q each represent 0, and o represents 1, at least one $R_1$ represents a substituted or unsubstituted, monovalent fused aromatic heterocyclic group having a ring formed of 8 to 24 atoms.

In the formulae (1) and (2), o, p, and q each represent 0 or 1 and s represents 1, 2, or 3. n represents 2, 3, or 4, and the material represented by the formula (2) includes a dimer using $L_3$ as a linking group for n=2, a trimer using $L_3$ as a linking group for n=3, or a tetramer using $L_3$ as a linking group for n=4.

In the formulae (1) and (2), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with $Ar_1$ through a carbon-carbon bond.

In the formula (1), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with $Ar_3$ through a carbon-carbon bond, provided that, when both $X_1$ and $X_2$ represent $CR_2R_3$, o and p each represent 0, q represents 1, and both $L_1$ and $L_2$ represent substituted or unsubstituted, monovalent or divalent aromatic hydrocarbon groups each having a ring formed of 6 to 24 carbon atoms, or when both $X_1$ and $X_3$ represent $CR_2R_3$, p and q each represent 0, o represents 1, and both $L_1$ and $L_2$ represent substituted or unsubstituted, monovalent or divalent aromatic hydrocarbon groups each having a ring formed of 6 to 24 carbon atoms, a case where $L_1$ and $L_2$ are simultaneously linked at para positions with respect to $Ar_2$ is excluded.

In the formula (2), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with $Ar_3$ through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has a ring formed of 3 to 24 atoms and which is linked with $Ar_3$ through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with $Ar_3$ through a carbon-carbon bond, provided that, when both $X_1$ and $X_2$ represent $CR_2R_3$, o and p each represent 0, q represents 1, and both $L_1$ and $L_2$ represent substituted or unsubstituted, monovalent, divalent, trivalent, or tetravalent aromatic hydrocarbon groups each having a ring formed of 6 to 24 carbon atoms, or when both $X_1$ and $X_3$ represent $CR_2R_3$, p and q each represent 0, o represents 1, and both $L_1$ and $L_3$ represent substituted or unsubstituted, monovalent, divalent, trivalent, or tetravalent aromatic hydrocarbon groups each having a ring formed of 6 to 24 carbon atoms, a case where $L_1$ and $L_3$ are simultaneously linked at para positions with respect to $Ar_2$ is excluded.

In the formulae (1) and (2), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (1), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_1$ and $X_2$ each represent O, S, or $CR_2R_3$, o and p each represent 0, q represents 1, and both $L_1$ and $L_2$ represent single bonds, or when both $X_1$ and $X_3$ each represent O, S, or $CR_2R_3$, p and q each represent 0, o represents 1, and both $L_1$ and $L_2$ represent single bonds, a case where $A_1$ and $A_2$ simultaneously represent hydrogen atoms is excluded; In the formulae (1) and (2), $A_1$, $A_2$, $L_1$, $L_2$, and $L_3$ are each free of any carbonyl group.

A case where the formula (1) has a structure represented by the following general formula (3) is excluded,

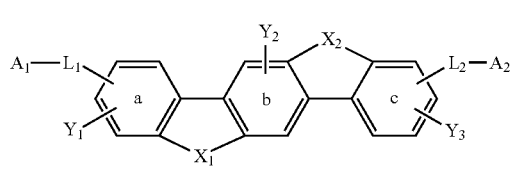

(3)

provided that, $X_1$, $X_2$, $A_1$, $A_2$, $L_1$, and $L_2$ in the formula (3) has the same meaning $X_1$, $X_2$, $A_1$, $A_2$, $L_1$, and $L_2$ in the formula (1), respectively.

In the formula (3), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with a benzene ring a, b, or c through a carbon-carbon bond, the number of each of $Y_1$ and $Y_3$ is 0, 1, 2, or 3, and the number of $Y_2$ is 0, 1, or 2.

A case where the formula (2) has a structure represented by the following general formula (4) is excluded,

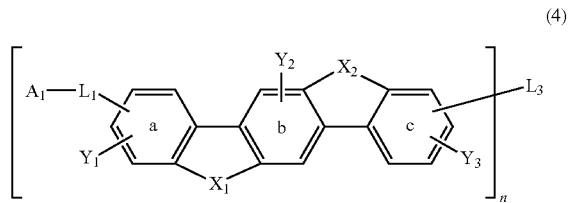

(4)

provided that, $X_1$, $X_2$, $R_1$, $L_1$, $L_3$, and n in the formula (4) has the same meaning $X_1$, $X_2$, $A_1$, $L_1$, $L_3$, and n in the formula (2), respectively.

In the formula (4), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.]

In addition, the present invention provides an organic EL device having one or more organic thin film layers including a light emitting layer between a cathode and an anode in which at least one layer of the organic thin film layers contains a material for an organic EL device as a compound having a π-conjugated heteroacene skeleton crosslinked with a carbon atom, nitrogen atom, oxygen atom, or sulfur atom. A material for an organic EL device represented by the above formula (1) or (2) is preferably used as the material for an organic EL device of the present invention.

Further, the material for an organic EL device is effective also as a material for an organic electron device such as an organic solar cell, organic semiconductor laser, a sensor using organic matter, or an organic TFT.

Effects of the Invention

According to the present invention, there can be provided an organic EL device which shows high luminous efficiency, is free of any pixel defect, and has a long lifetime, and a material for an organic EL device for realizing the device.

BEST MODE FOR CARRYING OUT THE INVENTION

A material for an organic EL device of the present invention is represented by the following general formula (1) or

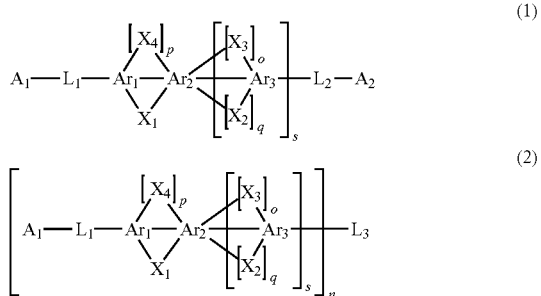

[In the formulae (1) and (2), $Ar_1$, $Ar_2$, and $Ar_3$ each independently represent a substituted or unsubstituted aromatic hydrocarbon group having a ring formed of 6 to 24 carbon atoms or a substituted or unsubstituted aromatic heterocyclic group having a ring formed of 3 to 24 atoms, provided that, $Ar_1$, $Ar_2$, and $Ar_3$ each may have one substituent Y or multiple substituents Ys, in the case of multiple substituents Ys, the substituent Ys may be different from each other, Y represents an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $Ar_1$, $Ar_2$, or $Ar_3$ through a carbon-carbon bond.

In the formulae (1) and (2), $X_1$, $X_2$, $X_3$, and $X_4$ each independently represent O, S, N—$R_1$, or $CR_2R_3$.

In the formulae (1) and (2), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon, atoms, or a substituted or unsubstituted aromatic heterocyclic group having a ring formed of 3 to 24 atoms, provided that, when both $X_1$ and $X_2$ represent N—$R_1$, o and p each represent 0, and q represents 1, or when both $X_1$ and $X_3$ represent N—$R_1$, p and q each represent 0, and o represents 1, at least one $R_1$ represents a substituted or unsubstituted, monovalent fused aromatic heterocyclic group having a ring formed of 8 to 24 atoms.

In the formulae (1) and (2), o, p, and q each represent 0 or 1, s represents 1, 2, or 3, when s represents 2 or 3, and the general formulae (1) and (2) are each represented as the following.

When s represents 2

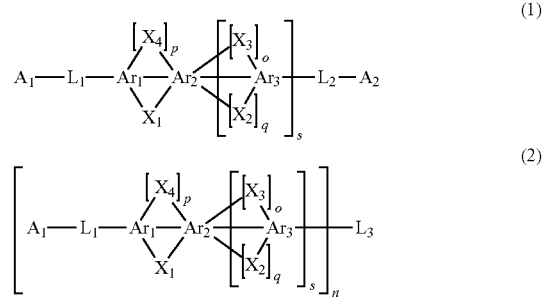

When s represents 3

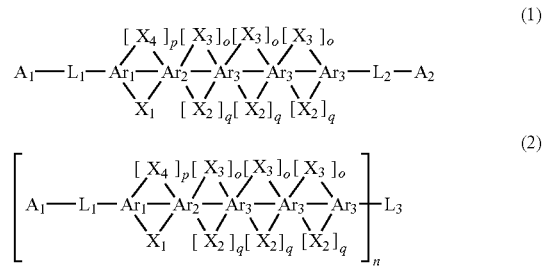

n represents 2, 3, or 4, and the material represented by the formula (2) includes a dimer using $L_3$ as a linking group for n=2, a trimer using $L_3$ as a linking group for n=3, or a tetramer using $L_3$ as a linking group for n=4.

In the formulae (1) and (2), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with $Ar_1$ through a carbon-carbon bond.

In the formula (1), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with $Ar_3$ through a carbon-carbon bond, provided that, when both $X_1$ and $X_2$ represent $CR_2R_3$, o and p each represent 0, q represents 1, and both $L_1$ and $L_2$ represent substituted or unsubstituted, monovalent or divalent aromatic hydrocarbon groups each having a ring formed of 6 to 24 carbon atoms, or when both $X_1$ and $X_3$ represent $CR_2R_3$, p and q each represent 0, o represents 1, and both $L_1$ and $L_2$ represent substituted or unsubstituted, monovalent or divalent aromatic hydrocarbon groups each having a ring formed of 6 to 24 carbon atoms, a case where $L_1$ and $L_2$ are simultaneously linked at para positions with respect to $Ar_2$ is excluded.

In the formula (2), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with $Ar_3$ through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has a ring formed of 3 to 24 atoms and which is linked with $Ar_3$ through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with $Ar_3$ through a carbon-carbon bond, provided that, when both $X_1$ and $X_2$ represent $CR_2R_3$, o and p each represent 0, g represents 1, and both $L_1$ and $L_3$ represent substituted or unsubstituted, monovalent, divalent, trivalent, or tetravalent aromatic hydrocarbon groups each having a ring formed of 6 to 24 carbon atoms, or when both $X_1$ and $X_3$ represent $CR_2R_3$, p and q each represent 0, o represents 1, and both $L_1$ and $L_3$ represent substituted or unsubstituted, monovalent, divalent, trivalent, or tetravalent aromatic hydrocarbon groups each having a ring formed of 6 to 24 carbon atoms, a case where $L_1$ and $L_3$ are simultaneously linked at para positions with respect to $Ar_2$ is excluded.

In the formulae (1) and (2), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (1), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_1$ and $X_2$ each represent O, S, or $CR_2R_3$, o and p each represent 0, q represents 1, and both $L_1$ and $L_2$ represent single bonds, or when both $X_1$ and $X_3$ each represent O, S, or $CR_2R_3$, p and q each represent 0, o represents 1, and both $L_1$ and $L_2$ represent single bonds, a case where $A_1$ and $A_2$ simultaneously represent hydrogen atoms is excluded.

In the formulae (1) and (2), $A_1$, $A_2$, $L_1$, $L_2$, and $L_3$ are each free of any carbonyl group.

A case where the formula (1) has a structure represented by the following general formula (3) is excluded,

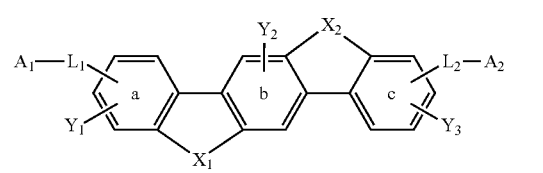

provided that, $X_1$, $X_2$, $A_1$, $A_2$, $L_1$, and $L_2$ in the formula (3) has the same meaning $X_1$, $X_2$, $A_1$, $A_2$, $L_1$, and $L_2$ in the formula (1), respectively.

In the formula (3), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with a benzene ring a, b, or c through a carbon-carbon bond, the number of each of $Y_1$ and $Y_3$ is 0, 1, 2, or 3, and the number of $Y_2$ is 0, 1, or 2.

A case where the formula (2) has a structure represented by the following general formula (4) is excluded,

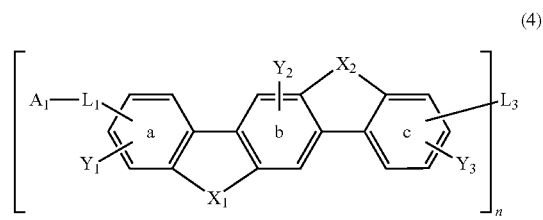

provided that, $X_1$, $X_2$, $A_1$, $L_1$, $L_3$, and n in the formula (4) has the same meaning $X_1$, $X_2$, $A_1$, $L_1$, $L_3$, and n in the formula (2), respectively.

In the formula (4), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with a benzene ring a, b, or c through a carbon-carbon bond, the number of each of $Y_1$ and $Y_3$ is 0, 1, 2, or 3, and the number of $Y_2$ is 0, 1, or 2.

When the benzene ring a is substituted by multiple $Y_1$s, the benzene ring b is substituted by multiple $Y_2$s, or the benzene ring c is substituted by multiple $Y_3$s in the formulae (3) and (4), each of the rings is represented as shown below.

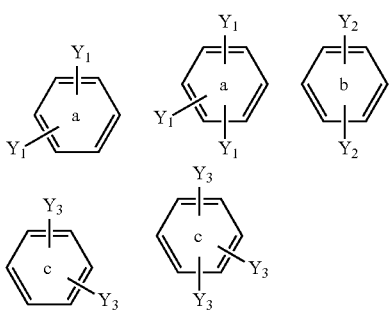

The material for an organic EL device represented by the general formula (1) is preferably a material for an organic EL device represented by any one of the following general formulae (5), (7) to (9), (13), (15), and (17), and the material for an organic EL device represented by the general formula (2) is preferably a material for an organic EL device represented by any one of the following general formulae (6), (10) to (12), (14), (1.6), and (18).

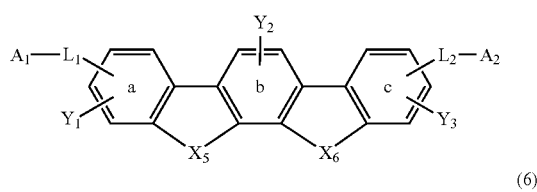

(5)

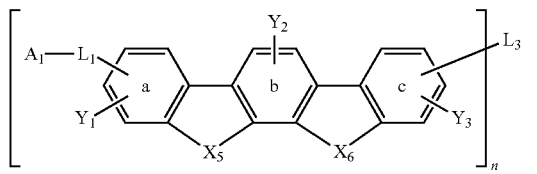

(6)

[In the formulae (5) and (6), $X_5$ and $X_6$ each independently represent O, S, N—$R_1$, or $CR_2R_3$.

In the formulae (5) and (6), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_5$ and $X_6$ represent N—$R_1$, at least one $R_1$ represents a substituted or unsubstituted, monovalent fused aromatic heterocyclic group having a ring formed of 8 to 24 atoms.

In the formula (6), n represents 2, 3, or 4, and the material represented by the formula (6) includes a dimer using $L_3$ as a linking group for n=2, a trimer using $L_3$ as a linking group for n=3, or a tetramer using $L_3$ as a linking group for n=4.

In the formulae (5) and (6), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (5), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with the benzene ring c through a carbon-carbon bond, provided that, when both $X_5$ and $X_6$ represent $CR_2R_3$ and both $L_1$ and $L_2$ represent substituted or unsubstituted, monovalent or divalent aromatic hydrocarbon groups each having a ring formed of 6 to 24 carbon atoms, a case where $L_1$ and $L_2$ are simultaneously linked at para positions with respect to a benzene ring b is excluded.

In the formulae (6), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with a benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with a benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond, provided that, when both $X_5$ and $X_6$ represent $CR_2R_3$ and both $L_1$ and $L_3$ represent substituted or unsubstituted, monovalent, divalent, trivalent, or tetravalent aromatic hydrocarbon groups each having a ring formed of 6 to 24 carbon atoms, a case where $L_1$ and $L_3$ are simultaneously linked at para positions with respect to the benzene ring b is excluded.

In the formulae (5) and (6), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (5), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_5$ and $X_6$ each represent O, S, or $CR_2R_3$ and both $L_1$ and $L_2$ represent single bonds, a case where $A_1$ and $A_2$ simultaneously represent hydrogen atoms is excluded.

In the formulae (5) and (6), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_3$ and $Y_3$ is 0, 1, 2, or 3, and the number of $Y_2$ is 0, 1, or 2.

In the formulae (5) and (6), $A_1$, $A_2$, $L_1$, $L_2$, and $L_3$ are each free of any carbonyl group.]

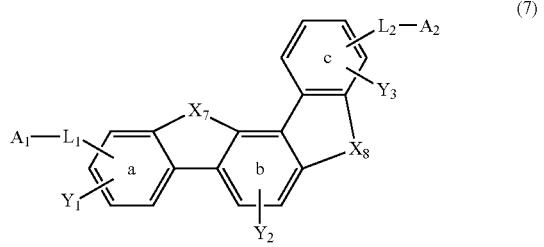

(7)

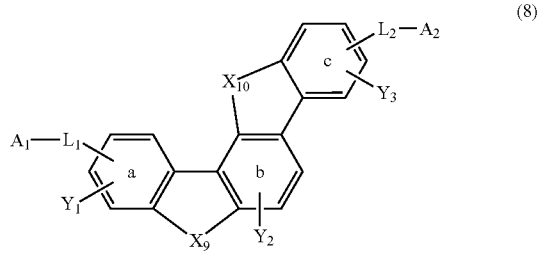

(8)

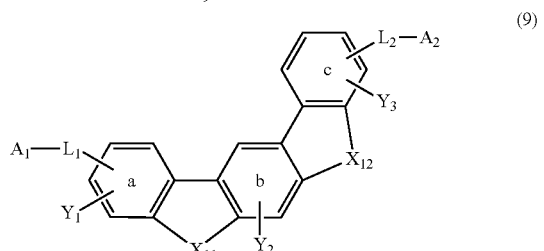

(9)

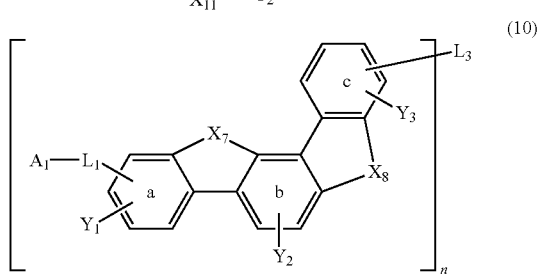

(10)

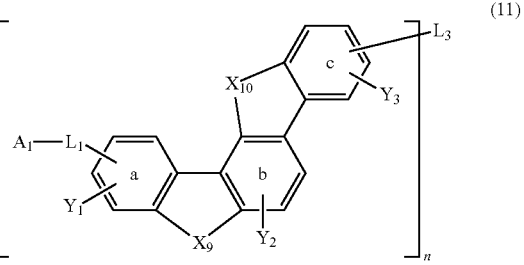

(11)

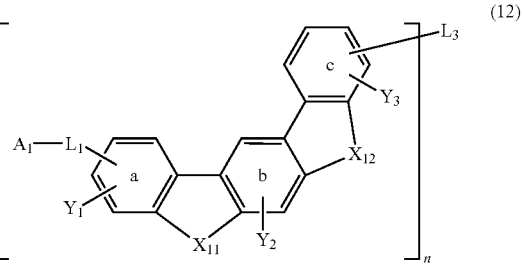

(12)

[In the formulae (7) to (12), $X_7$, $X_8$, $X_9$, $X_{10}$, $X_{11}$, and $X_{12}$ each independently represent O, S, N—$R_1$, or $CR_2R_3$.

In the formulae (7) to (12), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_7$ and $X_8$, both $X_9$ and $X_{10}$, and both $X_{11}$ and $X_{12}$ represent N—$R_1$, at least one $R_1$ represents a substituted or unsubstituted, monovalent fused aromatic heterocyclic group having a ring formed of 8 to 24 atoms.

In the formulae (10) to (12), n represents 2, 3, or 4, and the material represented by any one of the formulae (10) to (12) includes a dimer using $L_3$ as a linking group for n=2, a trimer using $L_3$ as a linking group for n=3, or a tetramer using $L_3$ as a linking group for n=4.

In the formulae (7) to (12), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formulae (7) to (9), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond, provided that, when both $X_7$ and $X_8$, both $X_9$ and $X_{10}$, or both $X_{11}$ and $X_{12}$ represent $CR_2R_3$ and both $L_1$ and $L_2$ represent substituted or unsubstituted, monovalent or divalent aromatic hydrocarbon groups each having a ring formed of 6 to 24 carbon atoms, a case where $L_1$ and $L_2$ are simultaneously linked at para positions with respect to a benzene ring b is excluded.

In the formulae (10) to (12), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond, provided that, when both $X_7$ and $X_8$, both $X_9$ and $X_{10}$, or both $X_{11}$ and $X_{12}$, represent $CR_2R_3$ and both and $L_3$ represent substituted or unsubstituted, monovalent, divalent, trivalent, or tetravalent aromatic hydrocarbon groups each having a ring formed of 6 to 24 carbon atoms, a case where $L_1$ and $L_3$ are simultaneously linked at para positions with respect to the benzene ring b is excluded.

In the formulae (7) to (12), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where A represents a hydrogen atom is excluded.

In the formulae (7) to (9), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $X_7$ and $X_8$, both $X_9$ and $X_{10}$, or both $X_{12}$ and $X_{12}$, represent O, S, or $CR_2R_3$ and both $L_1$ and $L_2$ represent single bonds, a case where $A_1$ and $A_2$ simultaneously represent hydrogen atoms is excluded.

In the formulae (7) to (12), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (7) to (12), $A_1$, $A_2$, $L_1$, $L_2$, and $L_3$ are each free of any carbonyl group.]

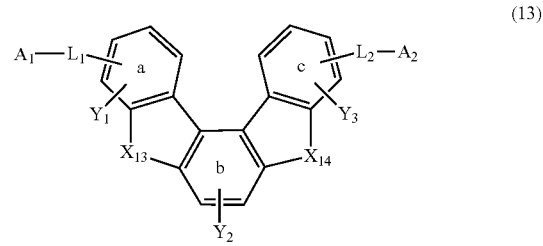

(13)

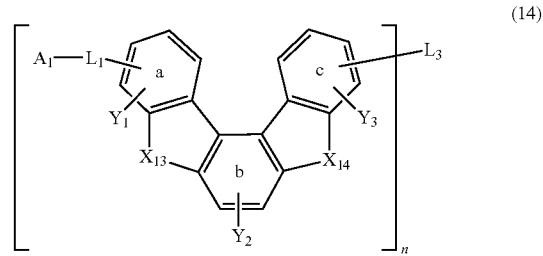

(14)

[In the formulae (13) and (14), $X_{13}$ and $X_{14}$ each independently represent O, S, N—$R_1$, or $CR_2R_3$.

In the formulae (13) and (14), $R_1$, $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms, provided that, when both $X_{13}$ and $X_{14}$ represent N—$R_1$, at least one $R_1$ represents a substituted or unsubstituted, monovalent fused aromatic heterocyclic group having a ring formed of 8 to 24 atoms.

In the formula (14), n represents 2, 3, or 4, and the material represented by the formula (14) includes a dimer using $L_3$ as a linking group for n=2, a trimer using $L_3$ as a linking group for n=3, or a tetramer using $L_3$ as a linking group for n=4.

In the formulae (13) and (14), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (13), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond, provided that, when both $X_{13}$ and $X_{14}$ represent $CR_2R_3$ and both $L_1$ and $L_2$ represent substituted or unsubstituted, monovalent or divalent aromatic hydrocarbon groups each having a ring formed of 6 to 24 carbon atoms, a case where $L_1$ and $L_2$ are simultaneously linked at para positions with respect to a benzene ring b is excluded.

In the formula (14), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond, provided that, when both $X_{13}$ and $X_{14}$ represent $CR_2R_3$ and both $L_1$ and $L_3$ represent substituted or unsubstituted, monovalent, divalent, trivalent, or tetravalent aromatic hydrocarbon groups each having a ring formed of 6 to 24 carbon atoms, a case where $L_1$ and $L_3$ are simultaneously linked at para positions with respect to the benzene ring b is excluded.

In the formulae (13) and (14), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (13), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when $X_{13}$ and $X_{14}$ each represent O, S, or $CR_2R_3$, and both $L_1$ and $L_2$ represent single bonds, a case where $A_3$ and $A_2$ simultaneously represent hydrogen atoms is excluded.

In the formulae (13) and (14), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (13) and (14), $A_1$, $A_2$, $L_1$, $L_2$, and $L_3$ are each free of any carbonyl group.]

The compounds represented by the general formulae (5) and (6) are each preferably a benzofurano dibenzofuran derivative represented by one of the following general formulae (15) and (16).

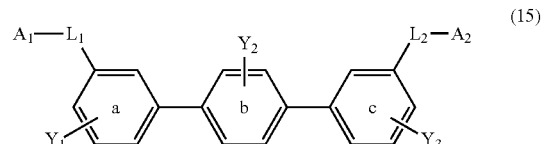

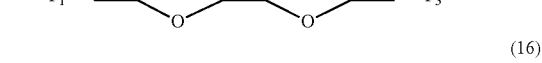

[In the formula (16), n represents 2, 3, or 4, and the material represented by the formula (16) includes a dimer using $L_3$ as a linking group for n=2, a trimer using $L_3$ as a linking group for n=3, or a tetramer using $L_3$ as a linking group for n=4.

In the formulae (15) and (16), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (15), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formula (16), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (15) and (16), $A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (15), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded.

In the formulae (15) and (16), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (15) and (16), $A_1$, $A_2$, $L_1$, $L_2$, and $L_3$ are each free of any carbonyl group.]

The compounds represented by the general formulae (9) and (12) are each preferably a benzofurano dibenzofuran derivative represented by one of the following general formulae (17) and (18).

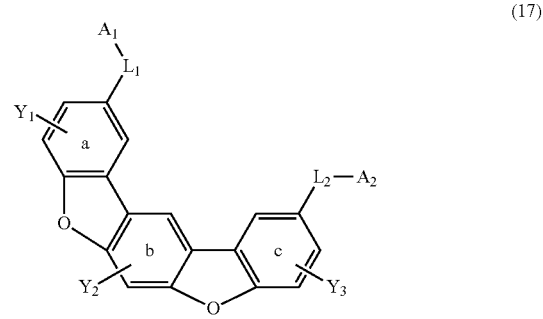

(17)

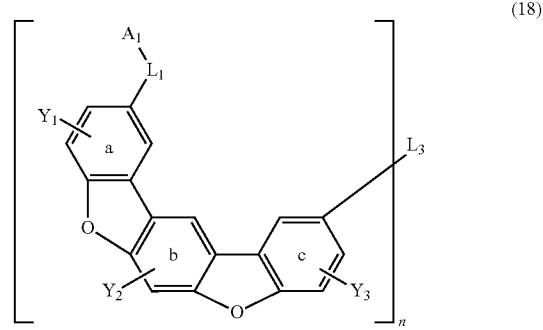

(18)

[In the formula (18), n represents 2, 3, or 4, and the material represented by the formula (18) includes a dimer using $L_3$ as a linking group for n=2, a trimer using $L_3$ as a linking group for n=3, or a tetramer using $L_3$ as a linking group for n=4.

In the formulae (17) and (18), $L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond.

In the formula (17), $L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond.

In the formula (18), when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond.

In the formulae (17) and (18), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded.

In the formula (17), $A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or an aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded, and, when both $L_1$ and $L_2$ represent single bonds, a case where $A_1$ and $A_2$ simultaneously represent hydrogen atoms is excluded.

In the formulae (17) and (18), $Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, the number of each of $Y_1$ and $Y_3$ is 0, 1, 2, or 3, and the number of $Y_2$ is 0, 1, or 2.

In the formulae (17) and (18), $A_1$, $A_2$, $L_1$, $L_2$, and $L_3$ are each free of any carbonyl group.]

In the general formulae (1) to (18), specific examples of each group are described below.

Examples of the substituted or unsubstituted aromatic hydrocarbon group having a ring formed of 6 to 24 carbon atoms represented by $Ar_1$ to $Ar_3$, Y, $Y_1$ to $Y_3$, $R_1$ to $R_3$, $L_1$ to $L_3$, and $A_1$ and $A_2$ include residues having corresponding valencies such as substituted or unsubstituted benzene, naphthalene, biphenyl, terphenyl, fluorene, phenanthrene, triphenylene, perylene, chrysene, fluoranthene, benzofluorene, bnezotriphenylene, benzochrysene, and anthracene. Preferred are benzene, naphthalene, biphenyl, terphenyl, fluorene, and phenanthrene.

Examples of the substituted or unsubstituted aromatic heterocyclic group having a ring formed of 3 to 24 atoms represented by $Ar_1$ to $Ar_3$, Y, $Y_1$ to $Y_3$, $R_1$ to $R_3$, $L_1$ to $L_3$, and $A_1$ and $A_2$ include residues having corresponding valencies such as pyridine, pyridazine, pyrimidine, pyrazine, 1,3,5-triazine, carbazole, dibenzofuran, dibenzothiophene, phenoxazine, phenothiazine, and dihydroacridine. Preferred are pyridine, pyridazine, pyrimidine, pyrazine, carbazole, dibenzofuran, dibenzothiophene, phenoxazine, and dihydroacridine. In addition, examples of at least one substituted or unsubstituted, monovalent fused aromatic heterocyclic group having a ring formed of 8 to 24 atoms represented by $R_1$ include aromatic heterocyclic groups each having a fused structure in examples of the aromatic heterocyclic groups.

Examples of the alkyl group, alkylene group, and trivalent or tetravalent alkane, each of which has 1 to 20 carbon atoms represented by Y, $Y_1$ to $Y_3$, $L_1$ to $L_3$, and $R_1$ to $R_3$ include a methyl group, an ethyl group, a propyl group, an isopropyl group, an n-butyl group, an s-butyl group, a t-butyl group, an isobutyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 2-methylpentyl group, a 1-pentylhexyl group, a 1-butylpentyl group, a 1-heptyloctyl group, and a 3-methylpentyl group or groups obtained by allowing those groups to have two to four valencies. Preferred are a methyl group, an ethyl group, a propyl group, an isopropyl group, an n-butyl group, an s-butyl group, an isobutyl group, a t-butyl group, n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 1-pentylhexyl group, a 1-butylpentyl group, and a 1-heptyloctyl group.

Examples of the substituted or unsubstituted cycloalkyl group, cycloalkylene group, and trivalent or tetravalent cycloalkane, each of which has a ring formed of 3 to 20 carbon atoms, represented by Y, $Y_1$ to $Y_3$, $L_1$ to $L_3$, $R_1$ to $R_3$, and $A_1$ and $A_2$ include a cyclopropyl group, a cyclobutyl group, a cyclopentyl group, a cyclohexyl group, and groups obtained by allowing those group to have two to four valencies. Preferred are a cyclobutyl group, a cyclopentyl group, and a cyclohexyl group.

Examples of the alkoxy group having 1 to 20 carbon atoms and represented by Y, $Y_1$ to $Y_3$ include a methoxy group, an ethoxy group, a methoxy group, an i-propoxy group, an n-propoxy group, an n-butoxy group, an s-butoxy group, and a t-butoxy group. Preferred are a methoxy group, an ethoxy group, a methoxy group, an i-propoxy group, and an n-propoxy group.

Examples of the silyl group having 1 to 20 carbon atoms represented by Y, $Y_1$ to $Y_3$, $L_1$ to $L_3$, $R_1$ to $R_3$, and $A_1$ and $A_2$ include a trimethyl silyl group, a triethyl silyl group, a tributyl silyl group, a trioctyl silyl group, a triisobutyl silyl group, a dimethylethyl silyl group, a dimethylisopropyl silyl group, a dimethylpropyl silyl group, a dimethylbutyl silyl group, a dimethyltertiary butyl silyl group, a diethylisopropyl silyl group, a phenyldimethyl silyl group, a diphenylmethyl silyl group, a diphenyl tertiary butyl group, a triphenyl silyl group, and groups obtained by allowing those groups to have two or three valencies. Preferred are a trimethyl silyl group, a triethyl silyl group, and a tributyl silyl group.

Examples of the aralkyl group having 7 to 24 carbon atoms represented by Y, $Y_1$ to $Y_3$, and $R_1$ to $R_3$ include a benzyl group, a phenethyl group, and a phenylpropyl group.

Examples of the substituent that can be substituted for the each group in the general formulae (1) to (18) include alkyl groups each having 1 to 10 carbon atoms (such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group), cycloalkyl groups each having a ring formed of 3 to 40 carbon atoms (such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group), alkoxy groups each having 1 to 6 carbon atoms (such as an ethoxy group, a methoxy group, an i-propoxy group, an n-propoxy group, an s-butoxy group, a t-butoxy group, a pentoxy group, and a hexyloxy group), cycloalkoxy groups each having a ring formed of 3 to 10 carbon atoms (such as a cyclopentoxy group and a cyclohexyloxy group), aromatic hydrocarbon groups each having a ring formed of 6 to 40 carbon atoms, aromatic heterocyclic groups having a ring formed of 3 to 40 atoms, amino groups substituted with aromatic hydrocarbon groups having a ring formed of 6 to 40 carbon atoms, ester groups having aromatic hydrocarbon groups having a ring formed of 6 to 40 carbon atoms, an ester group, cyano group, nitro group, and halogen atom, each of which has an alkyl group having 1 to 6 carbon atoms.

Of those, alkyl groups each having 1 to 6 carbon atoms, a phenyl group, a pyridyl group, a carbazolyl group, and a dibenzofuranyl group are preferred and the number of substituents is preferably 1 or 2.

In the material for an organic EL device represented by the general formula (2), (6), (10) to (12), (14), (16), or (18), n preferably represents 2.

In the general formula (5), (7) to (9), (13), (15), or (17), the total number of the substituents represented by $Y_1$, $Y_2$, and $Y_2$ is preferably 3 or less, and the total number of the substituents represented by $Y_1$, $Y_2$, and $Y_3$ in the structure of [ ]$_n$ in the general formula (6), (10) to (12), (14), (16) or (18) is preferably 3 or less.

In the general formula (1) or (2), $X_1$ and $X_2$, or $X_3$ and $X_4$ are each represented by N—$R_a$. N—$R_1$ of $X_1$ and N—$R_1$ of $X_2$, or N—$R_1$ of $X_3$ and N—$R_1$ of $X_4$ may be preferably different from each other.

In the general formula (5) or (6), $X_5$ and $X_6$ are each represented by N—$R_1$. N—$R_1$ of $X_5$ and N—$R_1$ or $X_6$ may be preferably different from each other.

In the general formulae (7) to (12), $X_7$ and $X_8$, $X_9$ and $X_{10}$, or $X_{11}$ and $X_{12}$, are each represented by N—$R_1$. N—$R_1$ of $X_7$ and N—$R_1$ of $X_8$, N—$R_1$ of $X_9$ and N—$R_1$ of $X_{10}$, or N—$R_1$ of $X_{13}$ and N—$R_1$ of $X_{12}$, may be preferably different from each other.

In the general formula (13) or (14), $X_{13}$ and $X_{14}$ are each represented by N—$R_3$. N—$R_1$ of $X_{13}$ and N—$R_1$ or $X_{14}$ may be preferably different from each other.

In the general formulae (1), (2), (5) to (14), both $X_1$ and $X_2$, both $X_3$ and $X_4$, both $X_5$ and $X_6$, both $X_7$ and $X_8$, both $X_9$ and $X_{10}$, both $X_{11}$ and $X_{12}$, both $X_{13}$ and $X_{14}$, and both $X_{15}$ and $X_{16}$ preferably represent oxygen atoms.

Specific examples of the material for an organic EL device represented by any one of the general formulae (1), (2), (5) to (18) of the present invention are shown below. However, the present invention is not limited to these exemplified compounds.

No. 1

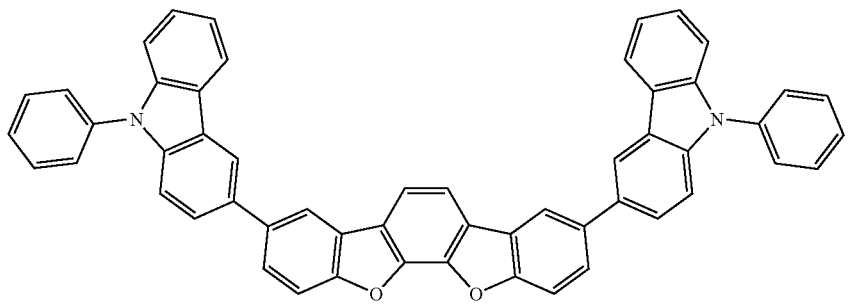

-continued
No. 2
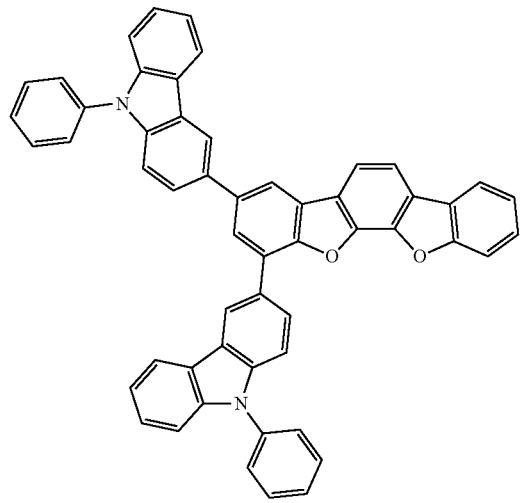
No. 3
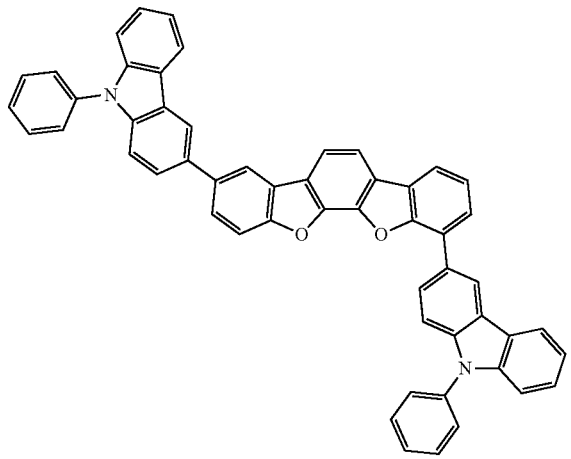
No. 4
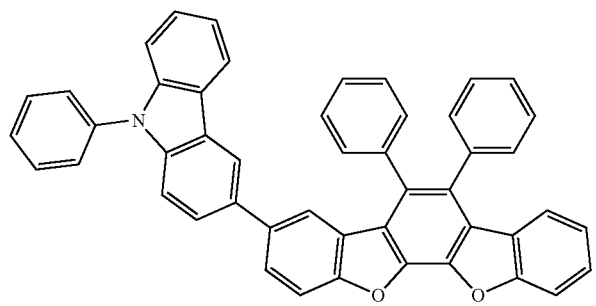
No. 5
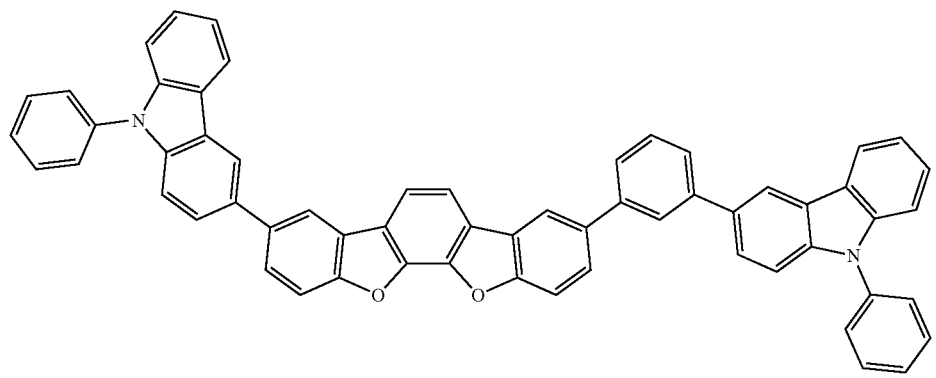
No. 6
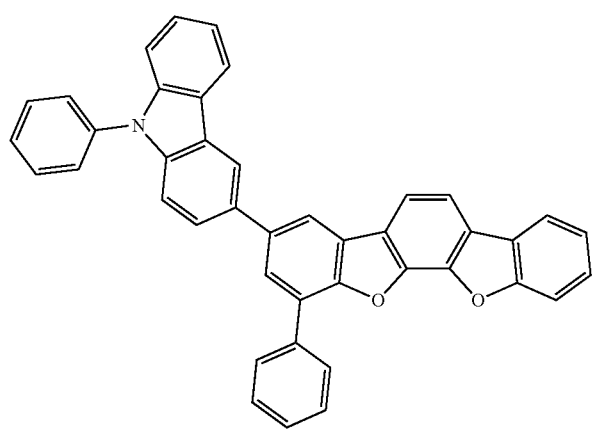

-continued
No. 7
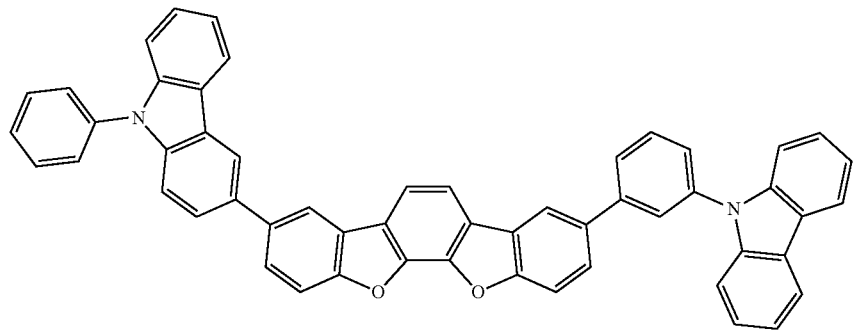
No. 8
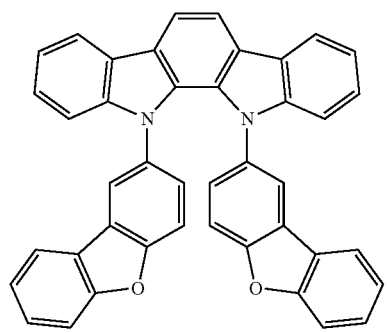
No. 9
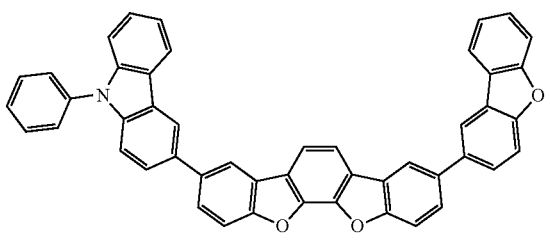
No. 10
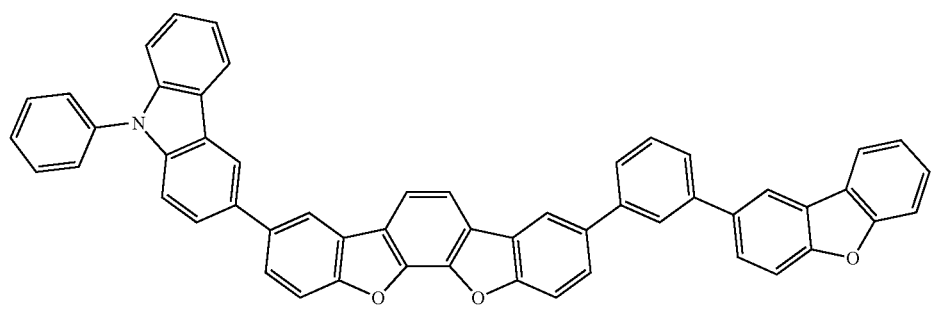
No. 11
No. 12
No. 13
No. 14
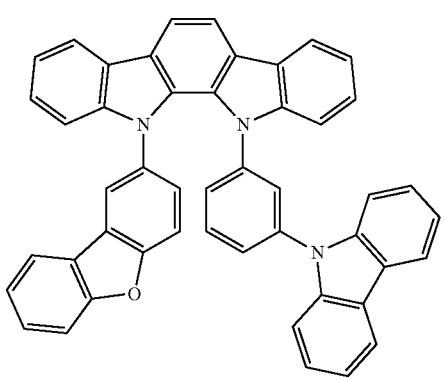

-continued
No. 15
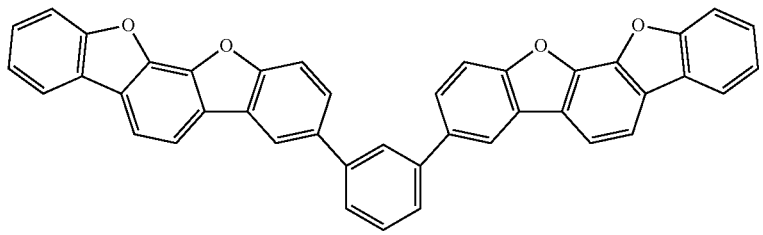
No. 16
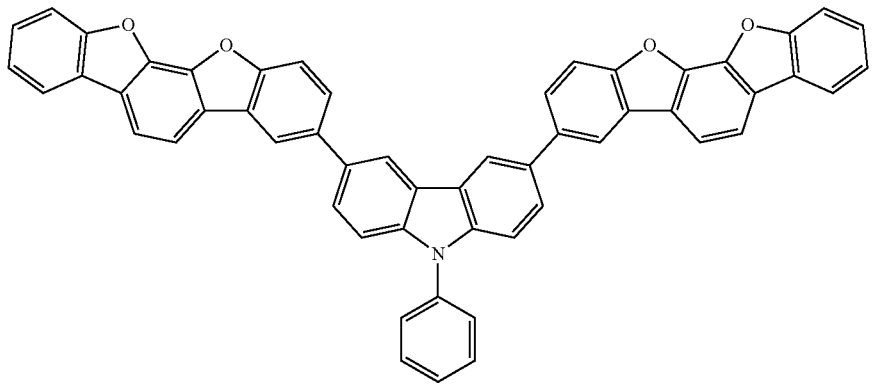
No. 17
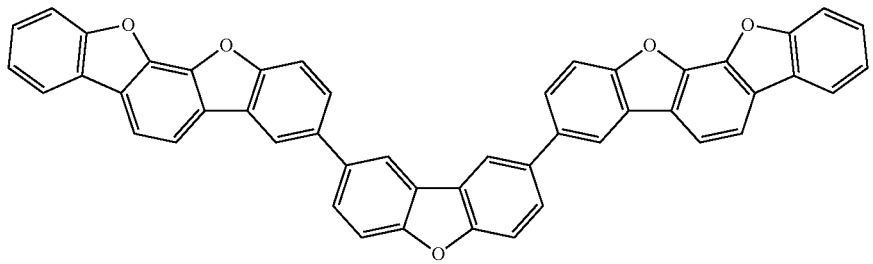
No. 18
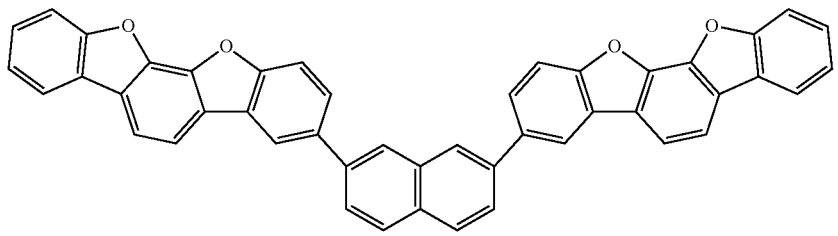
No. 19
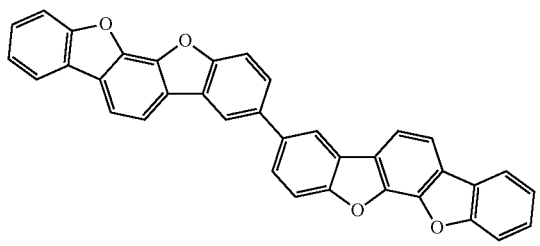
No. 20
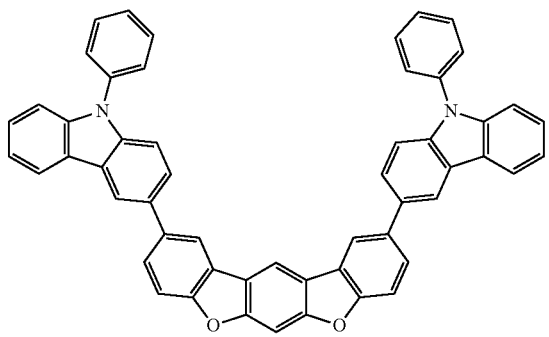

-continued
No. 21
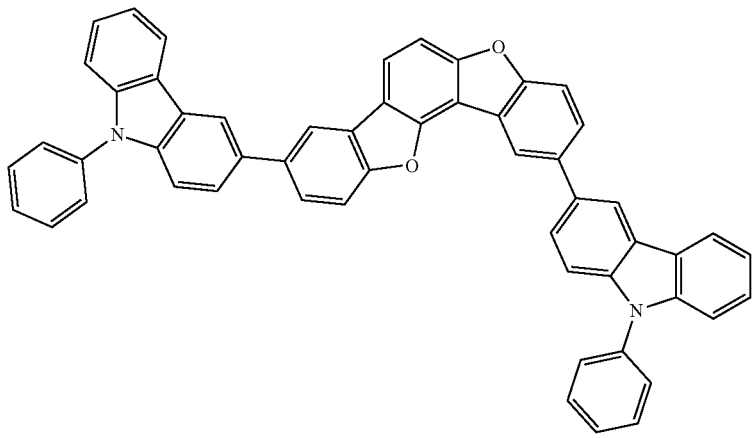
No. 22
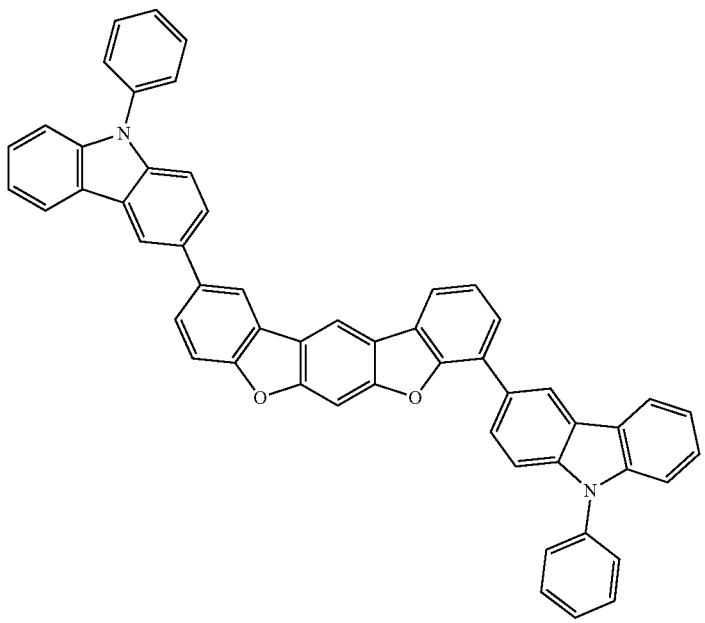
No. 23
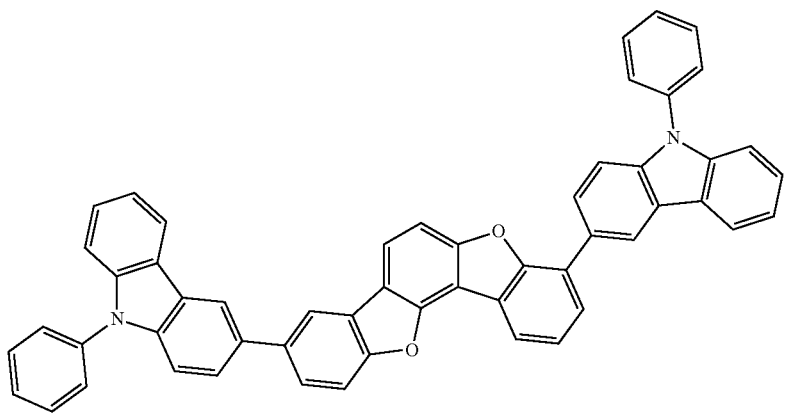

No. 24
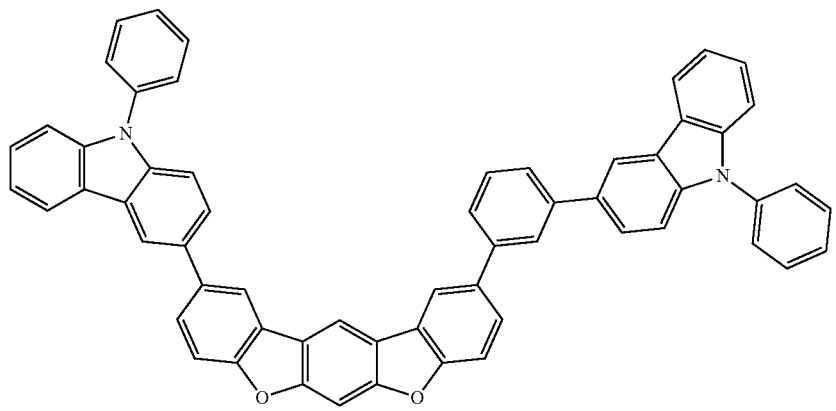
No. 25
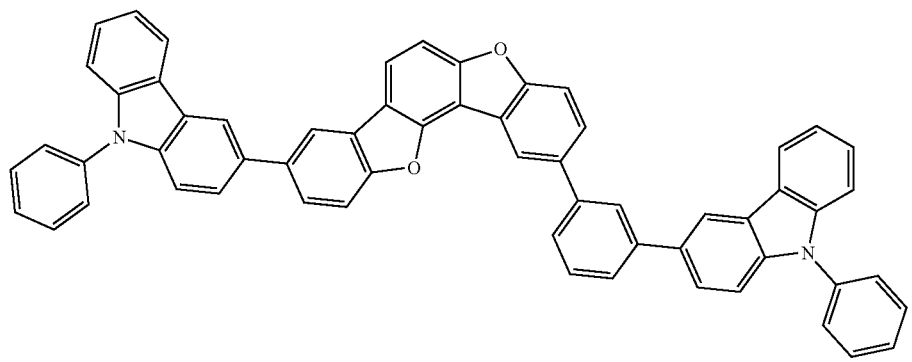
No. 26
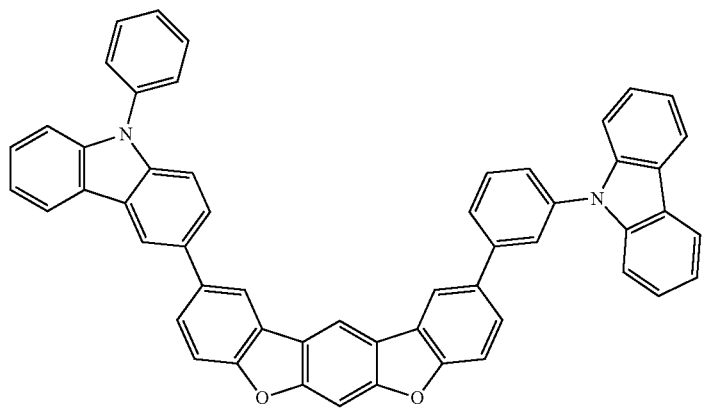
No. 27
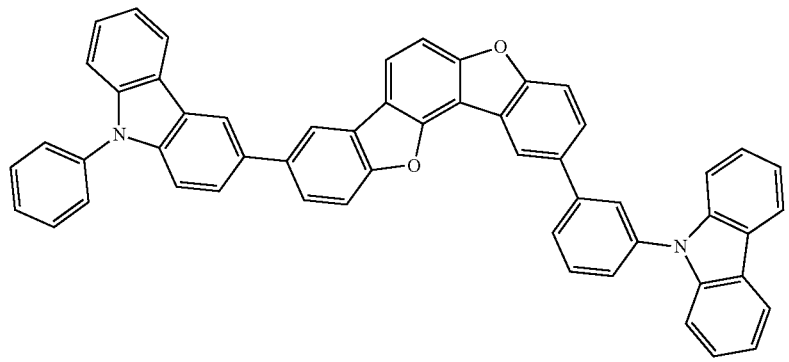

-continued
No. 28
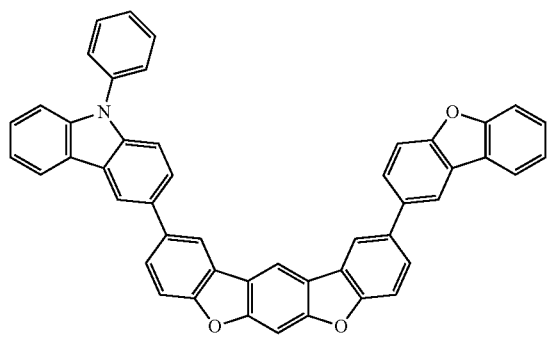
No. 29
No. 30
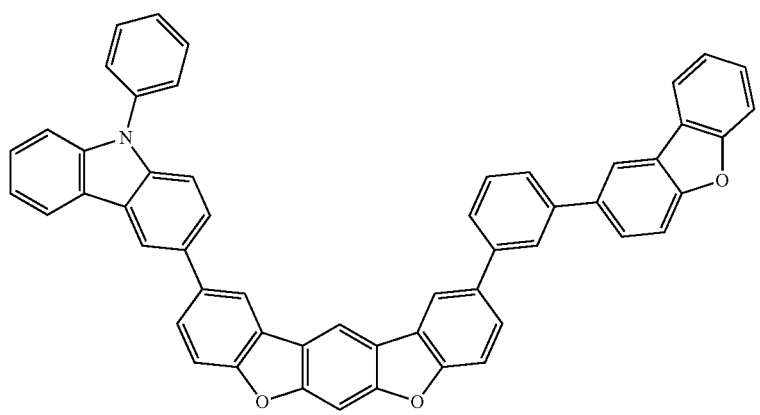
No. 31
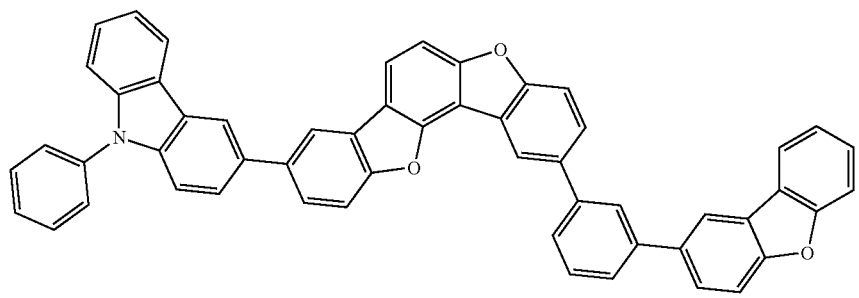

No. 32
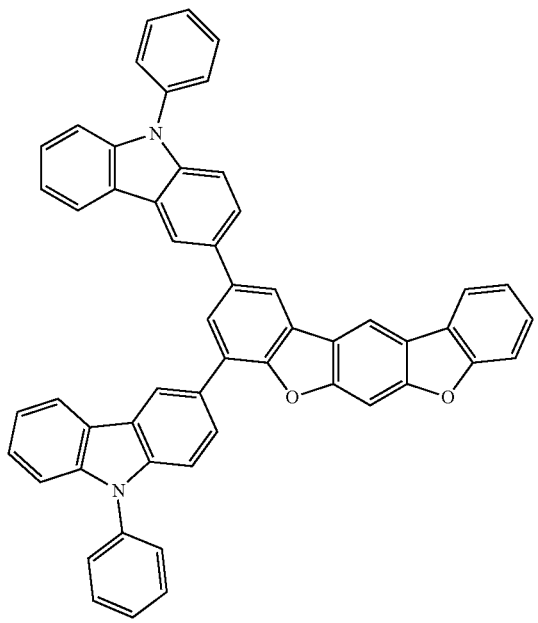
No. 33
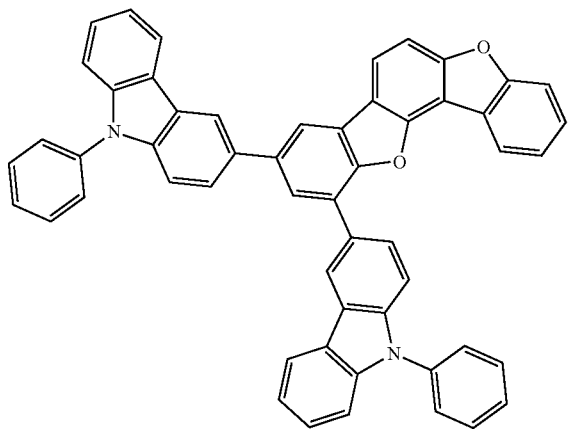
No. 34
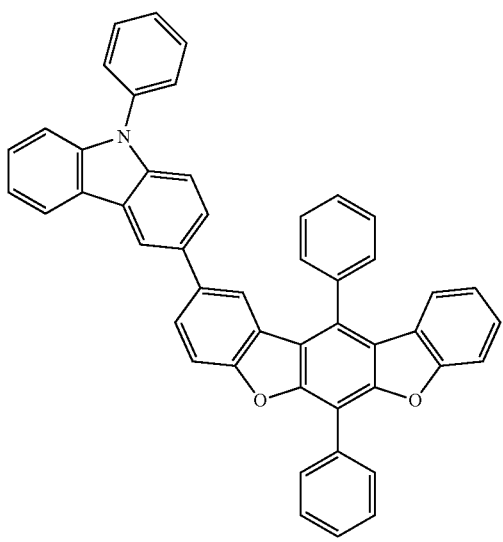
No. 35
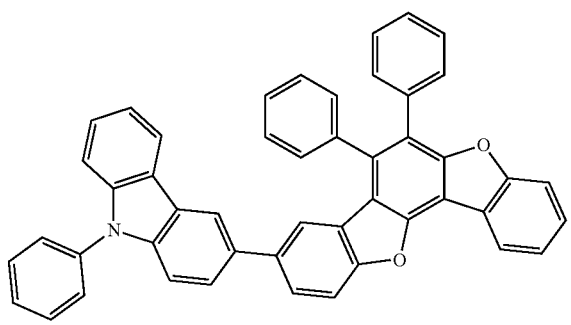

-continued
No. 36
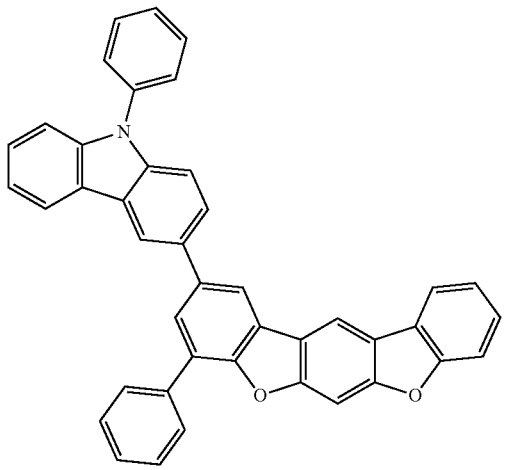
No. 37
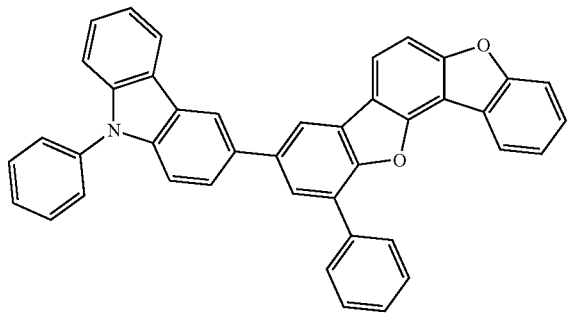
No. 38
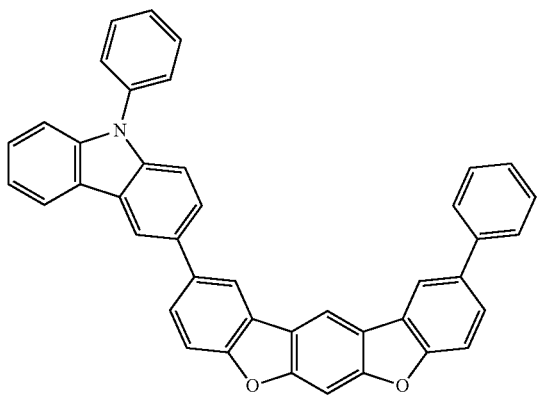
No. 39
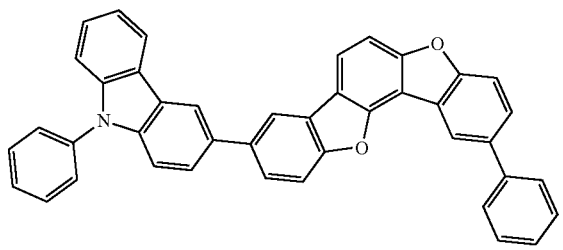
No. 40
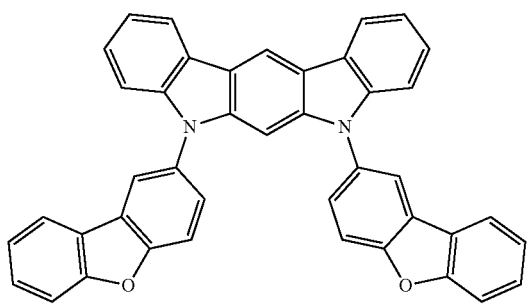
No. 41
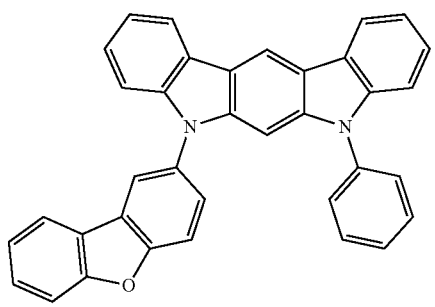
No. 42
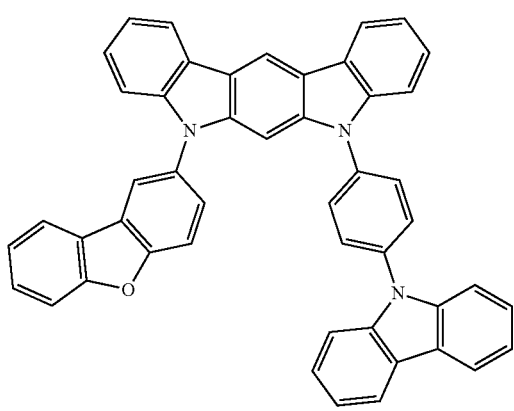
No. 43
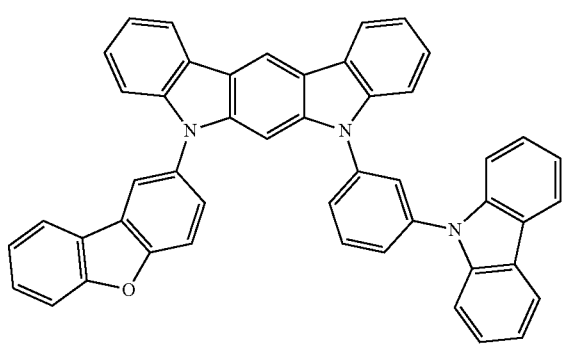

-continued
No. 44
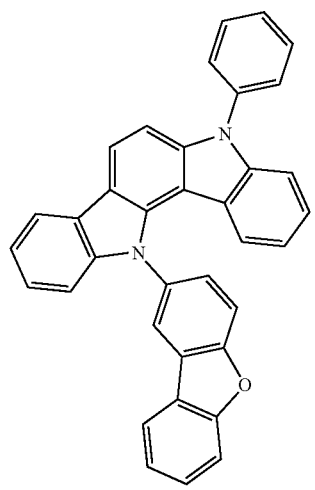
No. 45
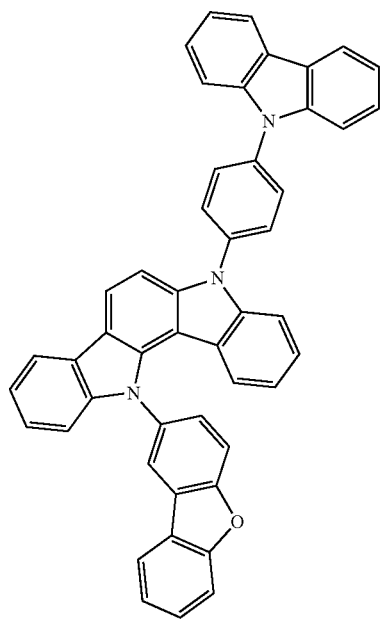
No. 46
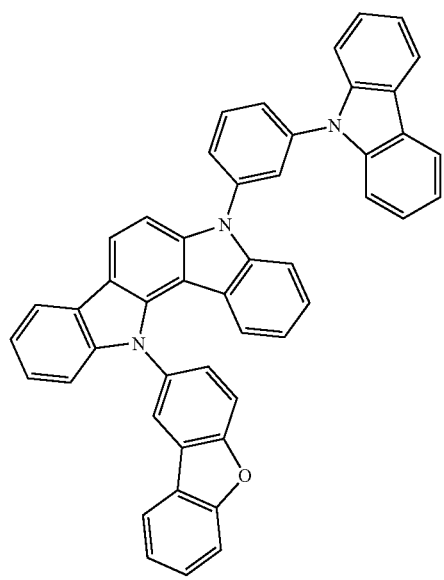
No. 47
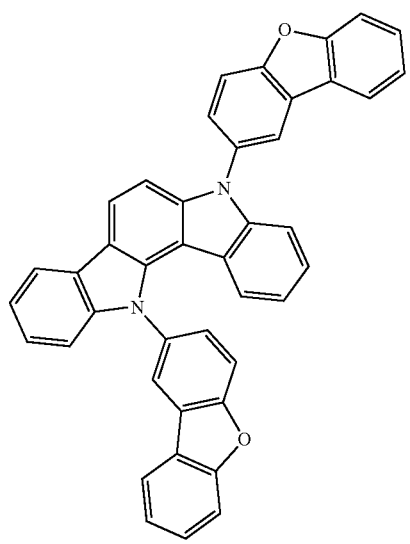
No. 48
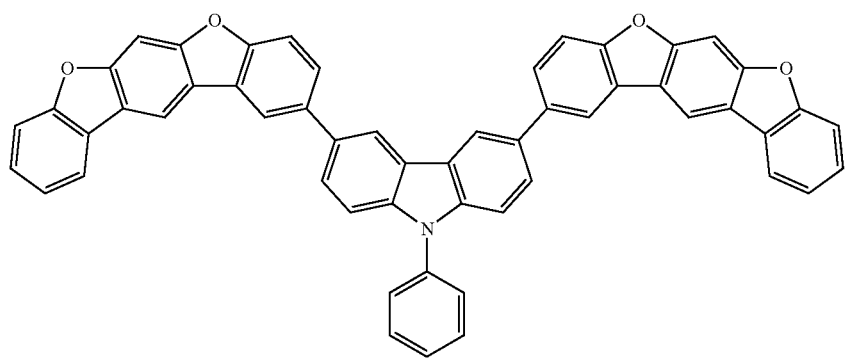

No. 49
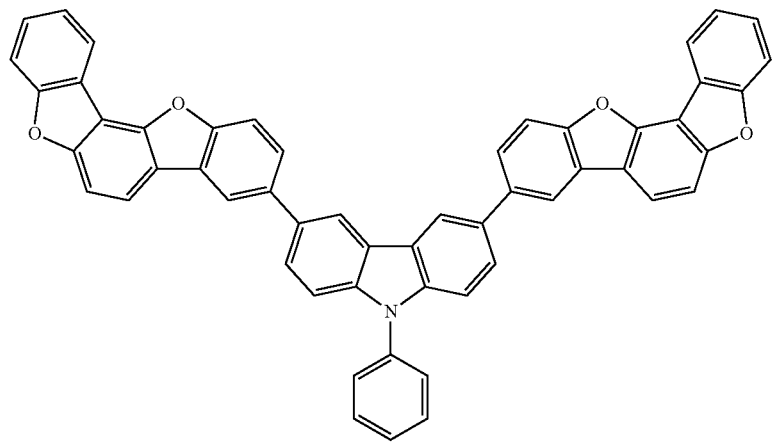
No. 50
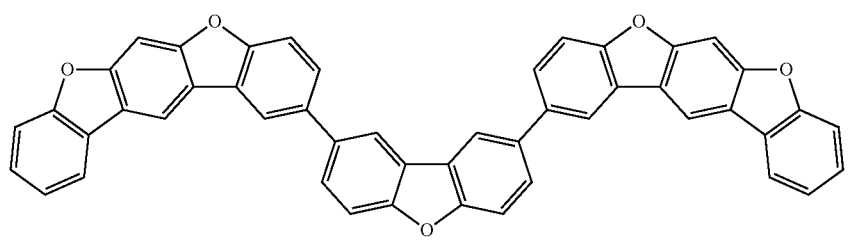
No. 51
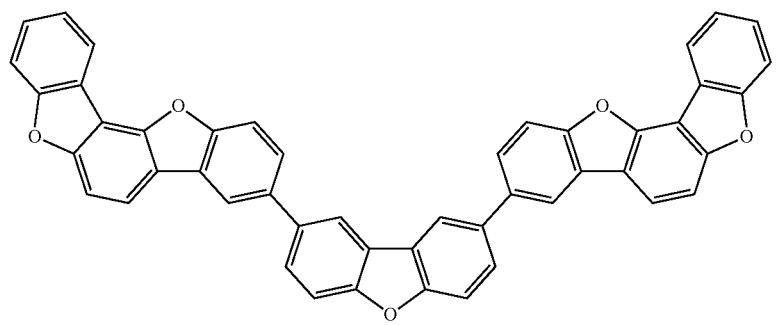
No. 52
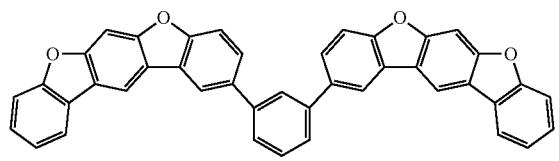
No. 53
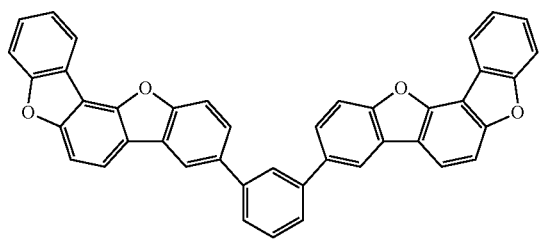

-continued
No. 54
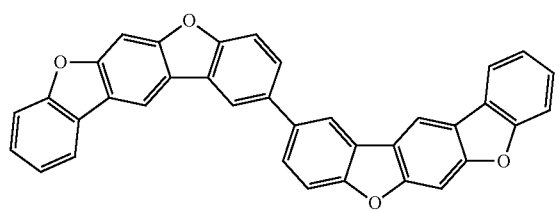
No. 55
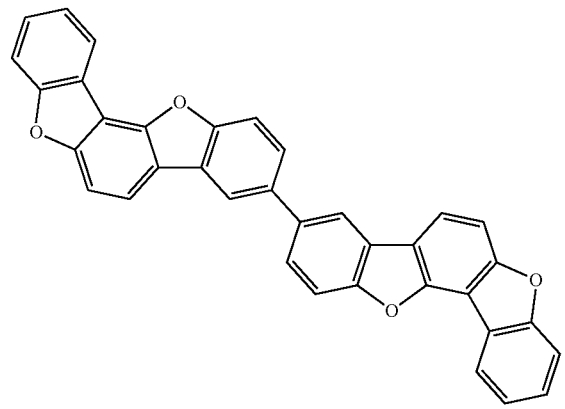
No. 56
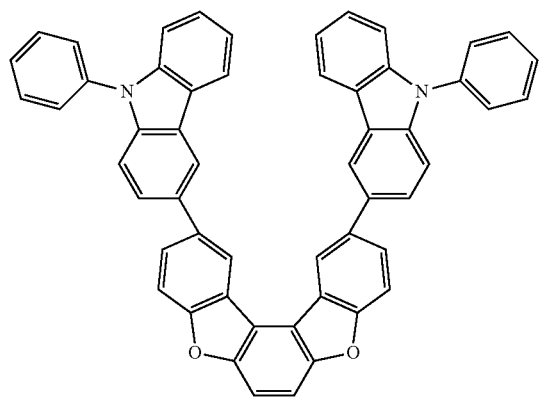
No. 57
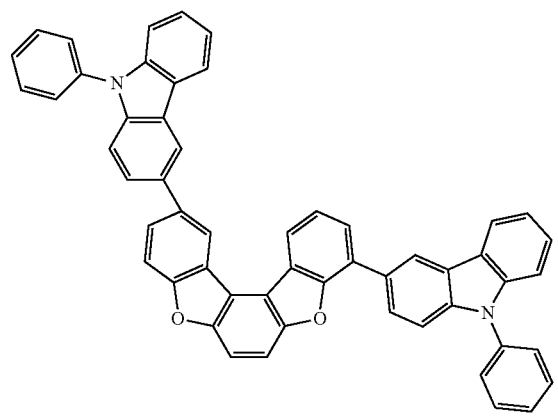
No. 58
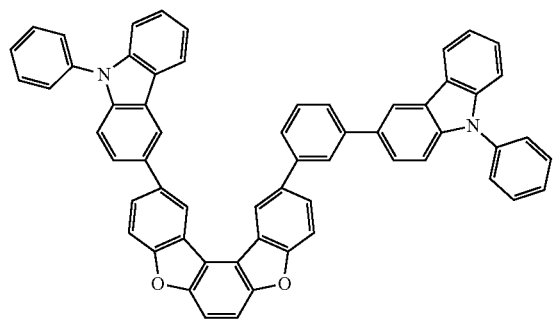
No. 59
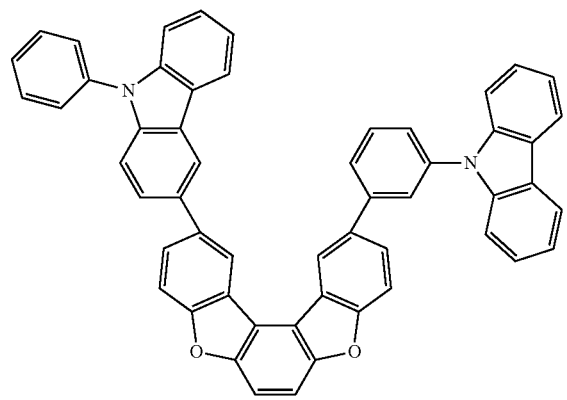

-continued
No. 60
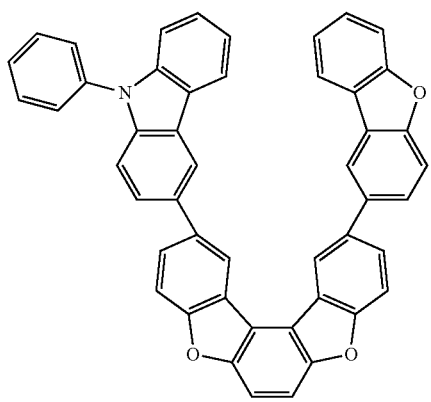
No. 61
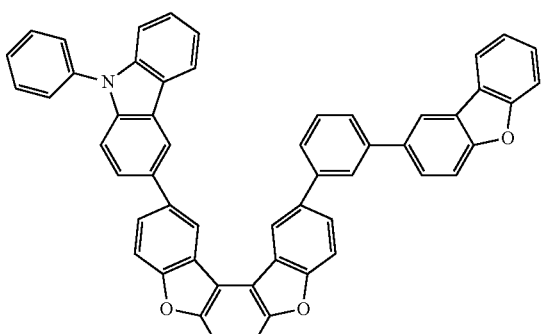
No. 62
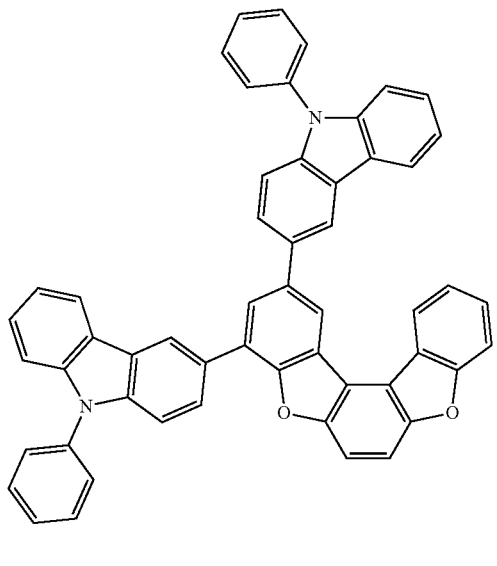
No. 63
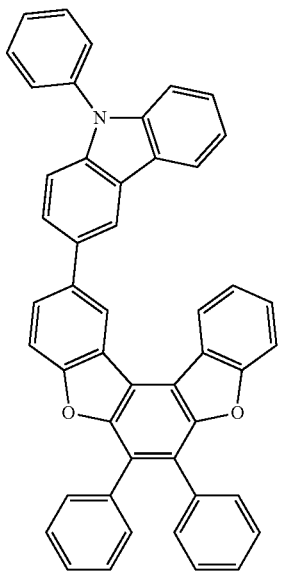
No. 64
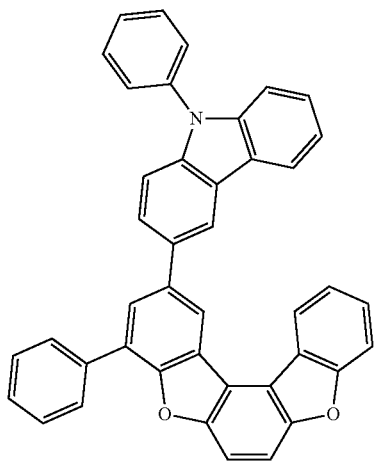
No. 65
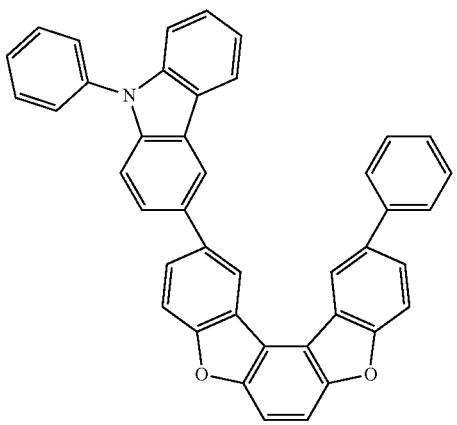

-continued
No. 66
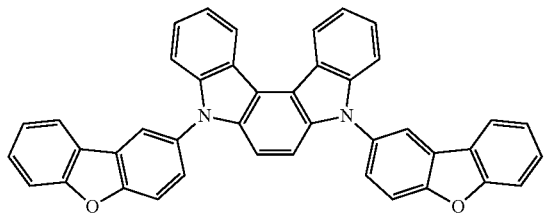
No. 67
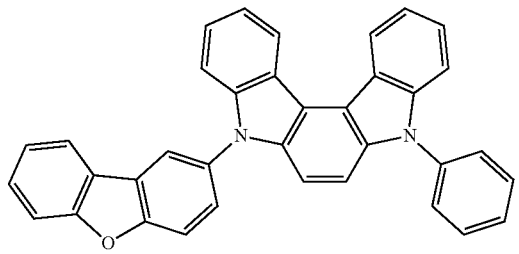
No. 68
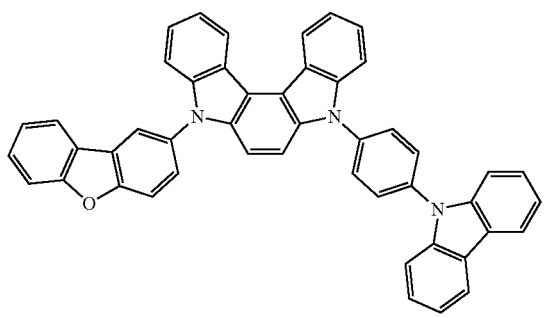
No. 69
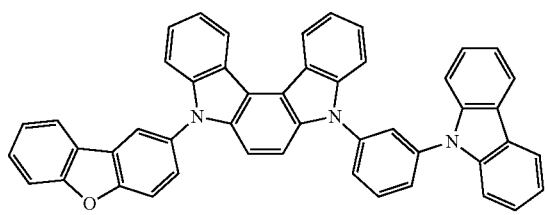
No. 70
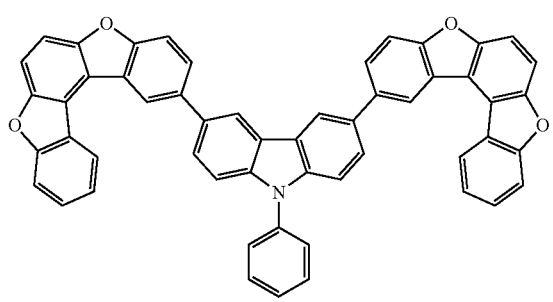
No. 71
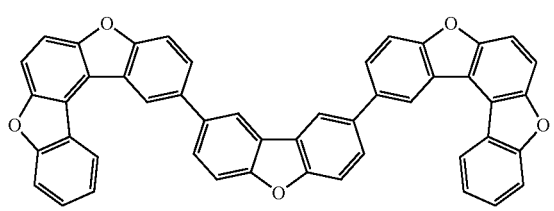
No. 72
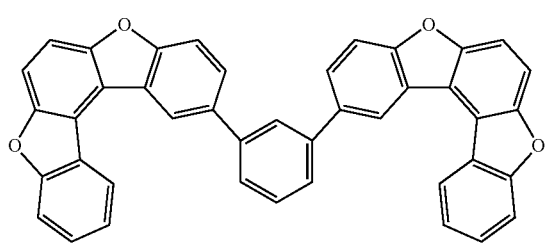
No. 73
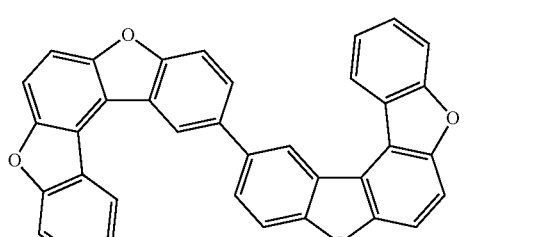
No. 74
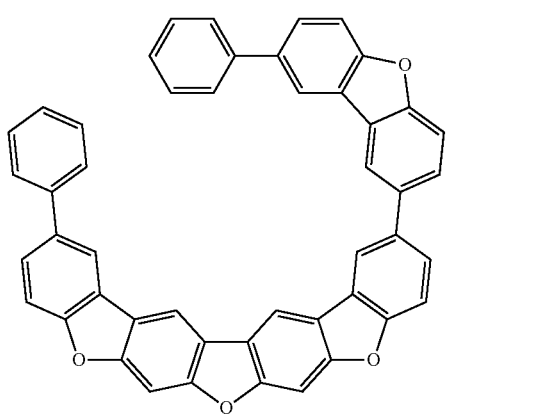
No. 75
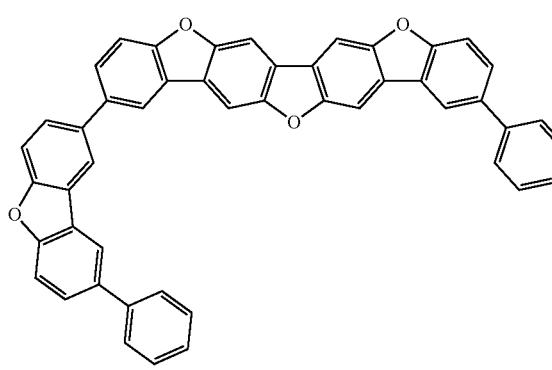

-continued
No. 76
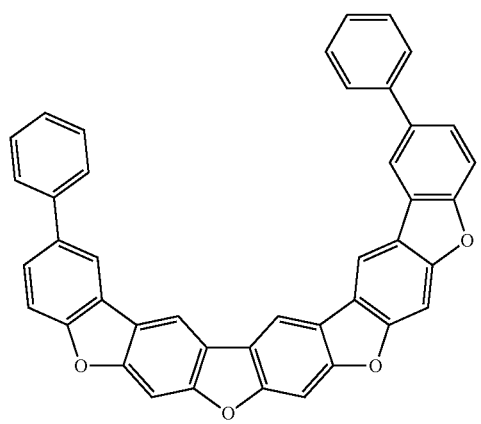
No. 77
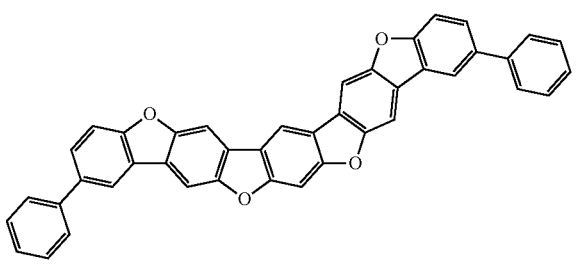
No. 78
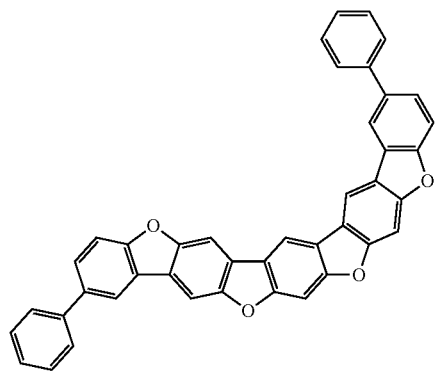
No. 79
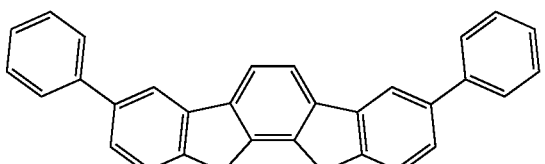
No. 80
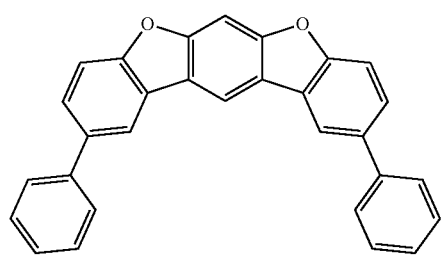
No. 81
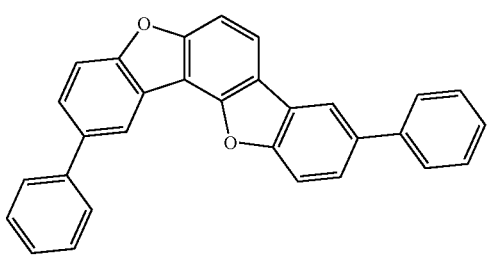

-continued
No. 82
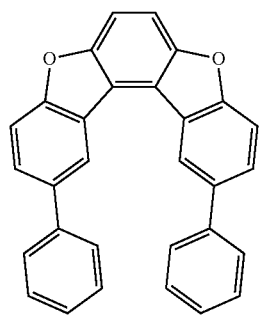
No. 83
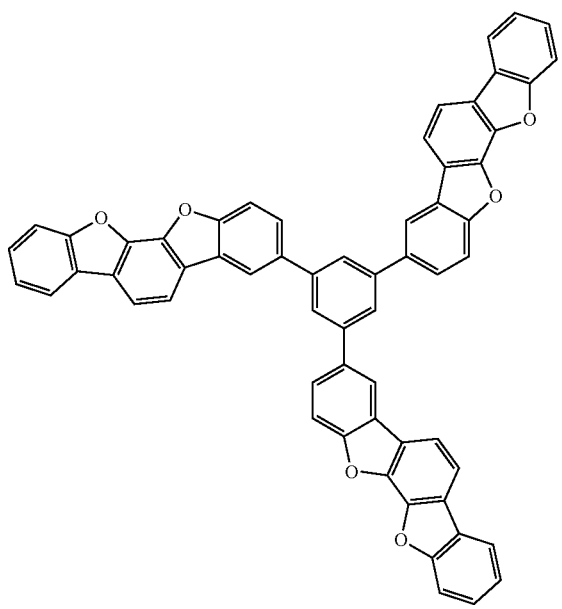
No. 84
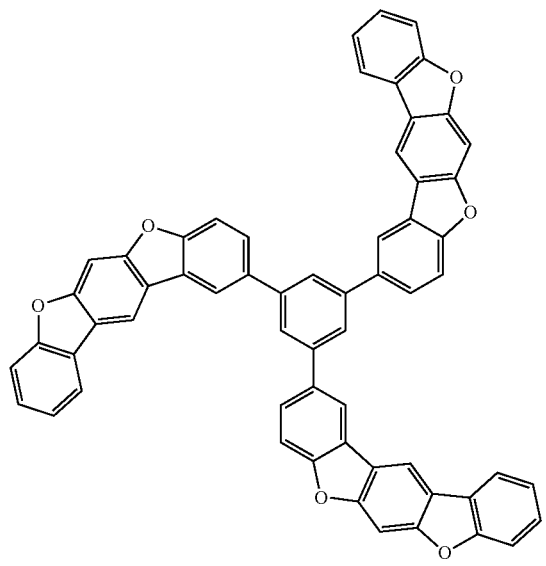
No. 85
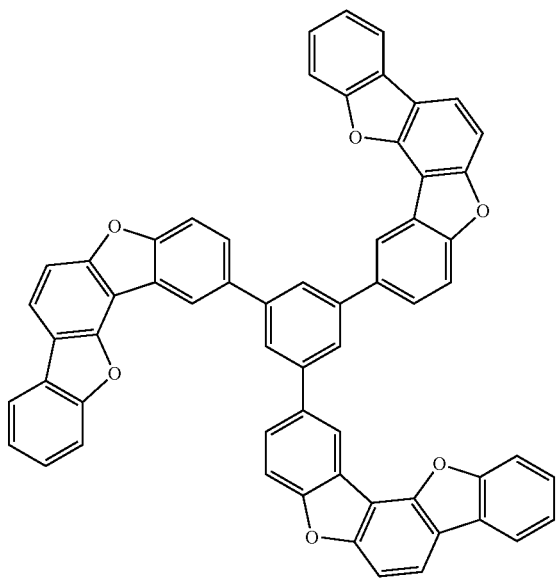

-continued
No. 86
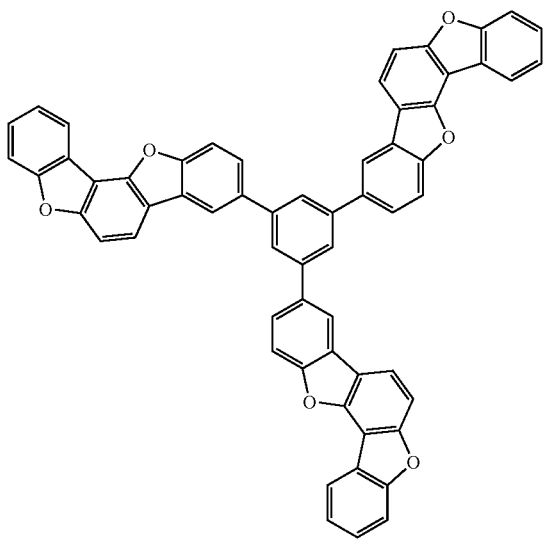
No. 87
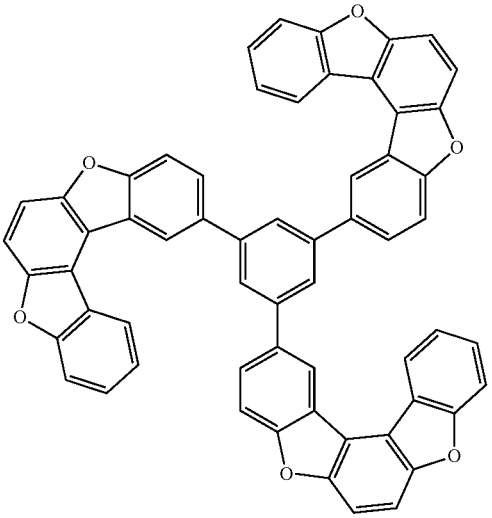
No. 88
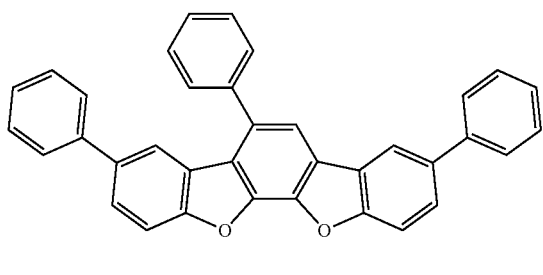
No. 89
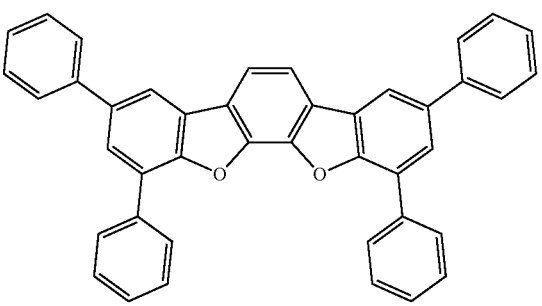
No. 90
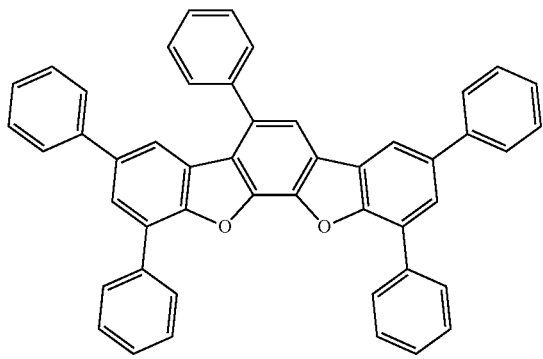
No. 91
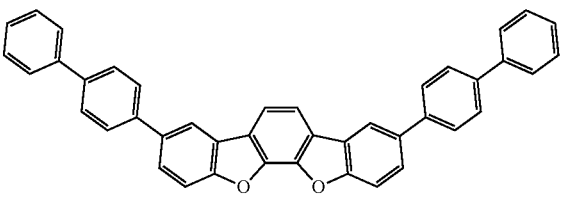
No. 92
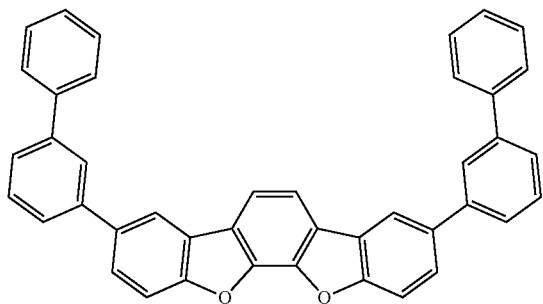

No. 93
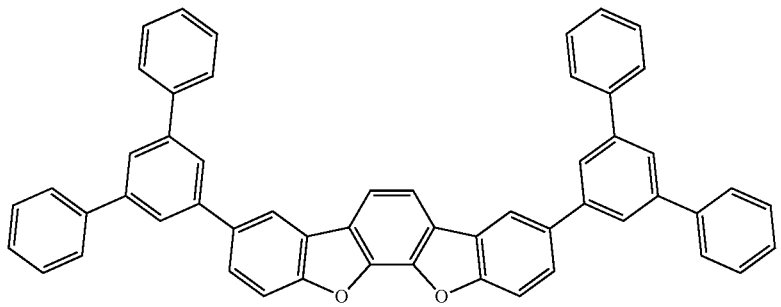
No. 94    No. 95
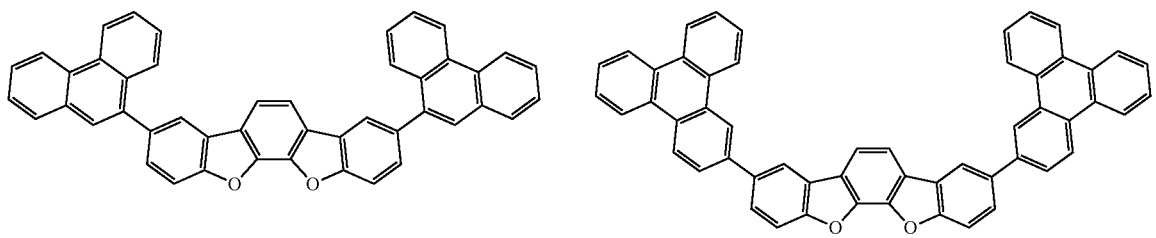
No. 96    No. 97
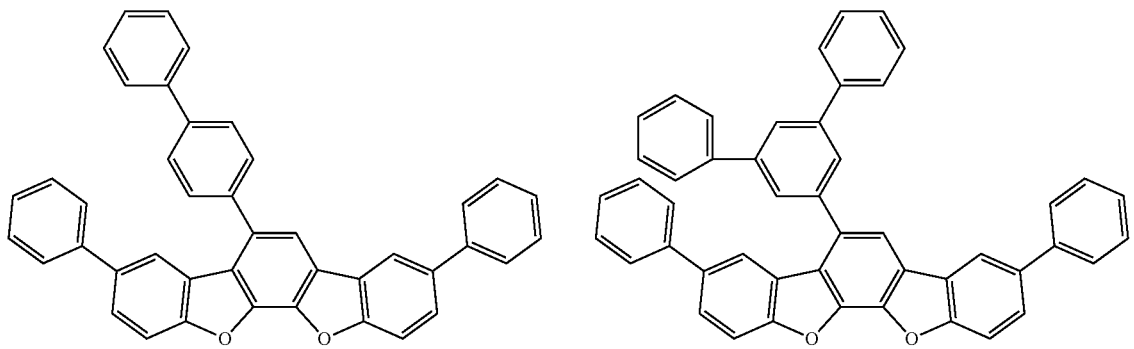
No. 98    No. 99
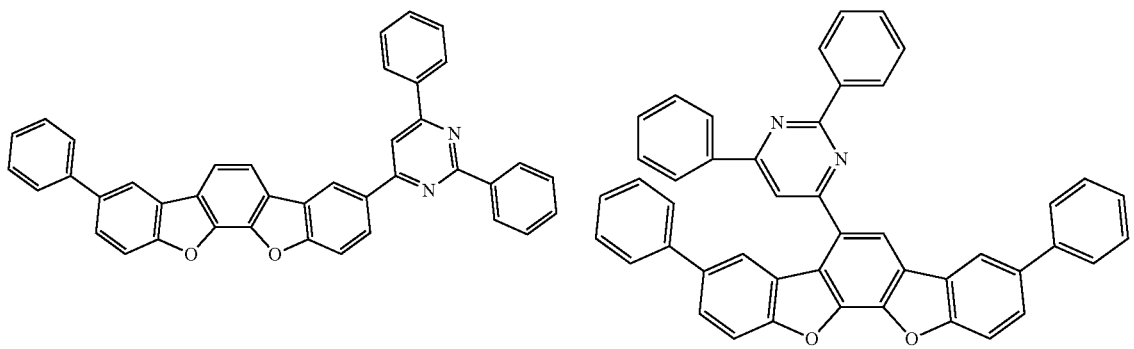

-continued
No. 100
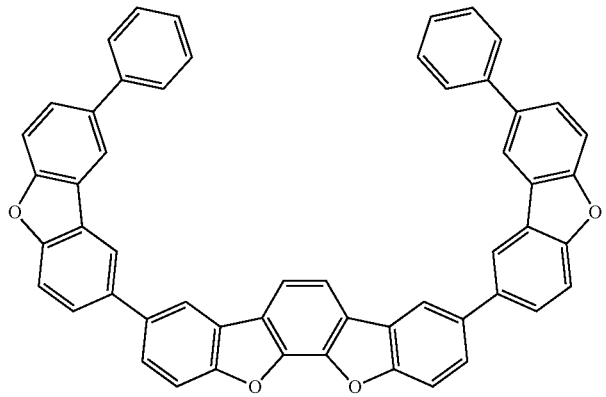
No. 101
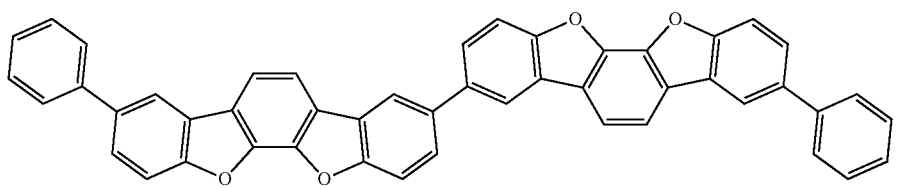
No. 102
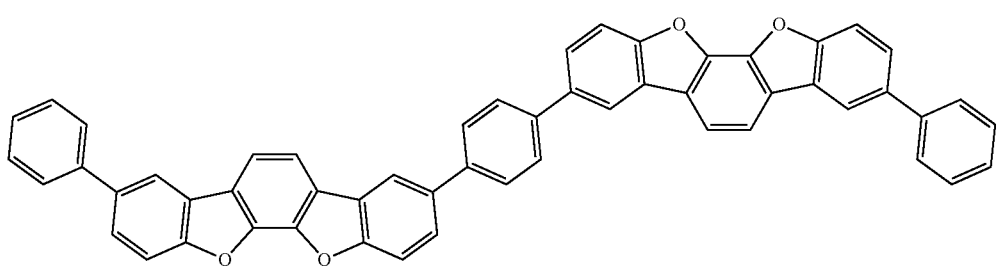
No. 103
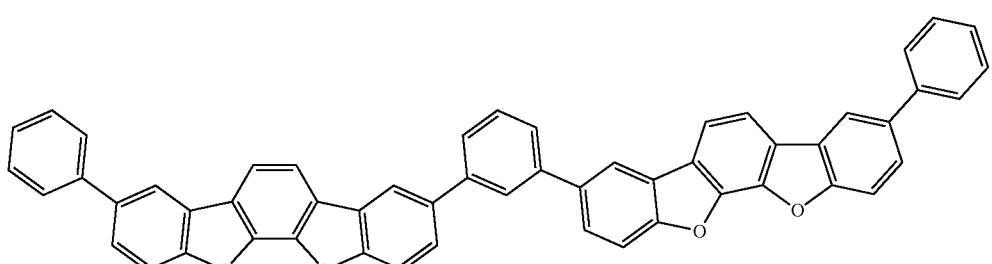
No. 104
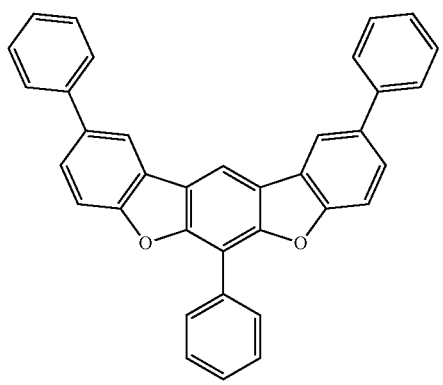
No. 105
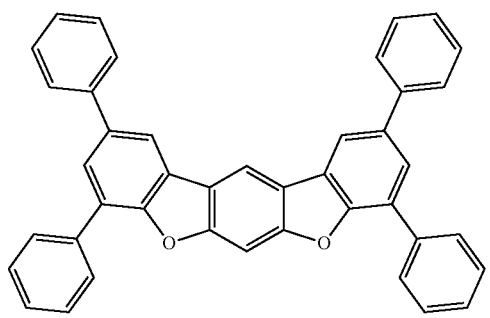

-continued
No. 106
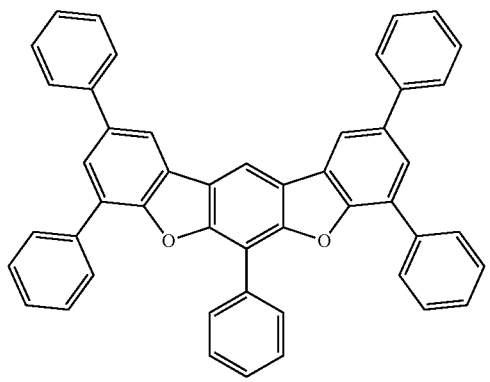
No. 107
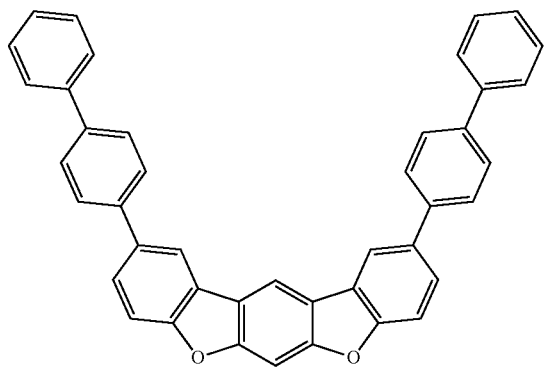
No. 108
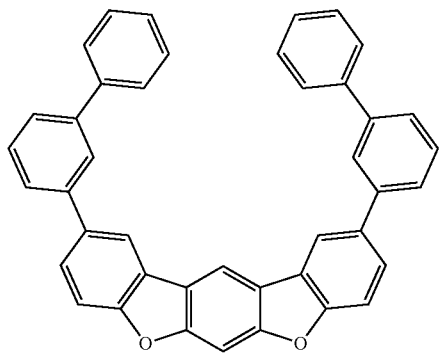
No. 109
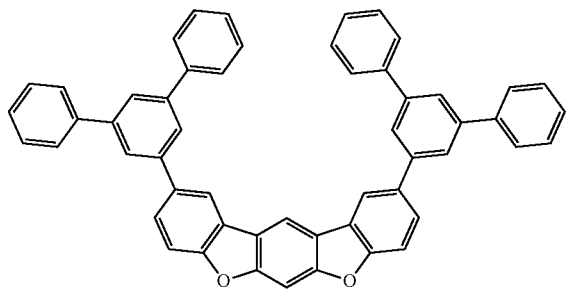
No. 110
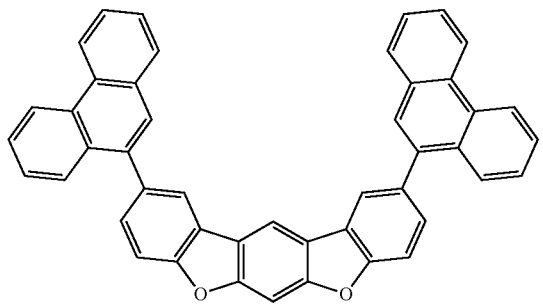
No. 111
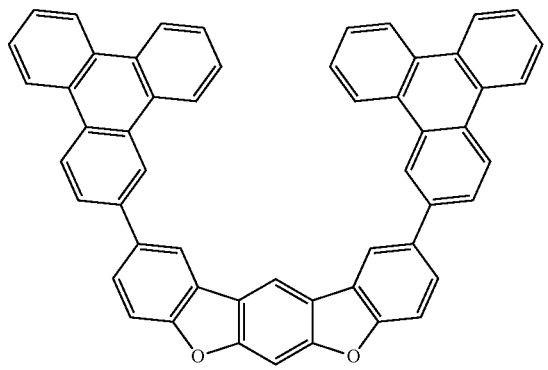

No. 112
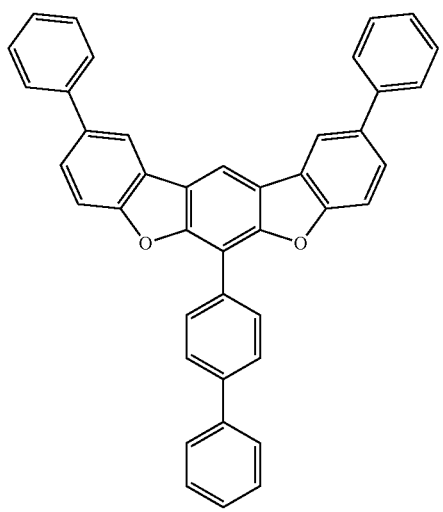
No. 113
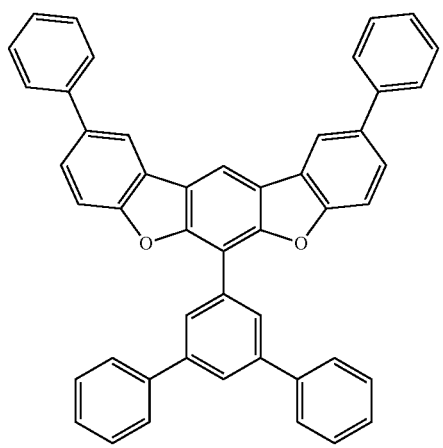
No. 114
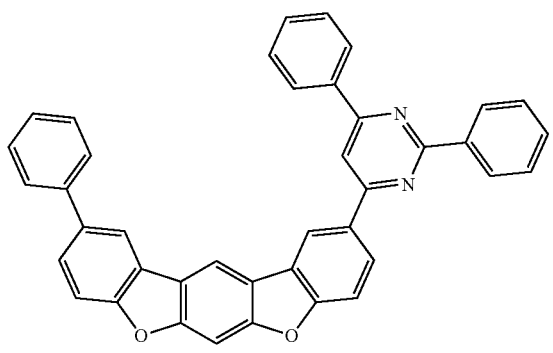
No. 115
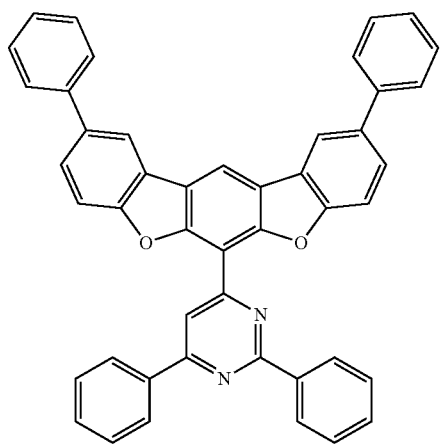
No. 116
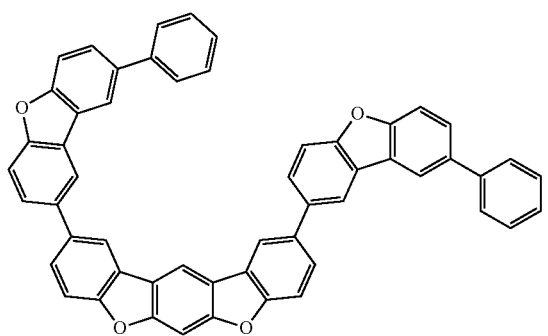
No. 117
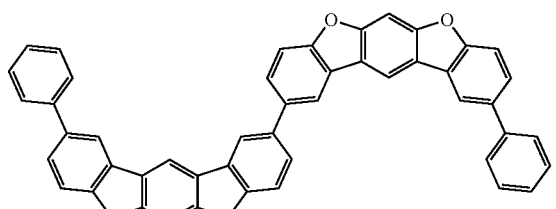

-continued
No. 118
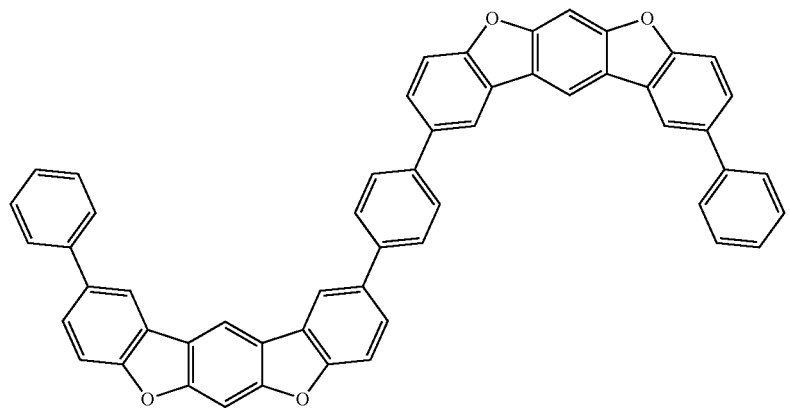
No. 119
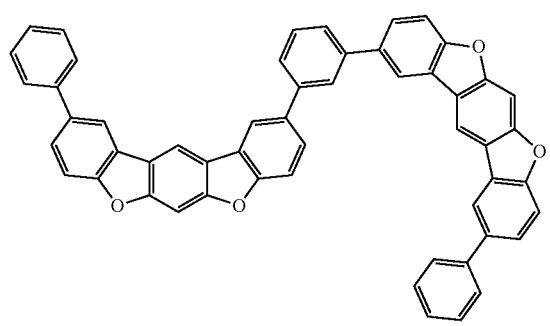
No. 120
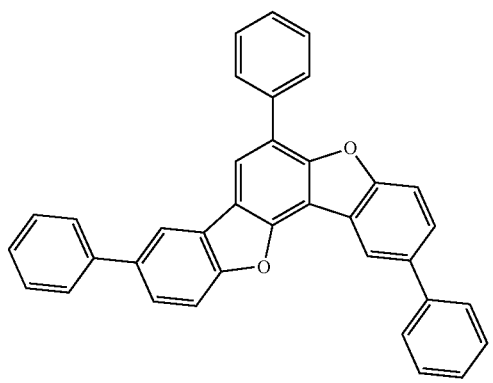
No. 121
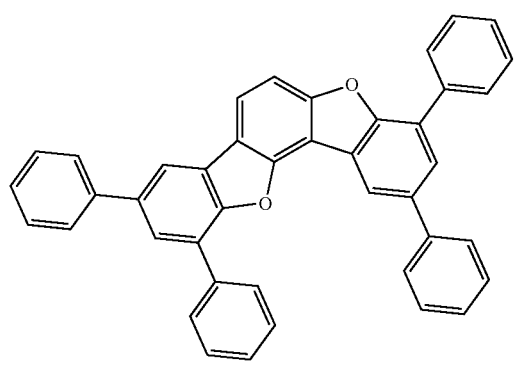
No. 122
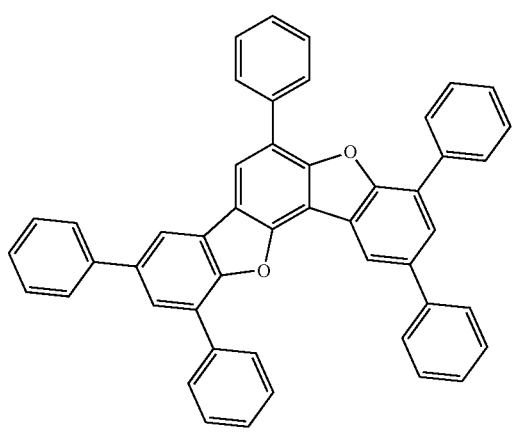

-continued
No. 123
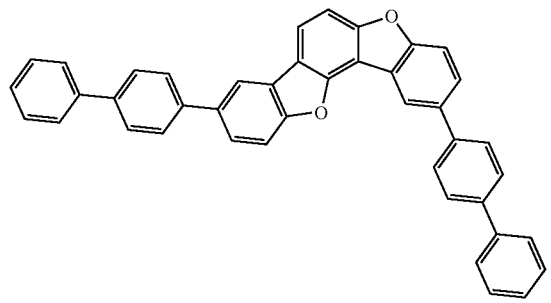
No. 124
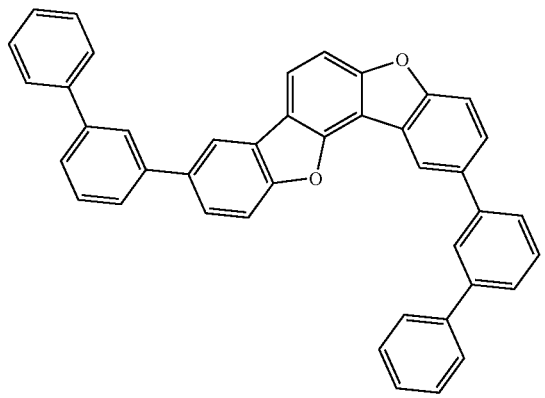
No. 125
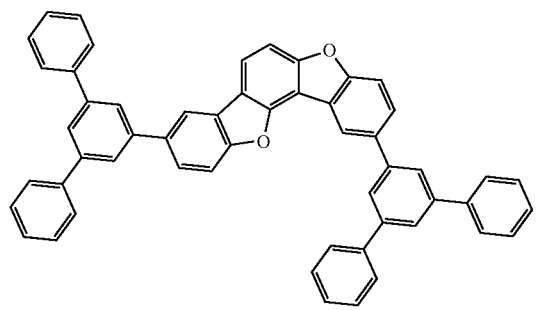
No. 126
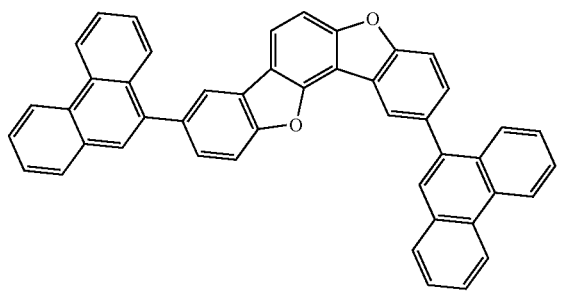
No. 127
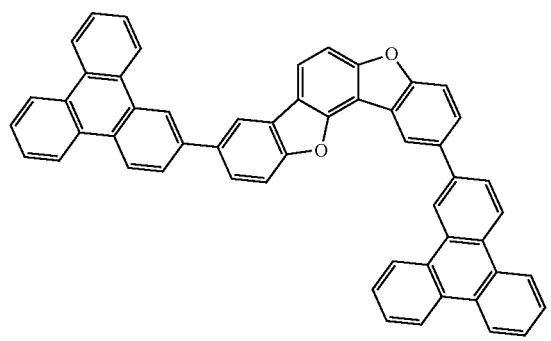
No. 128
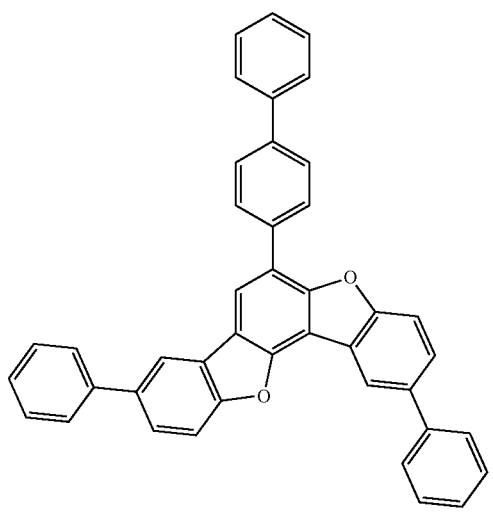

-continued
No. 129
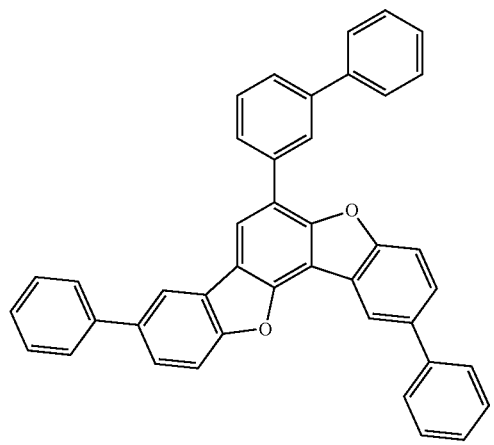
No. 130
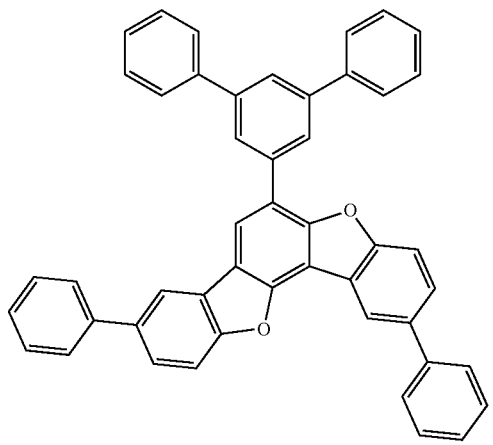
No. 131
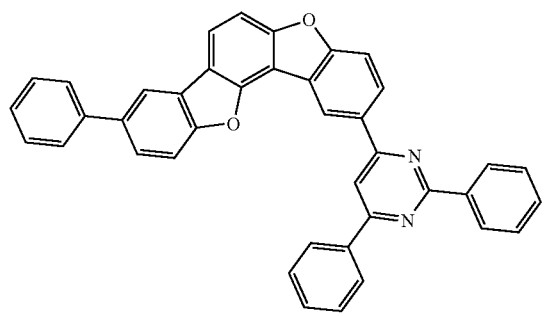
No. 132
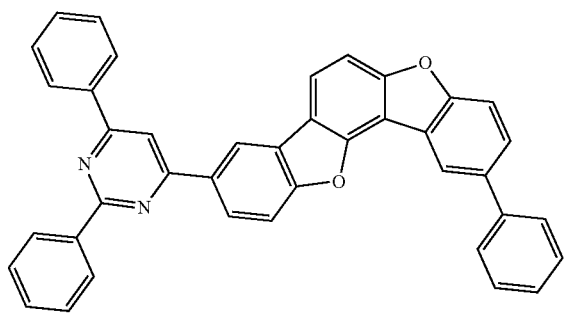
No. 133
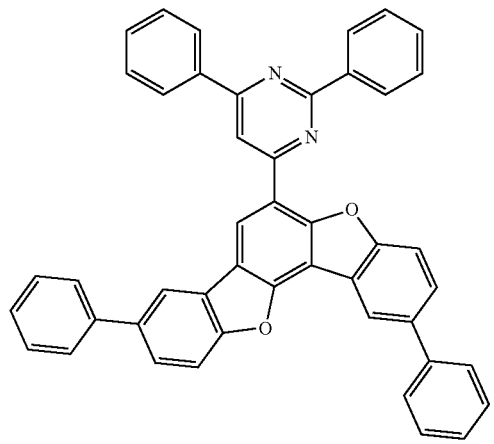

No. 134
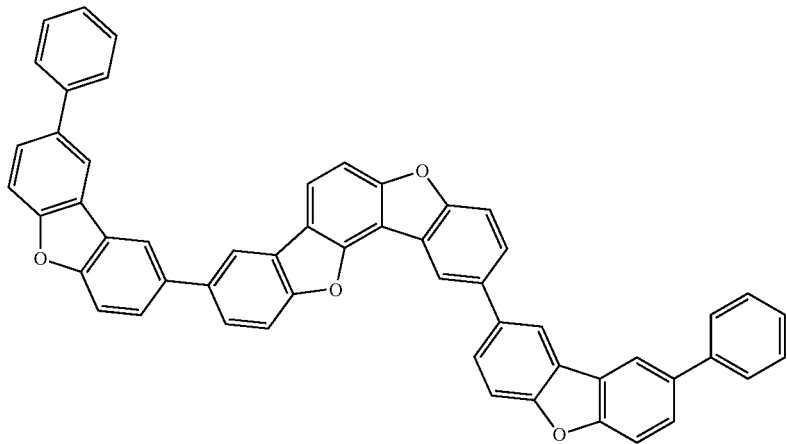
No. 135
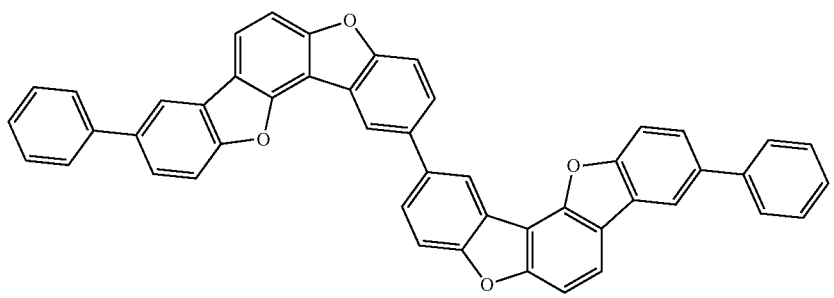
No. 136
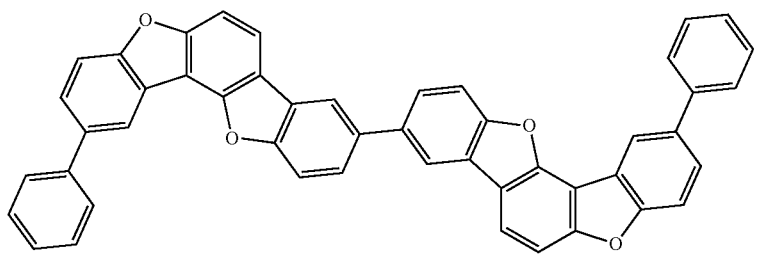
No. 137
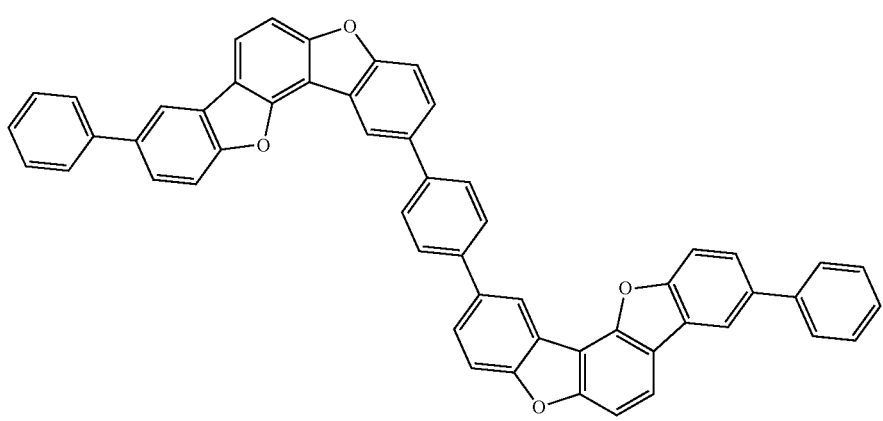

-continued
No. 138
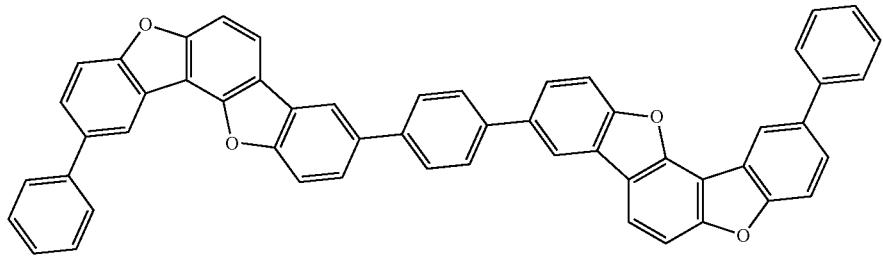
No. 139
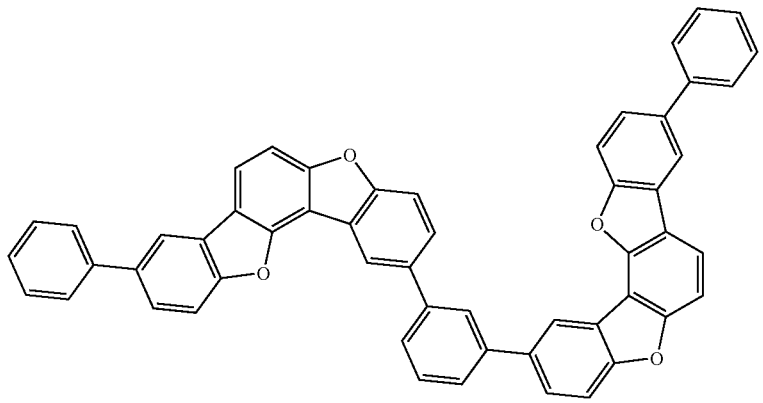
No. 140
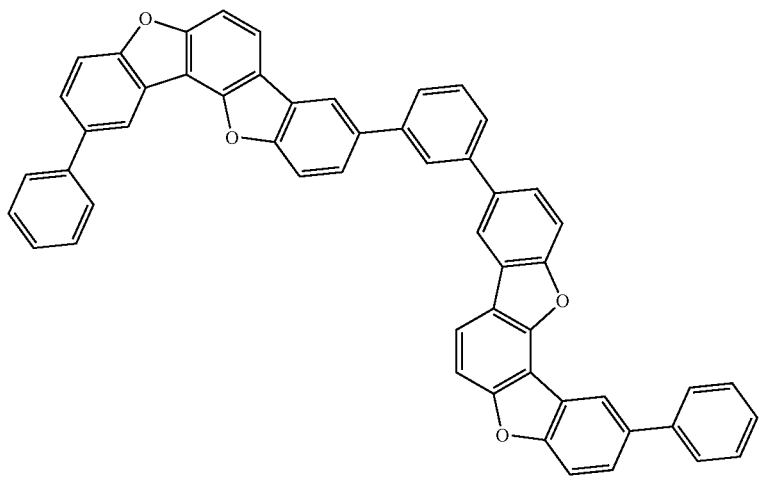
No. 141
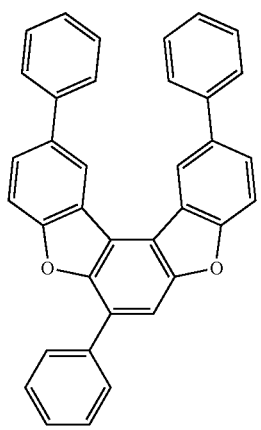
No. 142
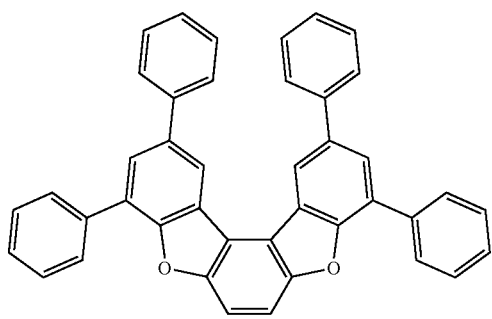

-continued
No. 143
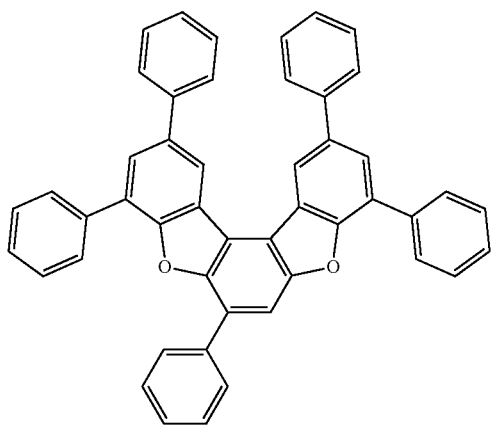
No. 144
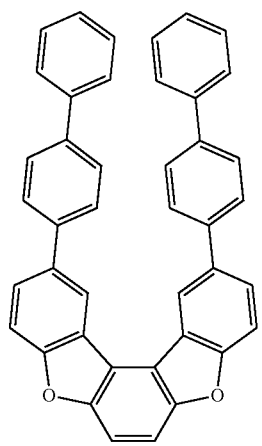
No. 145
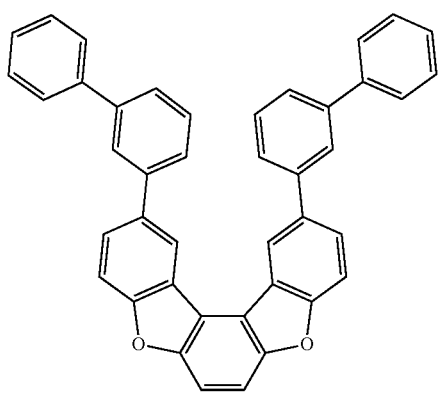
No. 146
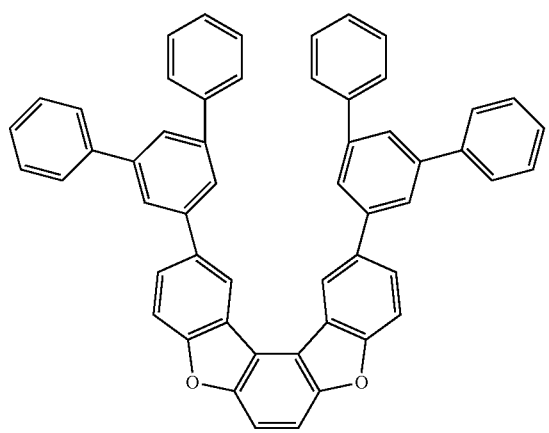
No. 147
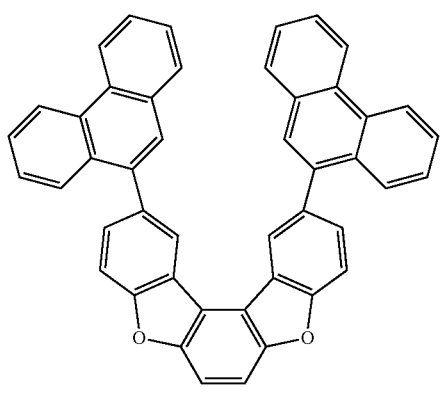
No. 148
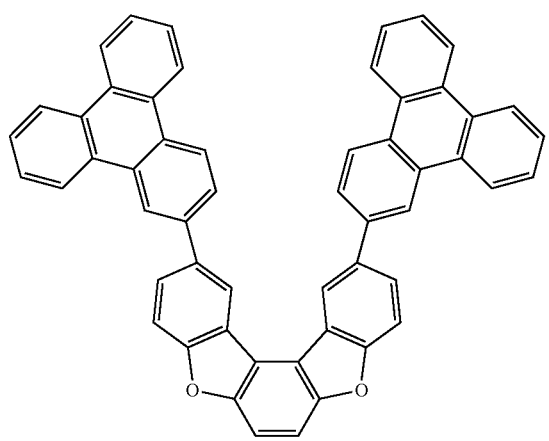

-continued
No. 149
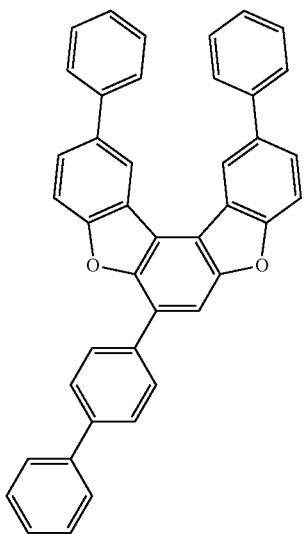
No. 150
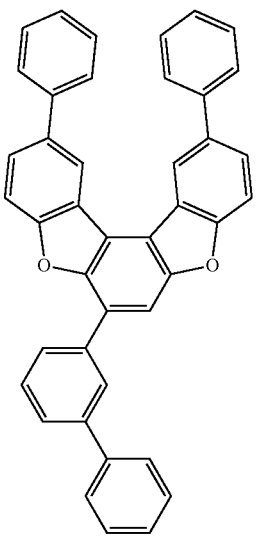
No. 151
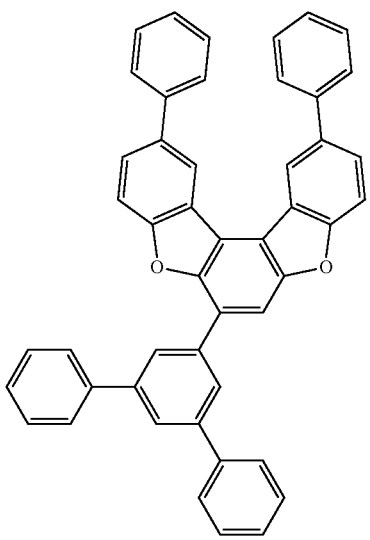
No. 152
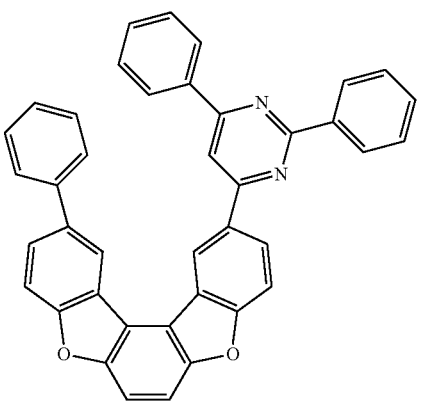
No. 153
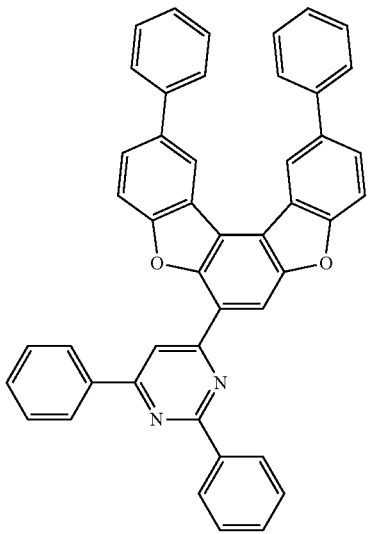
No. 154
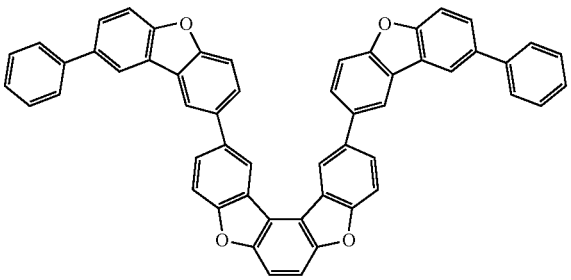

-continued
No. 155
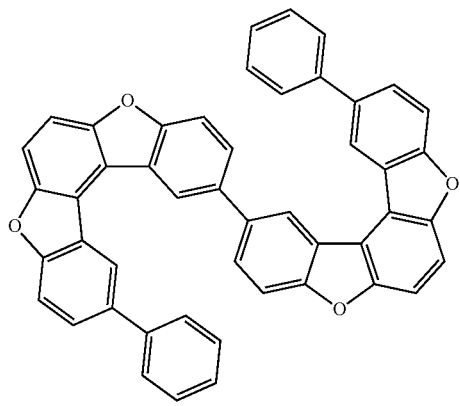
No. 156
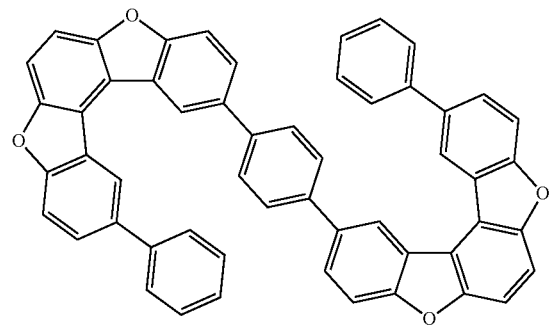
No. 157
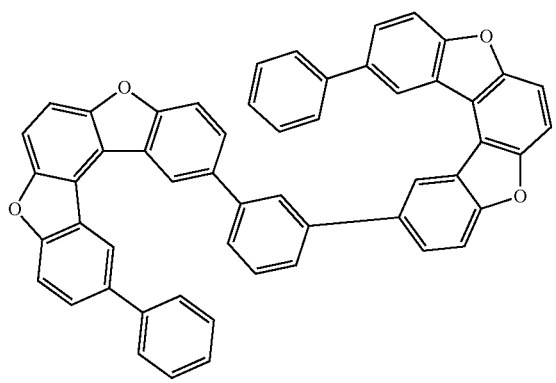
No. 158
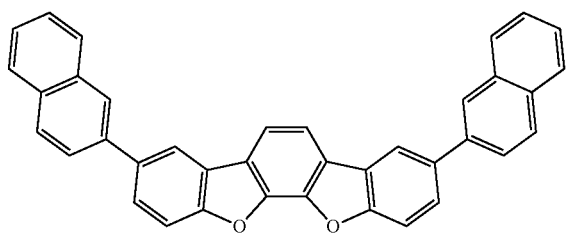
No. 159
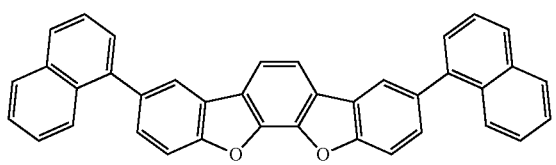
No. 160
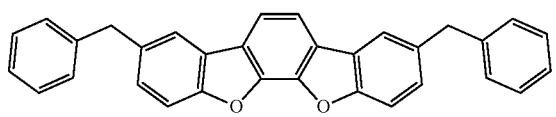
No. 161
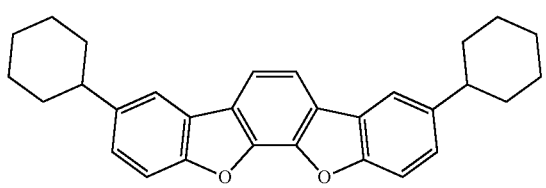
No. 162
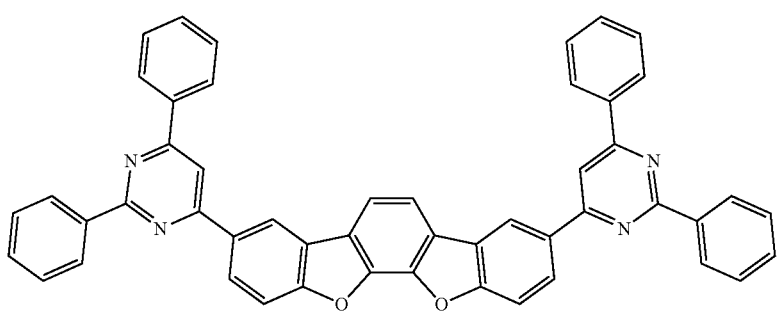

-continued
No. 163
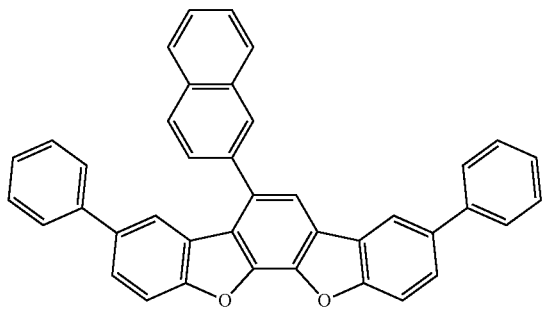
No. 164
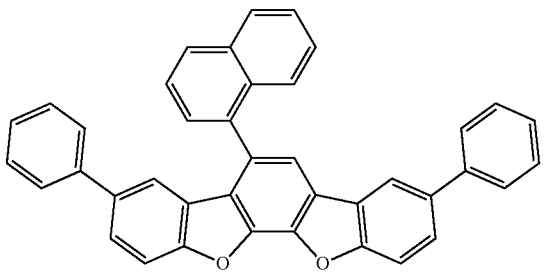
No. 165
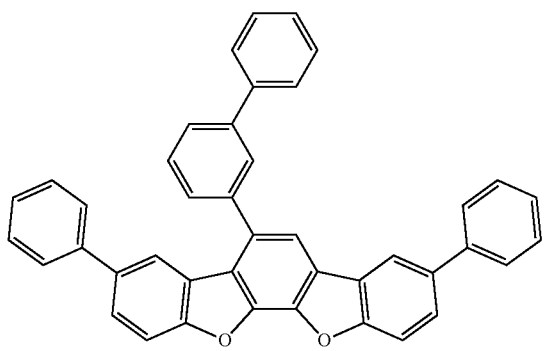
No. 166
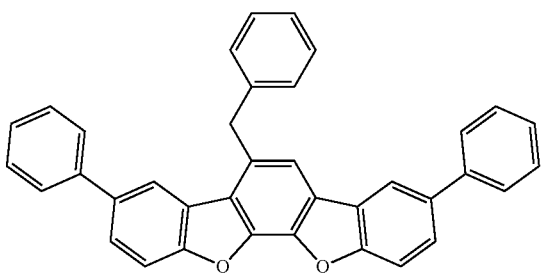
No. 167
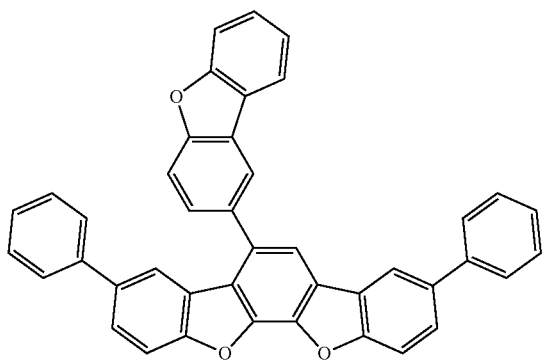
No. 168
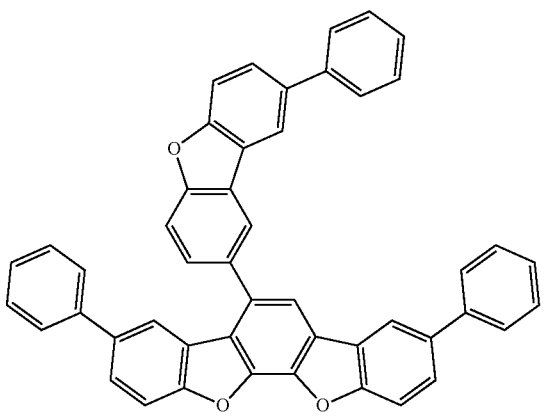
No. 169
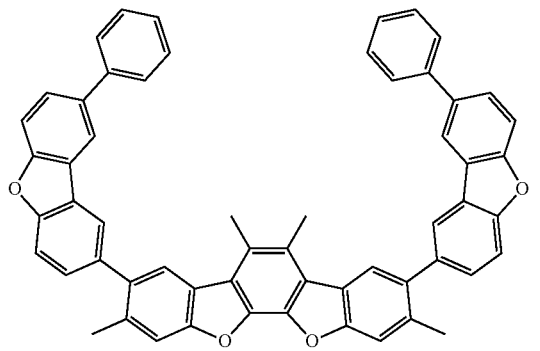
No. 170
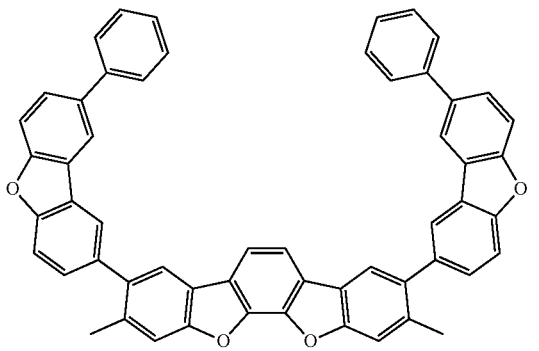

-continued
No. 171
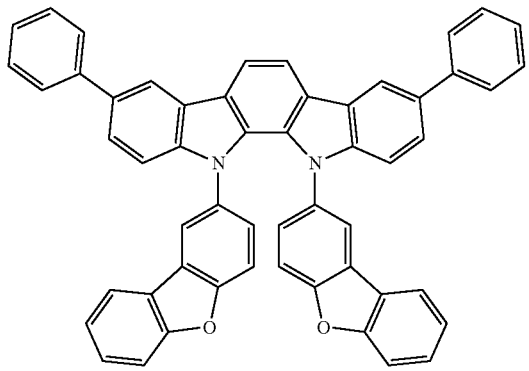
No. 172
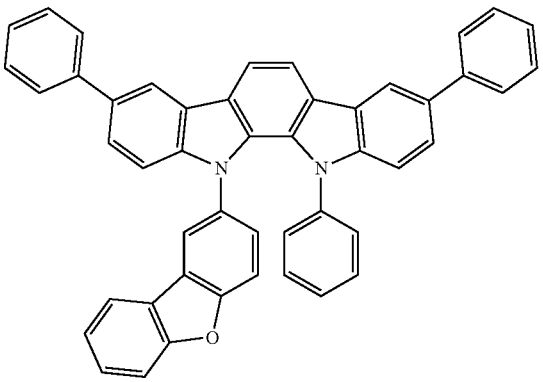
No. 173
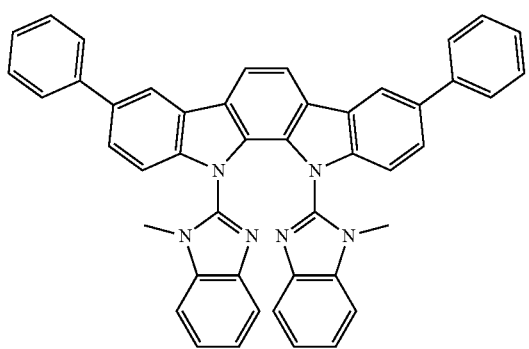
No. 174
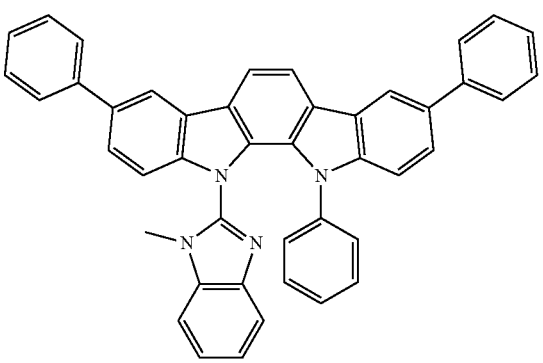
No. 175
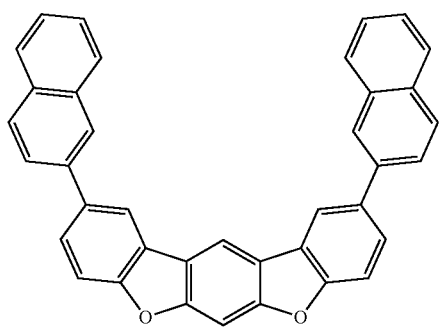
No. 176
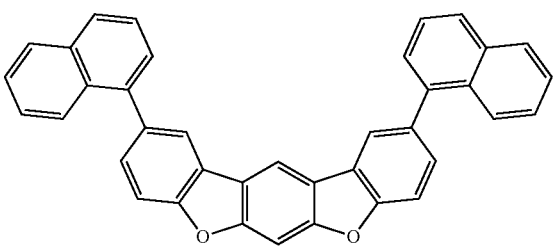
No. 177
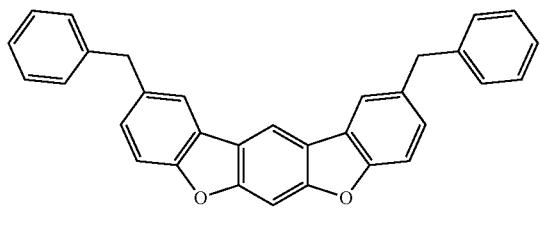
No. 178
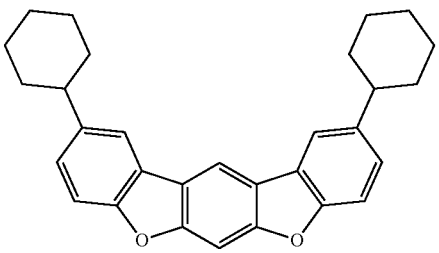

-continued
No. 179
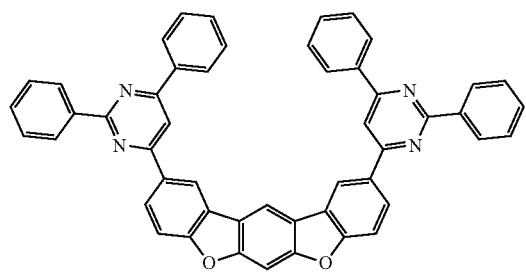
No. 180
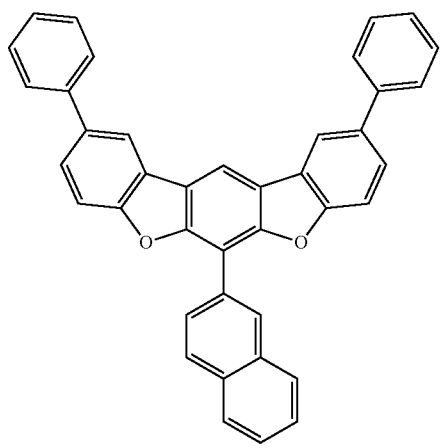
No. 181
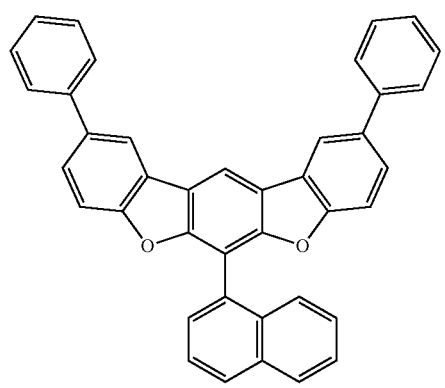
No. 182
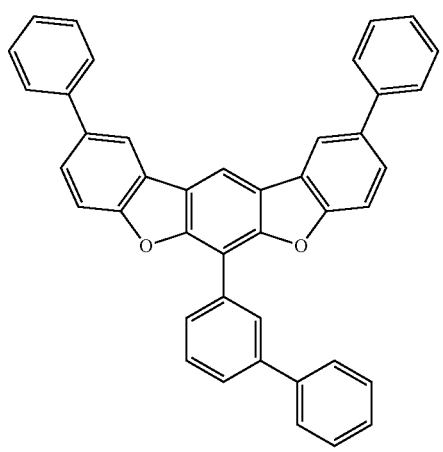
No. 183
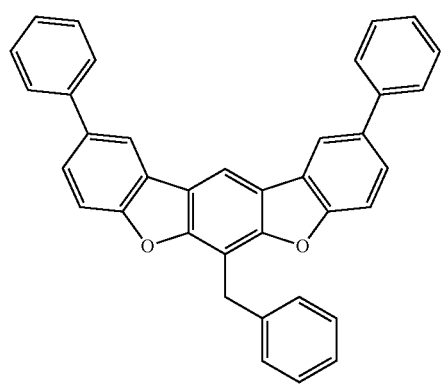
No. 184
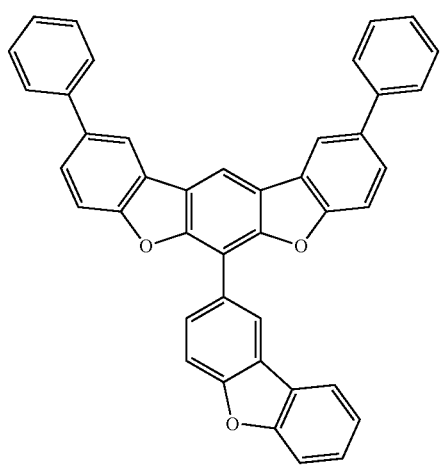

-continued
No. 185
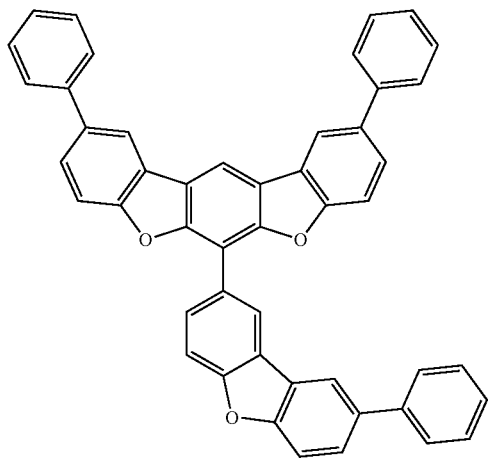
No. 186
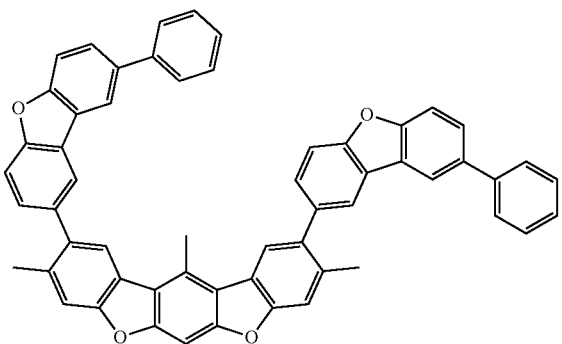
No. 187
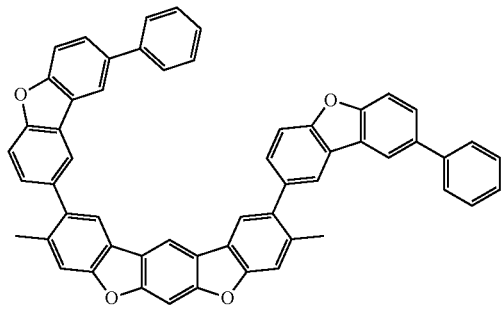
No. 188
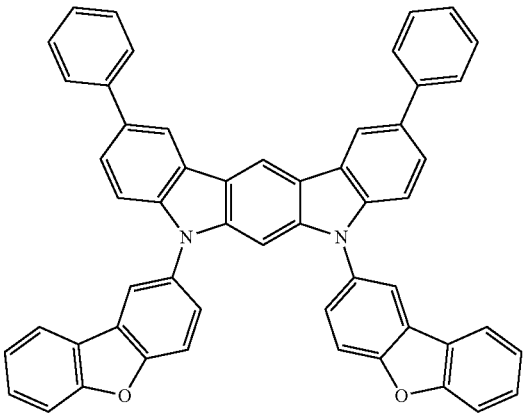
No. 189
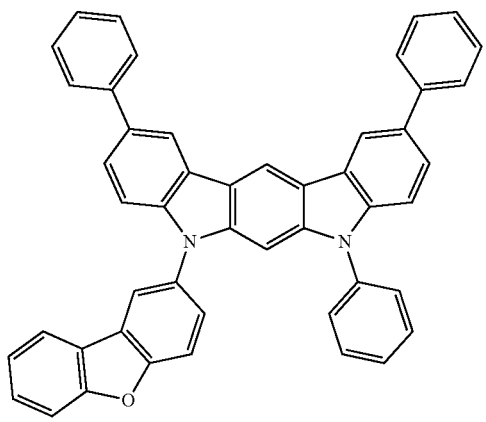
No. 190
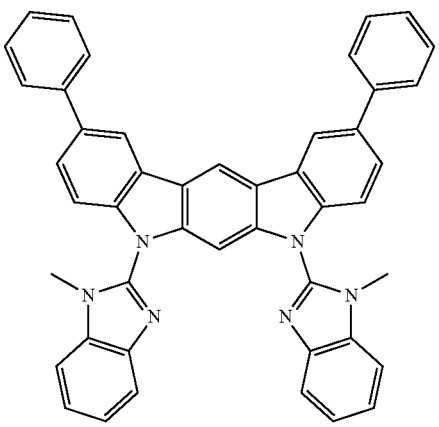

-continued
No. 191
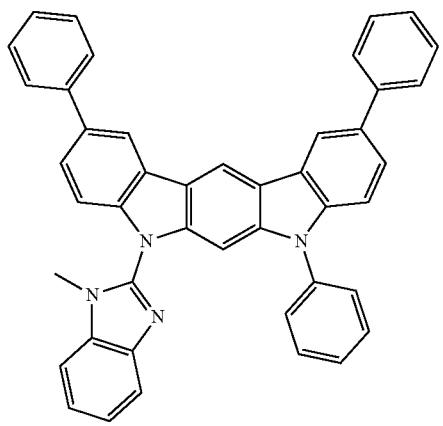
No. 192
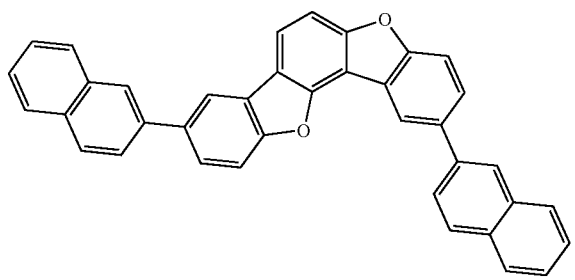
No. 193
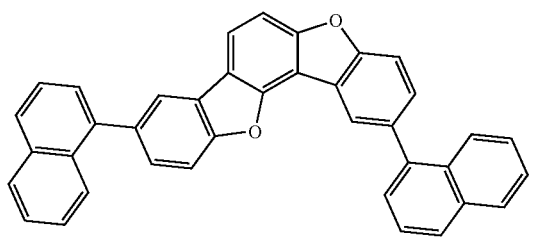
No. 194
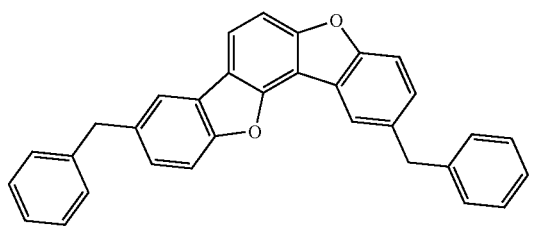
No. 195
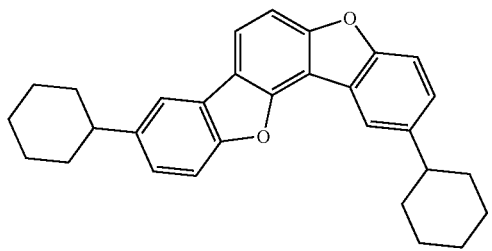
No. 196
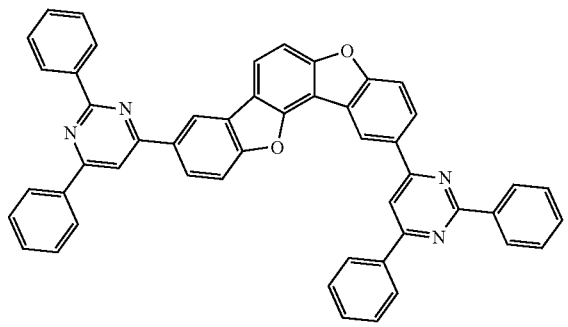
No. 197
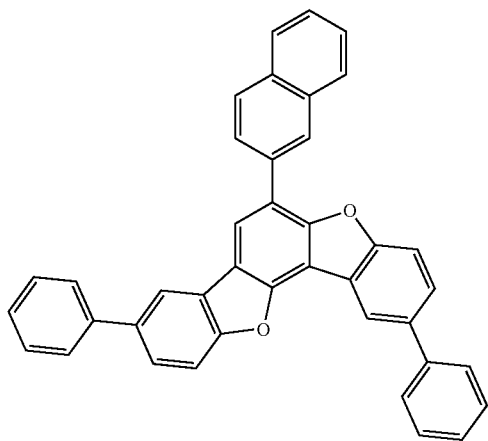
No. 198
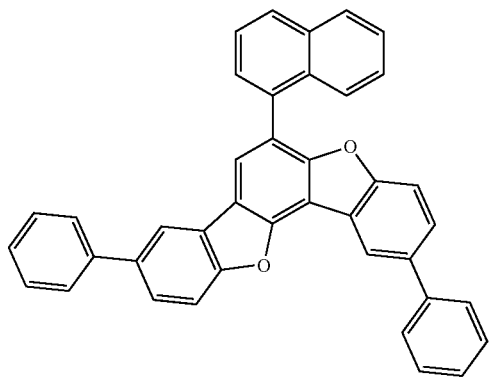

-continued
No. 199
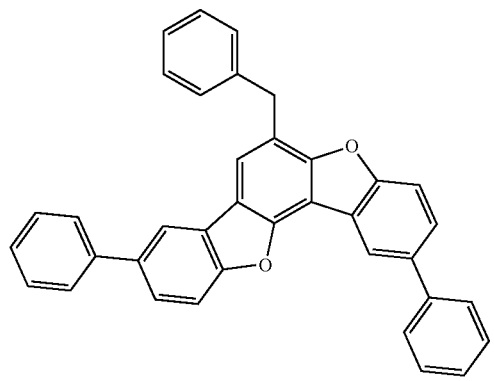
No. 200
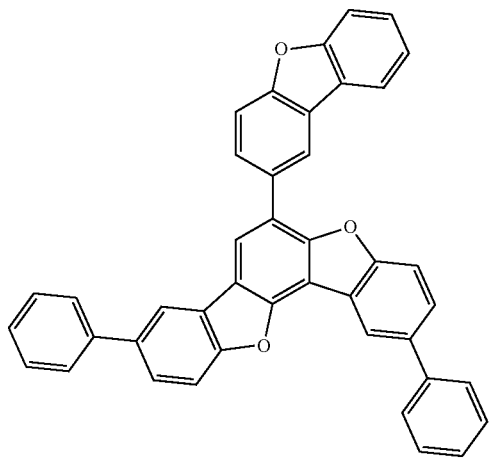
No. 201
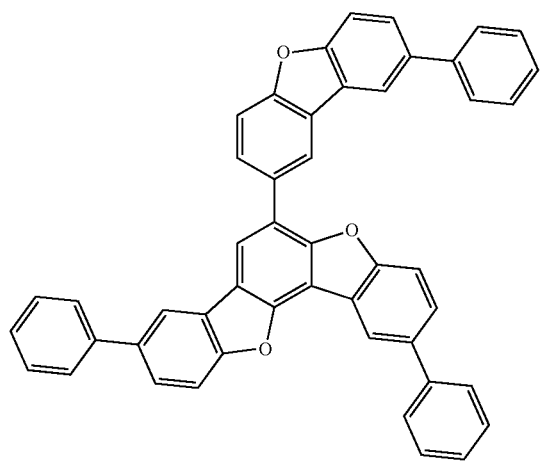
No. 202
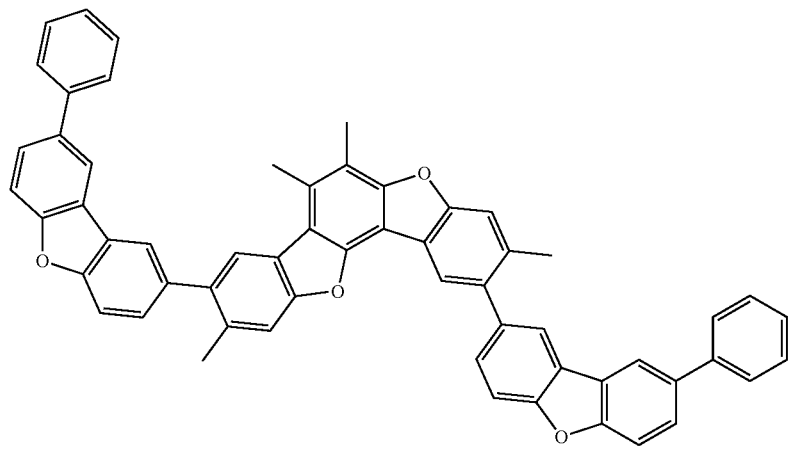

No. 203
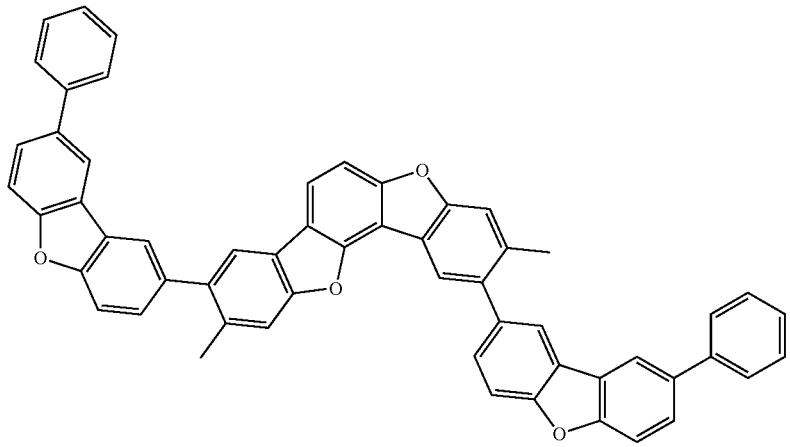
No. 204
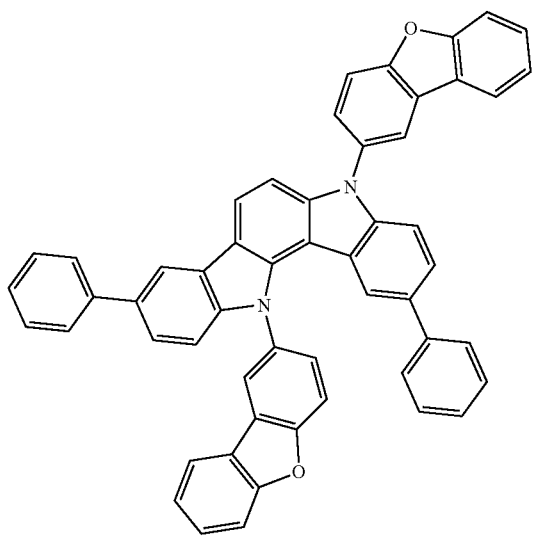
No. 205
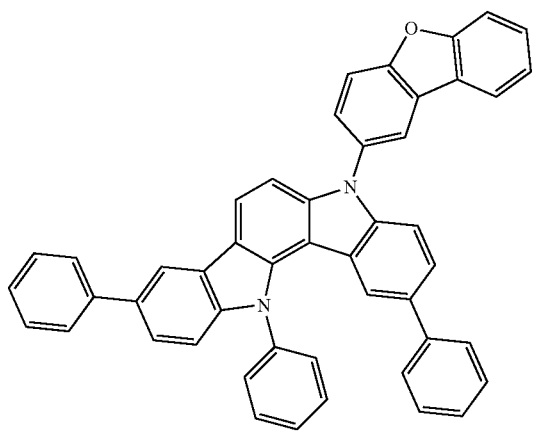
No. 206
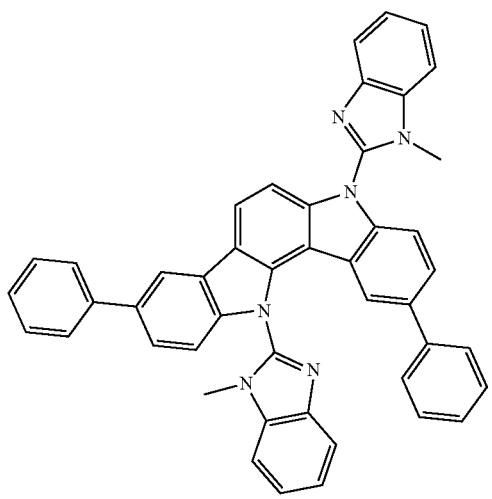
No. 207
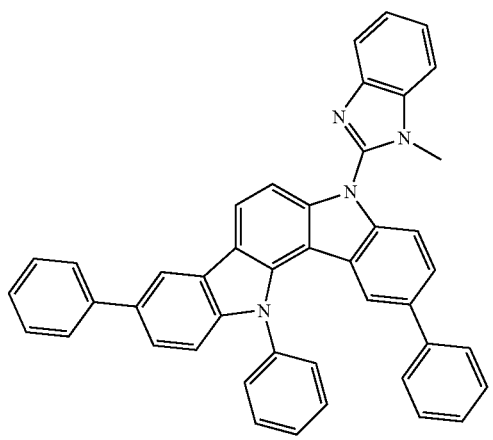

-continued
No. 208
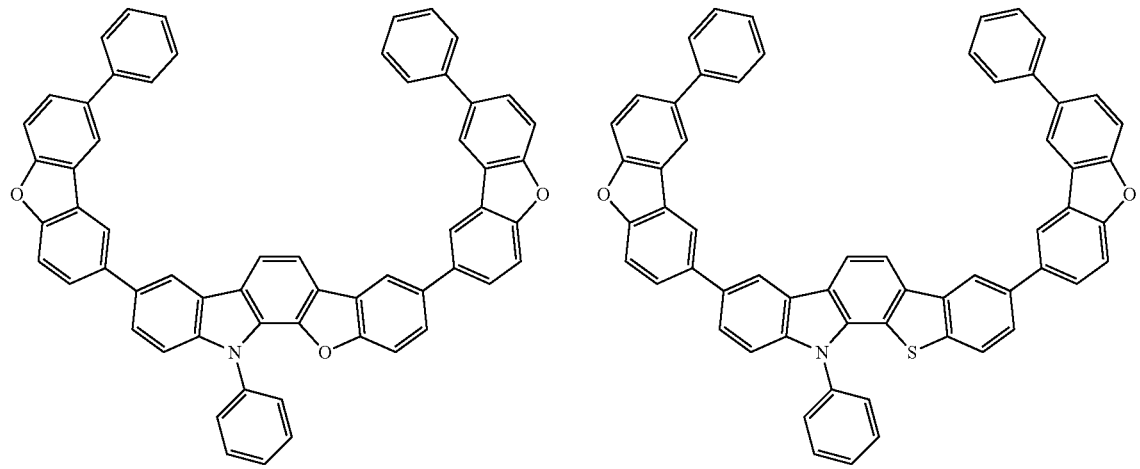
No. 209
No. 210
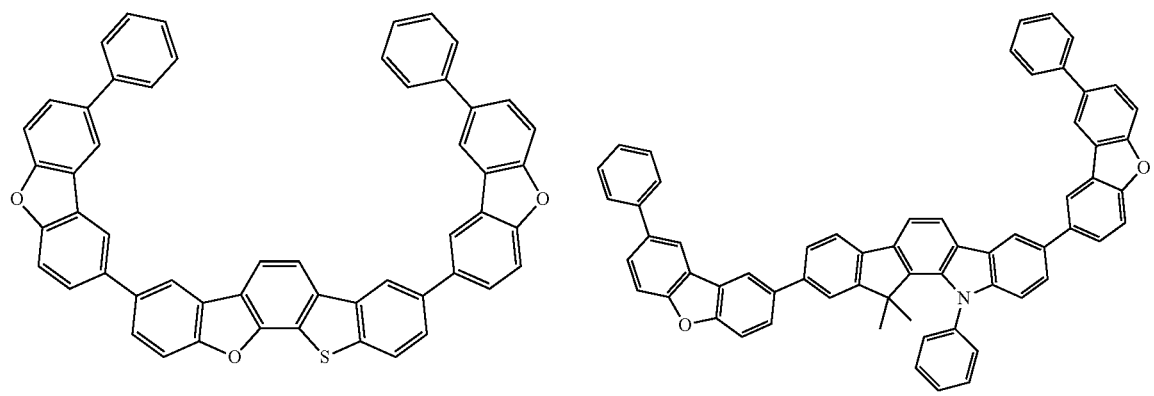
No. 211
No. 212
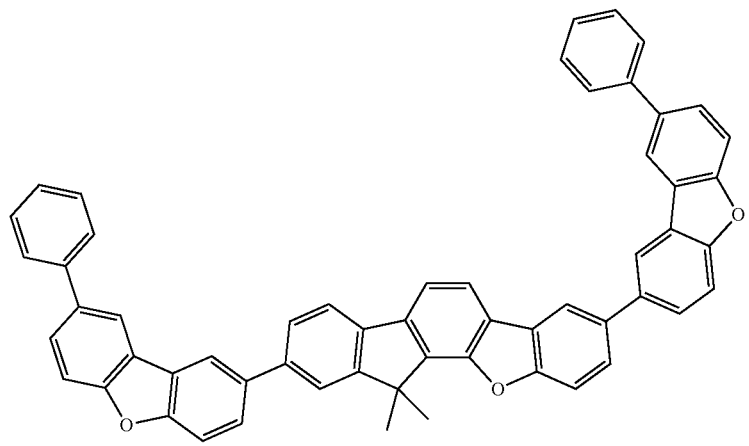

No. 213
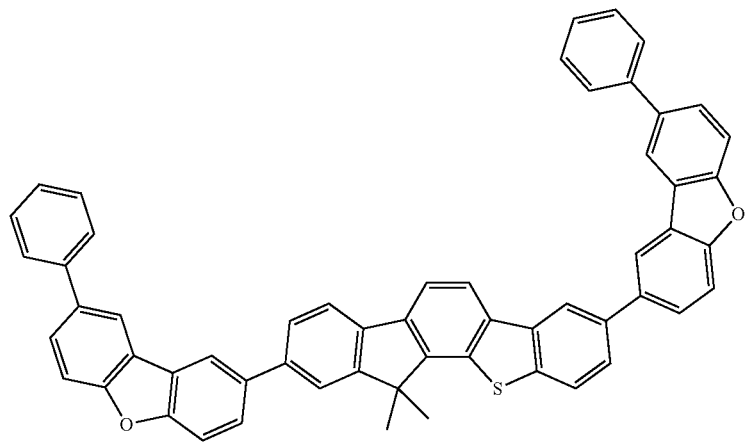
No. 214
No. 215
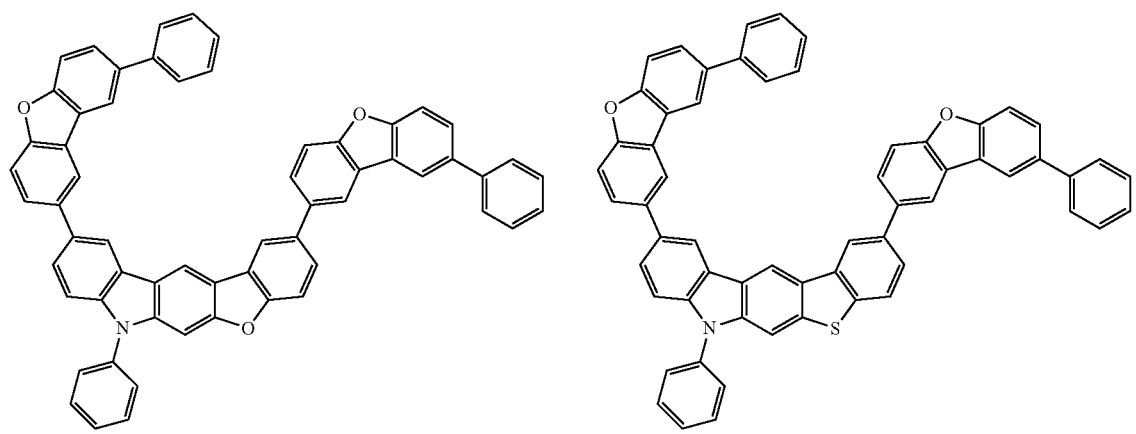
No. 216
No. 217
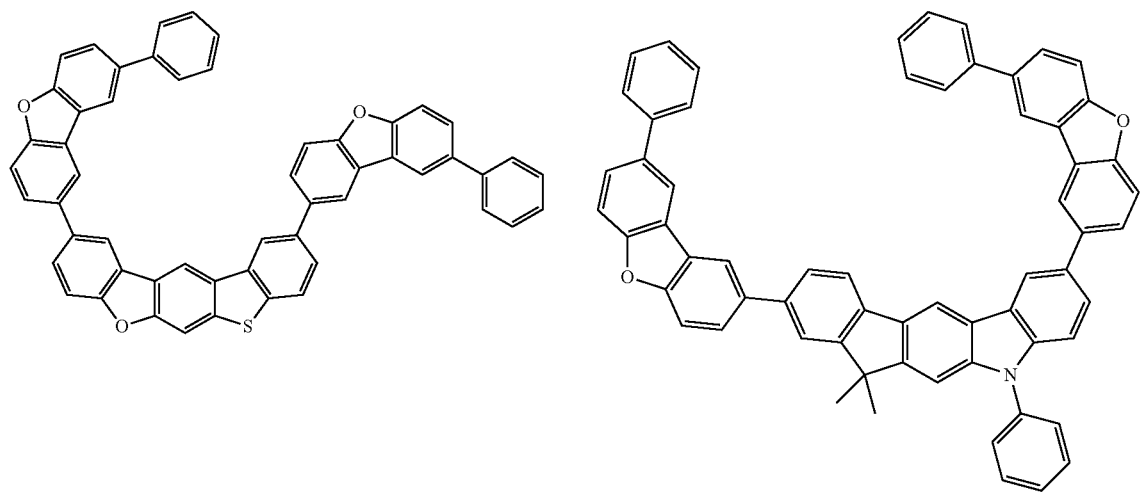

-continued
No. 218
No. 219
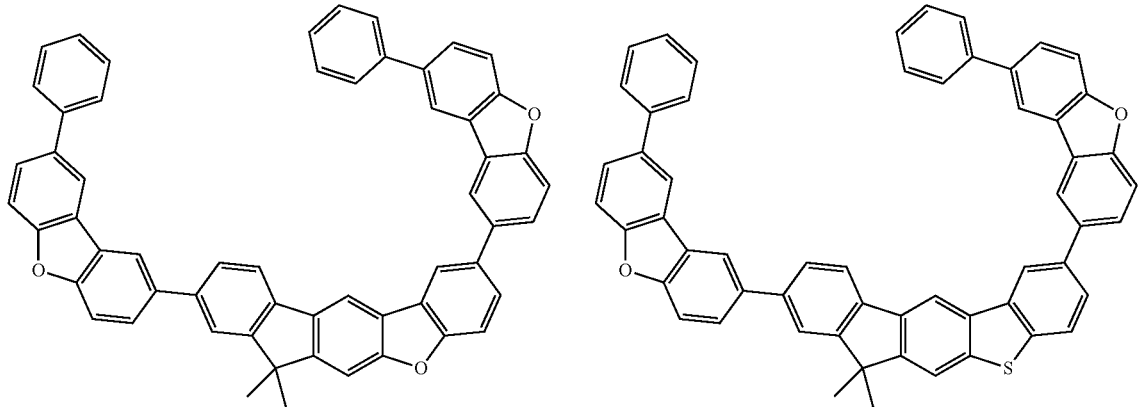
No. 220
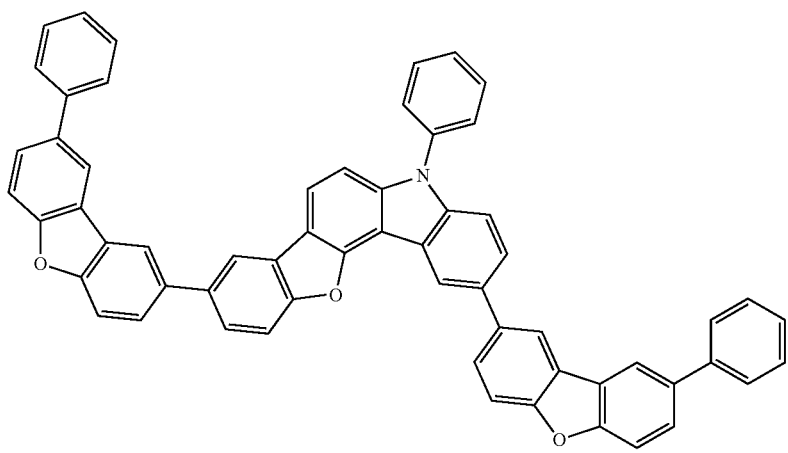
No. 221
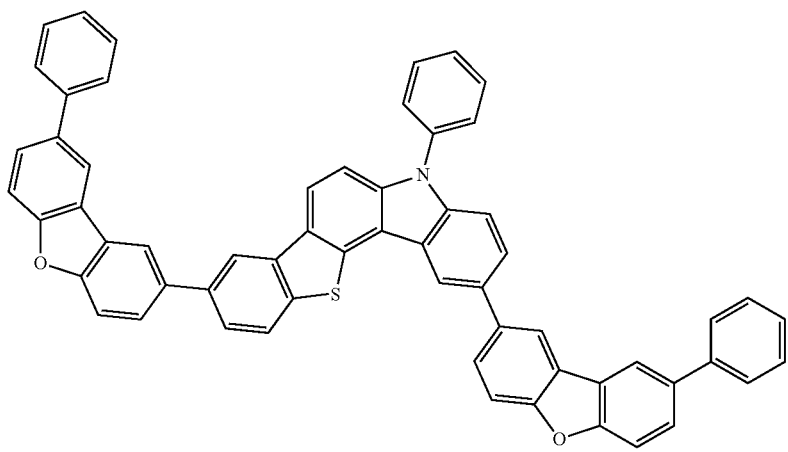

-continued
No. 222
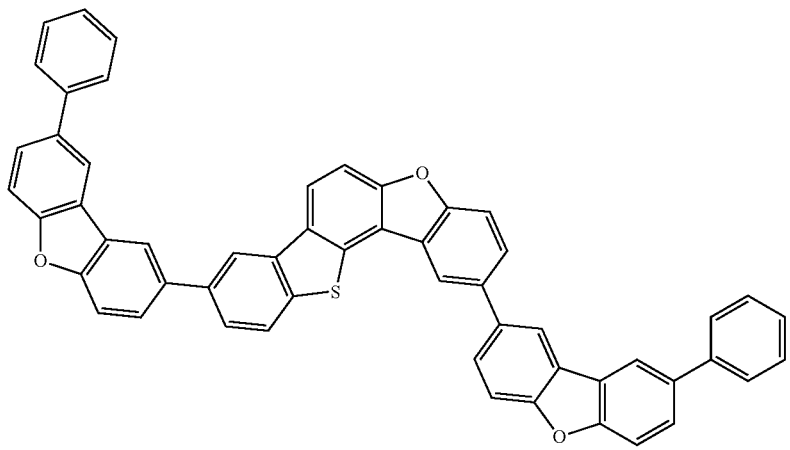
No. 223
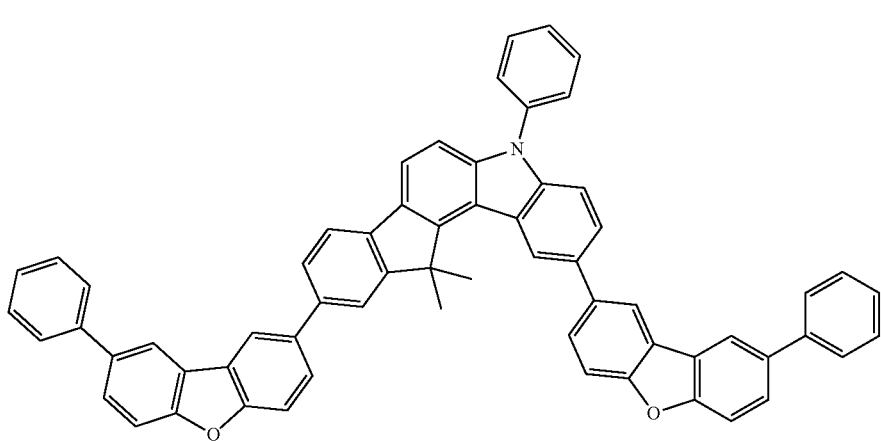
No. 224
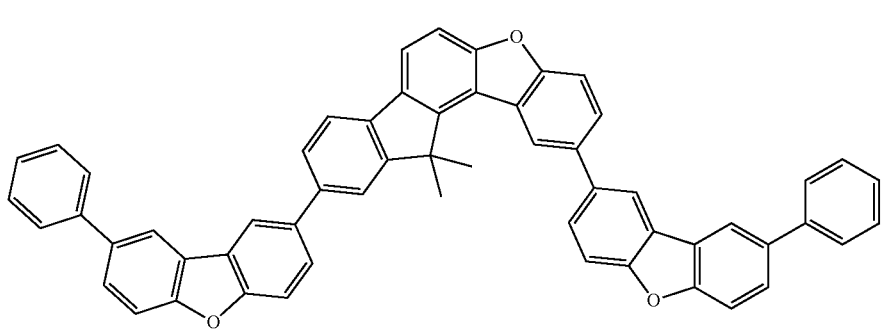
No. 225
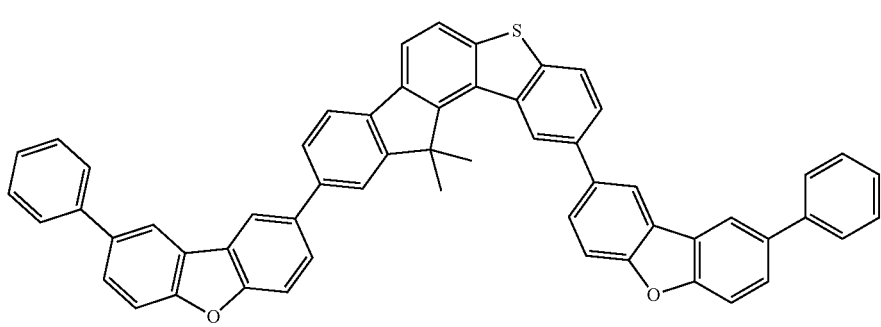

-continued
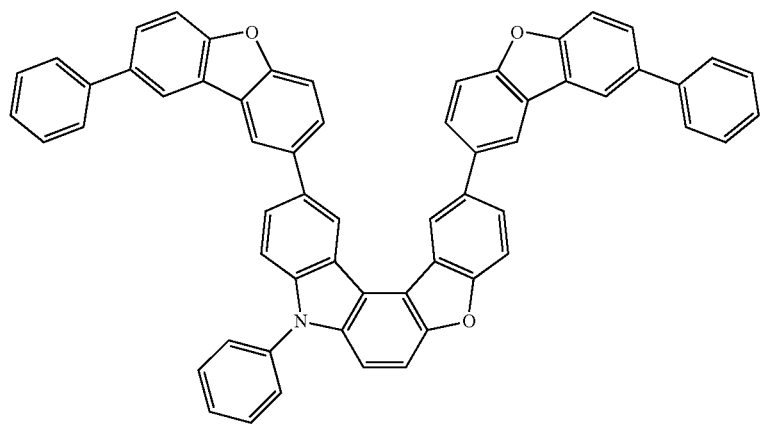
No. 226
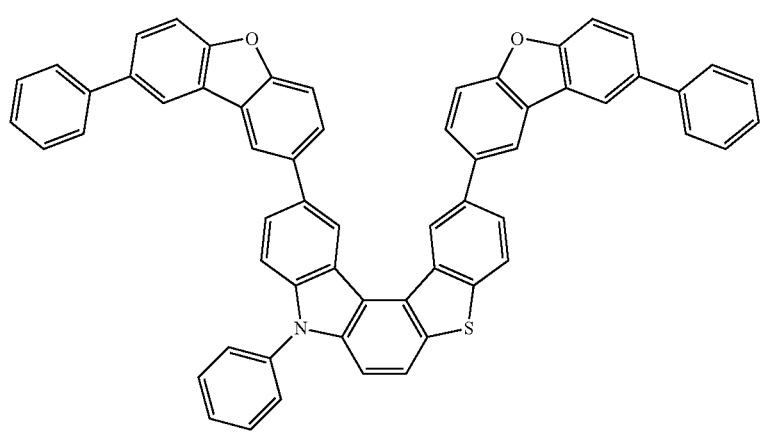
No. 227
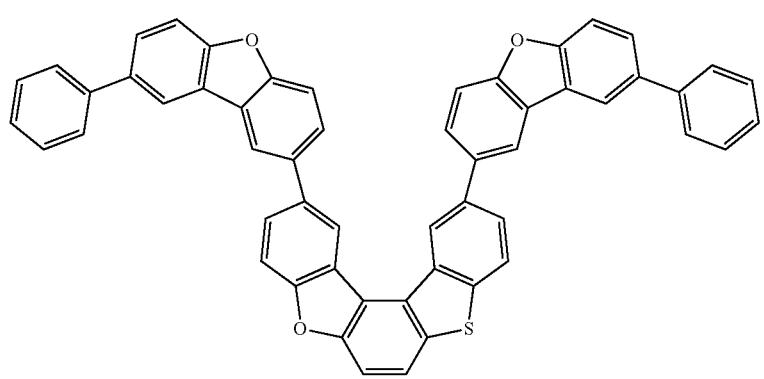
No. 228

-continued
No. 229
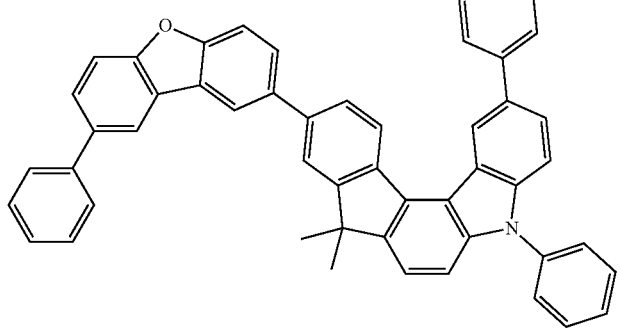
No. 230
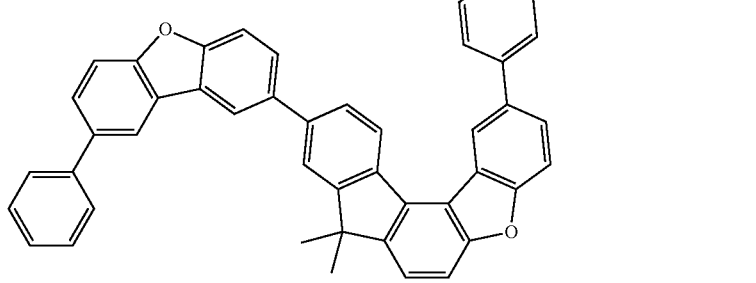
No. 231
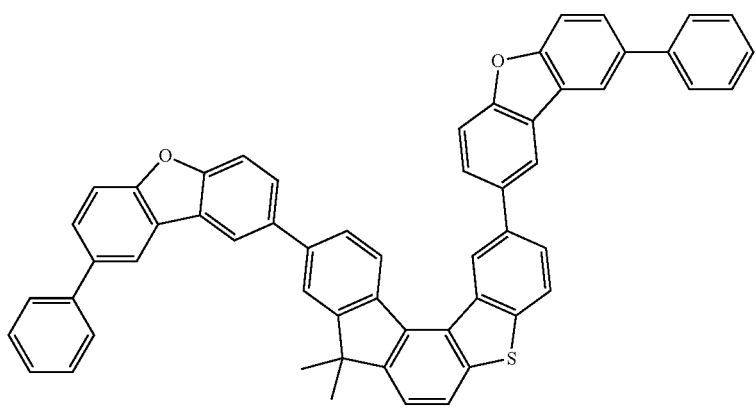
No. 232
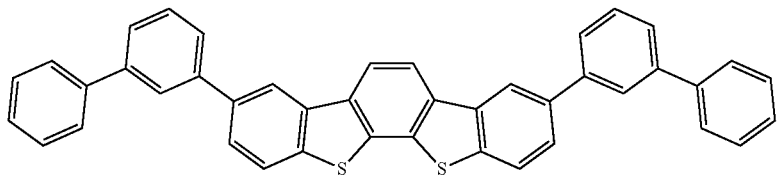

No. 233
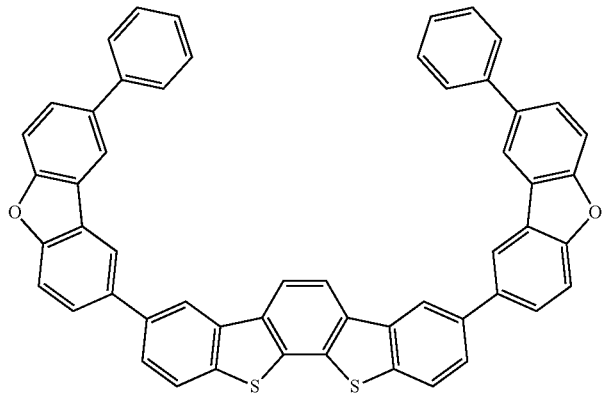
No. 234
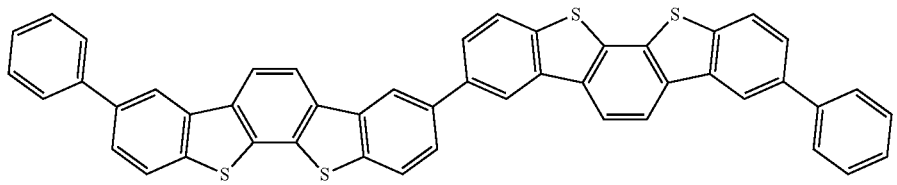
No. 235
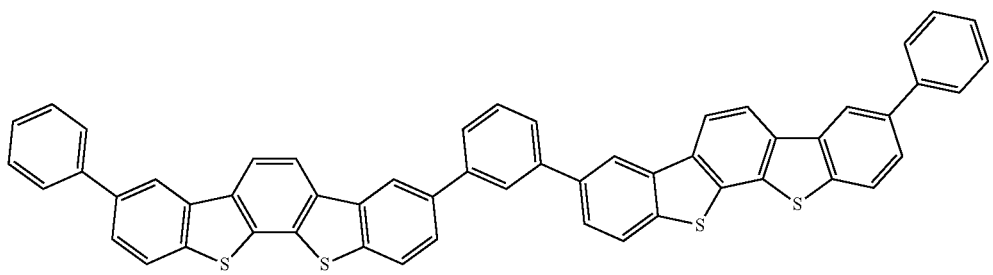
No. 236
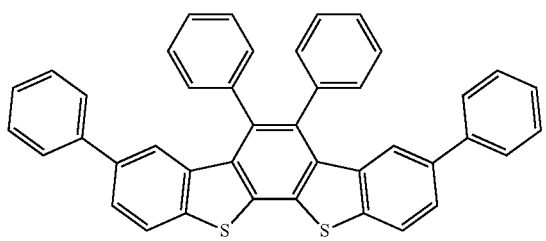
No. 237
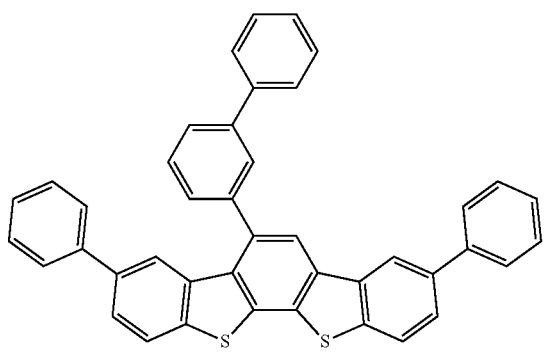
No. 238
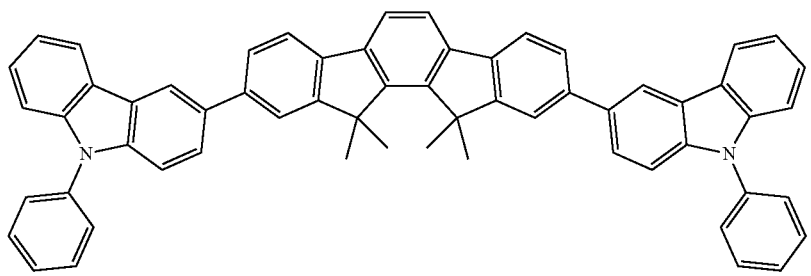

-continued
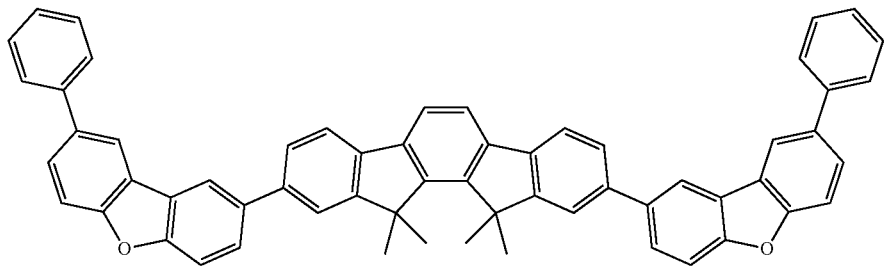
No. 239
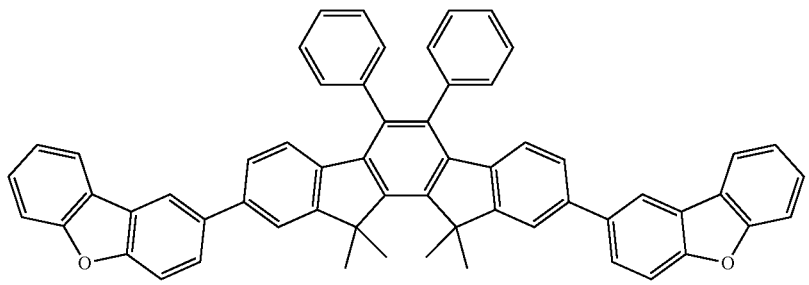
No. 240
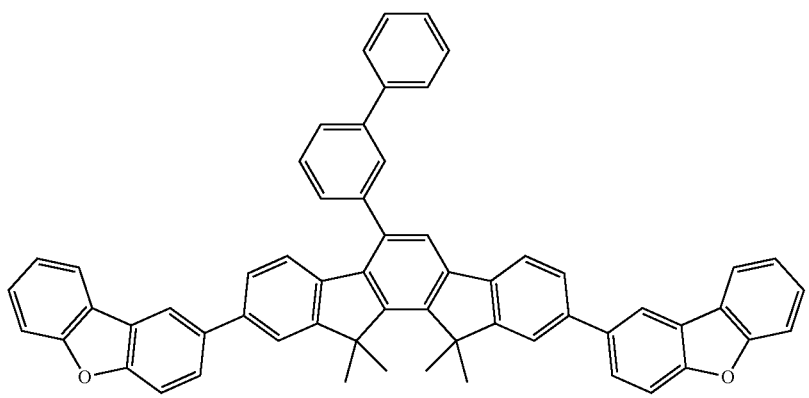
No. 241
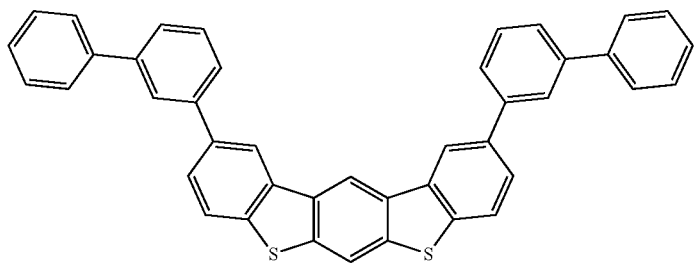
No. 242
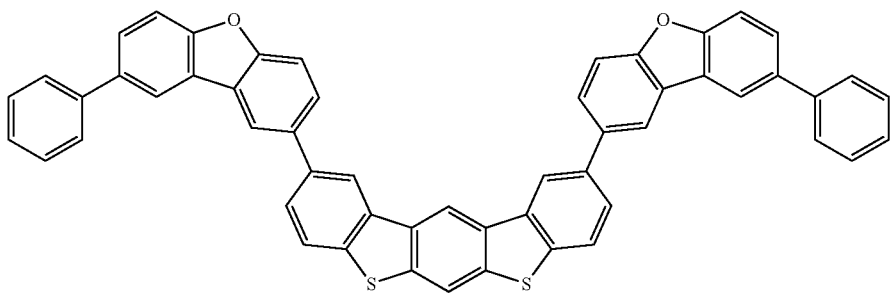
No. 243

-continued
No. 244
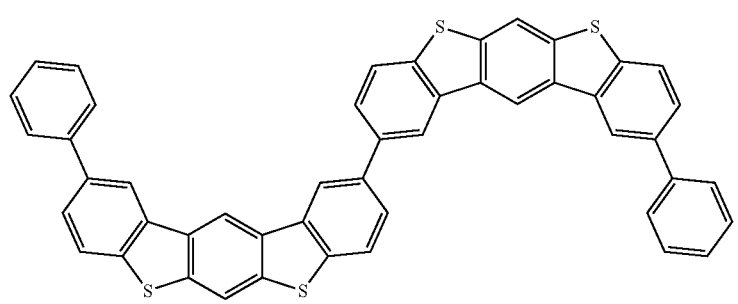
No. 245
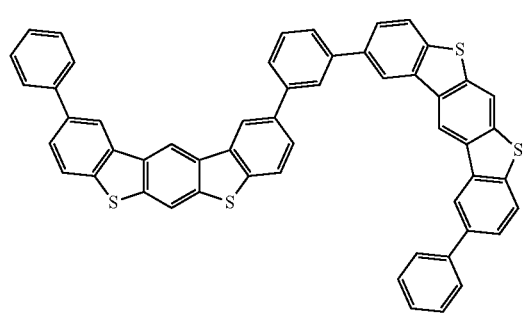
No. 246
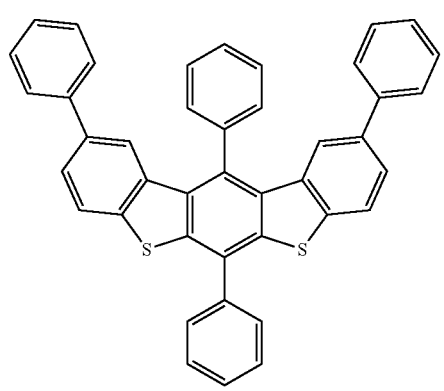
No. 247
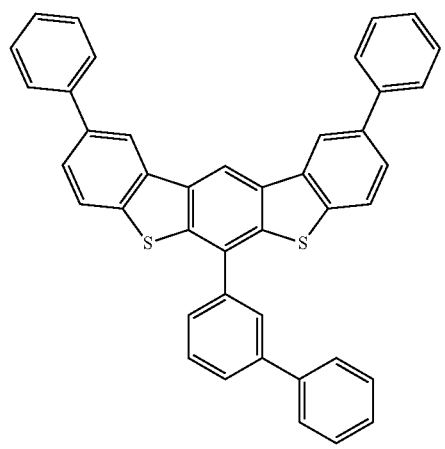
No. 248
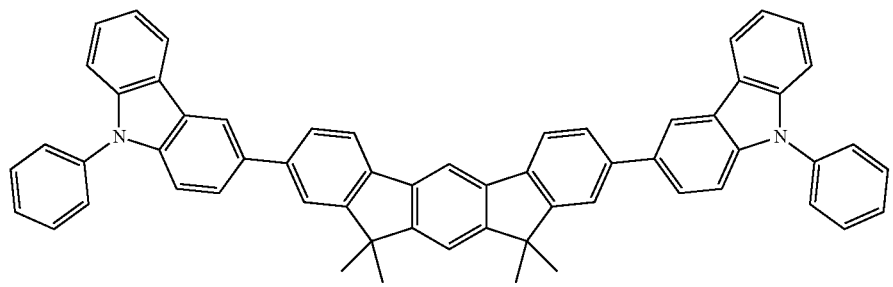

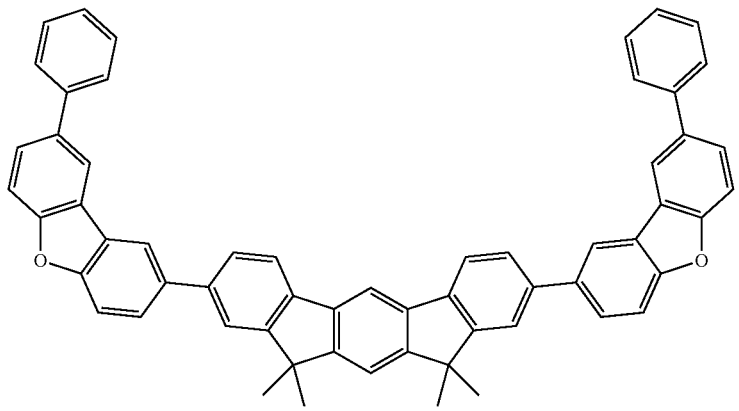
No. 249
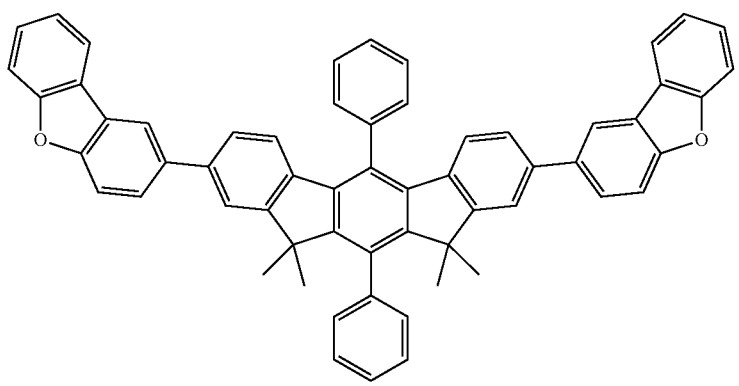
No. 250
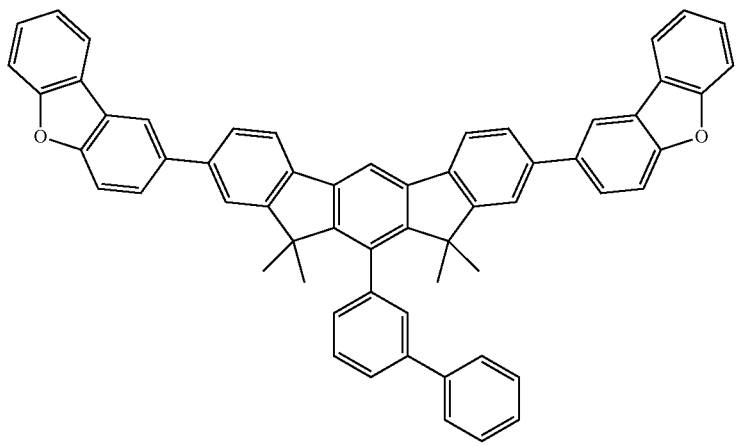
No. 251
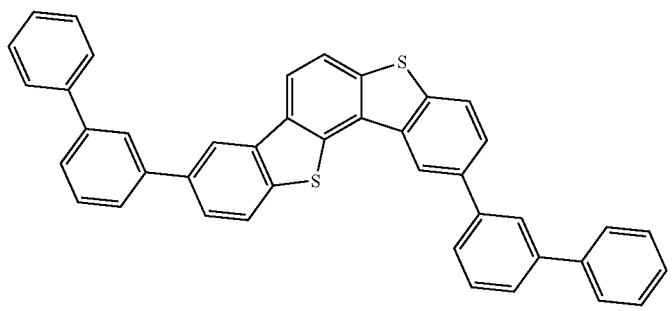
No. 252

-continued
No. 253
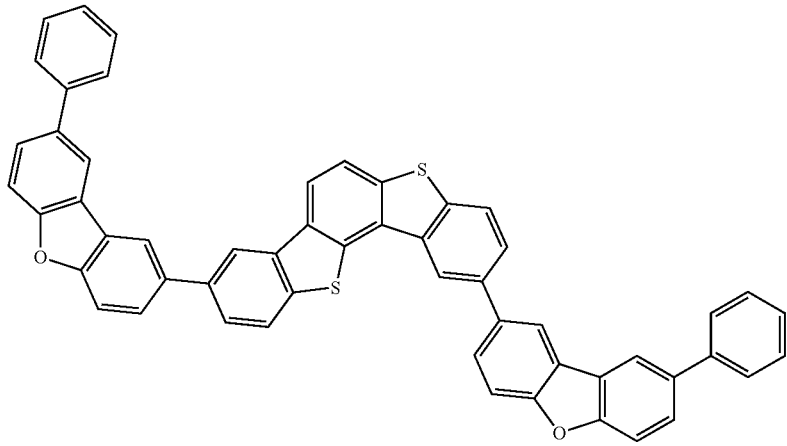
No. 254
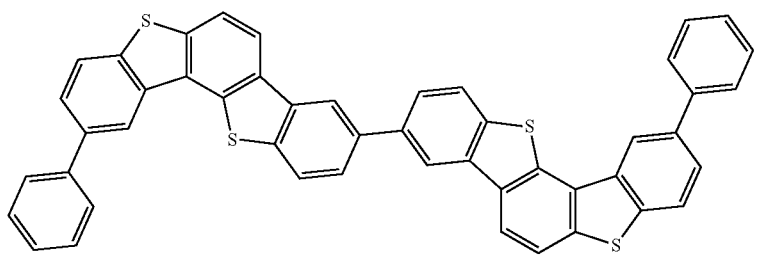
No. 255
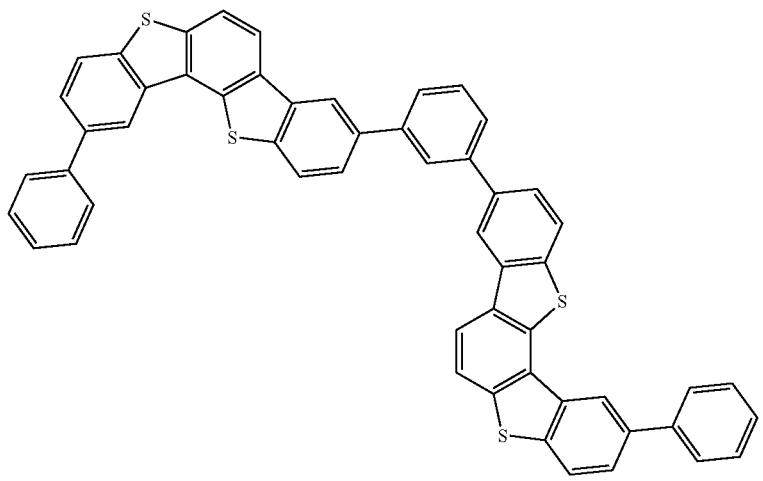
No. 256
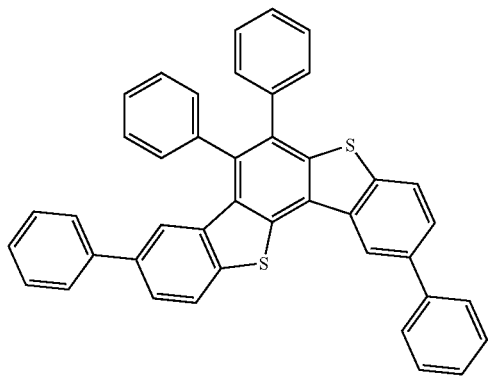
No. 257
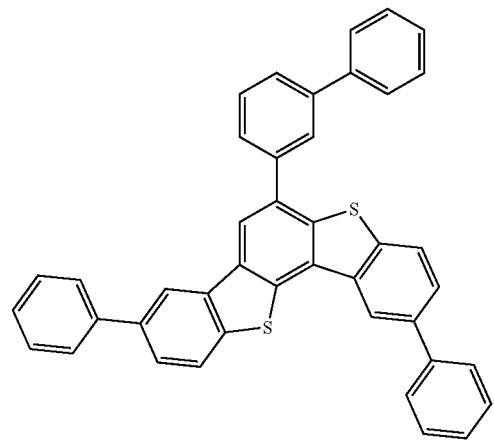

No. 258
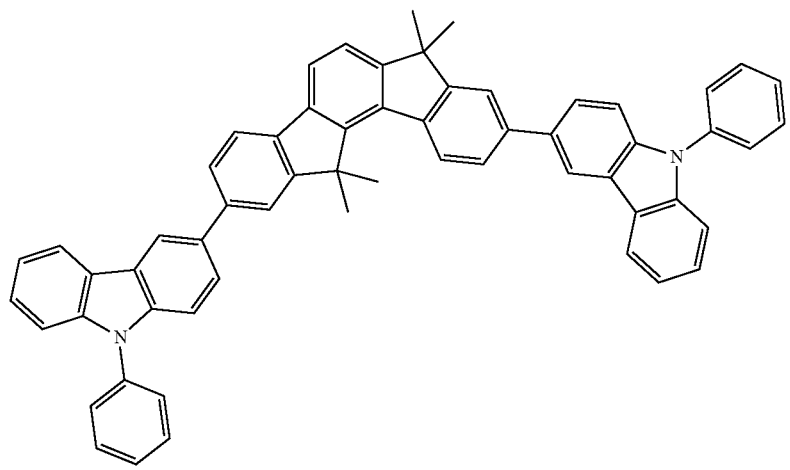
No. 259
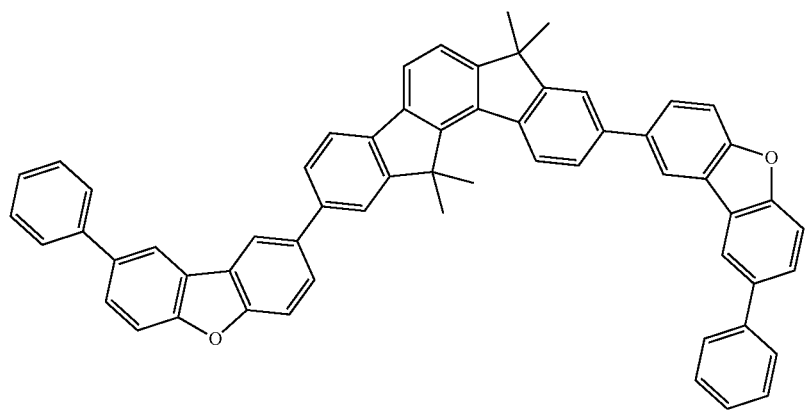
No. 260 No. 261
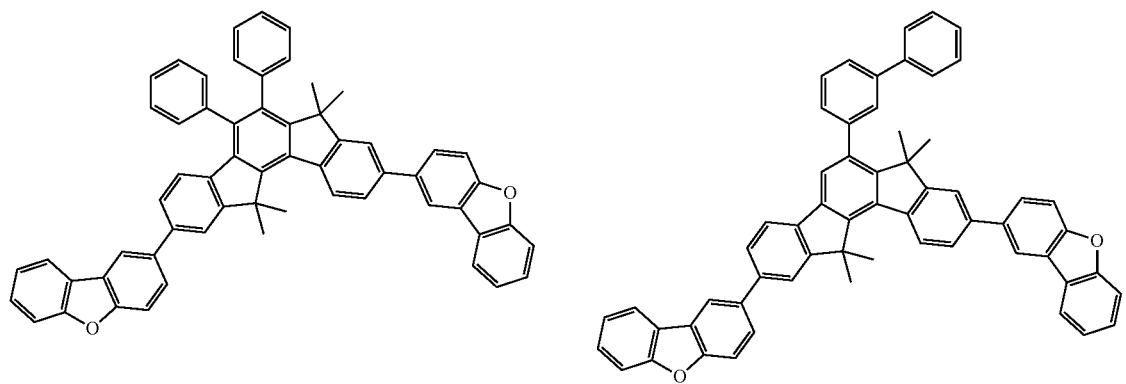

-continued
No. 262
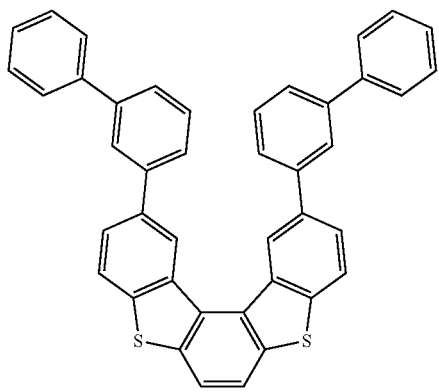
No. 263
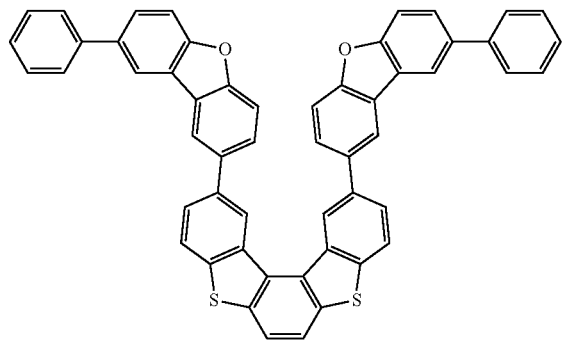
No. 264
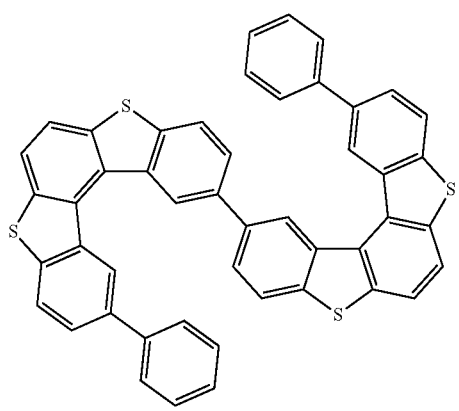
No. 265
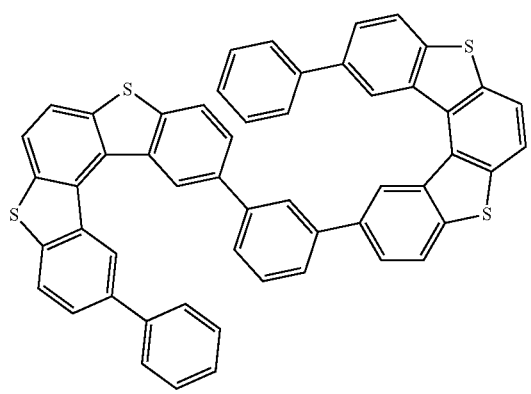
No. 266
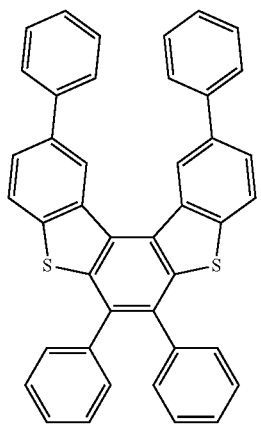
No. 267
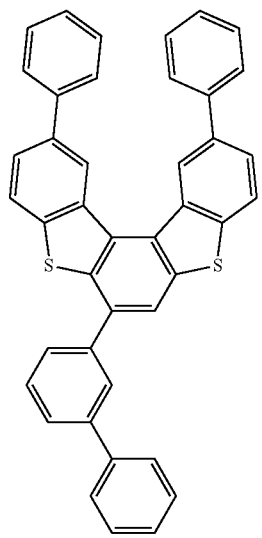

No. 268
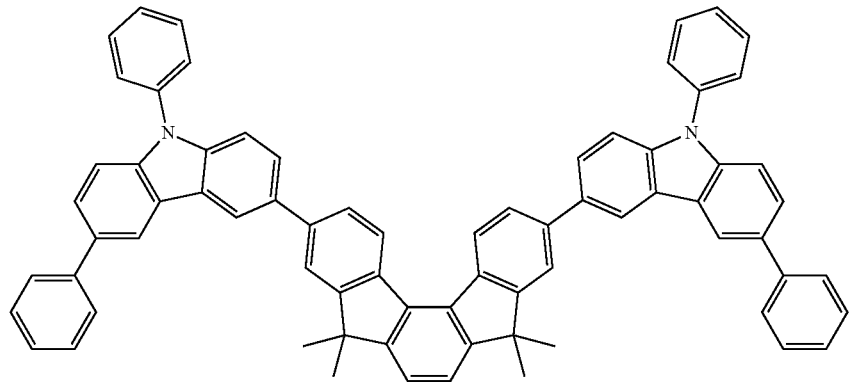
No. 269
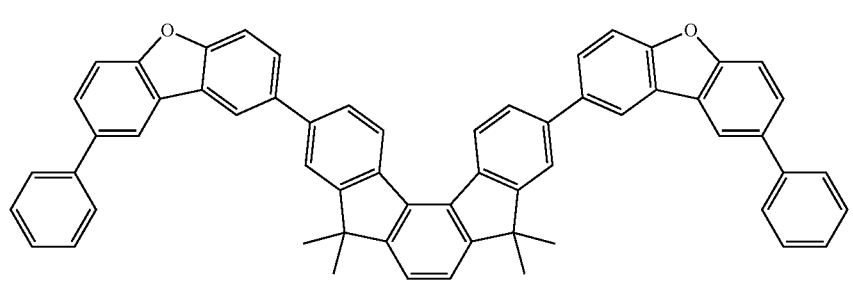
No. 270
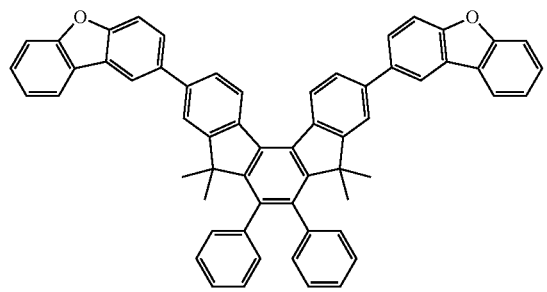
No. 271
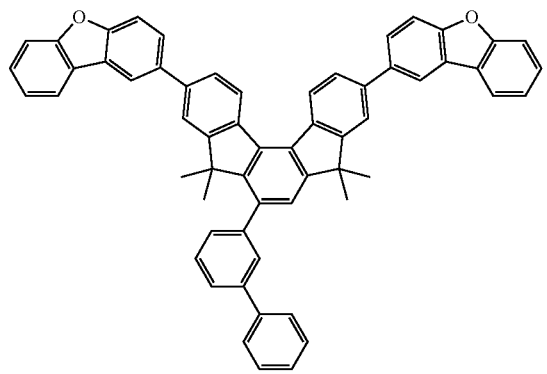

-continued
No. 272
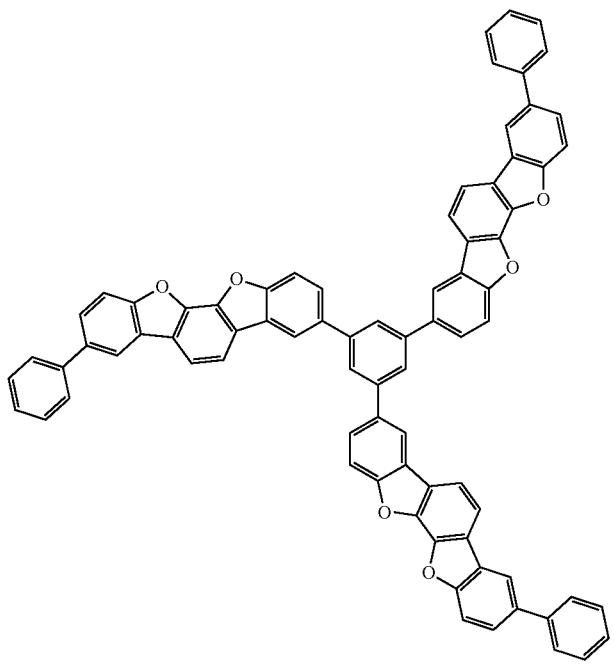
No. 273
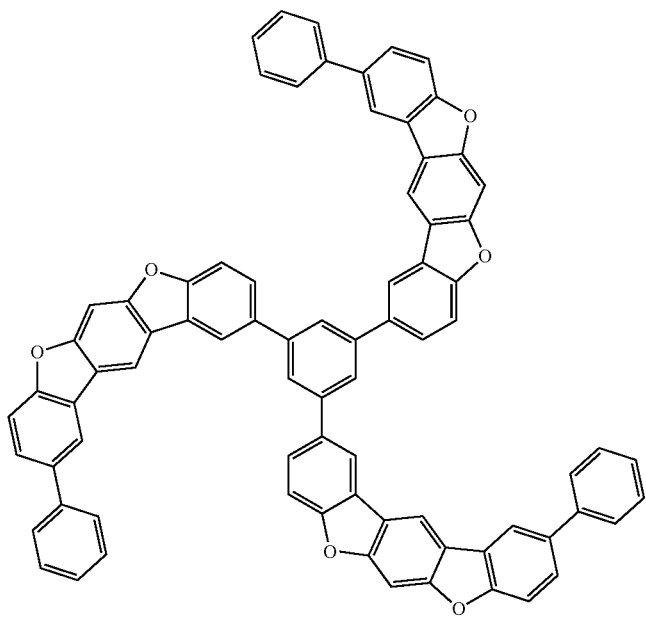

-continued
No. 274
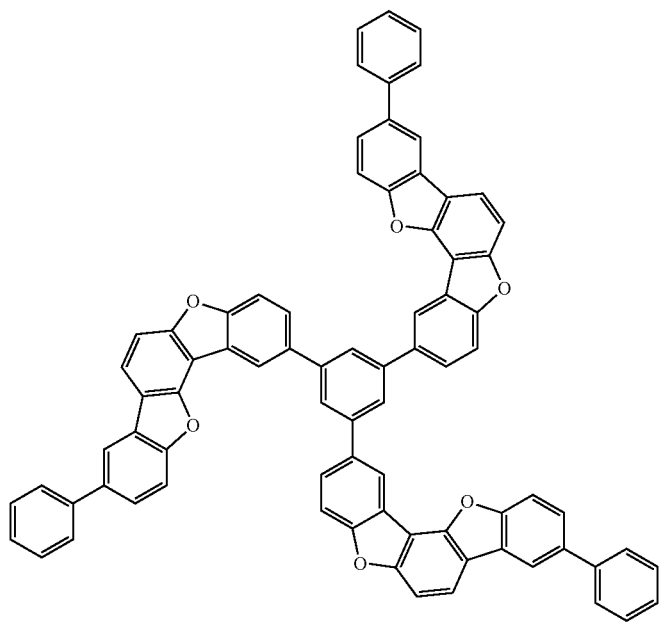
No. 275
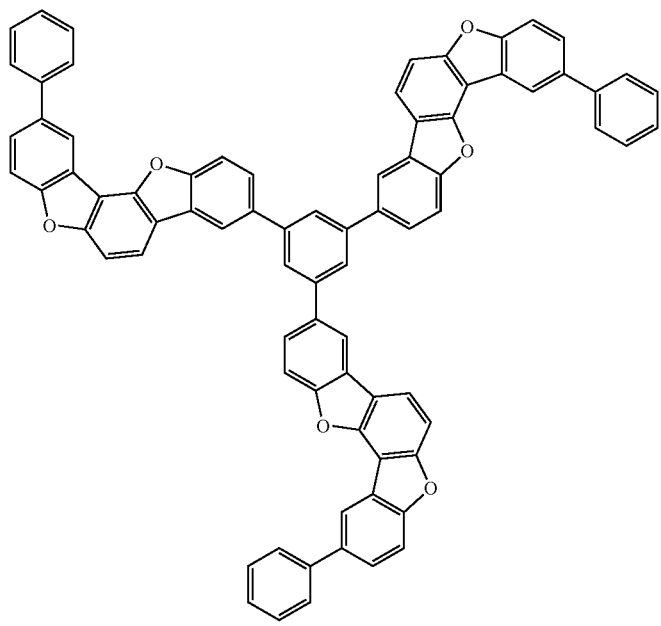

-continued
No. 276
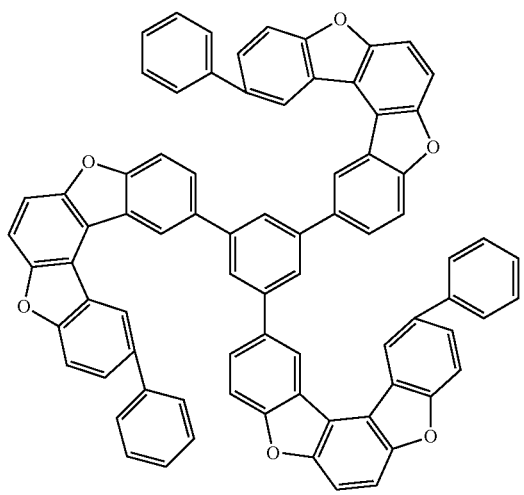
No. 277
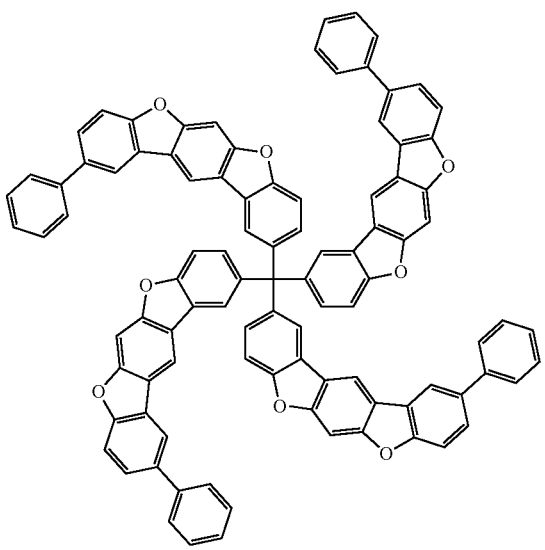
No. 278
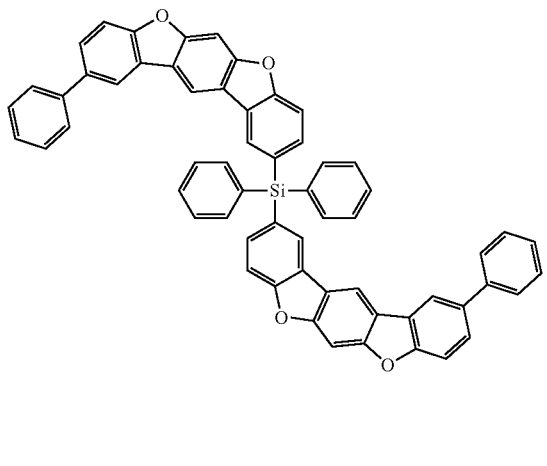
No. 279
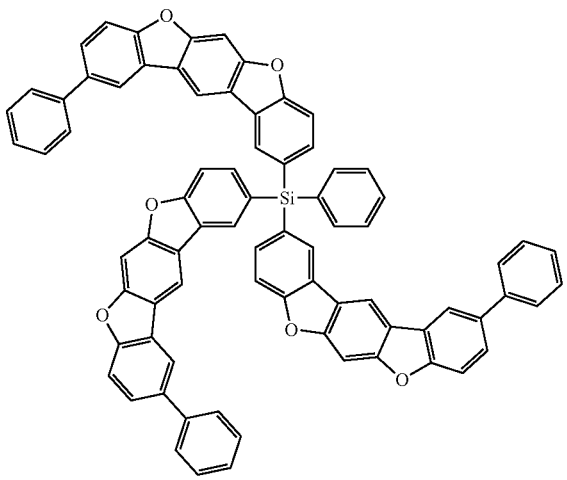
No. 280
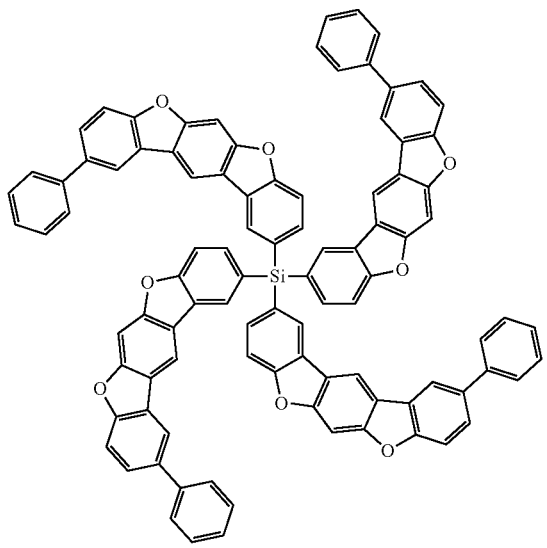
No. 281
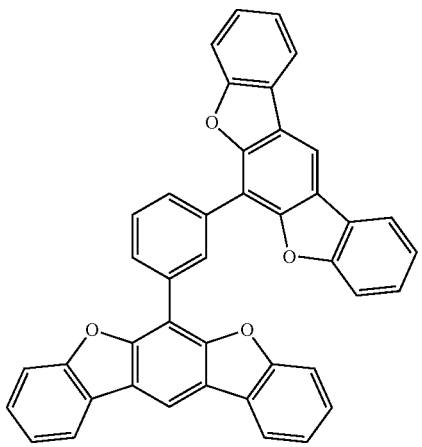

No. 282
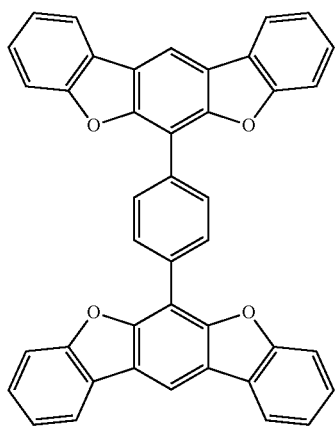
No. 283
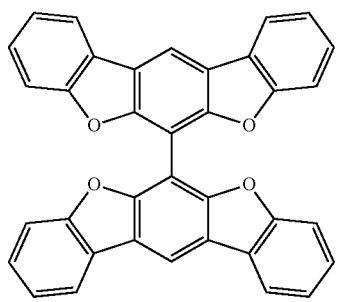
No. 284
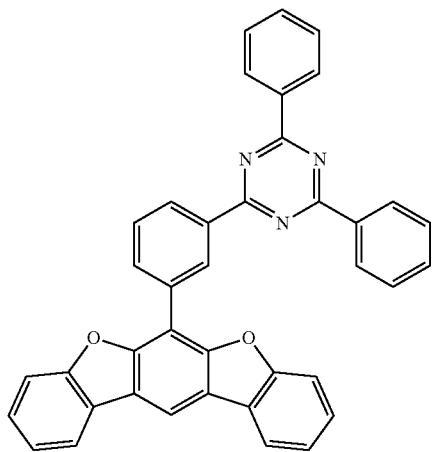
No. 285
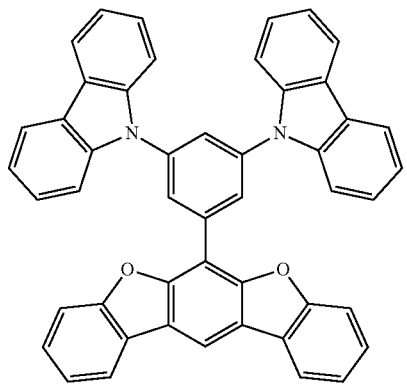
No. 286
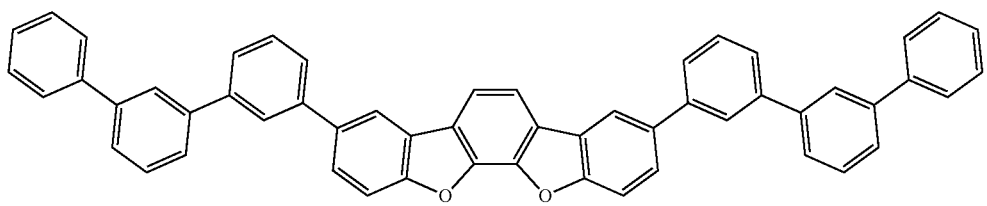
No. 287
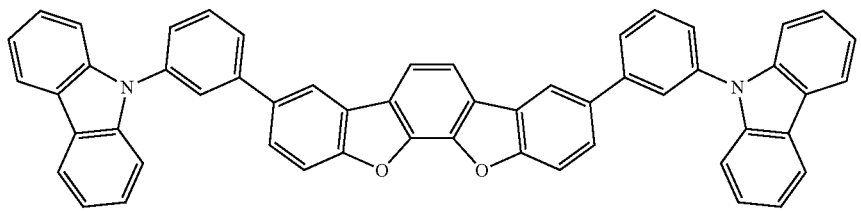

-continued
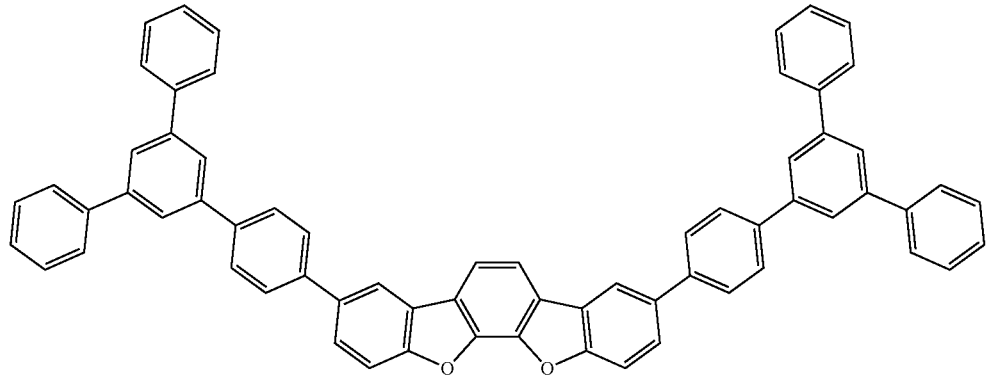
No. 288
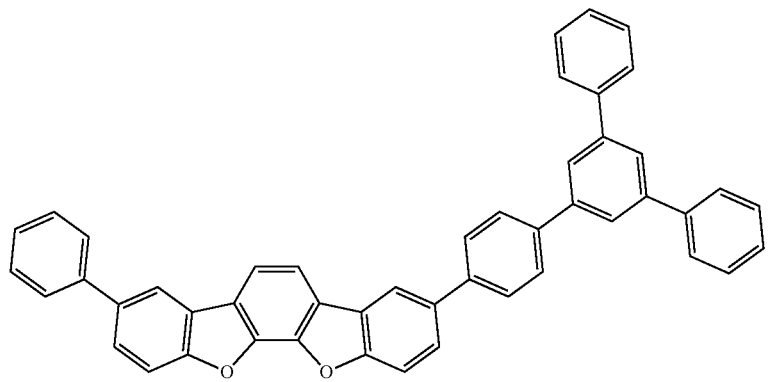
No. 289
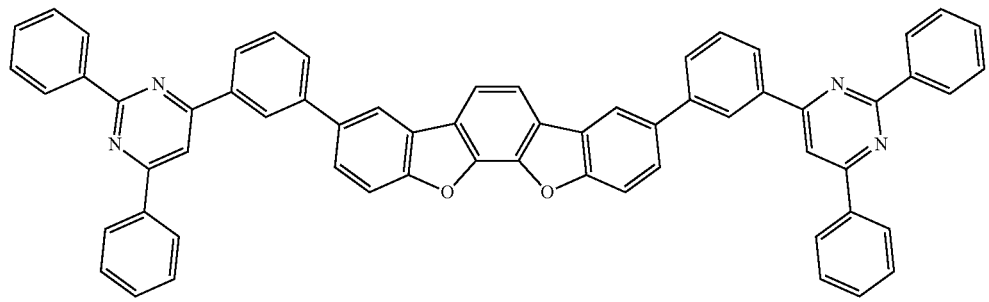
No. 290
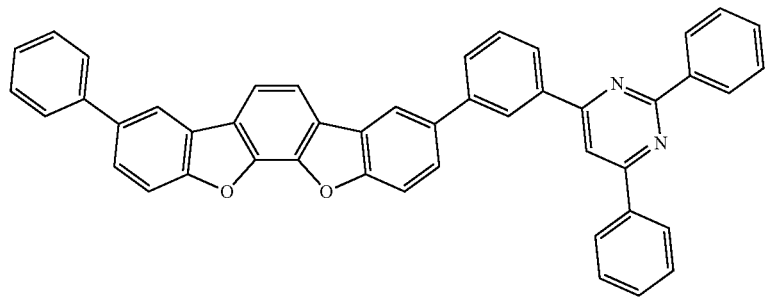
No. 291

-continued
No. 292
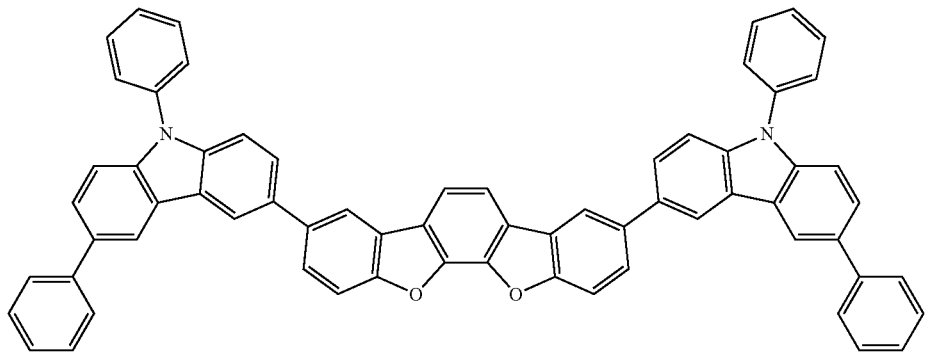
No. 293
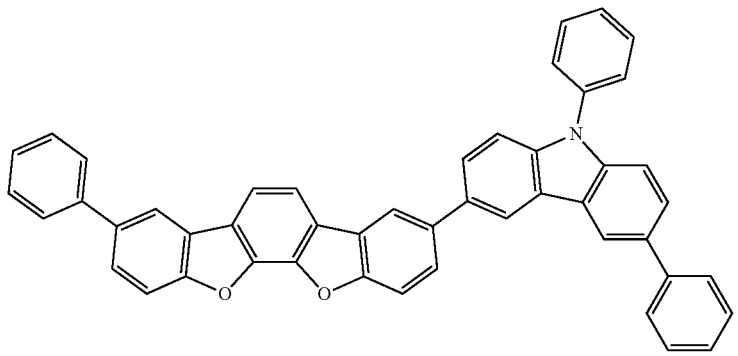
No. 294
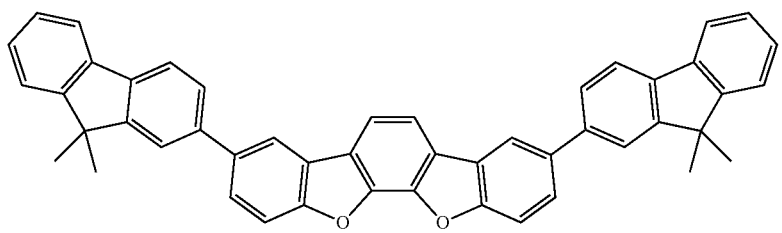
No. 295
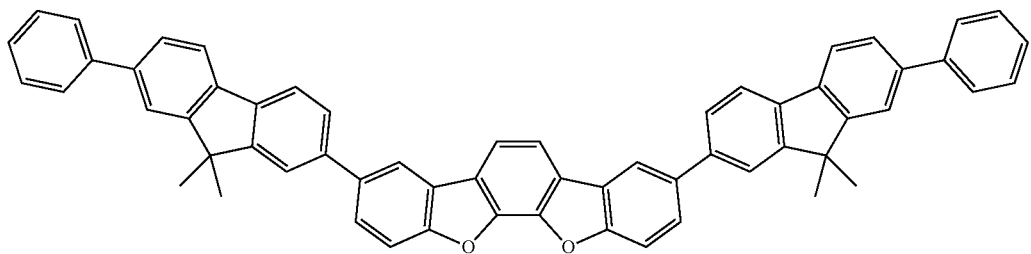

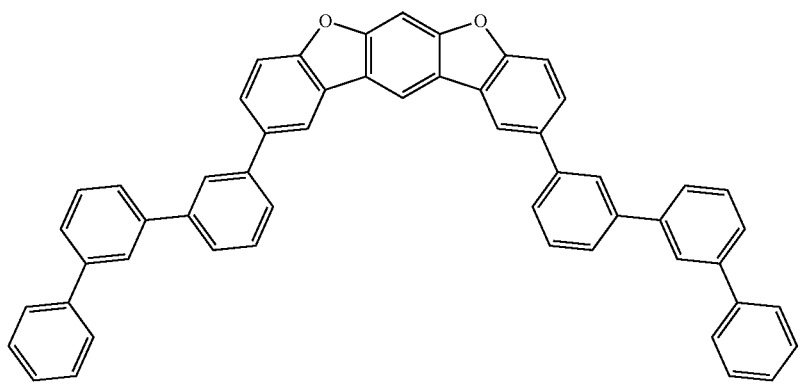
No. 296
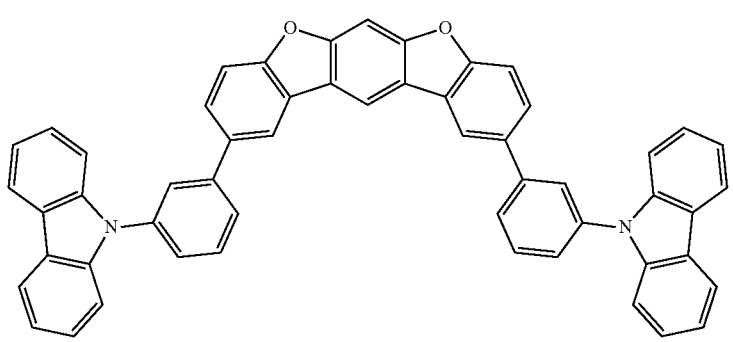
No. 297
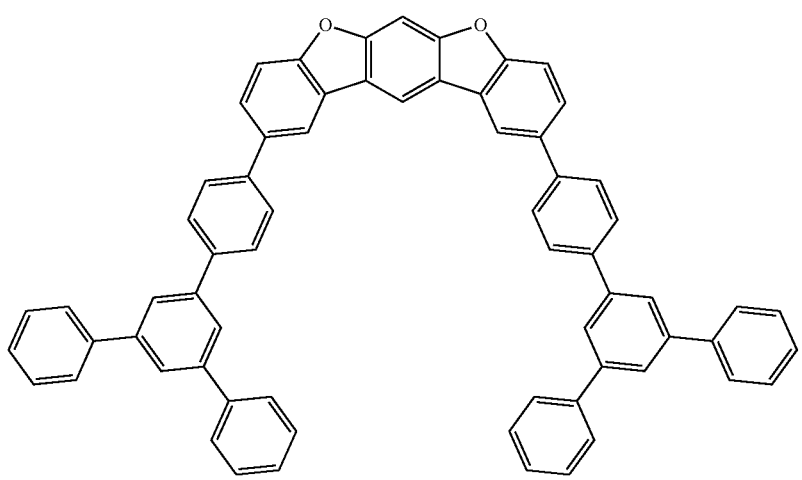
No. 298
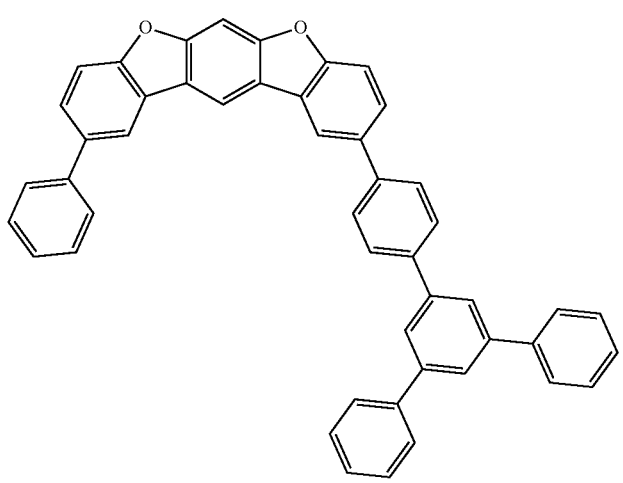
No. 299

-continued
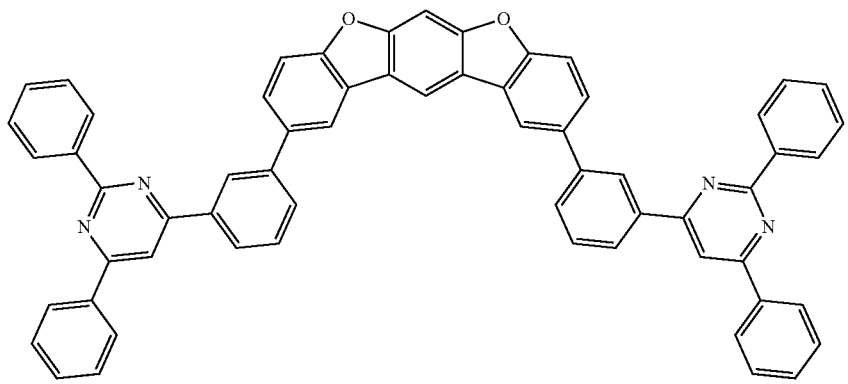
No. 300
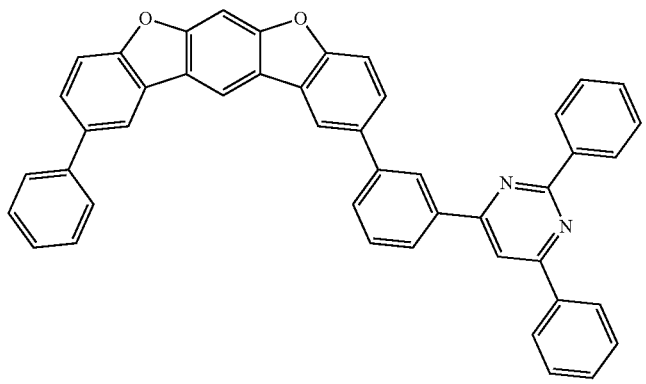
No. 301
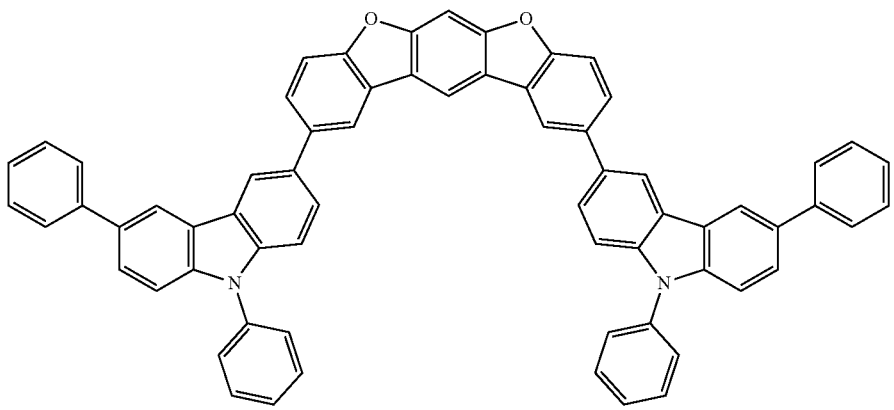
No. 302
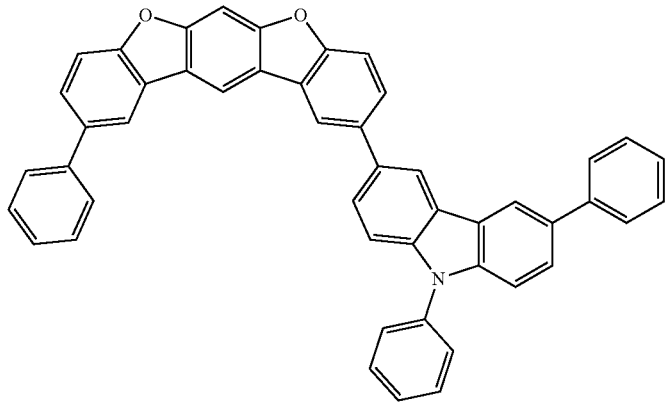
No. 303

-continued
No. 304
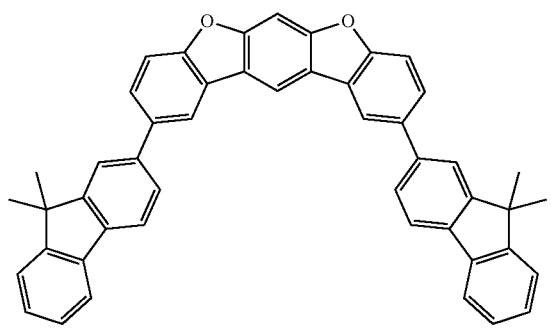
No. 305
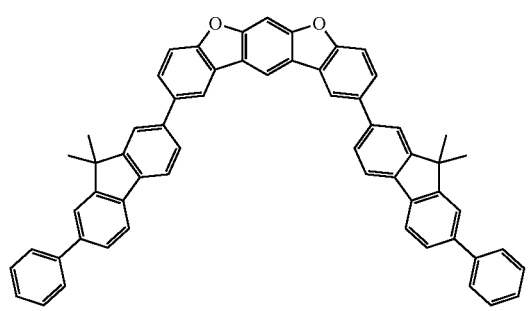
No. 306
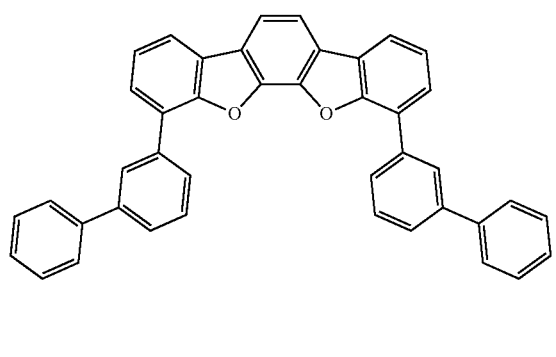
No. 307
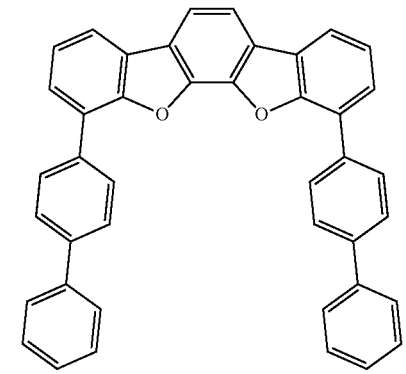
No. 308
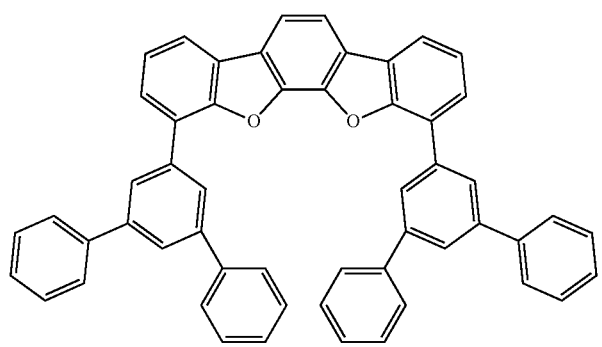
No. 309
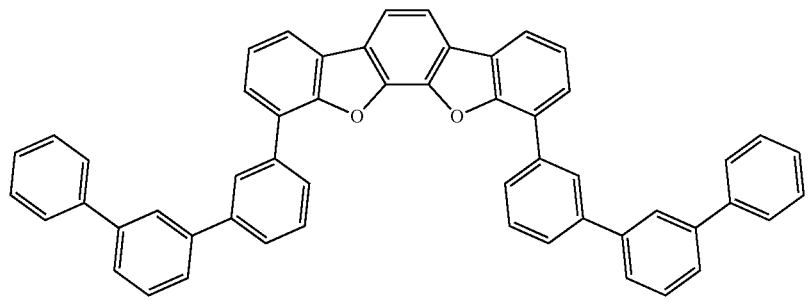

-continued
No. 310
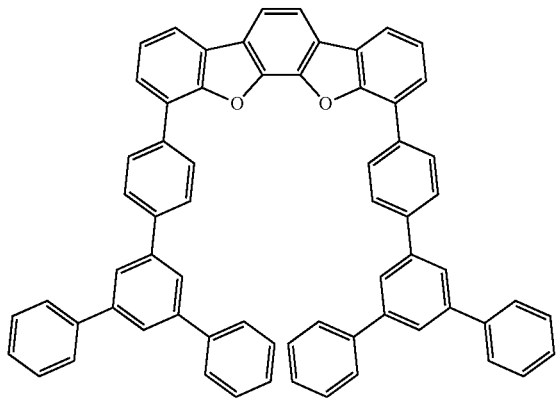
No. 311
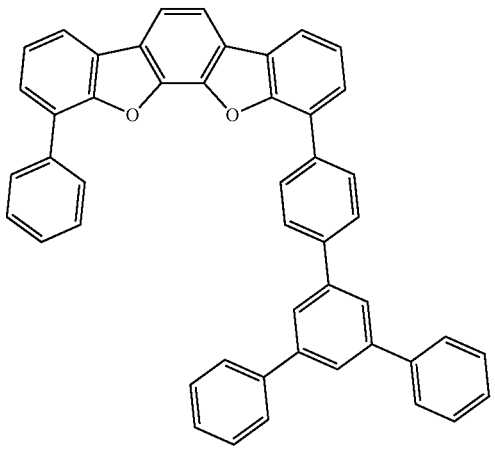
No. 312
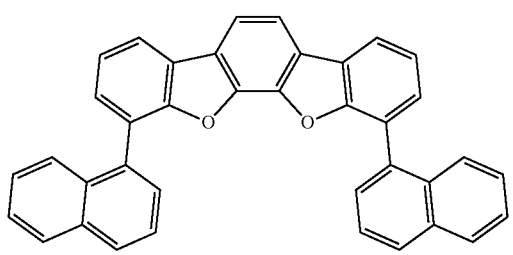
No. 313
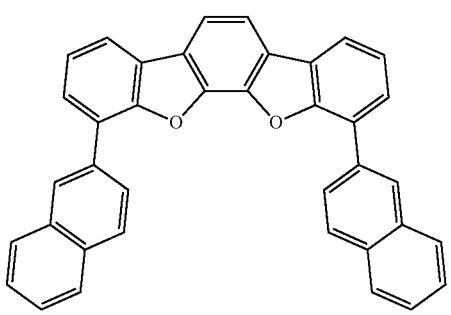
No. 314
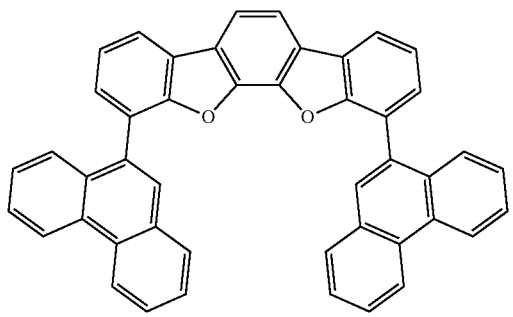
No. 315
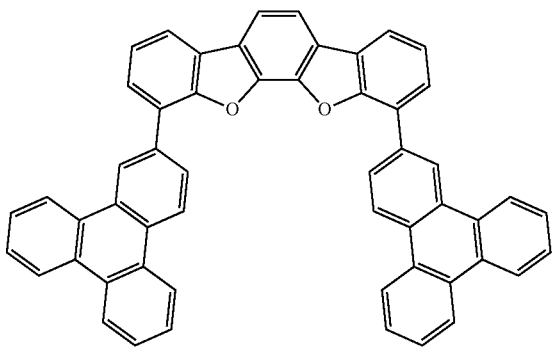
No. 316
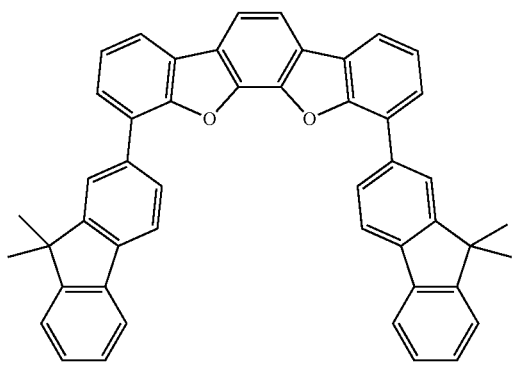
No. 317
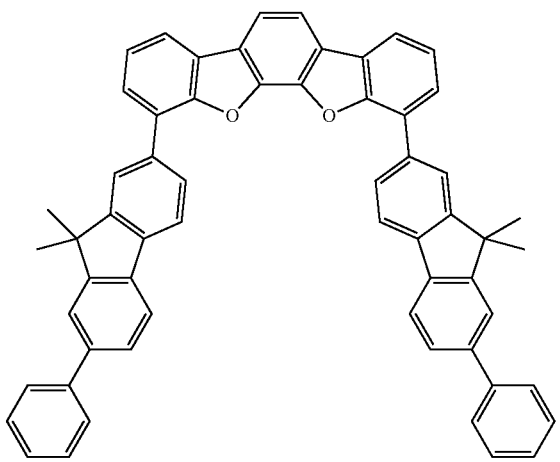

No. 318
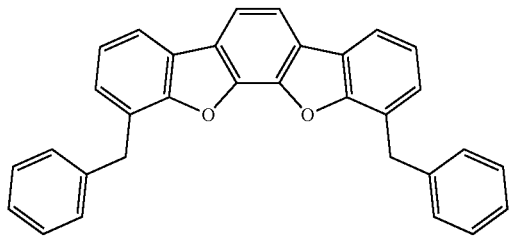
No. 319
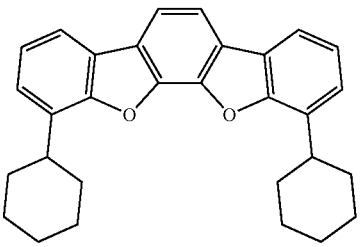
No. 320
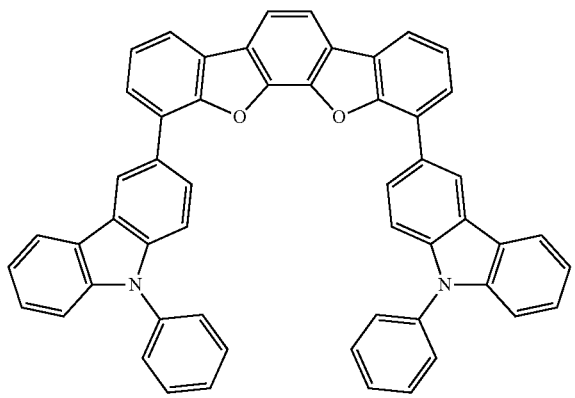
No. 321
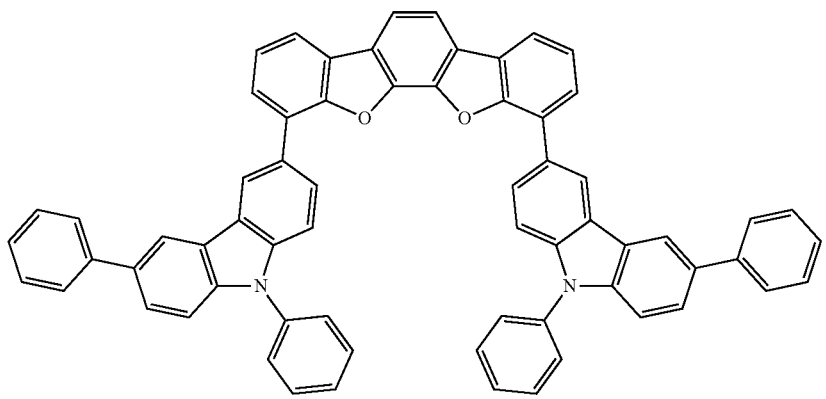
No. 322
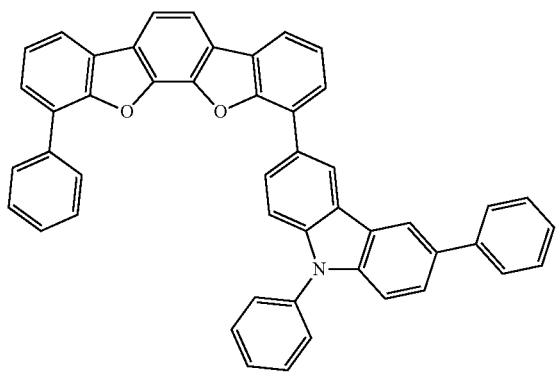
No. 323
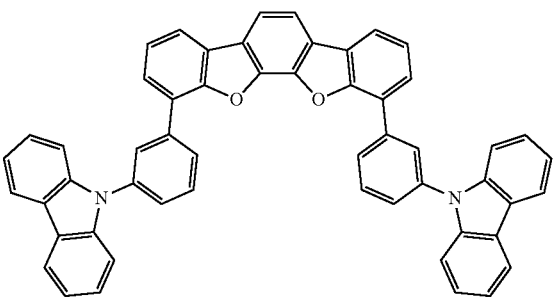

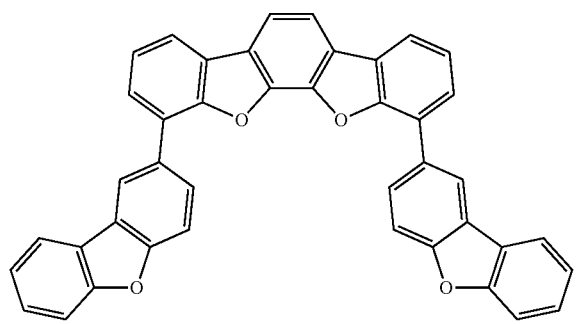
No. 324
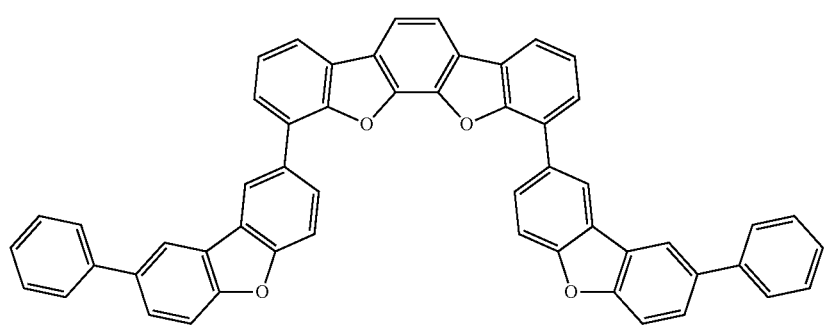
No. 325
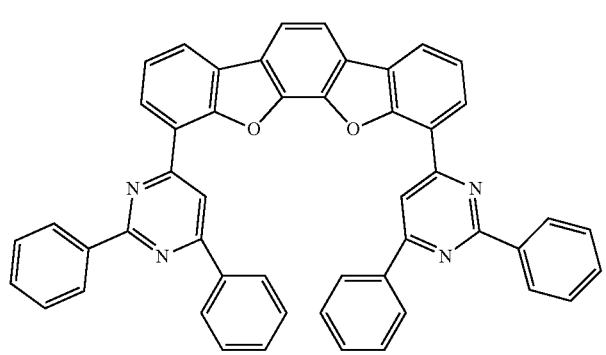
No. 326
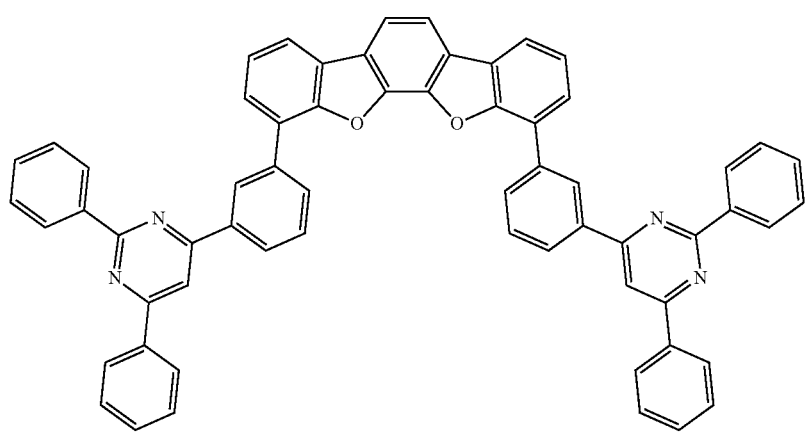
No. 327

-continued
No. 328
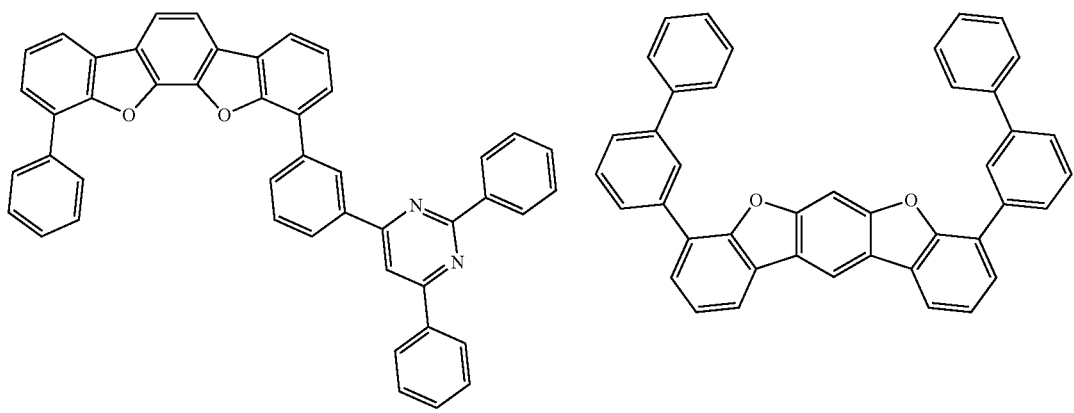
No. 329
No. 330
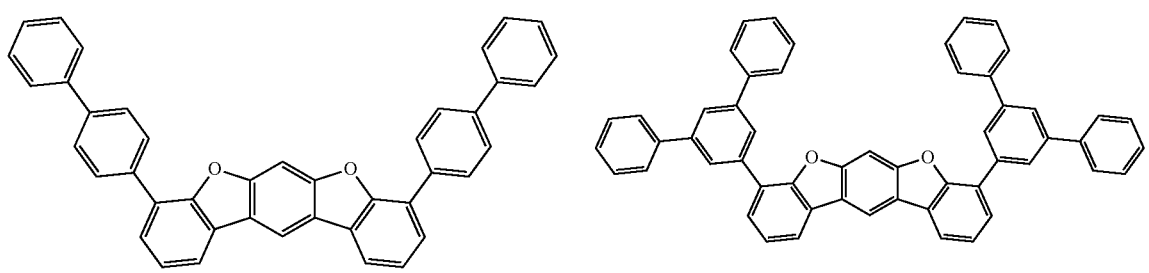
No. 331
No. 332
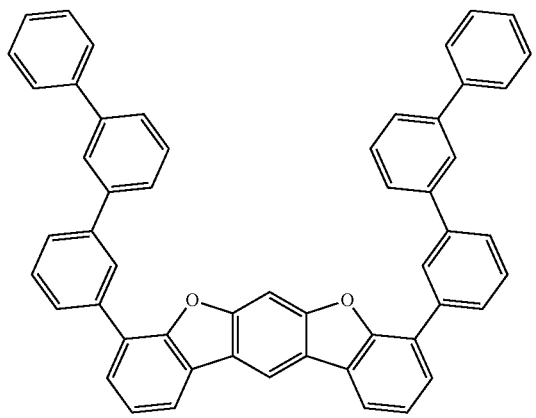
No. 333
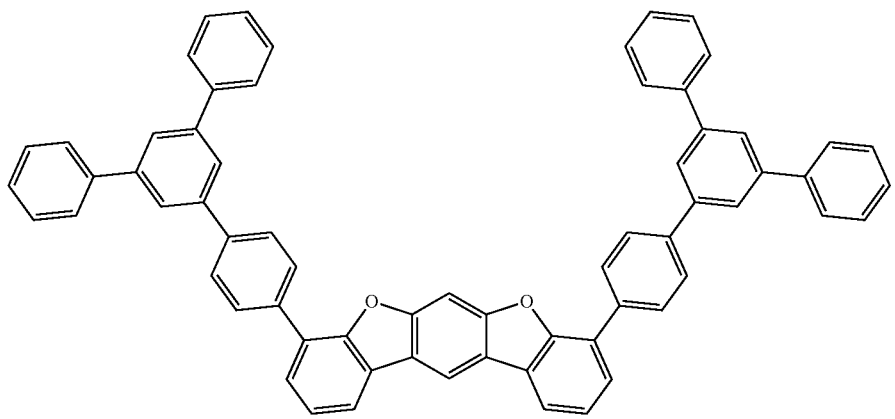

-continued
No. 334
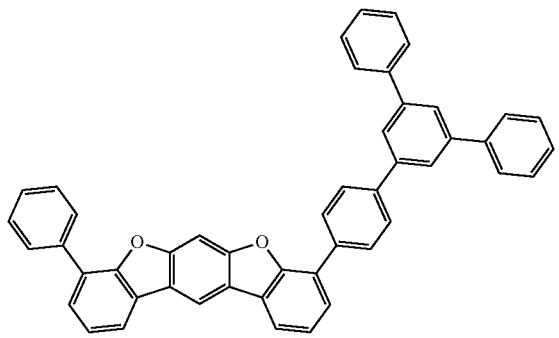
No. 335
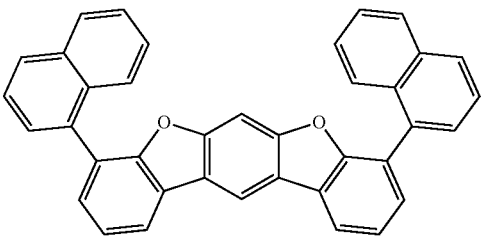
No. 336
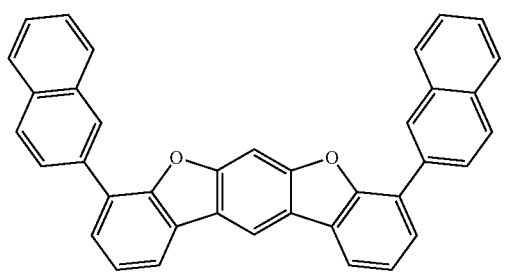
No. 337
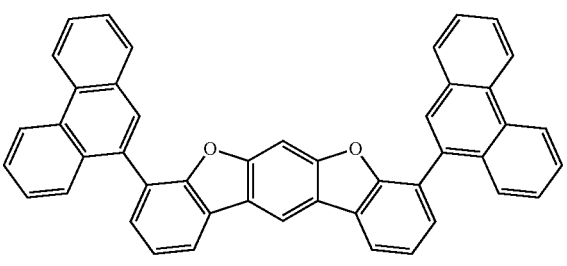
No. 338
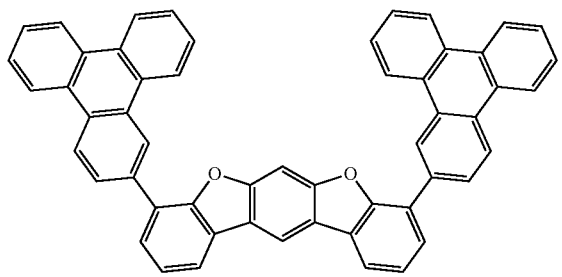
No. 339
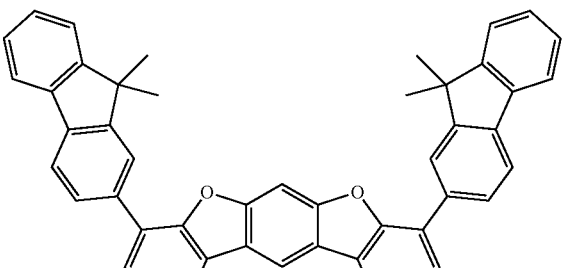
No. 340
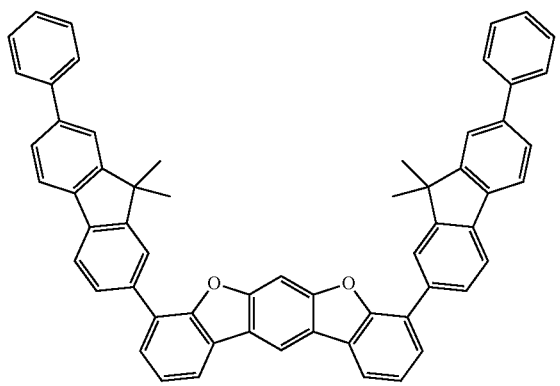
No. 341
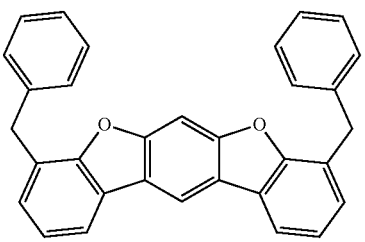
No. 342
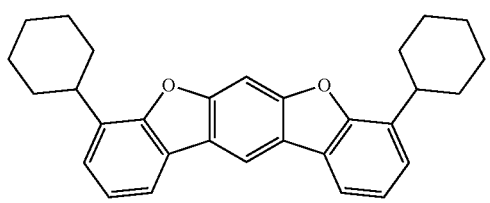
No. 343
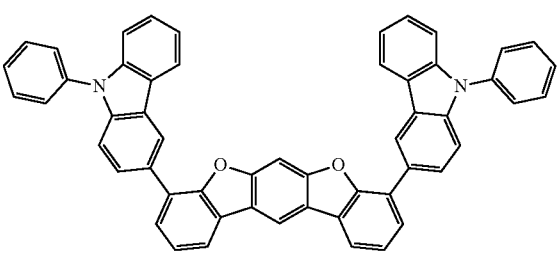

No. 344
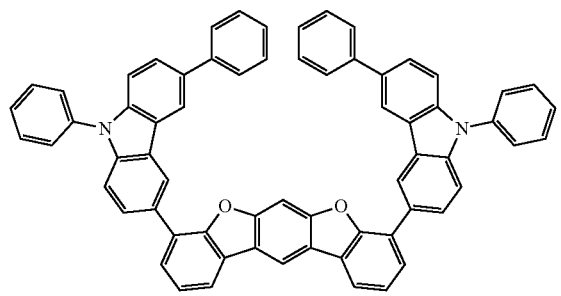
No. 345
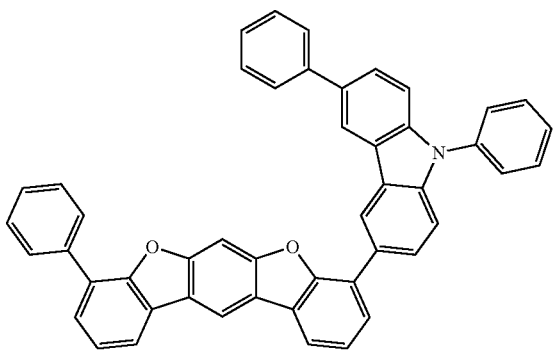
No. 346
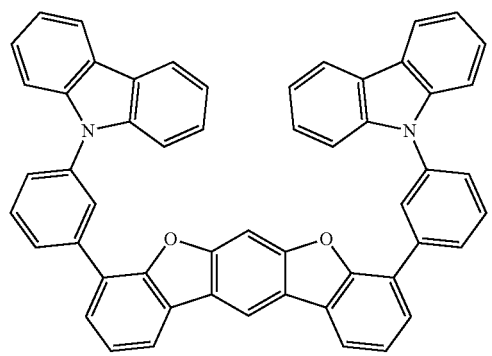
No. 347
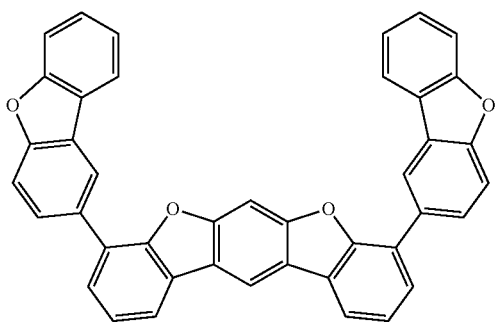
No. 348
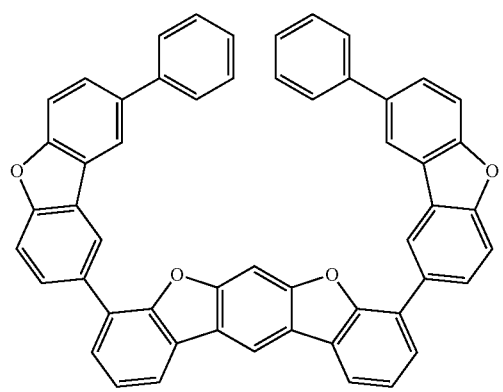
No. 349
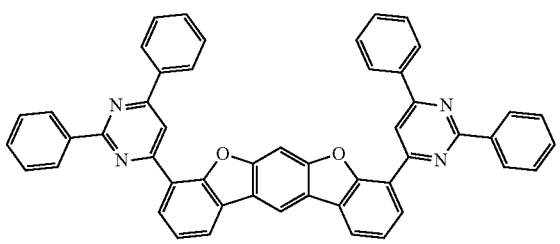
No. 350
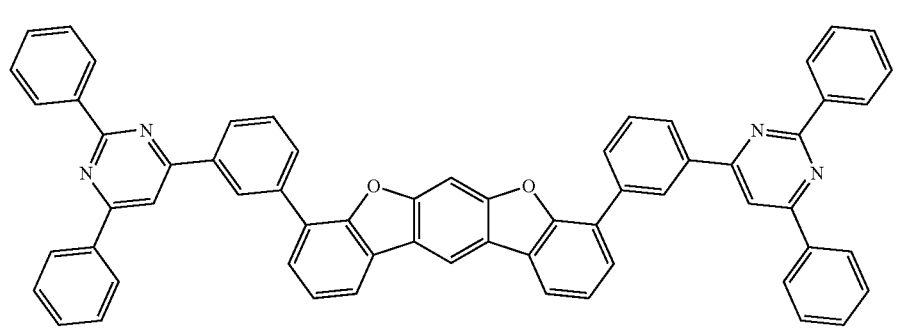

-continued
No. 351
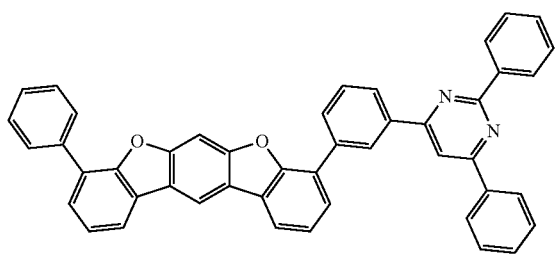
No. 352
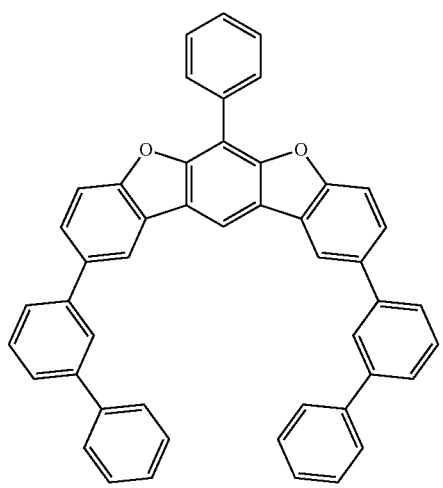
No. 353
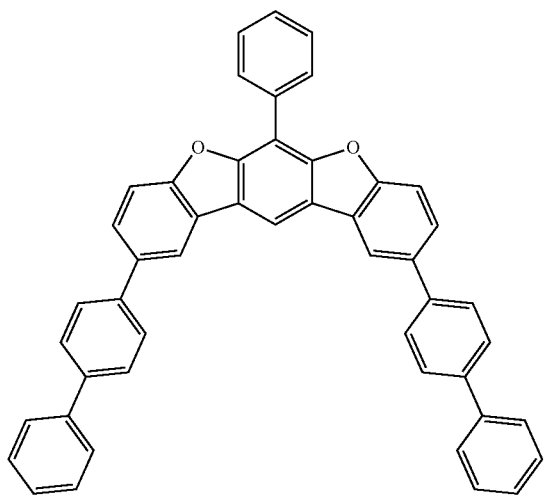
No. 354
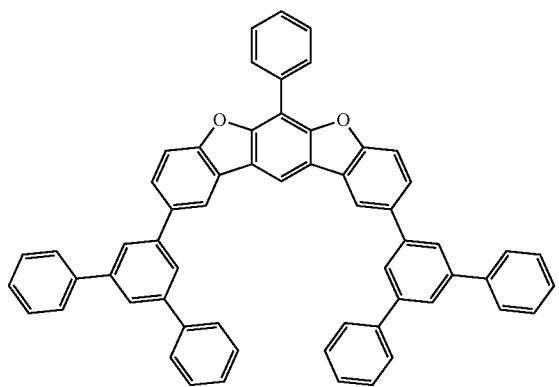
No. 355
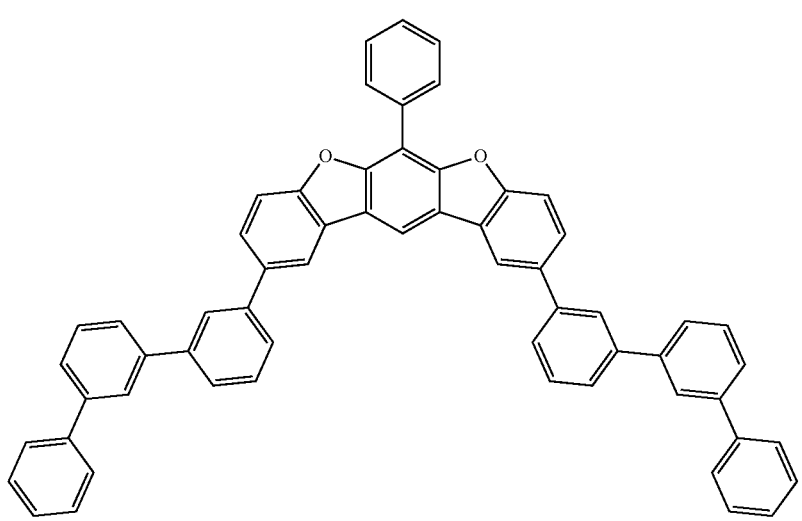

-continued
No. 356
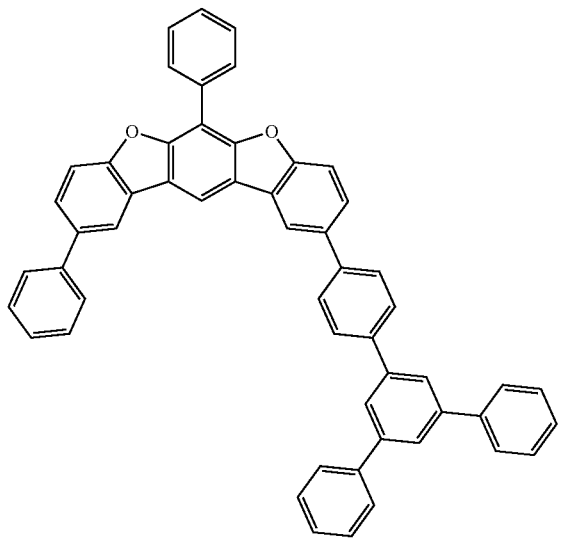
No. 357
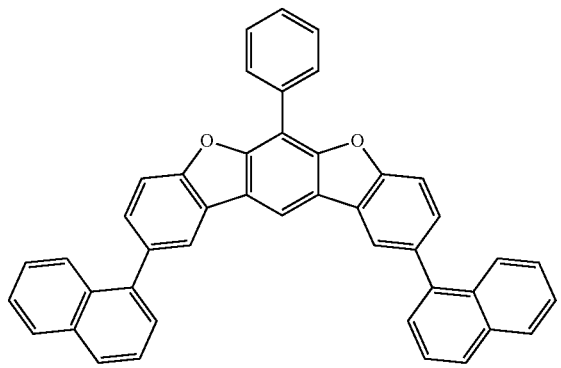
No. 358
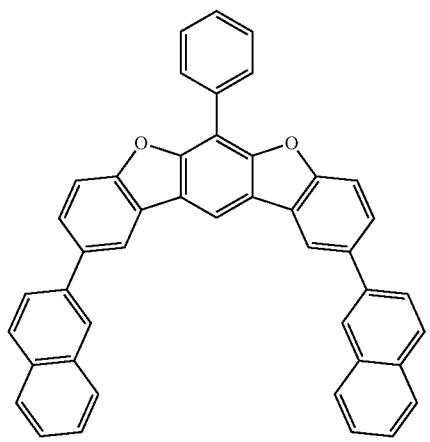
No. 359
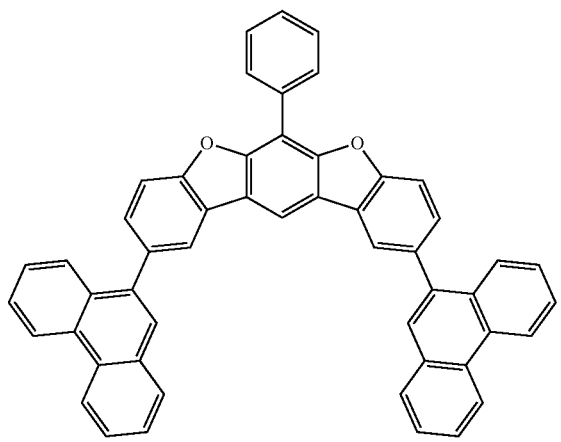
No. 360
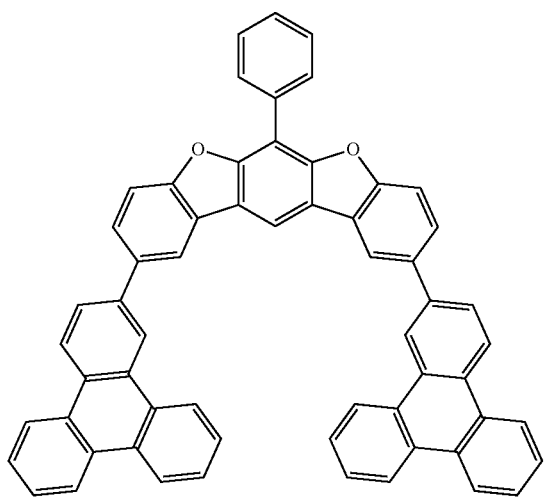
No. 361
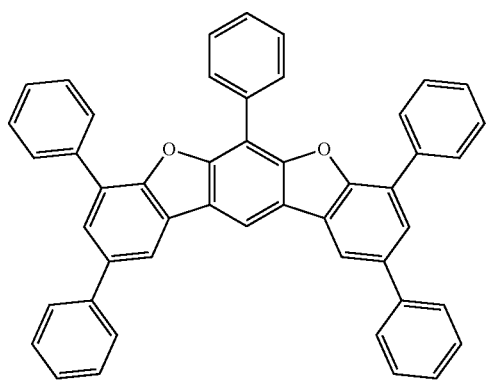

-continued
No. 362
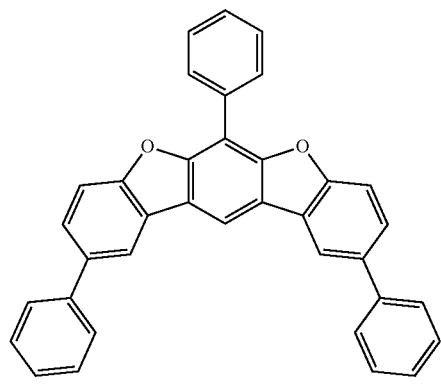
No. 363
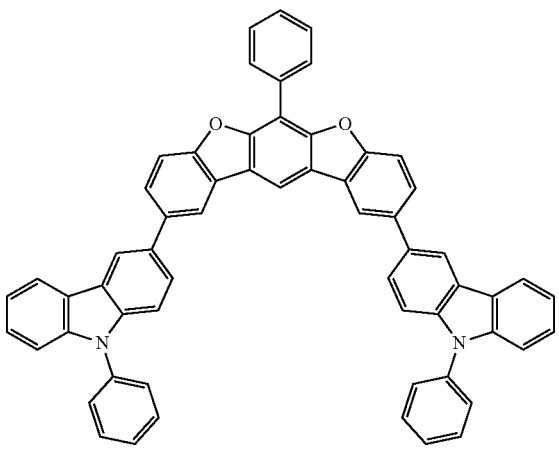
No. 364
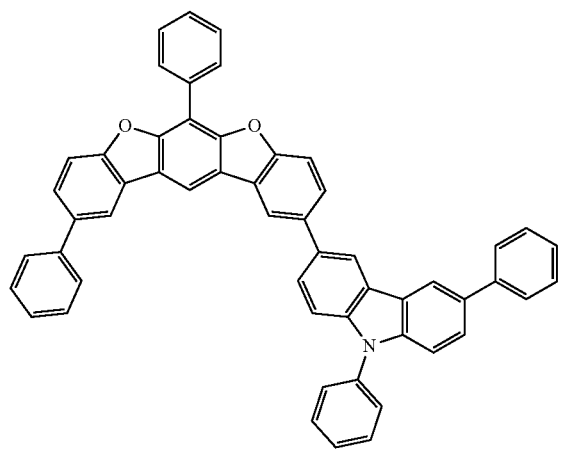
No. 365
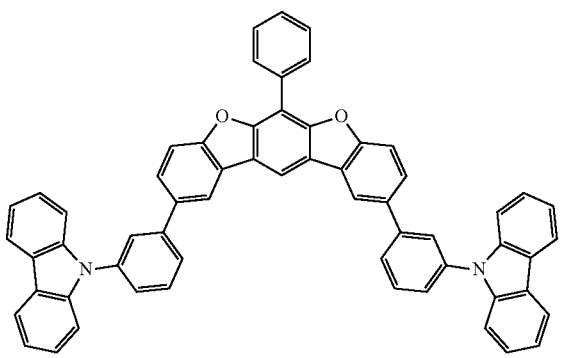
No. 366
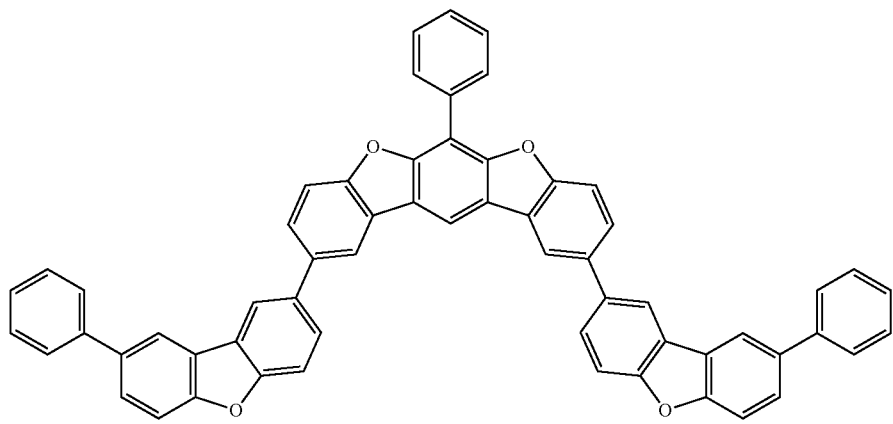

-continued
No. 367
No. 368
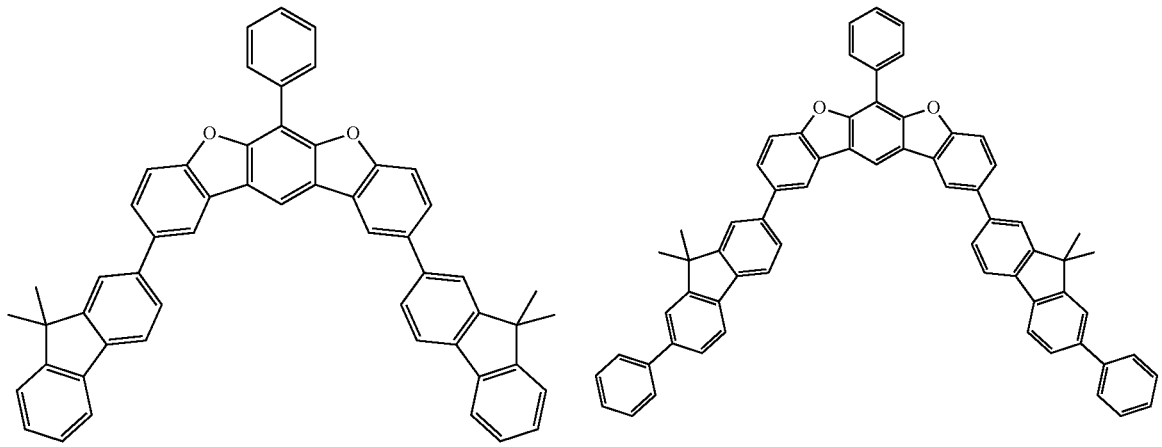
No. 369
No. 370
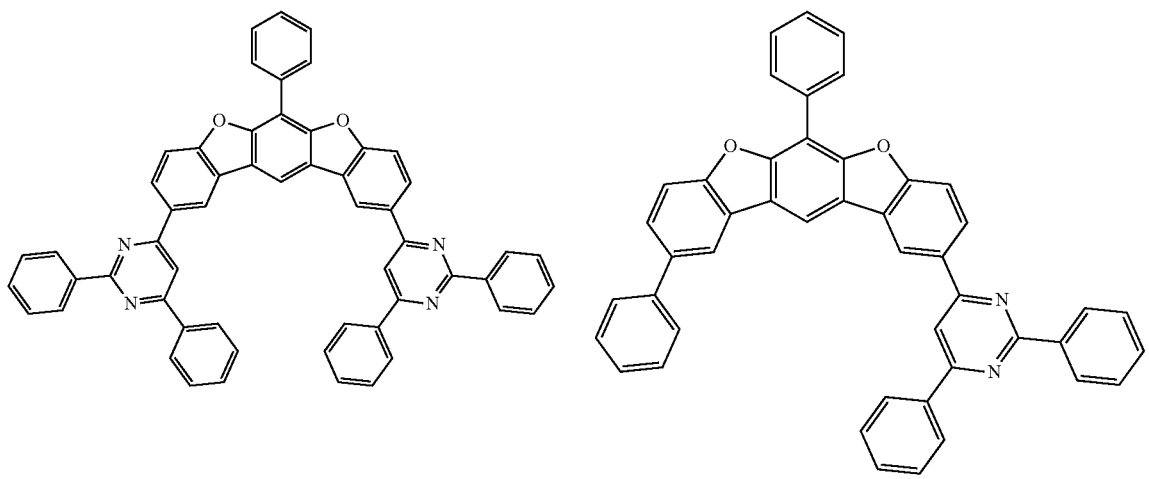
No. 371
No. 372
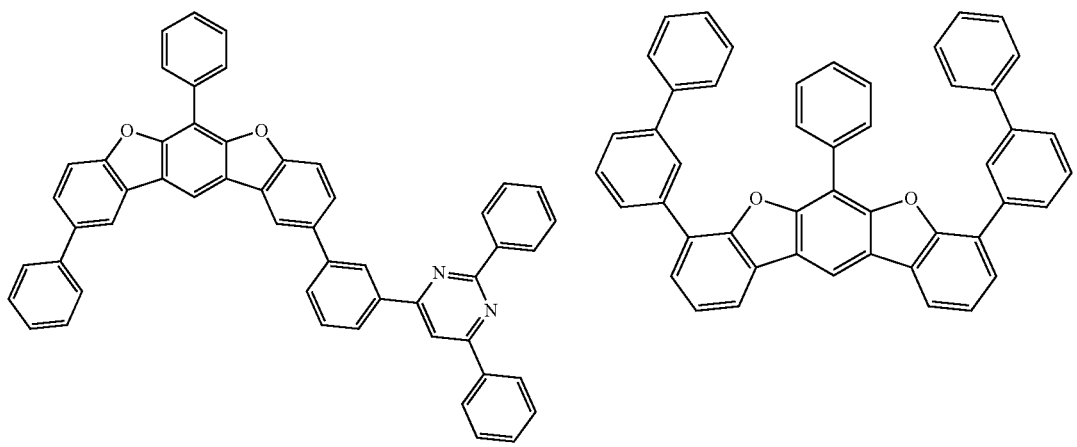

-continued
No. 373
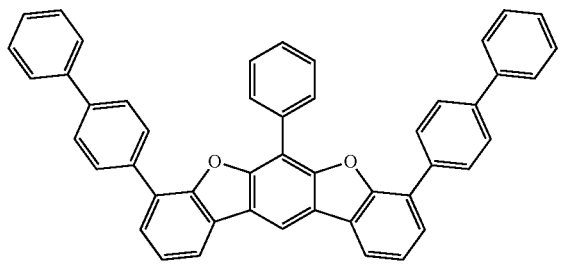
No. 374
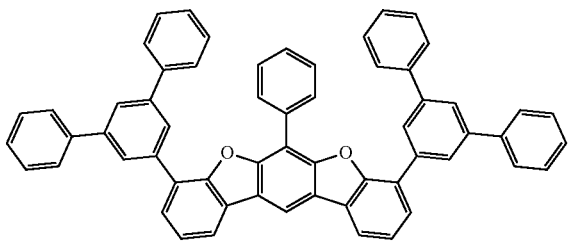
No. 375
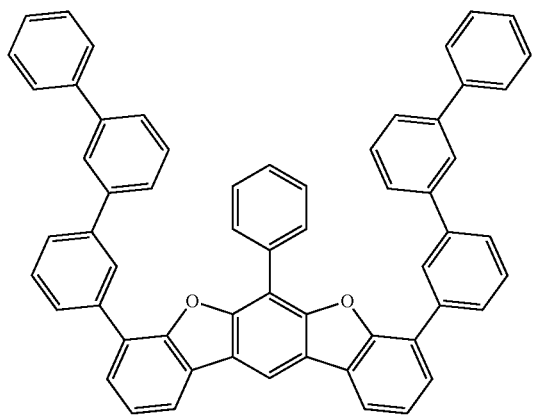
No. 376
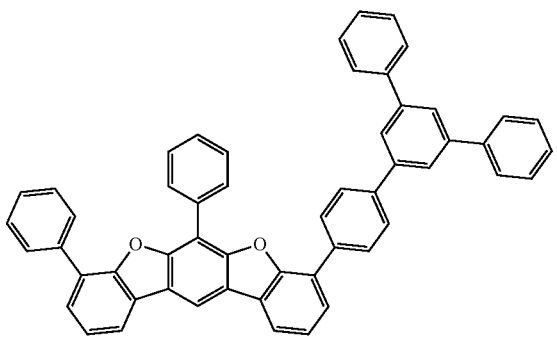
No. 377
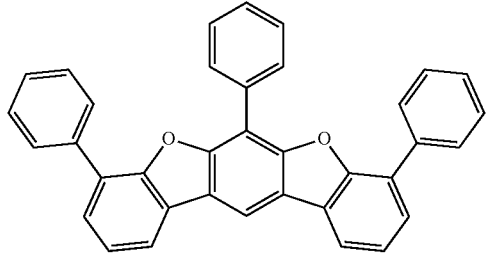
No. 378
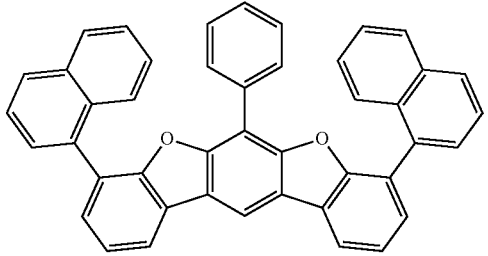
No. 379
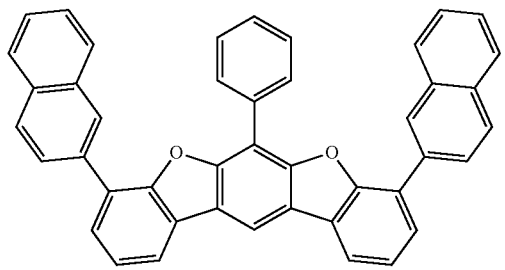
No. 380
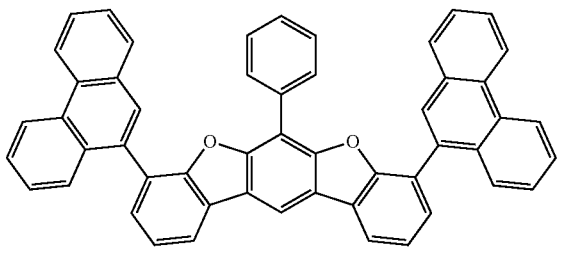
No. 381
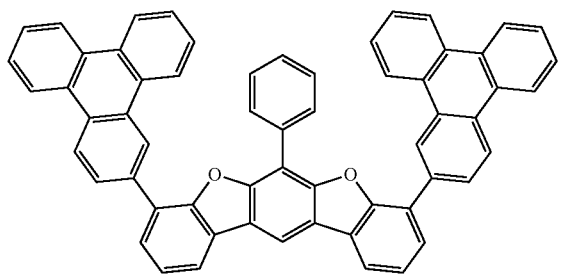
No. 382
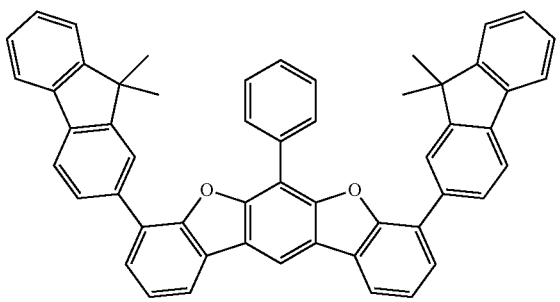

-continued
No. 383
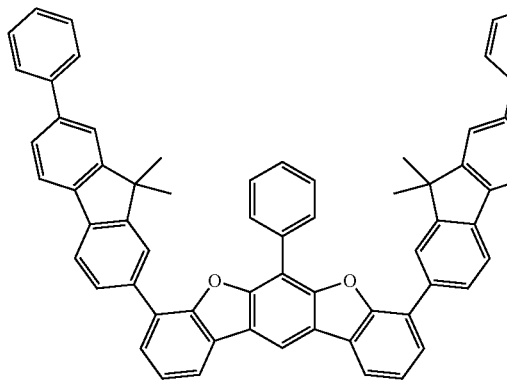
No. 384
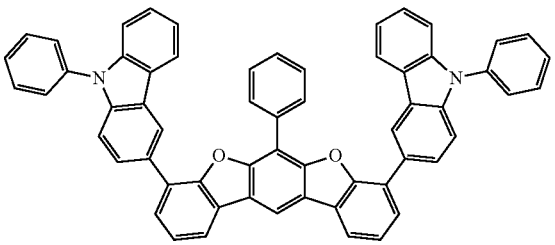
No. 385
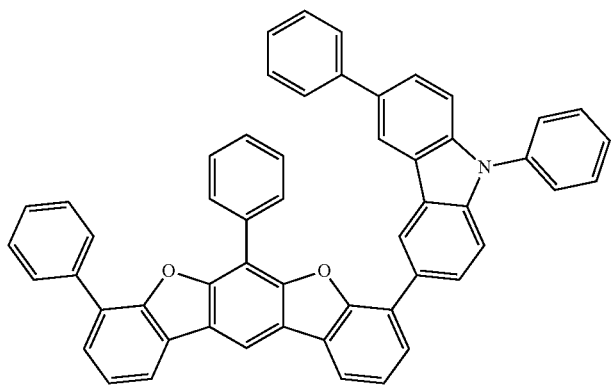
No. 386
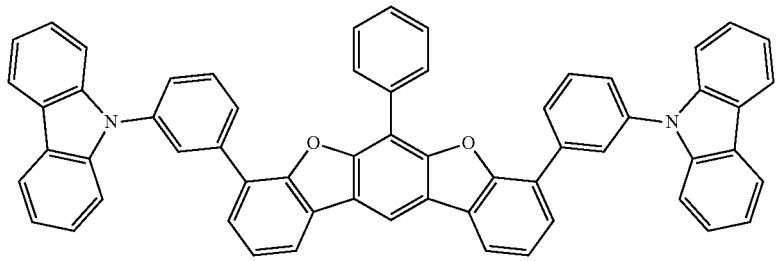
No. 387
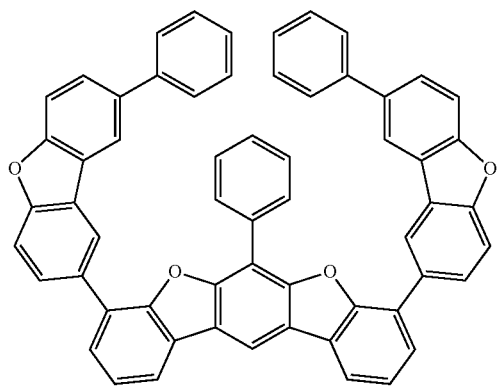
No. 388
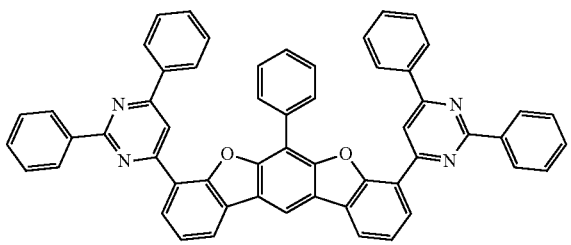

-continued
No. 389
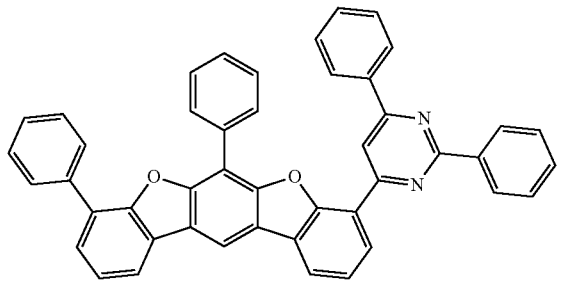
No. 390
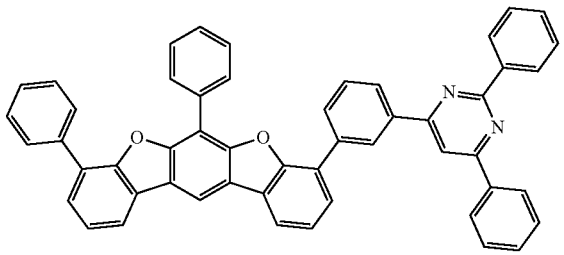
No. 391
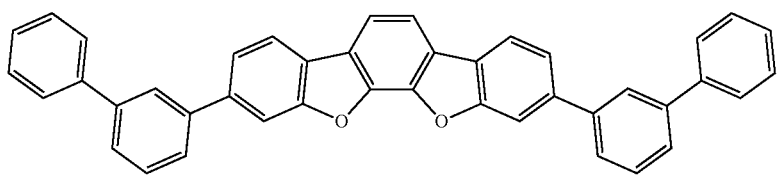
No. 392
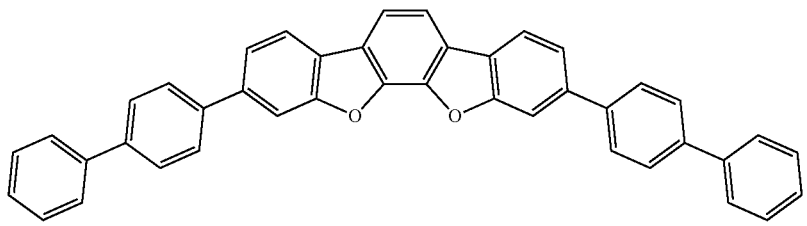
No. 393
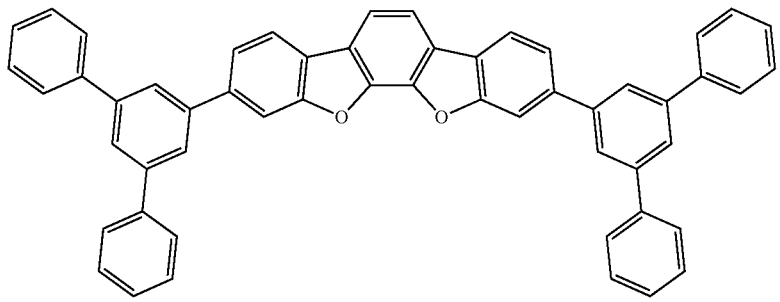
No. 394
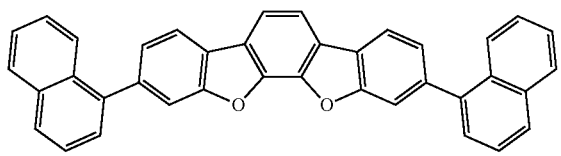
No. 395
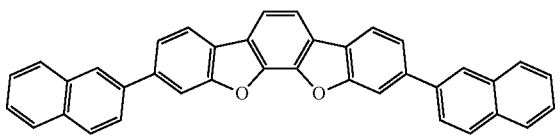
No. 396
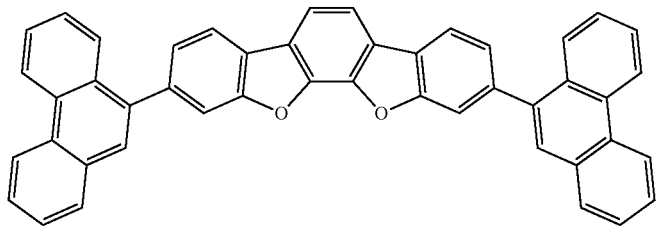

-continued
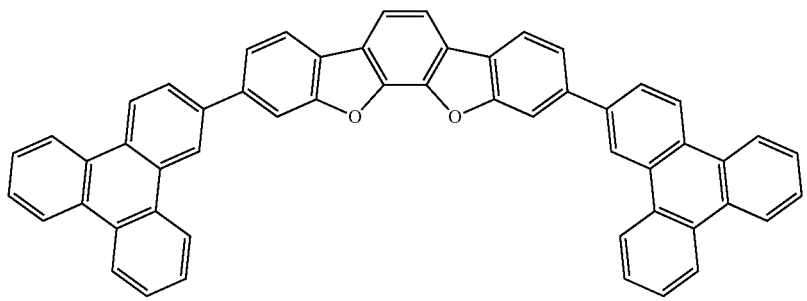
No. 397
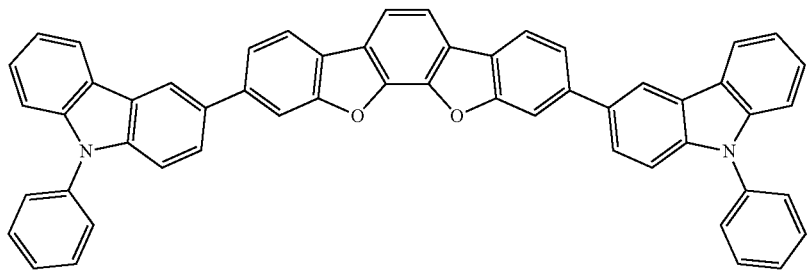
No. 398
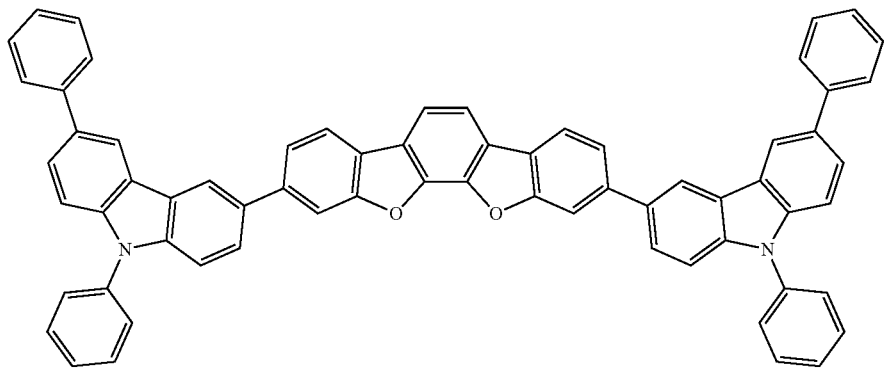
No. 399
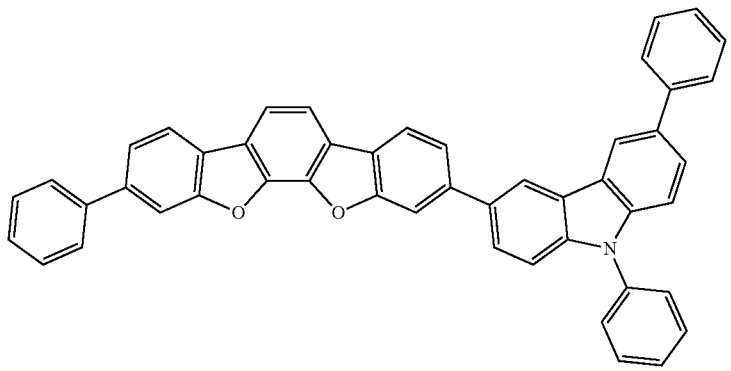
No. 400
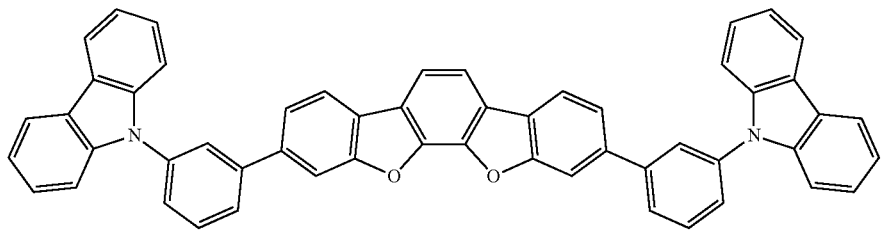
No. 401

No. 402
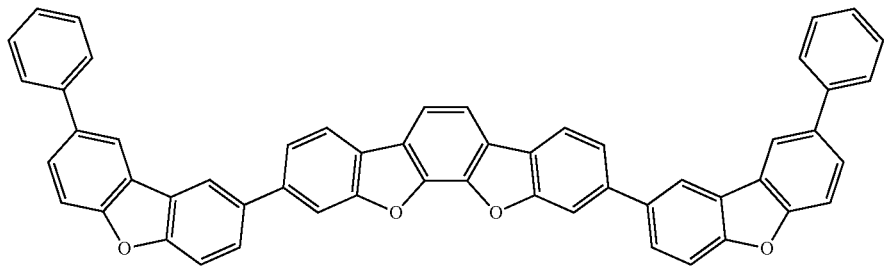
No. 403
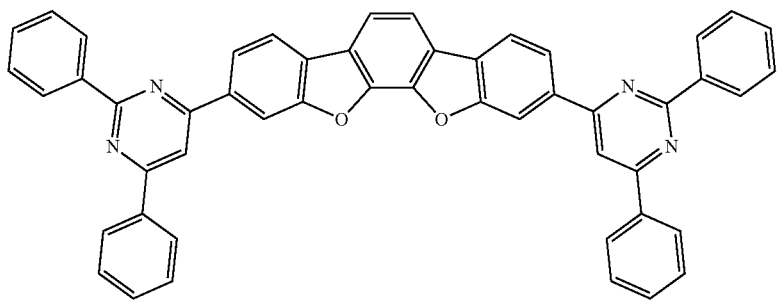
No. 404
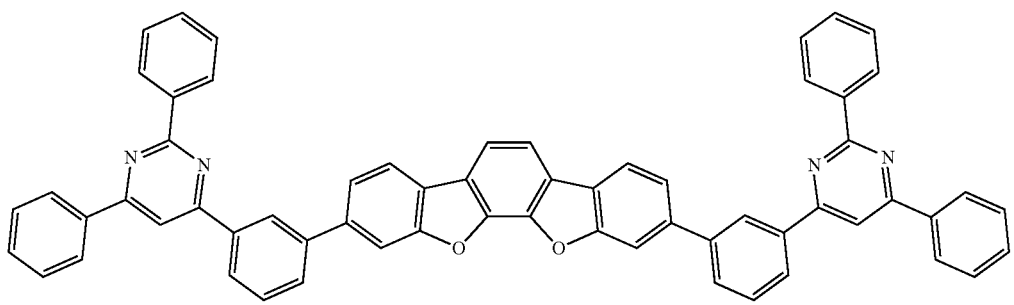
No. 405
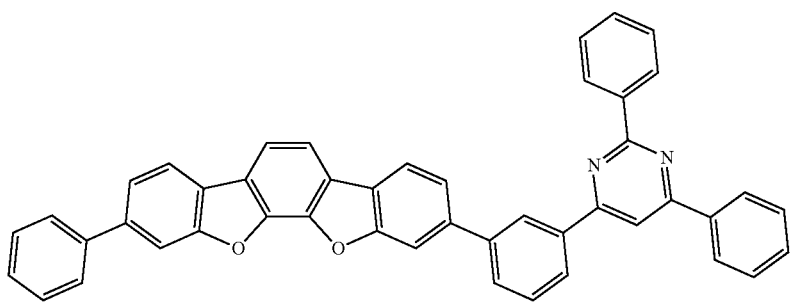
No. 406
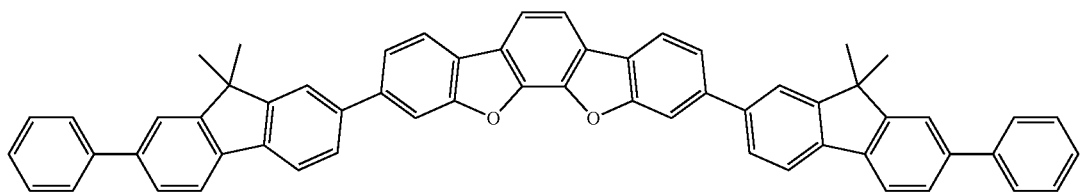
No. 407
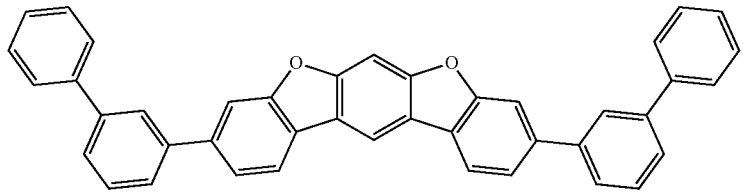

No. 408
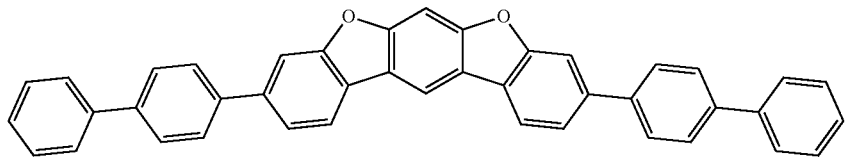
No. 409
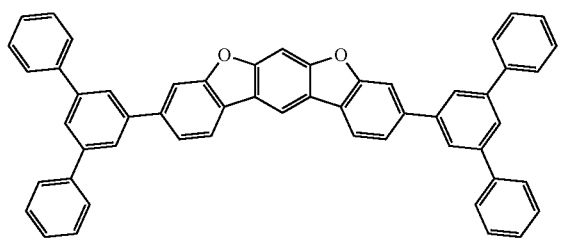
No. 410
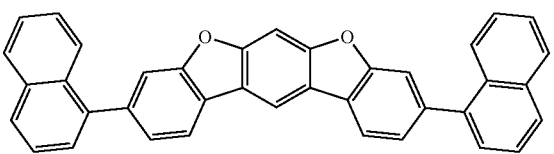
No. 411
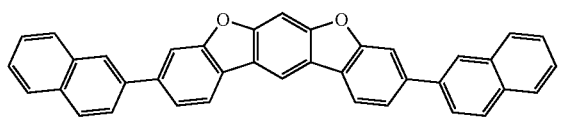
No. 412
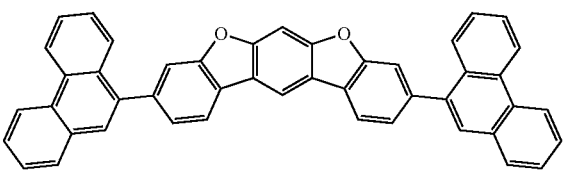
No. 413
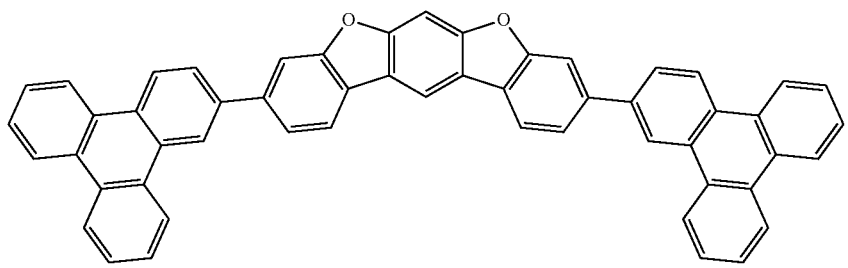
No. 414
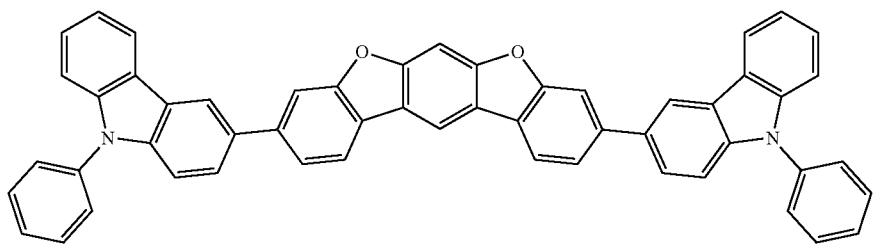
No. 415
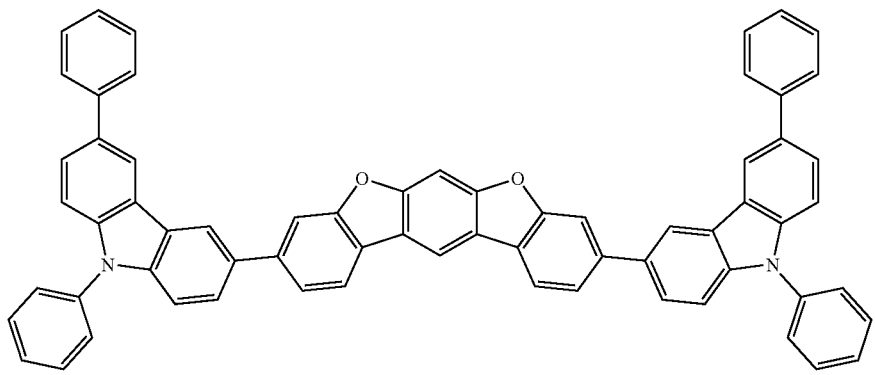

No. 416
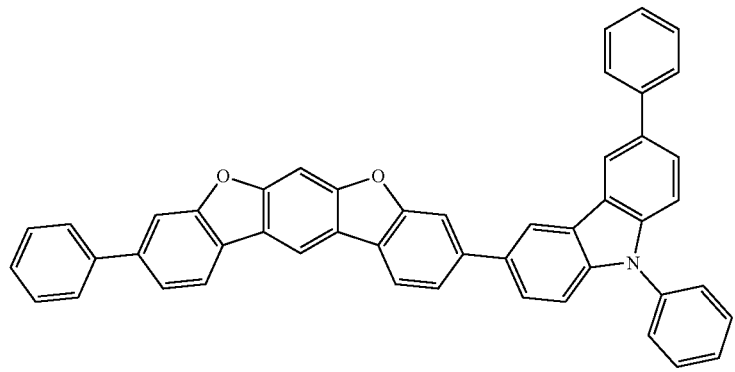
No. 417
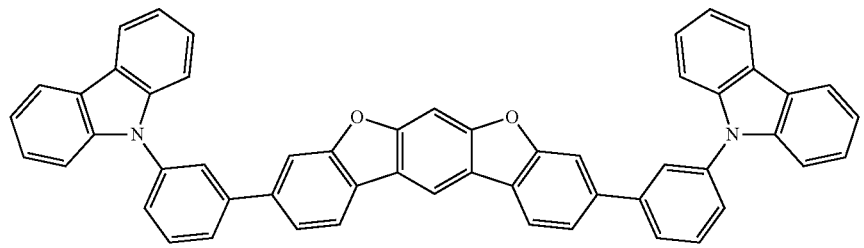
No. 418
No. 419
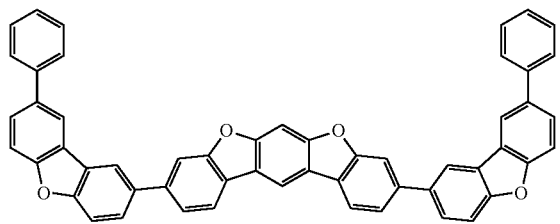 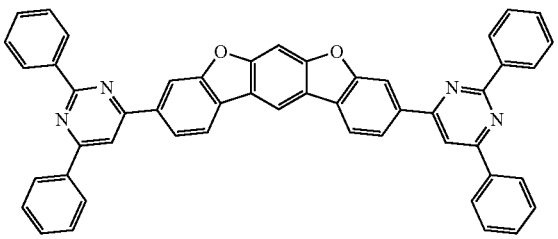
No. 420
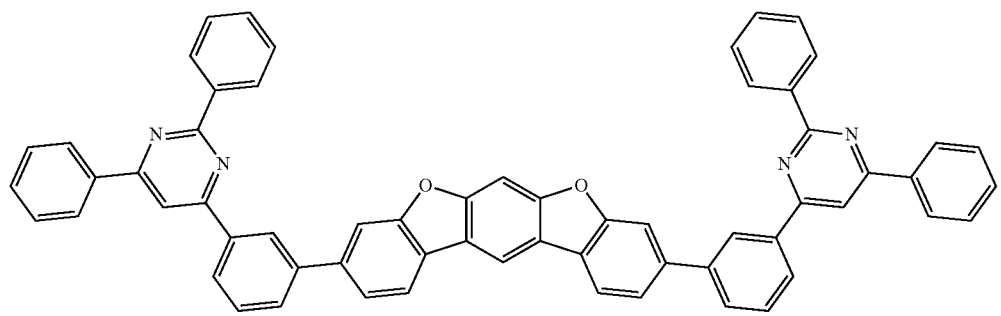
No. 421
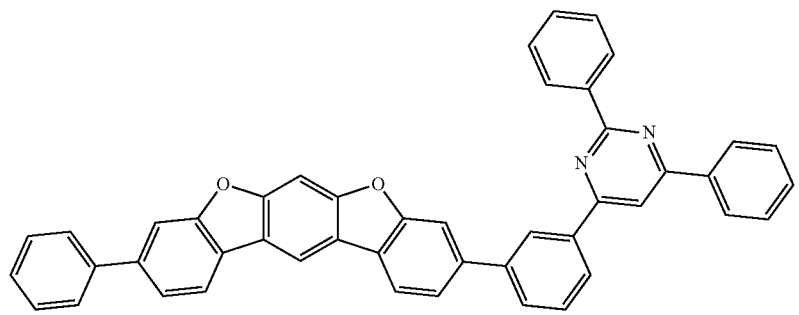

-continued
No. 422
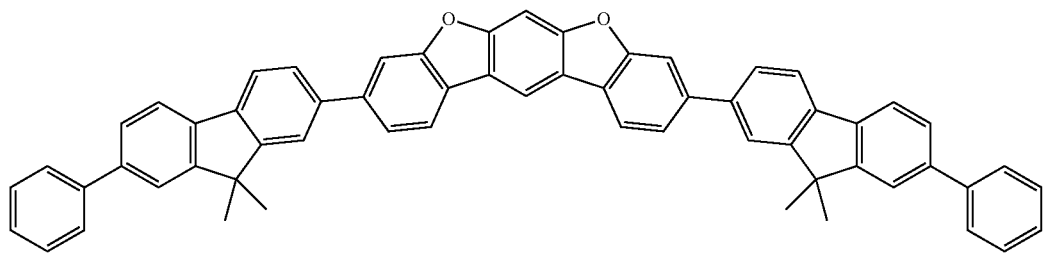
No. 423
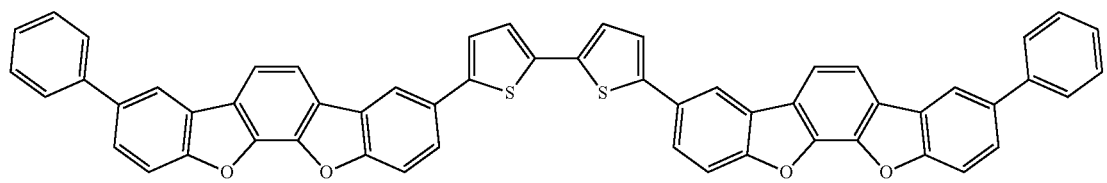
No. 424
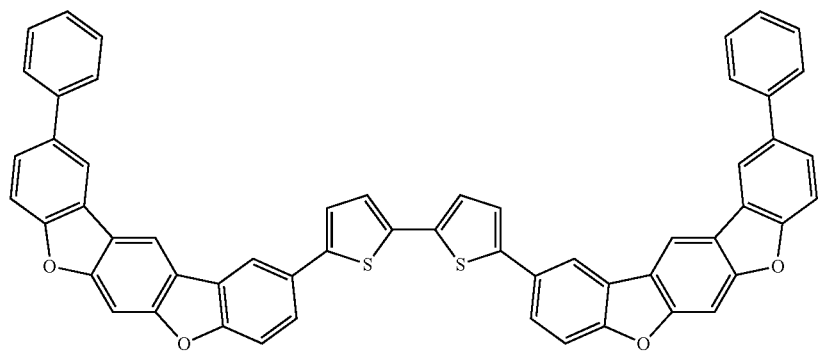
No. 425
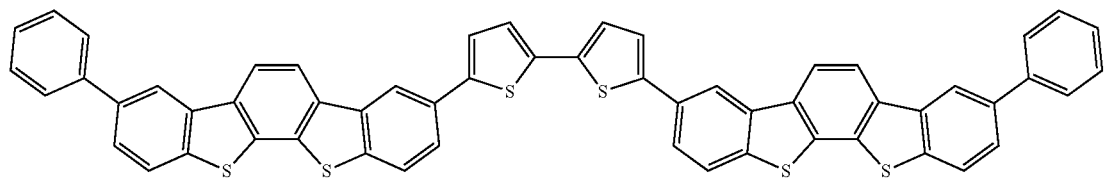
No. 426
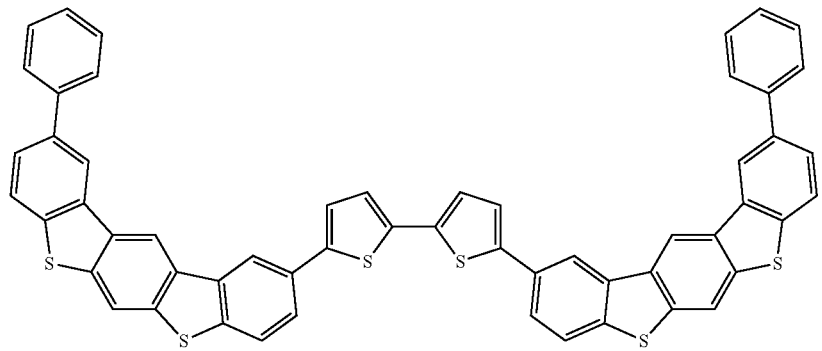
No. 427
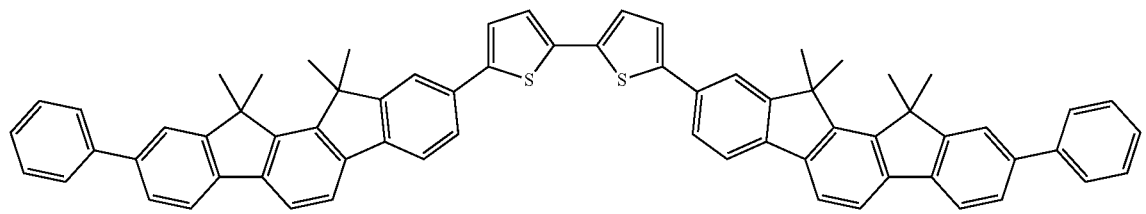

-continued
No. 428
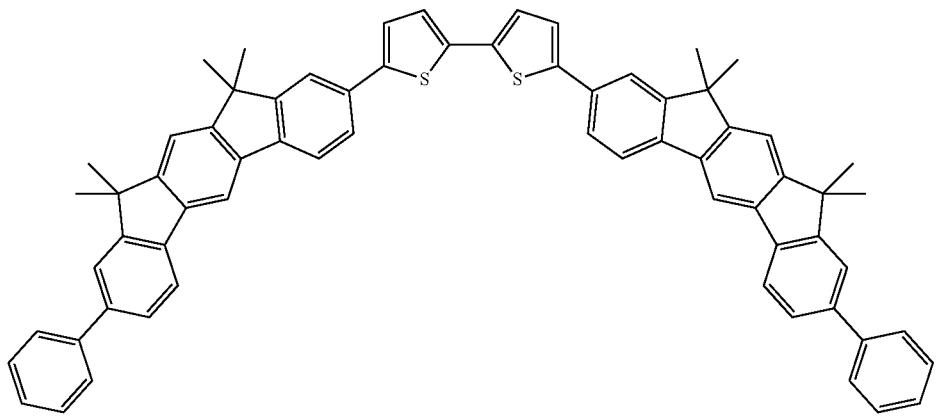
No. 429
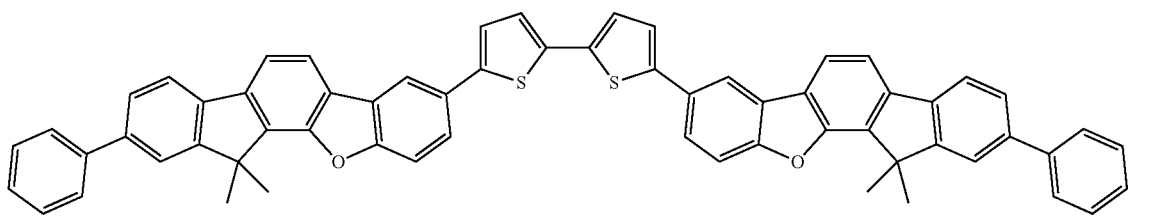
No. 430
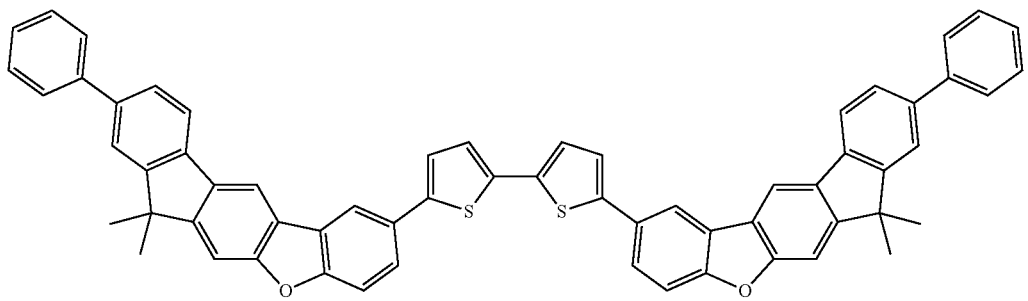
No. 431
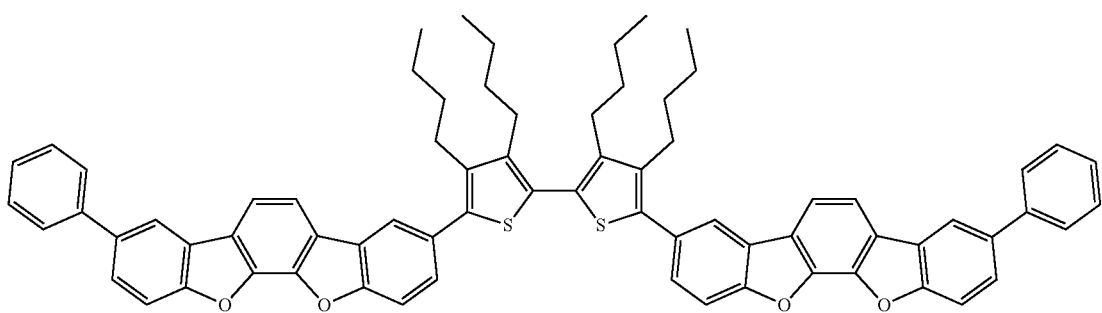
No. 432
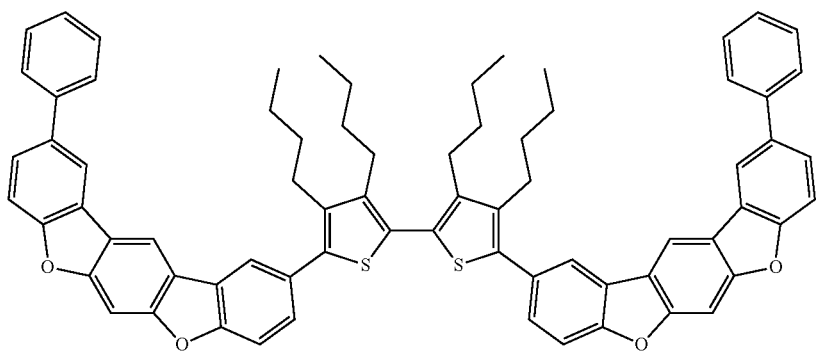

No. 433
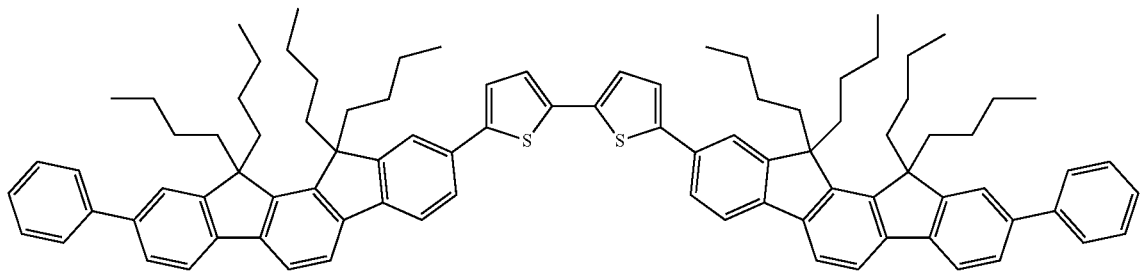
No. 434
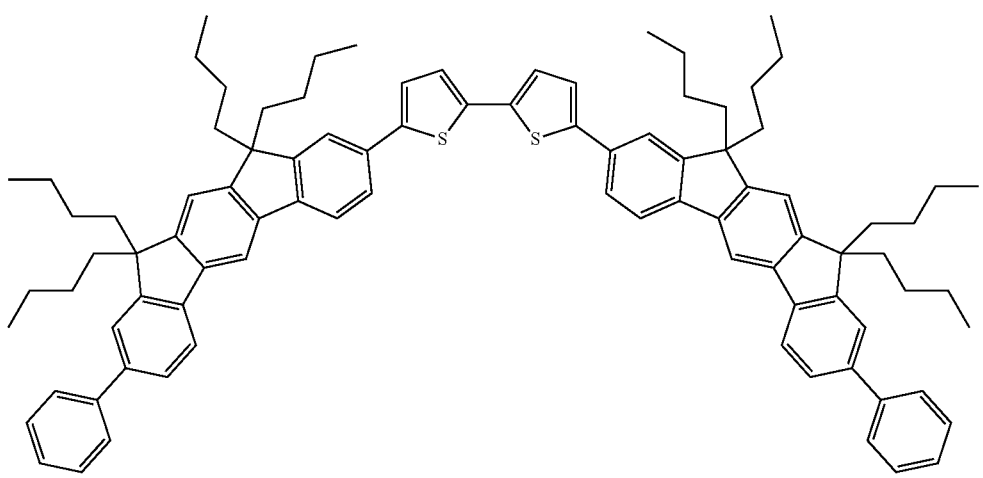
No. 435
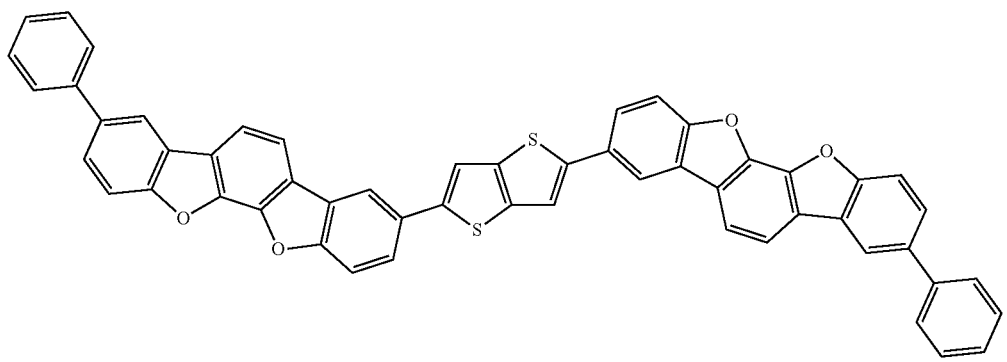

No. 436
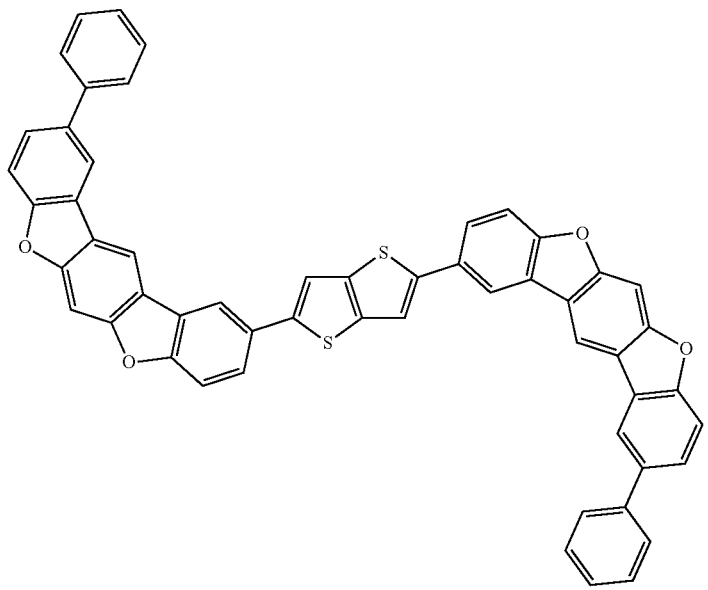
No. 437
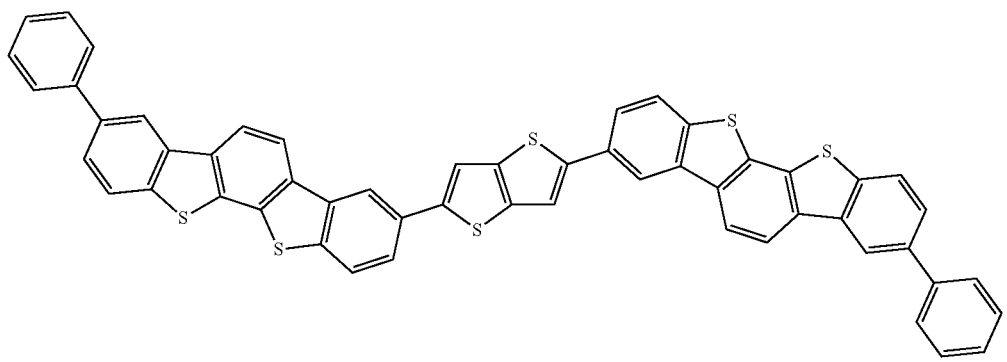
No. 438
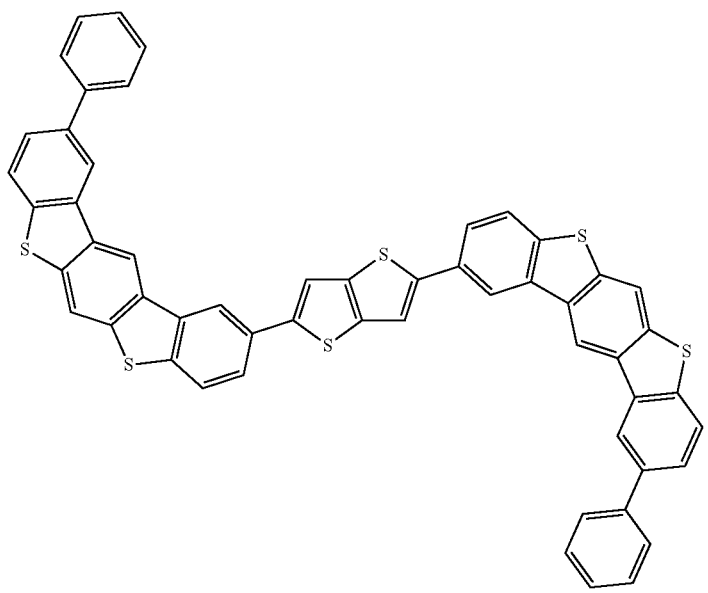

No. 439
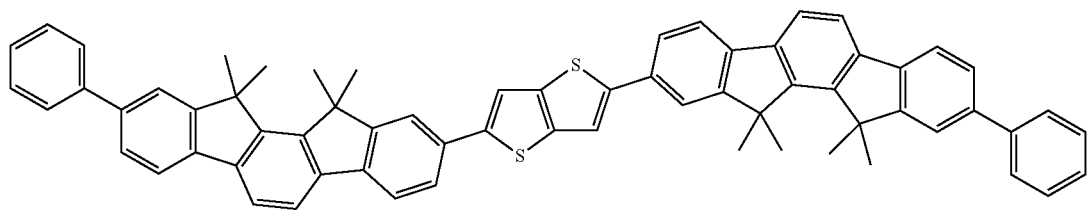
No. 440
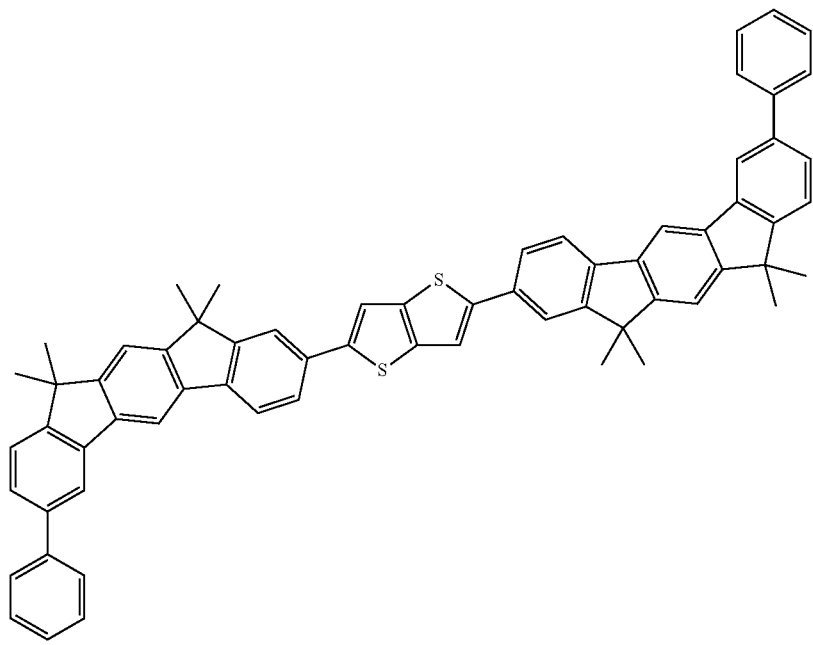
No. 441
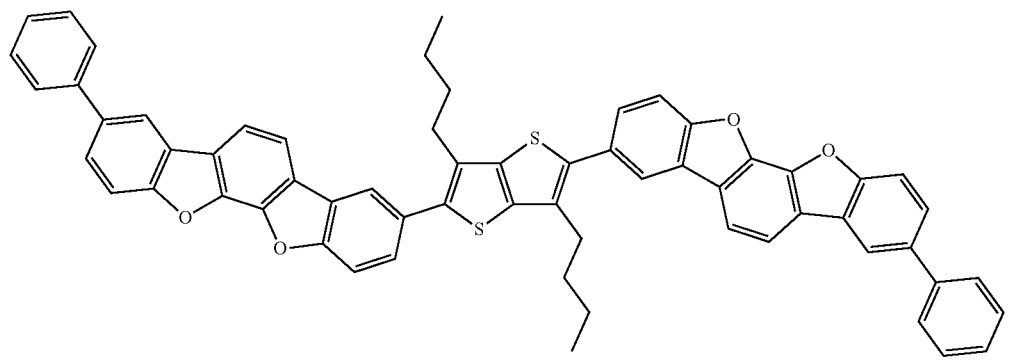

No. 442
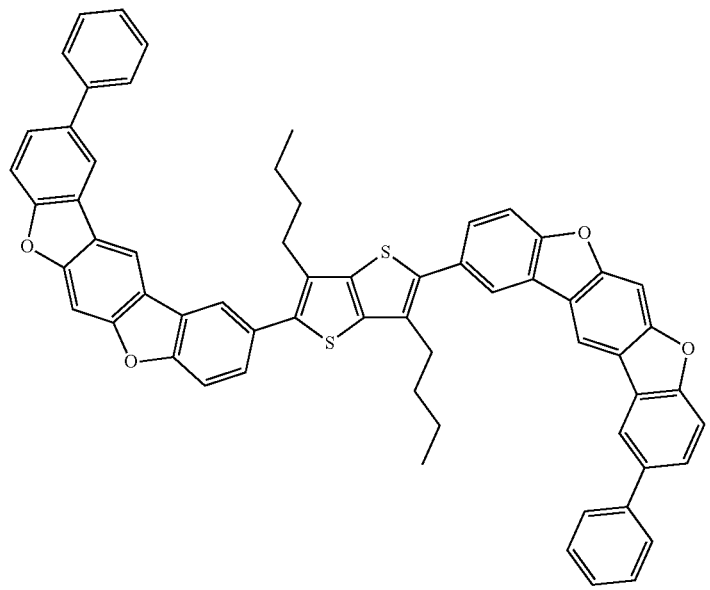
No. 443
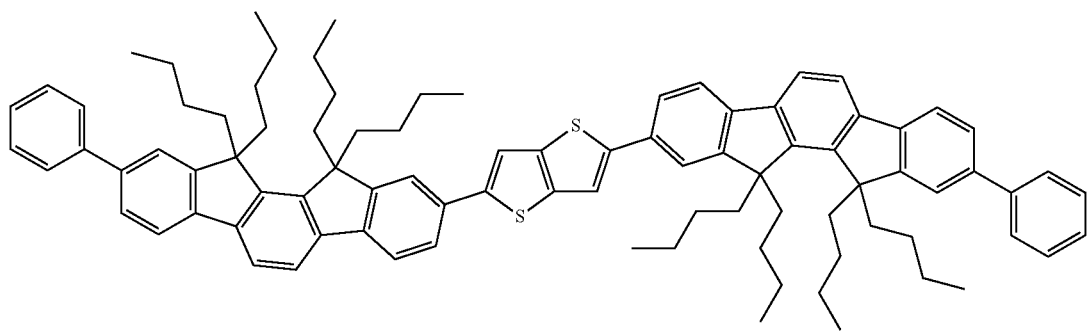
No. 444
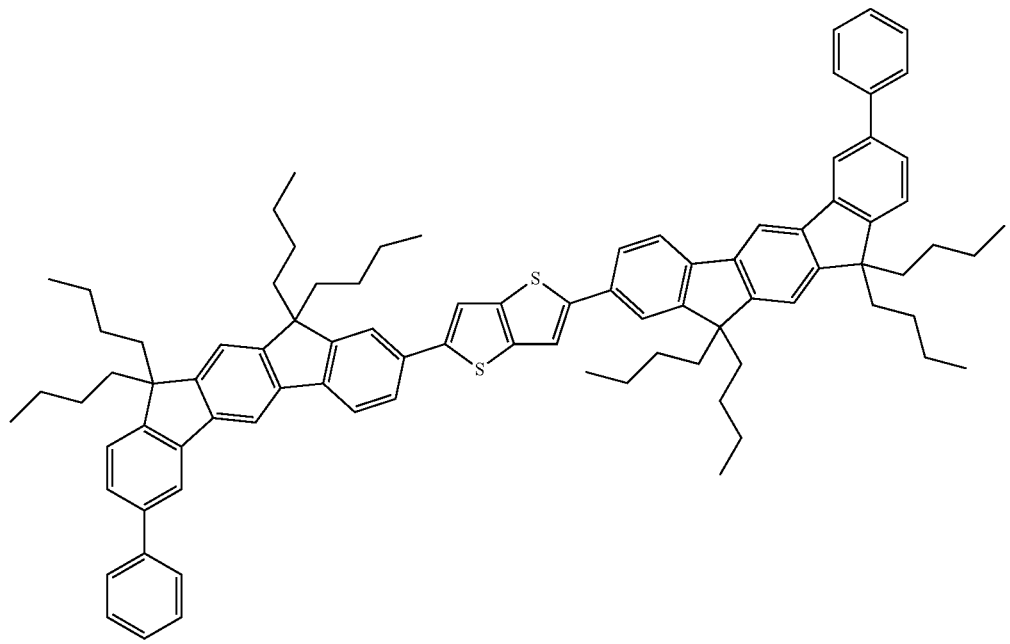

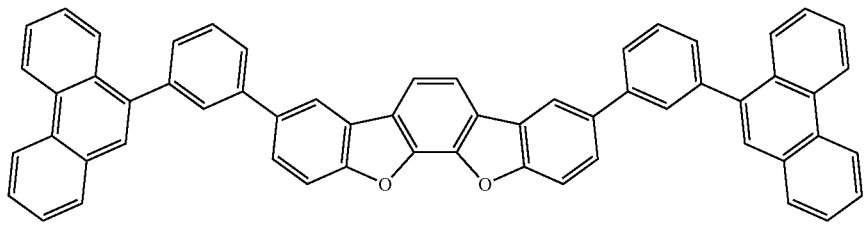
No. 445
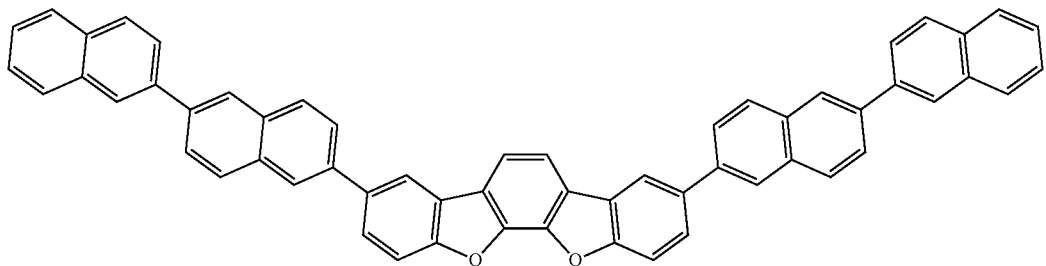
No. 446
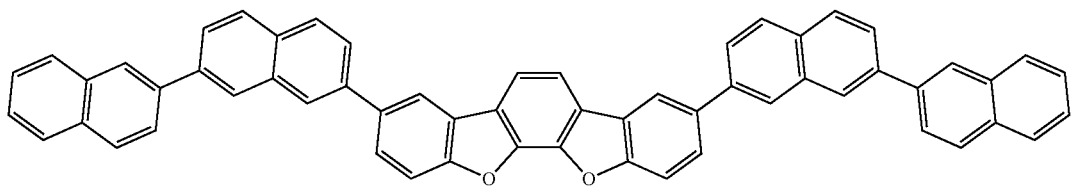
No. 447
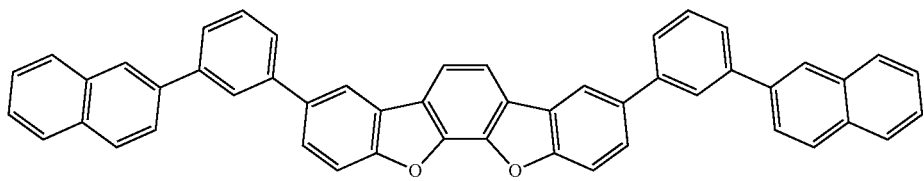
No. 448
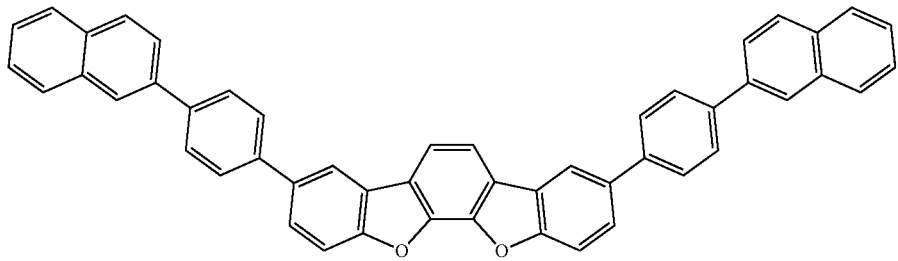
No. 449
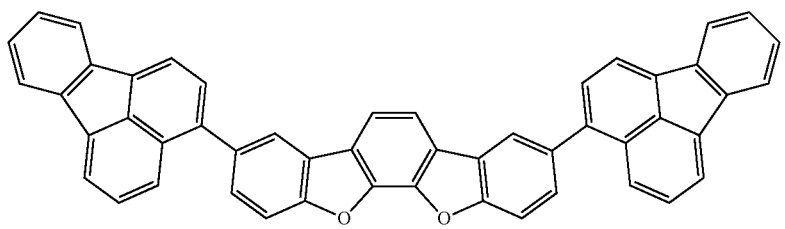
No. 450

-continued
No. 451
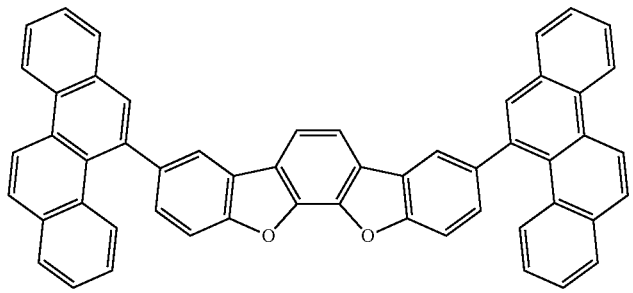
No. 452
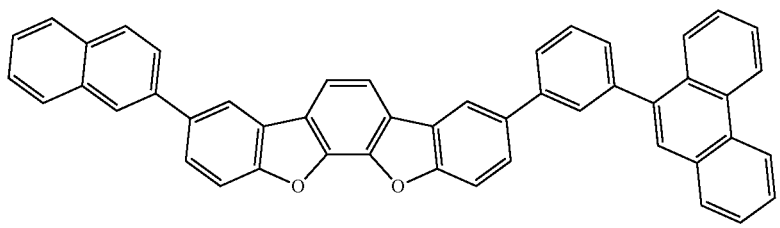
No. 453
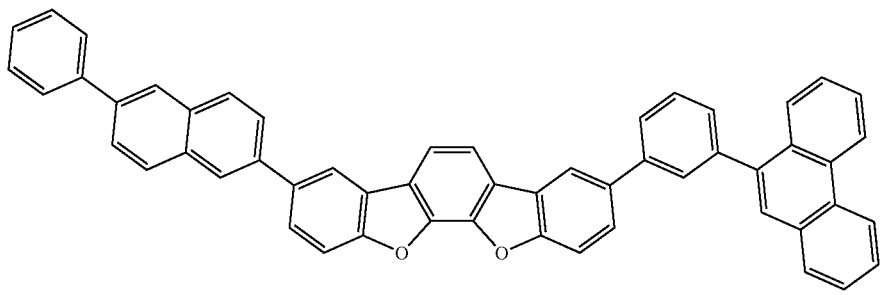
No. 454
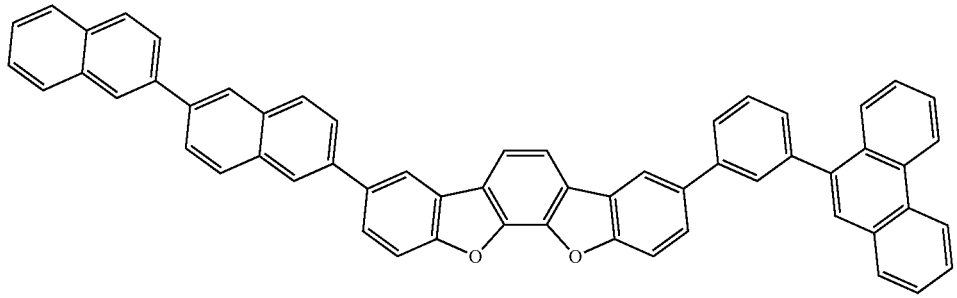
No. 455
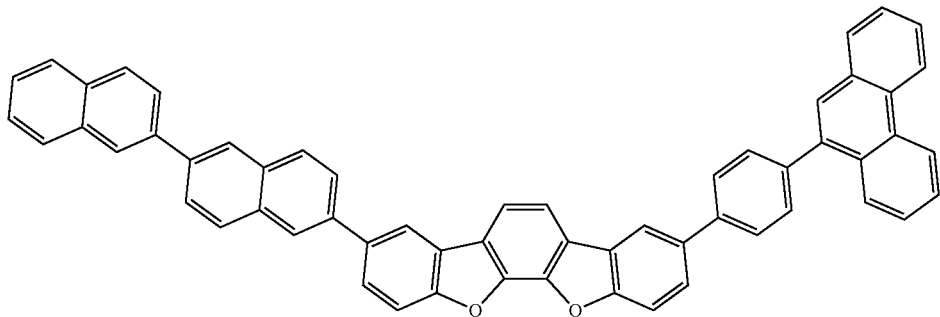

No. 456
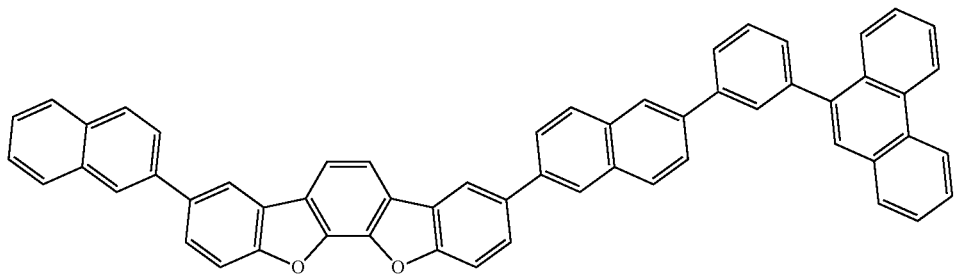
No. 457
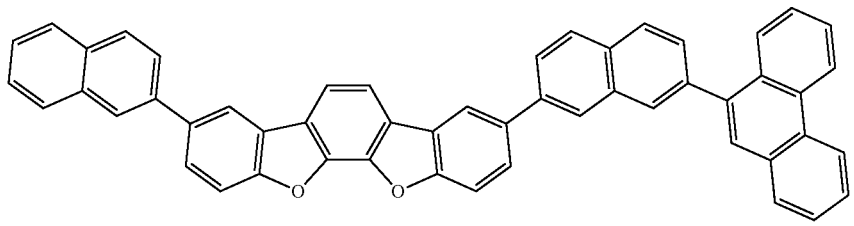
No. 458
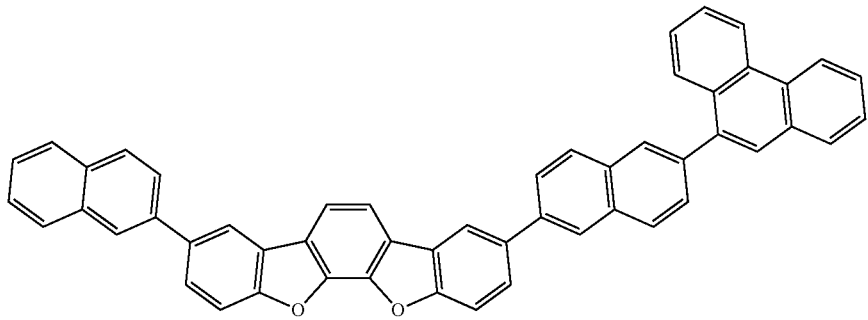
No. 459
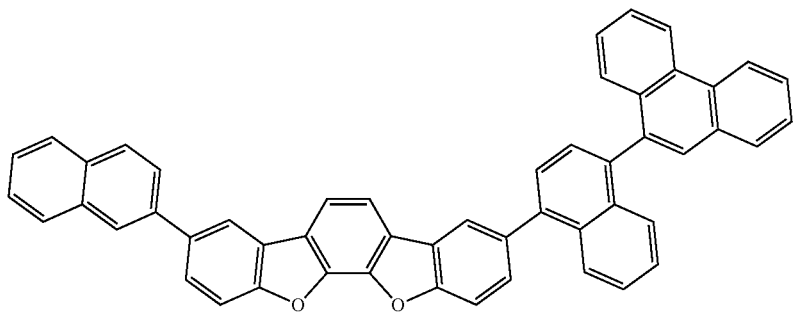
No. 460
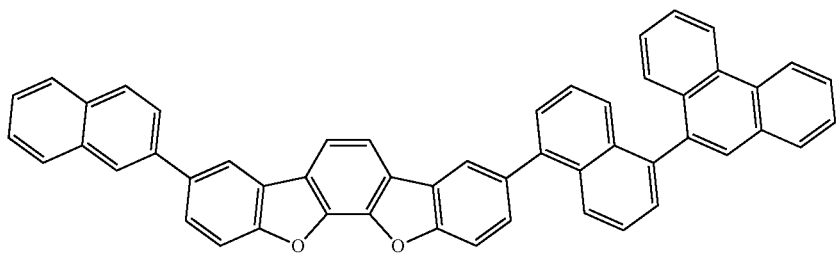

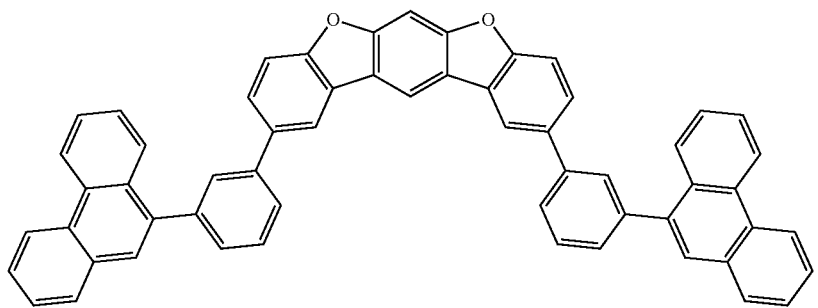
No. 461
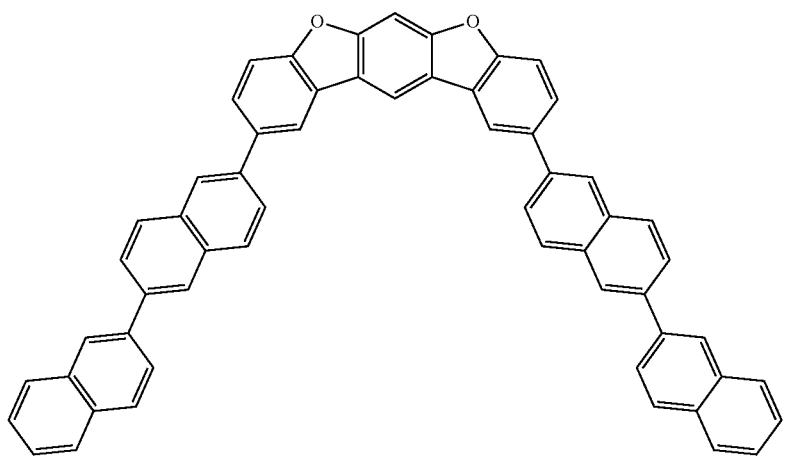
No. 462
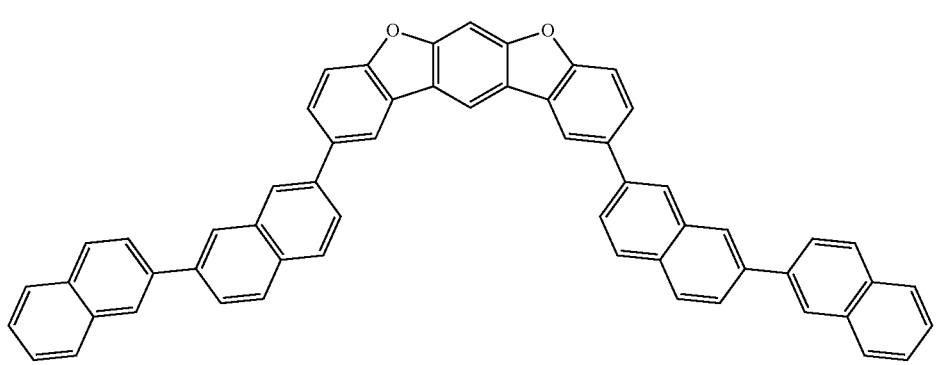
No. 463
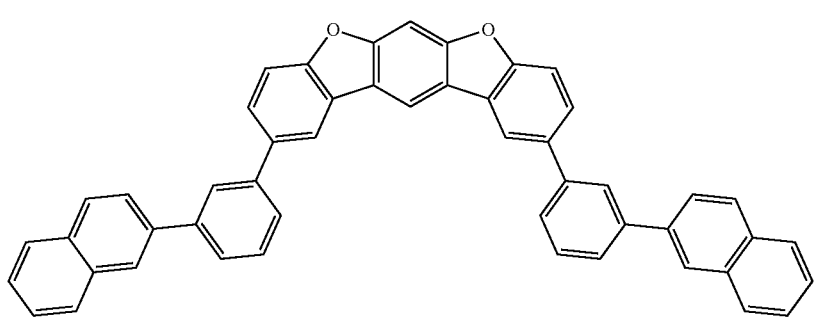
No. 464

-continued
No. 465
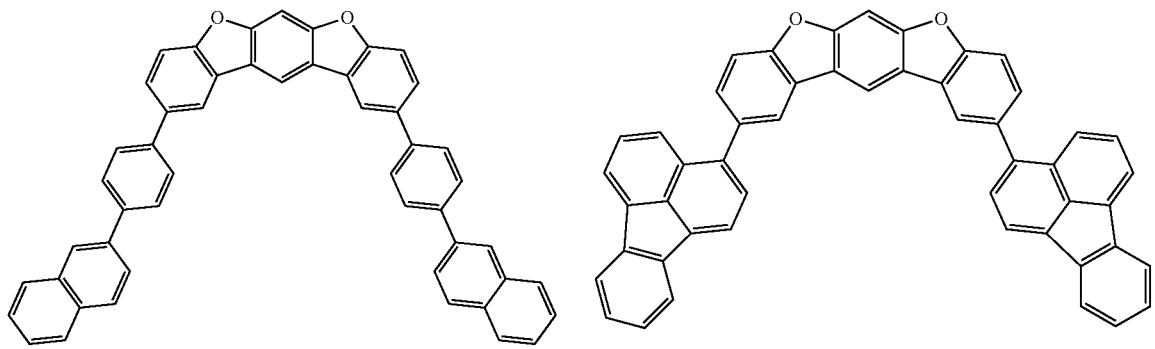
No. 466
No. 467
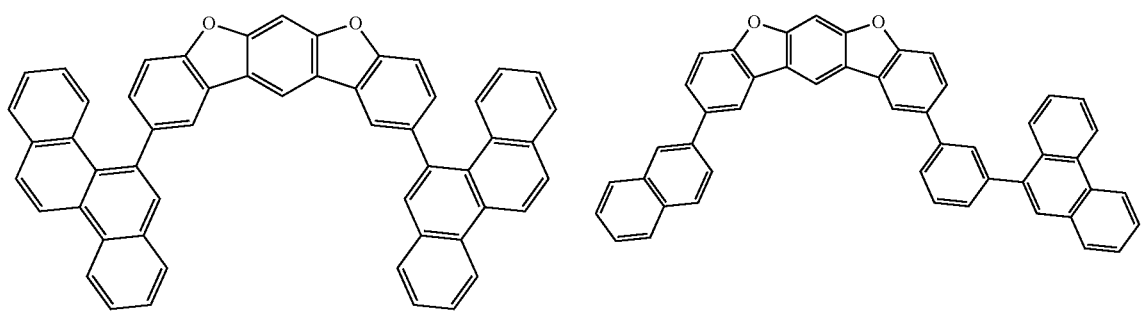
No. 468
No. 469
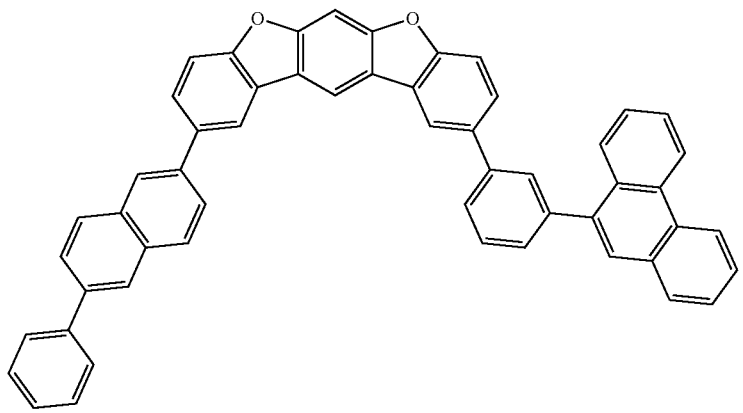
No. 470
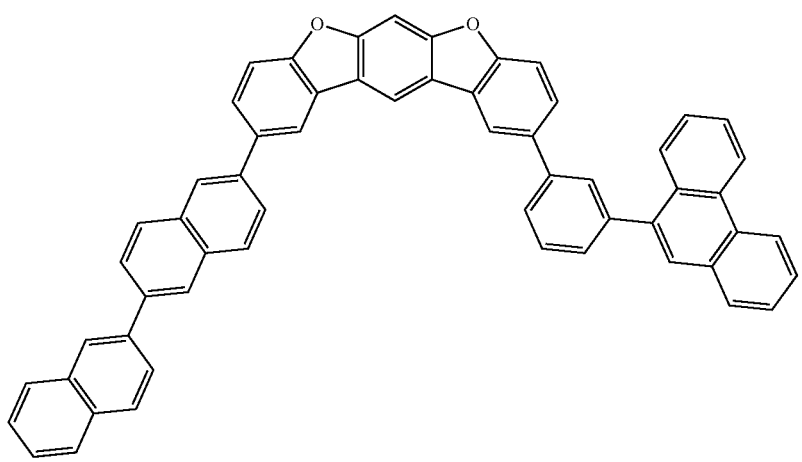

-continued
No. 471
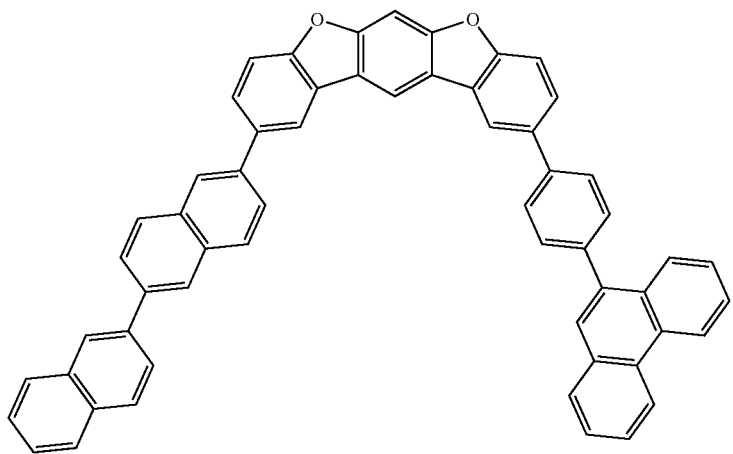
No. 472
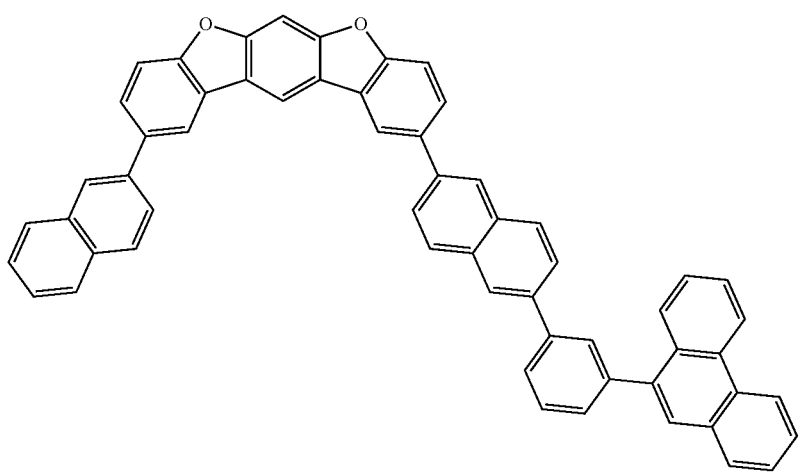
No. 473
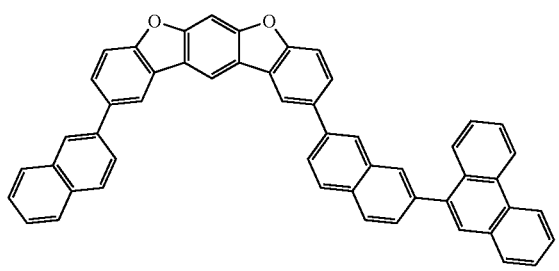
No. 474
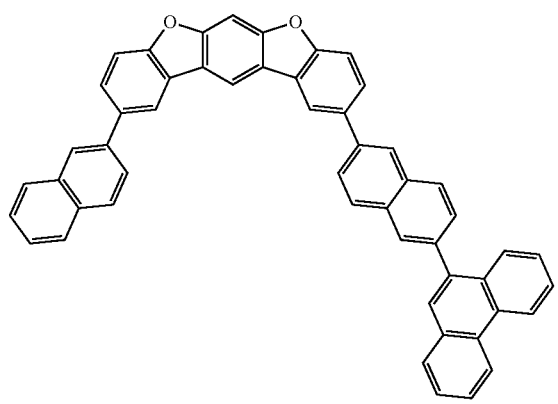

No. 475

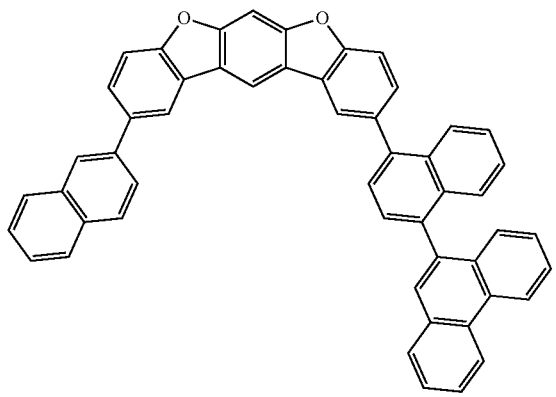

No. 476

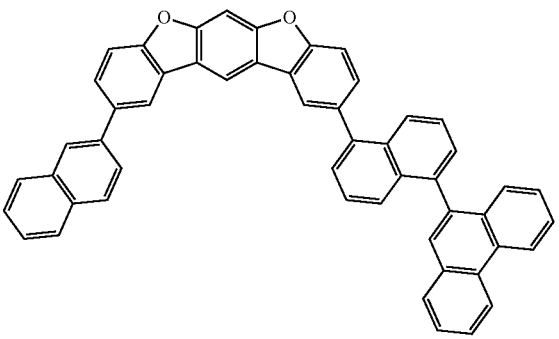

Next, an organic EL device of the present invention will be described.

The organic EL device of the present invention has one or more organic thin film layers including a light emitting layer between a cathode and an anode, and at least one layer of the organic thin film layers contains a material for an organic EL device serving as a compound having a π-conjugated heteroacene skeleton crosslinked with a carbon atom, nitrogen atom, oxygen atom, or sulfur atom. Specific examples of the π-conjugated heteroacene skeleton are shown below.

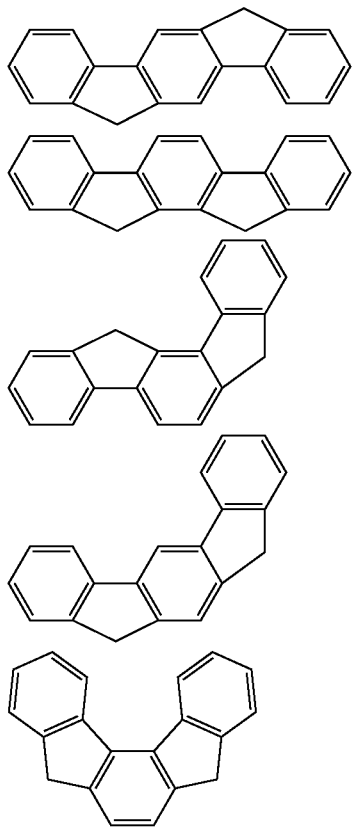

Indenofluorene (crosslinked with a carbon atom)

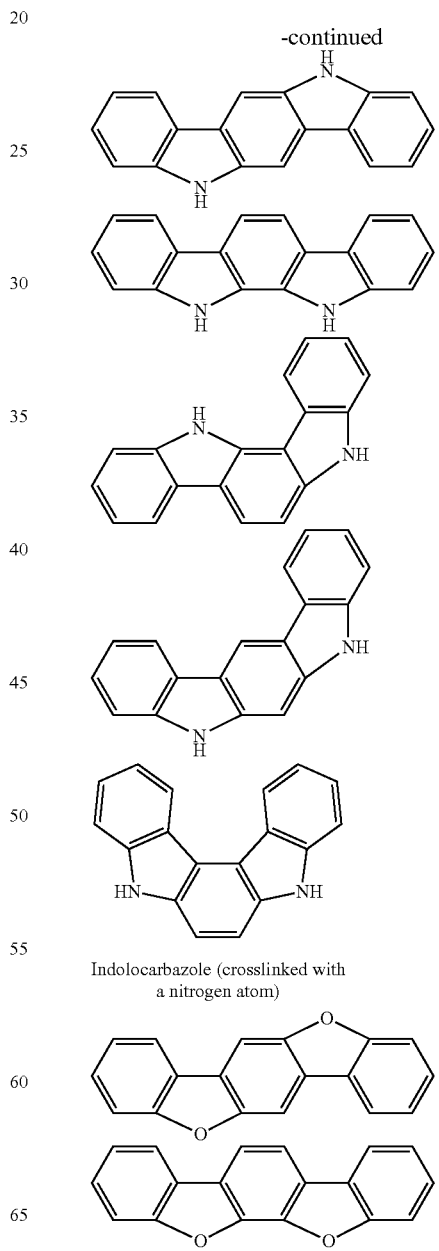

Indolocarbazole (crosslinked with a nitrogen atom)

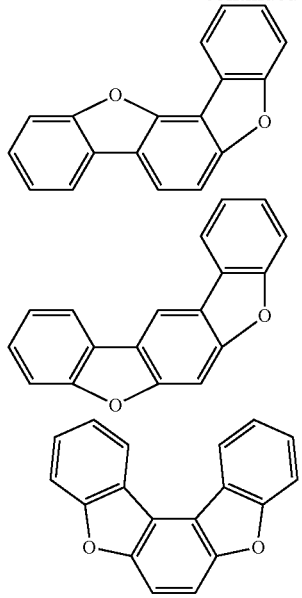

Benzofuranodibenzofuran (crosslinked with a oxygen atom)

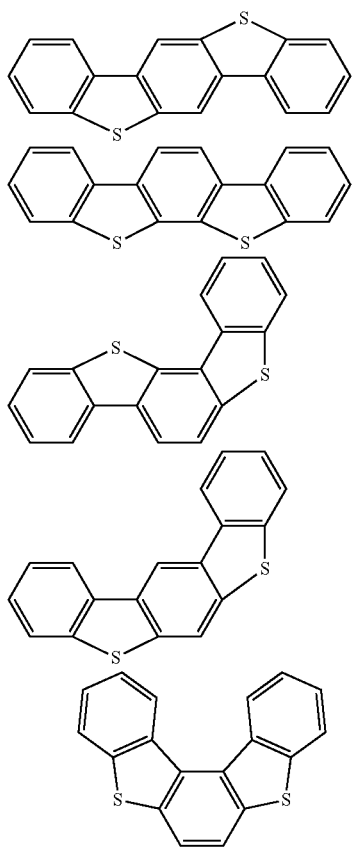

Benzothiophenodibenzothiophene (crosslinked with a sulfur atom)

In addition to the foregoing, a π-conjugated heteroacene skeleton crosslinked with a combination of two or more of a carbon atom, a nitrogen atom, an oxygen atom, and a sulfur atom is also permitted. Specific examples of the π-conjugated heteroacene skeleton are shown below.

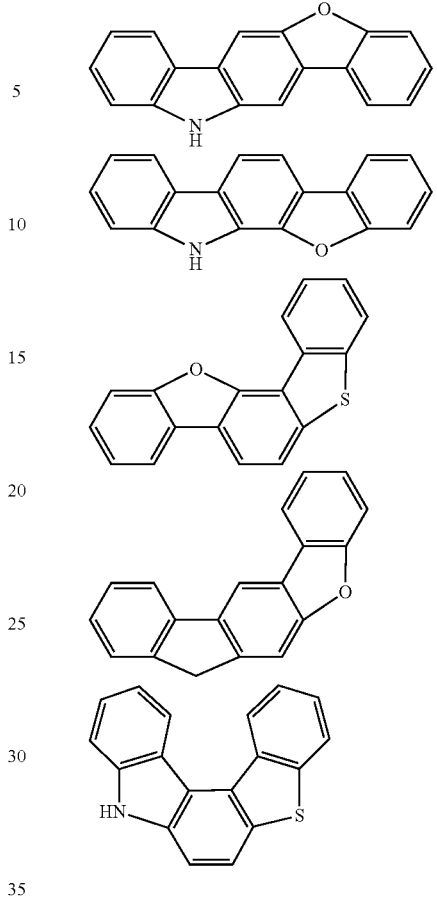

In addition, the above-mentioned material for an organic EL device of the present invention is preferably used as the material for an organic EL device.

The organic EL device may have an electron transporting layer between the light emitting layer and the cathode, and the electron transporting layer may contain the material for an organic EL device. Further, both the light emitting layer and the electron transporting layer each preferably contain the material for an organic EL device.

Alternatively, the organic EL device may have a hole transporting layer between the light emitting layer and the anode, and the hole transporting layer may contain the material for an organic EL device.

Further, the material for an organic EL device of the present invention is preferably incorporated into at least the light emitting layer. When the material is used in the light emitting layer, the lifetime of the organic EL device can be lengthened. When the material is used in the electron transporting layer or the electron injecting layer, the voltage at which the device is driven can be reduced. The material is preferably incorporated into each of two or more layers including the light emitting layer and the electron transporting layer or the electron injecting layer at the same time because both the reduced voltage and the lengthened lifetime can be achieved.

In particular, in addition to the electron transporting layer or the electron injecting layer, the light emitting layer preferably include the material for an organic EL device of the present invention as a host material. The light emitting layer preferably includes the material for an organic EL device represented by the general formula (5) or (6), or the general formula (9) or (12) as a host material, and more preferably includes the material for an organic EL device represented by the general formula (15) or (16), or the general formula (17) or (18) as a host material.

A multi-layer type organic EL device is obtained by laminating multiple layers; for example, the device is formed of an anode, a hole transporting layer (a hole injecting layer), a light emitting layer, and a cathode, of an anode, a light emitting layer, an electron transporting layer (an electron injecting layer), and a cathode, of an anode, a hole transporting layer (a hole injecting layer), a light emitting layer, an electron transporting layer (an electron injecting layer), and a cathode, or of an anode, a hole transporting layer (a hole injecting layer), a light emitting layer, a hole barrier layer, an electron transporting layer (an electron injecting layer), and a cathode.

In the organic EL device of the present invention, the light emitting layer preferably contains the material for an organic EL device as a host material. In addition, it is preferred that the light emitting layer be composed of a host material and a phosphorescent material, and the host material be the material for an organic EL device.

In addition, the material for an organic EL device may be a host material to be used together with a phosphorescent material, or may be an electron transporting material to be used together with a phosphorescent material. The material has a triplet energy gap of preferably 2.2 to 3.2 eV, or more preferably 2.5 to 3.2 eV.

The phosphorescent material is preferably a compound containing iridium (Ir), osmium (Os), ruthenium (Ru), or platinum (Pt) because the compound has a high phosphorescent quantum yield, and can additionally improve the external quantum efficiency of the light emitting device. The material is more preferably a metal complex such as an iridium complex, an osmium complex, a ruthenium complex, or a platinum complex. Of those, the iridium complex and the platinum complex are still more preferable, and an orthometalated iridium complex is most preferable. Specific examples of the metal complex such as an iridium complex, an osmium complex, a ruthenium complex, or a platinum complex are shown below.

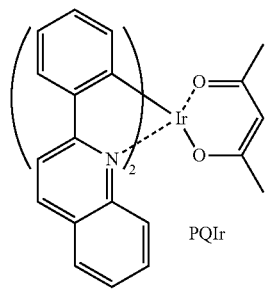

PQIr

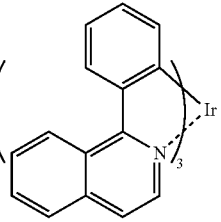

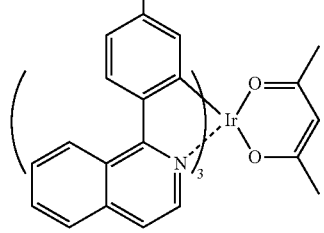

-continued

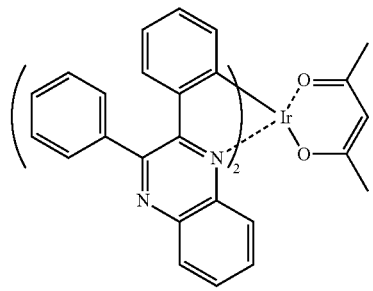

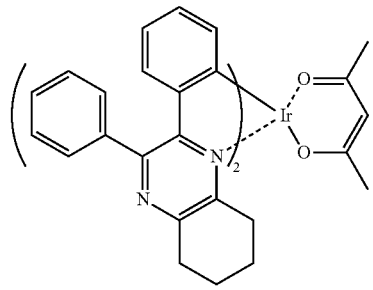

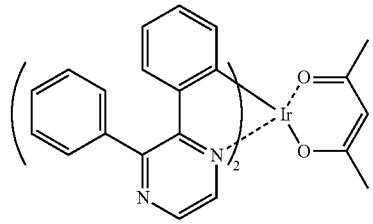

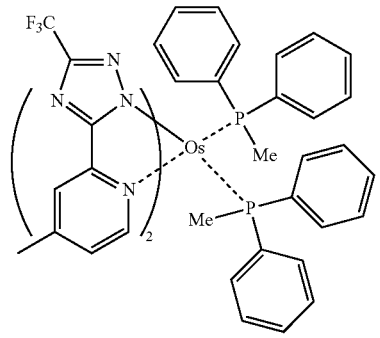

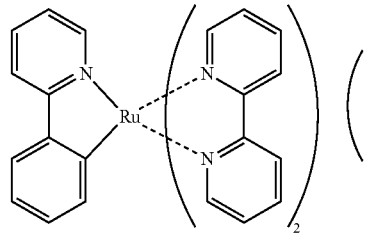

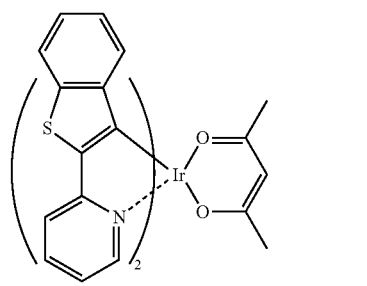

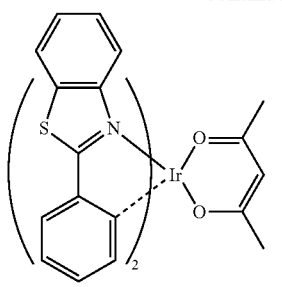
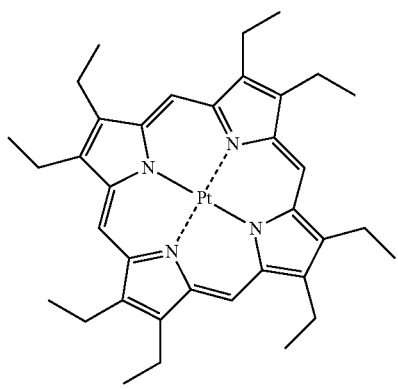
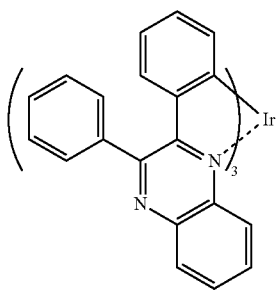
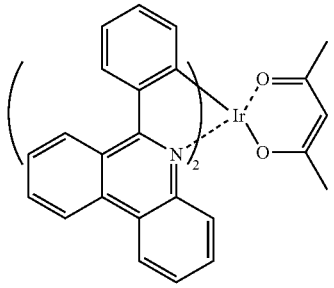
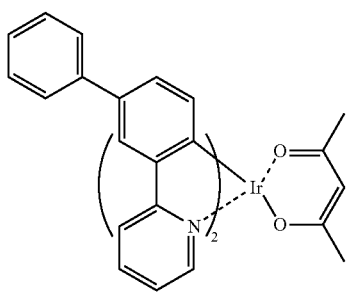
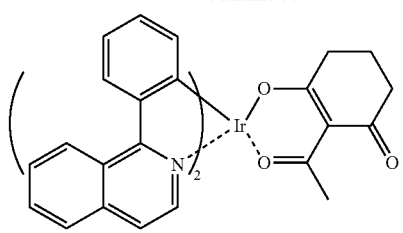
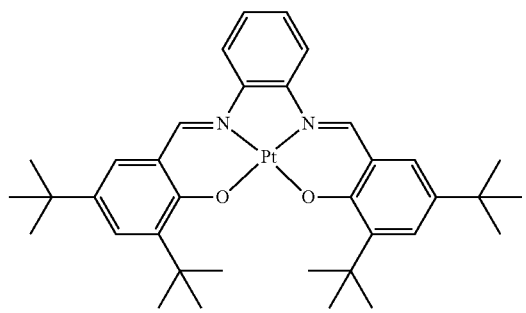
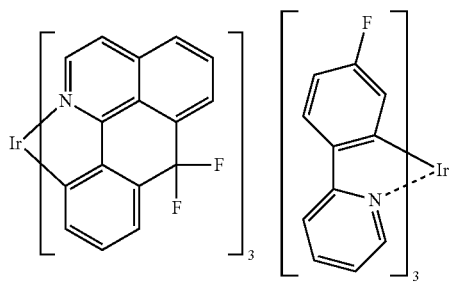
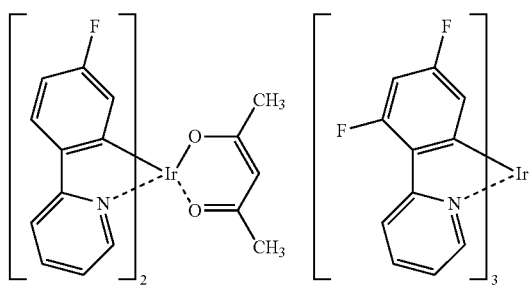
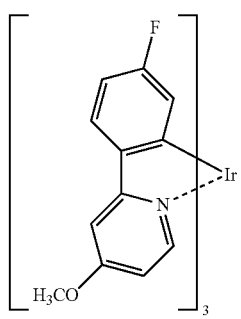
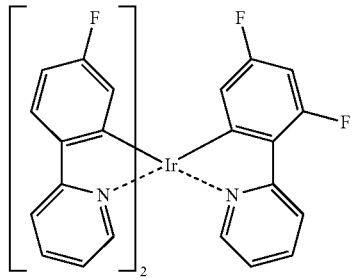

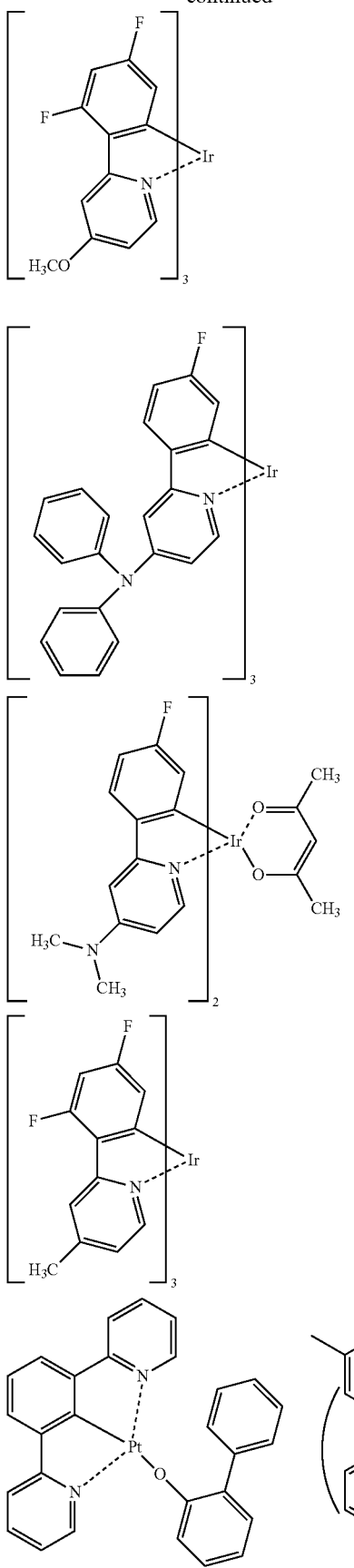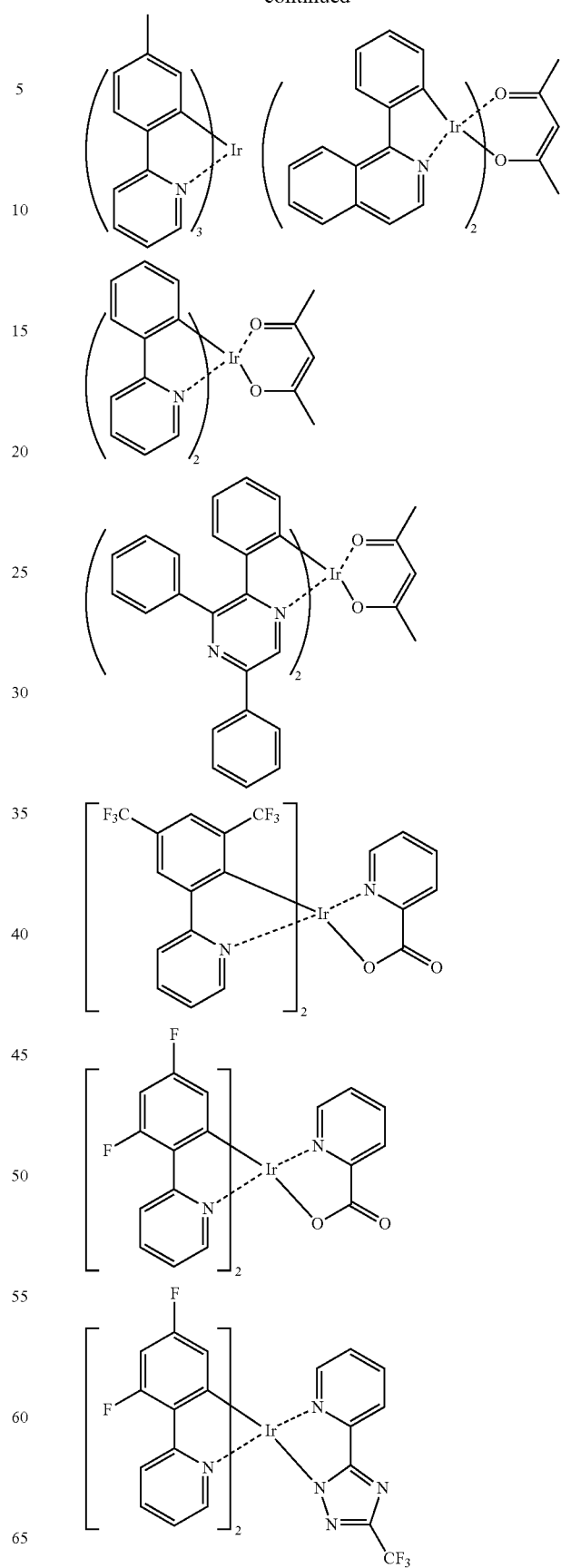

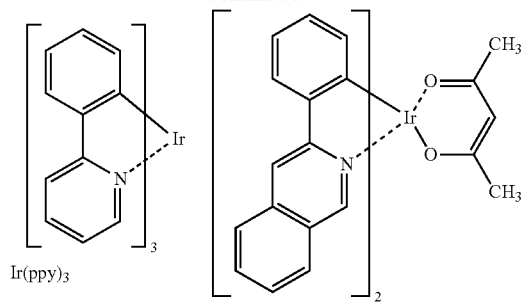
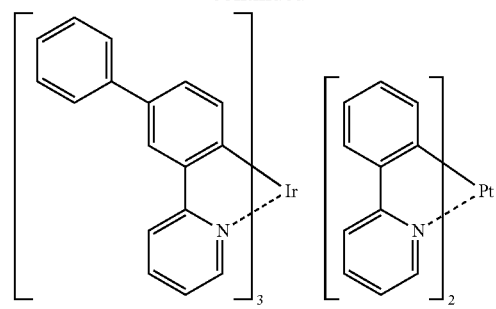
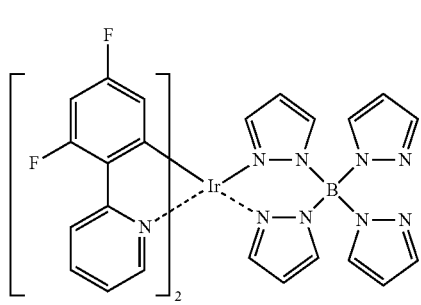
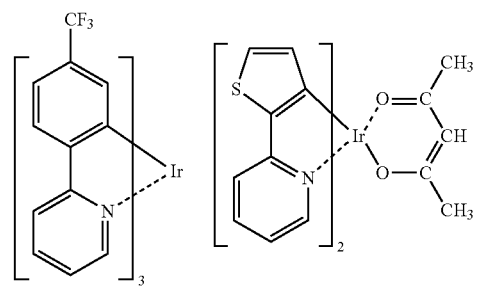
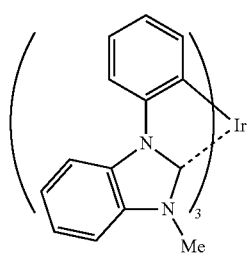
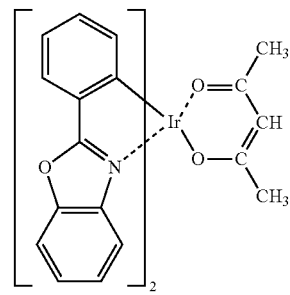
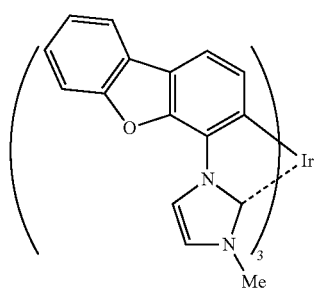
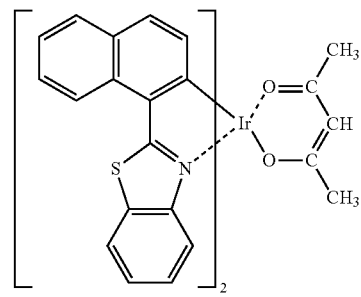
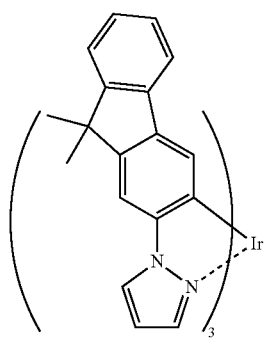
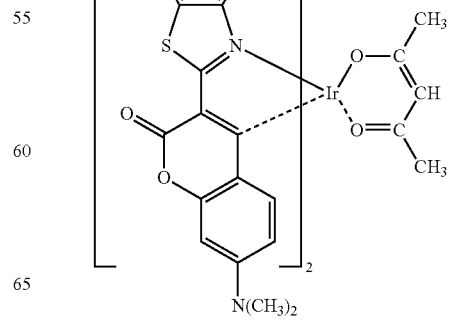

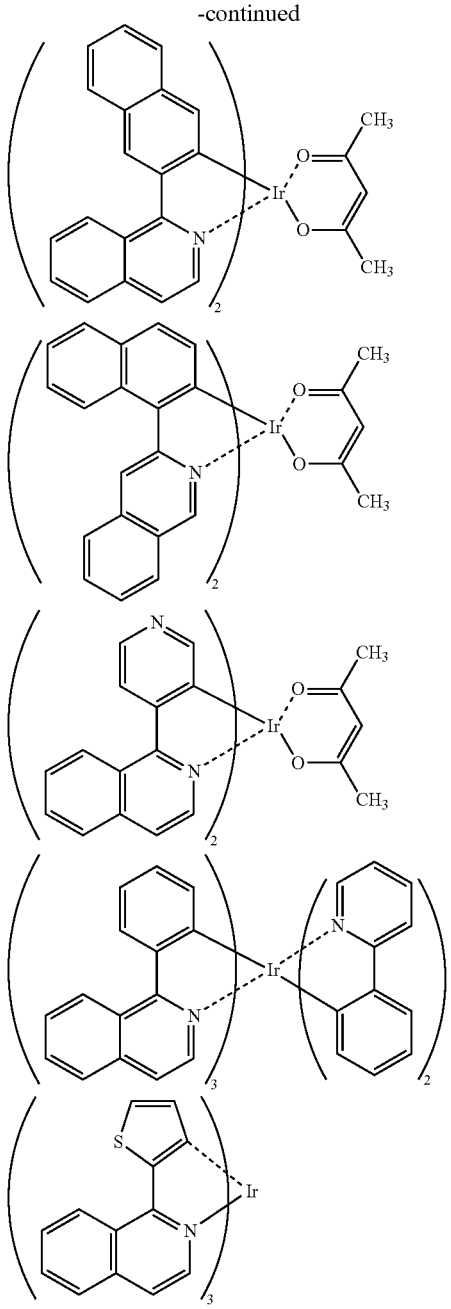

In addition, the organic EL device of the present invention is preferably such that the light emitting layer contains a host material and a phosphorescent material, and contains a metal complex having a local maximum luminous wavelength of 500 nm or less. Further, the material of the present invention can be used together with a fluorescent dopant. The material can be used together with a blue, green, or red fluorescent dopant. In particular, the material can be more preferably used together with the blue or green fluorescent dopant. Further, the material can be preferably used also as an electron transporting material for a fluorescent organic EL device.

The organic EL device of the present invention preferably has a reductive dopant in an interfacial region between the cathode and an organic thin layer (for example, an electron injecting layer or a light emitting layer). Examples of the reductive dopant include at least one kind selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Preferred examples of the alkali metal include an alkali metal having a work function of 2.9 eV or less, such as Na having a work function of 2.36 eV, K having a work function of 2.28 eV, Rb having a work function of 2.16 eV, and Cs having a work function of 1.95 eV. Of those, K, Rb, and Cs are more preferable, Rb or Cs is still more preferable, and Cs is most preferable.

Preferred examples of the alkali earth metal include an alkali earth metal having a work function of 2.9 eV or less, such as Ca having a work function of 2.9 eV, Sr having a work function of 2.0 to 2.5 eV, and Ba having a work function of 2.52 eV.

Preferred examples of the rare earth metal include a rare earth metal having a work function of 2.9 eV or less, such as Sc, Y, Ce, Tb, and Yb.

Of those metals, a preferable metal has a particularly high reductive ability, so improvement of light emission intensity and long life of organic EL device can be attained by adding a relatively small amount of the metal to an electron injecting region.

Examples of the alkali metal compound include an alkali oxide such as $Li_2O$, $Cs_2O$, or $K_2O$, and an alkali halide such as LiF, NaF, CsF, or KF. Of those, LiF, $Li_2O$, or NaF is preferable.

Examples of the alkali earth metal compound include BaO, SrO, CaO, and mixtures thereof such as $Ba_mSr_{1-m}O$ ($0<m<1$) and $Ba_mCa_{1-m}O$ ($0<m<1$). Of those, BaO, SrO, and CaO are preferable.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferable.

The alkali metal complex, alkali earth metal complex, and rare earth metal complex are not particularly limited as long as they each include as a metal ion at least one of alkali metal ions, alkali earth metal ions, and rare earth metal ions. Meanwhile, preferable examples of a ligand include, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfluborane, bipyridyl, phenanthroline, phthalocyanine, porphyrin, cyclopentadiene, β-diketones, azomethines, and derivatives thereof.

For the addition form of the reductive dopant, it is preferable that the reductive dopant be formed in a shape of a layer or an island in the interfacial region. A preferable example of the forming method includes a method in which an organic substance which is a light emitting material or an electron injecting material for forming the interfacial region is deposited at the same time as the reductive dopant is deposited by a resistant heating deposition method, thereby dispersing the reductive dopant in the organic substance. The disperse concentration by molar ratio of the organic compound to the reductive dopant is 100:1 to 1:100, and is preferably 5:1 to 1:5.

In a case where the reductive dopant is formed into the shape of a layer, the light emitting material or electron injecting material which serves as an organic layer in the interface is formed into the shape of a layer. After that, the reductive dopant is solely deposited by the resistant heating deposition method to form a layer preferably having a thickness of 0.1 to 15 nm.

In a case where the reductive dopant is formed into the shape of an island, the light emitting material or electron injecting material which serves as an organic layer in the interface is formed into the shape of an island. After that, the reductive dopant is solely deposited by the resistant heating deposition method to form an island preferably having a thickness of 0.05 to 1 nm.

When the organic EL device of the present invention has an electron injecting layer between the light emitting layer and the cathode, an electron transporting material to be used in the electron injecting layer is preferably an aromatic heterocyclic compound containing one or more heteroatoms in anyone of its molecules, or particularly preferably a nitrogen-containing ring derivative.

The nitrogen-containing ring derivative is preferably, for example, a nitrogen-containing ring metal chelate complex represented by the following general formula (A).

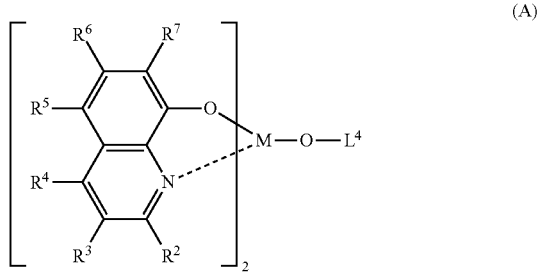

(A)

$R^2$ to $R^7$ each independently represent a hydrogen atom, a halogen atom, an amino group, a hydrocarbon group each having 1 to 40 carbon atoms, an alkoxy group, an aryloxy group, an alkoxycarbonyl group, or a heterocyclic group, each of which may be substituted.

Examples of the halogen atom represented by $R^2$ to $R^7$ include a fluorine atom, a chlorine atom, a bromine atom, and an iodine atom.

Examples of the amino group that may be substituted and represented by $R^2$ to $R^7$ include an alkylamino group, an arylamino group, and an aralkylamino group. Examples of the alkyl group in the alkylamino group include alkyl groups each having 1 to 40 carbon atoms such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, a iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, and a 1,2,3-trinitropropyl group. Preferred are alkyl groups each having 1 to 20 carbon atoms and more preferred are alkyl groups each having 1 to 10 carbon atoms.

Examples of the aryl group in the arylamino group include aryl groups each having a ring formed of 6 to 40 carbon atoms such as a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group. Preferred are aryl groups each having a ring formed of 6 to 20 carbon atoms and more preferred are aryl groups each having a ring formed of 6 to 10 carbon atoms.

Examples of the aralkyl group in the aralkylamino group include aralkyl groups each having 7 to 40 carbon atoms such as a benzyl group, a 1-phenylethyl group, a 2-phenylethyl group, a 1-phenyl isopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Preferred are aralkyl groups each having 7 to 20 carbon atoms and more preferred are aralkyl groups each having 7 to 10 carbon atoms.

Examples of the hydrocarbon groups each having 1 to 40 carbon atoms represented by $R^2$ to $R^7$ include substituted or unsubstituted alkyl groups, alkenyl groups, cycloalkyl groups, aryl groups, and aralkyl groups.

As the alkyl groups, the same examples of the alkyl groups in the above-mentioned alkylamino group are given, and alkyl groups each having 1 to 20 carbon atoms are preferred and alkyl groups each having 1 to 10 carbon atoms are more preferred.

Examples of the alkenyl group include alkenyl groups each having 2 to 40 carbon atoms such as a vinyl group, an allyl group, a 1-butenyl group, a 2-butenyl group, a 3-butenyl group, a 1,3-butanedienyl group, a 1-methylvinyl group, a styryl group, a 2,2-diphenyl vinyl group, a 1,2-diphenyl vinyl group, a 1-methylaryl group, a 1,1-dimethylaryl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. Preferred are alkenyl groups each having 2 to 20 carbon atoms and more preferred are alkenyl groups each having 2 to 10 carbon atoms.

Examples of the cycloalkyl groups include cycloalkyl groups each having a ring formed of 3 to 40 carbon atoms such as a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. Preferred are cycloalkyl groups each having a ring formed of 3 to 10 carbon atoms are preferred.

As the aryl groups, the same examples of the aryl groups in the above-mentioned arylamino groups are given. Preferred are aryl groups each having a ring formed of 6 to 20 carbon atoms and more preferred are aryl groups each having a ring formed of 6 to 10 carbon atoms.

As the aralkyl groups, the same examples of the aralkyl groups in the above-mentioned aralkylamino groups are given. Preferred are aralkyl groups each having 7 to 20 carbon atoms and more preferred are aralkyl groups each having 7 to 10 carbon atoms.

As the alkoxy group that represented by $R^2$ to $R^7$ and may be substituted, the same examples of the alkyl groups in the above-mentioned alkylamino groups are given as alkyl group moieties. Preferred are alkoxy groups each having 1 to 20 carbon atoms and more preferred alkoxy groups each having 1 to 10 carbon atoms.

As the aryloxy group that represented by $R^2$ to $R^7$ and may be substituted, aryloxy groups each having the same aryl group in the above-mentioned arylamino group as an aryl group moiety are given. Preferred are aryl groups each having a ring formed of 6 to 20 carbon atoms and more preferred are aryl groups each having a ring formed of 6 to 10 carbon atoms.

As the alkoxycarbonyl group that represented by $R^2$ to $R^7$ and may be substituted, alkoxycarbonyl groups each having the same alkyl group in the above-mentioned alkylamino group as the alkyl group moiety are given. Preferred are alkoxycarbonyl groups each having 2 to 20 carbon atoms and more preferred are alkoxycarbonyl groups each having 2 to 10 carbon atoms.

The heterocyclic group that represented by $R^2$ to $R^7$ and may be substituted is a monocycle or a fused ring. The heterocyclic group preferably has a ring formed of 1 to 20 carbon atoms, more preferably has a ring formed of 1 to 12 carbon atoms, and still more preferably has a ring formed of 2 to 10 carbon atoms. The heterocyclic group is an aromatic heterocyclic group having at least one hetero atom selected form a nitrogen atom, an oxygen atom, a sulfur atom, and selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, and azepine. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

M represents aluminum (Al), gallium (Ga), or indium (In). Indium is preferred.

$L^4$ in the formula (A) is a group represented by the following formula (A') or (A").

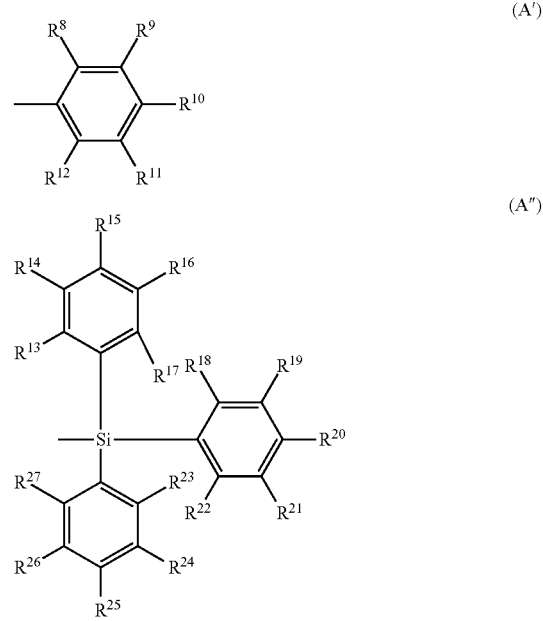

(In the formula, $R^8$ to $R^{12}$ each independently represent a hydrogen atom, or a substituted or unsubstituted hydrocarbon group having 1 to 40 carbon atoms, and adjacent groups may form a cyclic structure. In addition, $R^{13}$ to $R^{27}$ each independently represent a hydrogen atom, or a substituted or unsubstituted hydrocarbon group having 1 to 40 carbon atoms, and adjacent groups may form a cyclic structure.)

As the hydrocarbon group having 1 to 40 carbon atoms represented by $R^8$ to $R^{12}$ in the formula (A') and $R^{13}$ to $R^{27}$ in the formula (A"), the same specific examples of $R^2$ to $R^7$ are given.

In addition, examples of the divalent group in $R^8$ to $R^{12}$ and $R^{13}$ to $R^{27}$ in the case where adjacent groups form a cyclic structure include a tetramethylene group, a pentamethylene group, a hexamethylene group, a diphenylmethane-2,2'-diyl group, a diphenyethane-3,3'-diyl group, and diphenylpropane-4,4'-diyl group.

Specific examples of the nitrogen-containing ring metal chelate complex represented by the formula (A) are shown below. However, the present invention is not limited to these exemplified compounds.

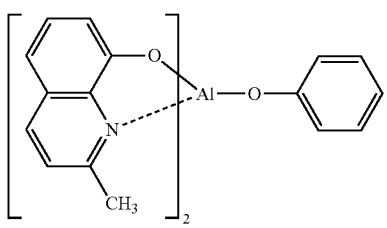 (A-1)
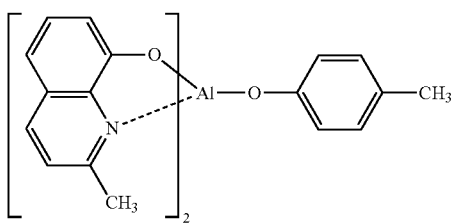 (A-2)
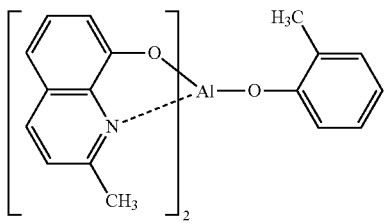 (A-3)
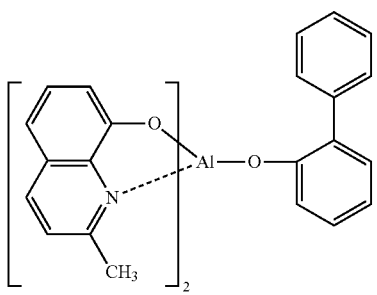 (A-4)
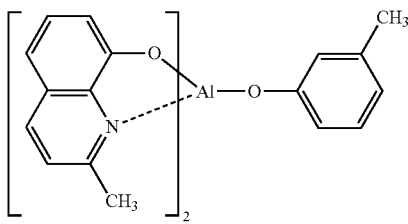 (A-5)
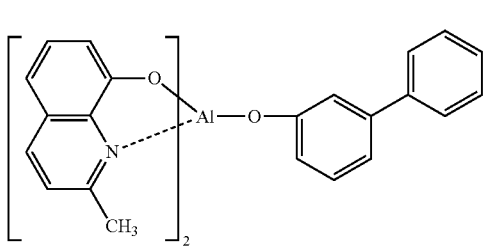 (A-6)
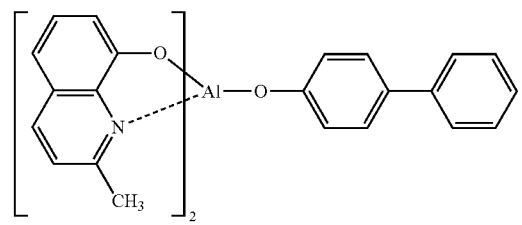 (A-7)
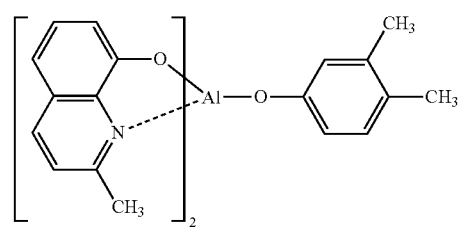 (A-8)
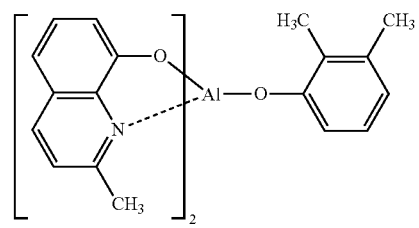 (A-9)
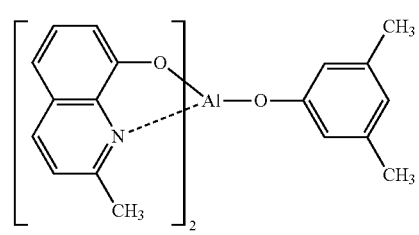 (A-10)
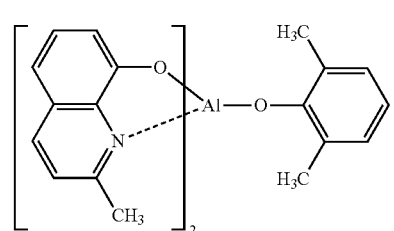 (A-11)
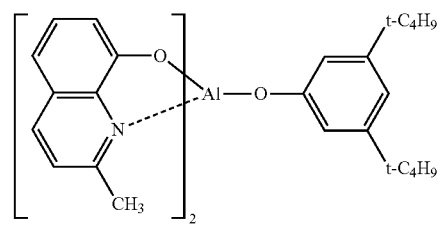 (A-12)
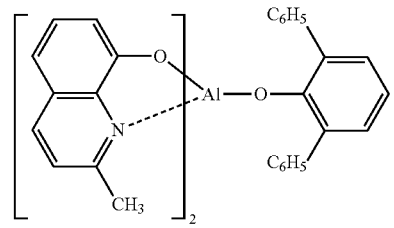 (A-13)

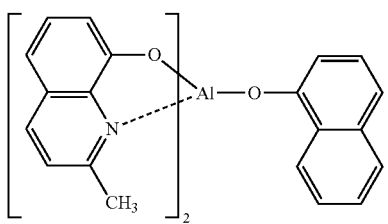
(A-14)
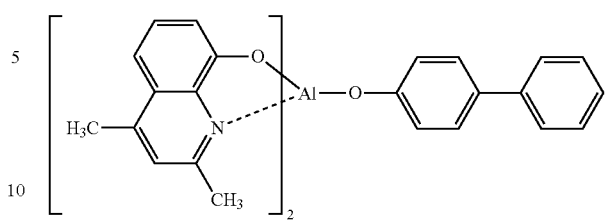
(A-20)
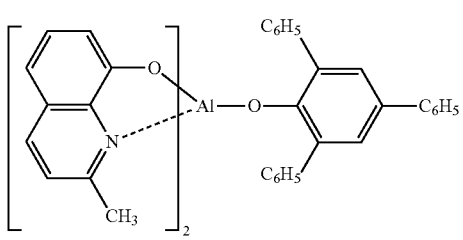
(A-15)
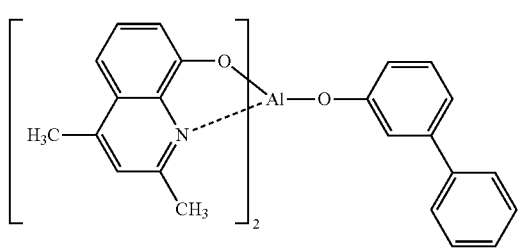
(A-21)
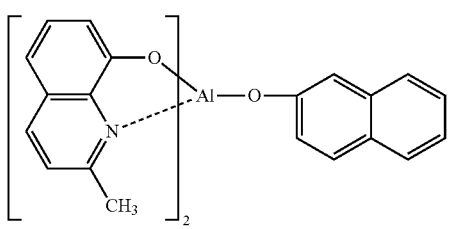
(A-16)
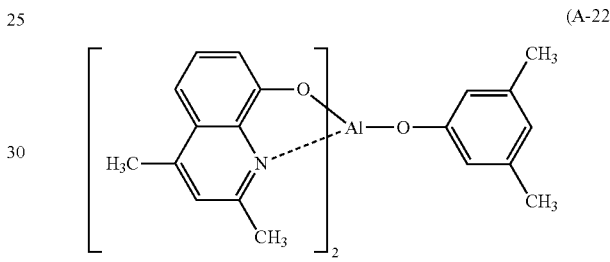
(A-22)
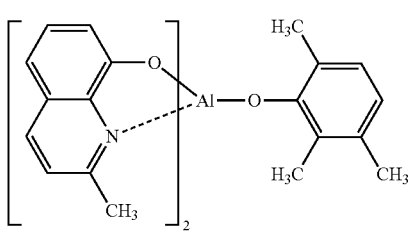
(A-17)
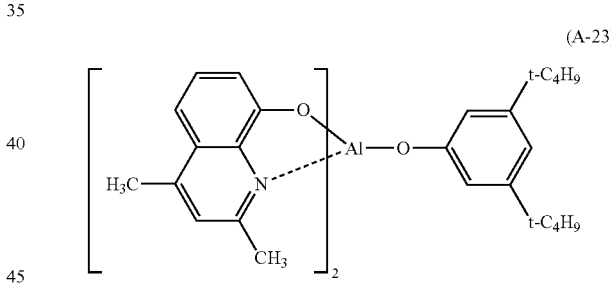
(A-23)
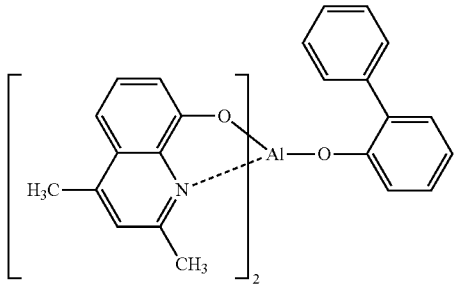
(A-18)
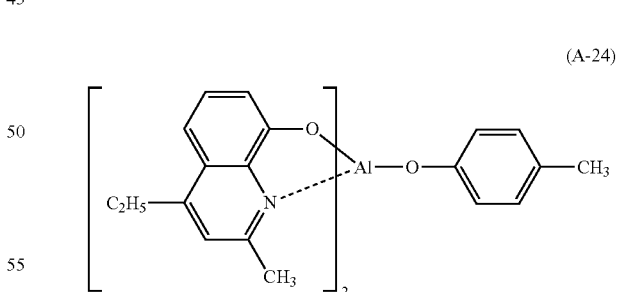
(A-24)
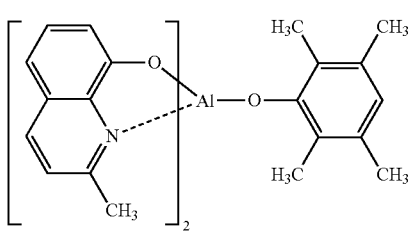
(A-19)
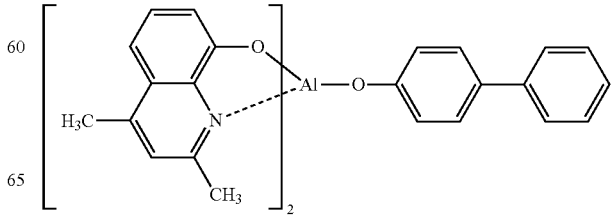
(A-25)

(A-26)
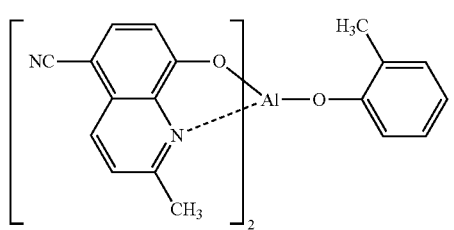
(A-27)
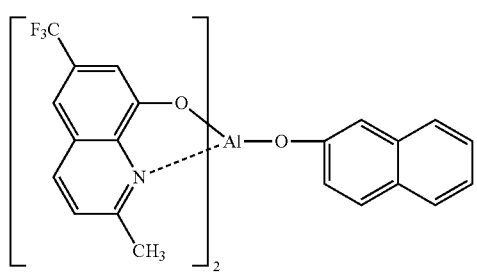
(A-28)
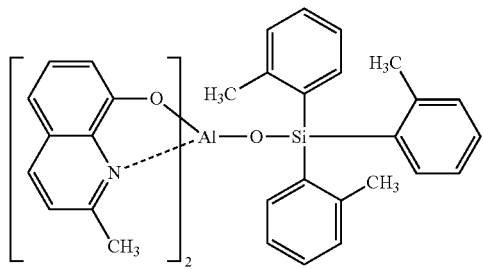
(A-29)
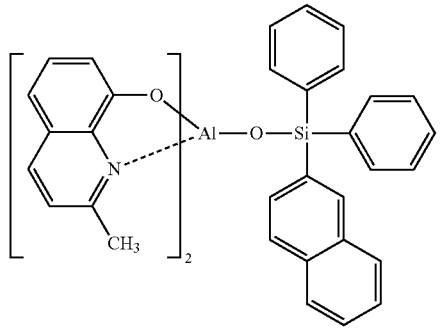
(A-30)
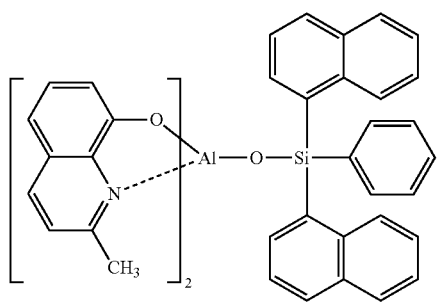
(A-31)
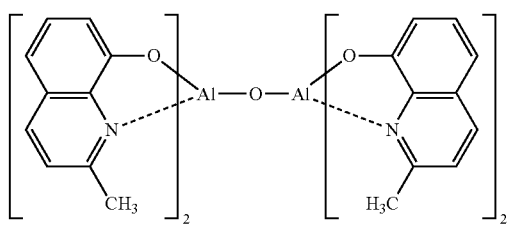
(A-32)
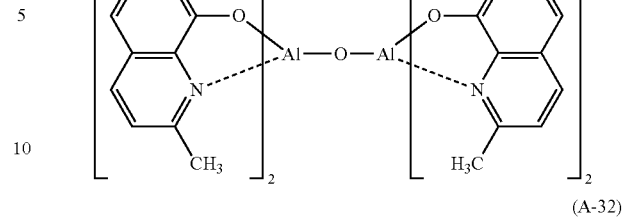
(A-33)
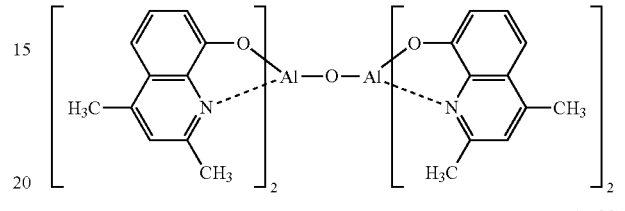
(A-34)
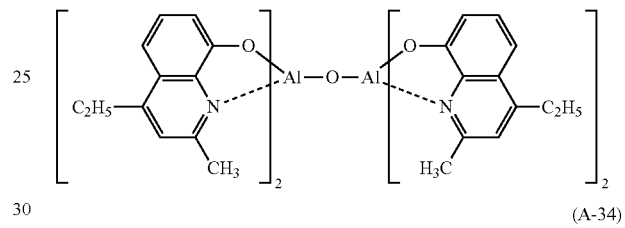
(A-35)
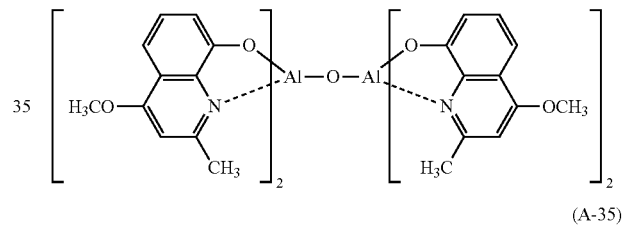
(A-36)
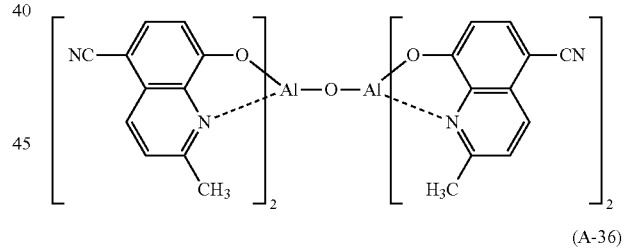
A nitrogen-containing heterocyclic derivative is a nitrogen-containing heterocyclic derivative composed of an organic compound having any one of the following general formulae, and a nitrogen-containing compound which is not a metal complex is also an example of the derivative. Examples of the derivative include a five- or six-membered ring containing a skeleton represented by the following formula (a) and a derivative of a structure represented by the following formula (b).

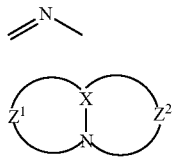

(In the formula (b), X represents a carbon atom or a nitrogen atom, and $Z^1$ and $Z^2$ each independently represent an atomic group capable of forming a nitrogen-containing heterocycle.)

An organic compound having a nitrogen-containing aromatic polycycle composed of a five- or six-membered ring is preferable. In the case of such nitrogen-containing aromatic polycycle having multiple nitrogen atoms, a nitrogen-containing aromatic polycyclic aromatic organic compound having a skeleton obtained by combining the above formulae (a) and (b) or the above formulae (a) and (c) is more preferable.

The nitrogen-containing group of the nitrogen-containing organic compound is selected from, for example, nitrogen-containing heterocyclic groups represented by the following general formulae.

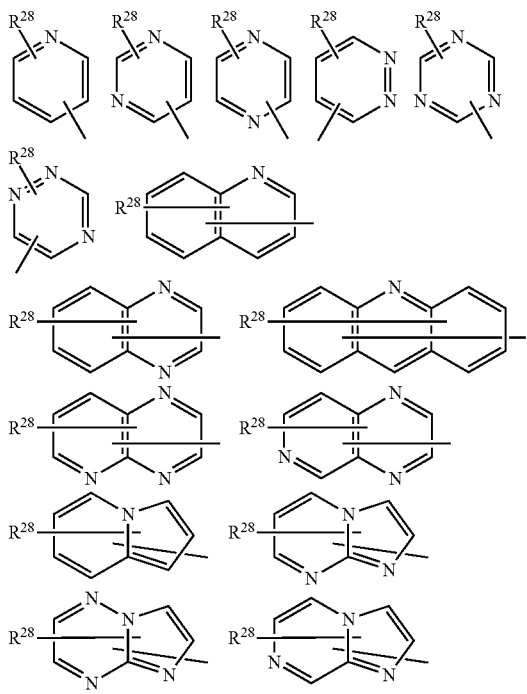

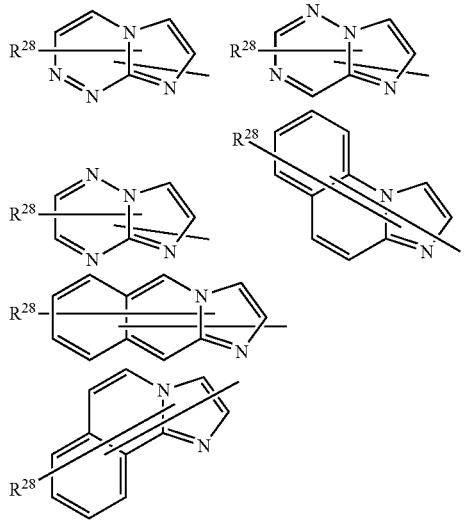

(In each of the formulae, $R^{28}$ represents an aryl group having 6 to 40 carbon atoms, a heteroaryl group having 3 to 40 carbon atoms, an alkyl group having 1 to 20 carbon atoms, or an alkoxy group having 1 to 20 carbon atoms, n represents an integer of 0 to 5, and, when n represents an integer of 2 or more, multiple $R^{28}$s may be identical to or different from each other).

Further, a preferable specific compound is, for example, a nitrogen-containing heterocyclic derivative represented by the following formula.

$HAr^a$-$L^6$-$Ar^b$—$Ar^c$ (In the formula, $HAr^a$ represents a nitrogen-containing heterocycle which has 3 to 40 carbon atoms and which may have a substituent, $L^6$ represents a single bond, an arylene group which has 6 to 40 carbon atoms and which may have a substituent, or a heteroarylene group which has 3 to 40 carbon atoms and which may have a substituent, $Ar^b$ represents a divalent aromatic hydrocarbon group which has 6 to 40 carbon atoms and which may have a substituent, and $Ar^c$ represents an aryl group which has 6 to 40 carbon atoms and which may have a substituent, or a heteroaryl group which has 3 to 40 carbon atoms and which may have a substituent.)

$HAr^a$ is selected from, for example, the following group.

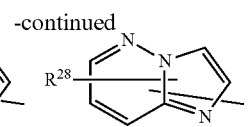

-continued
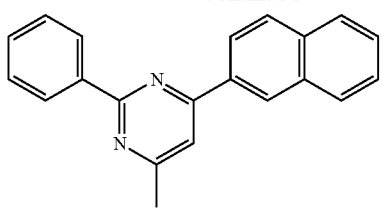
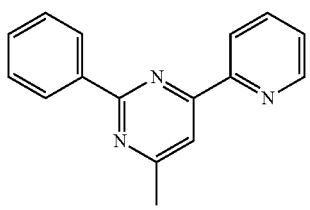
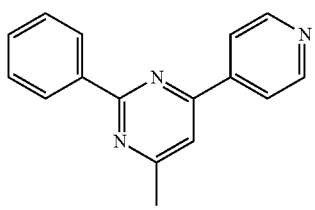
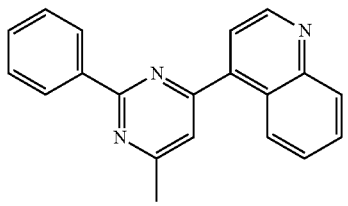
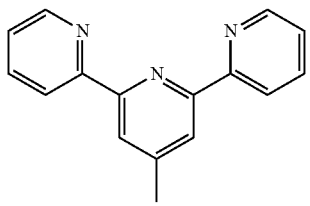
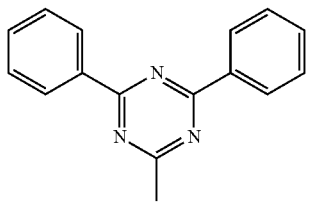
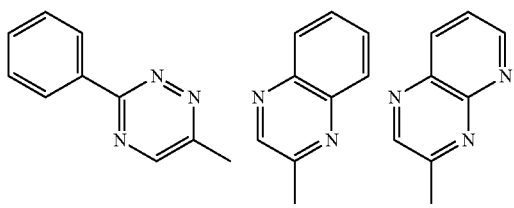
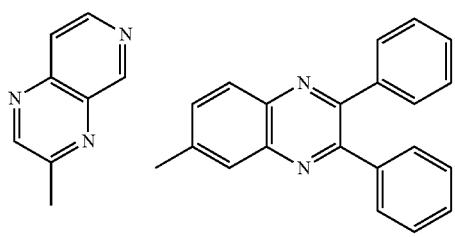
-continued
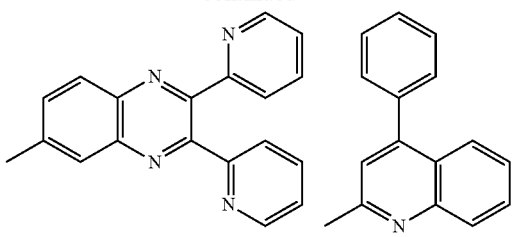
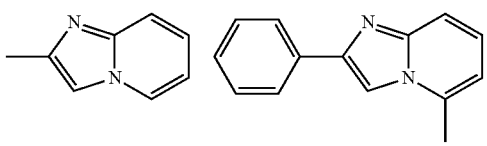
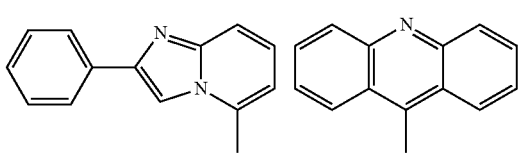
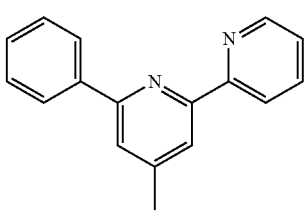
$L^6$ is selected from, for example, the following group.
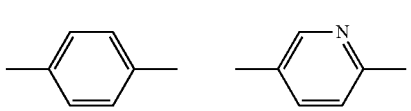
$Ar^e$ is selected from, for example, the following group.
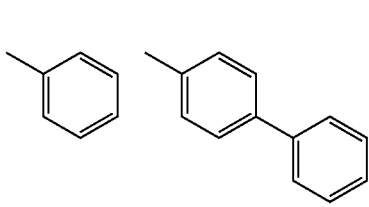
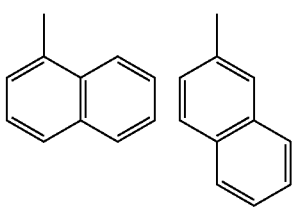

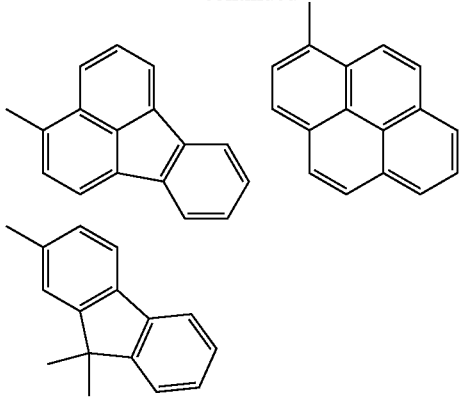

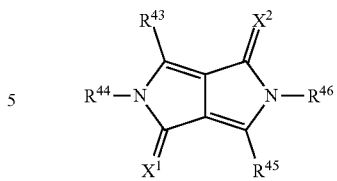

(In the formula, $R^{43}$ to $R^{46}$ each independently represent a hydrogen atom, a substituted or unsubstituted aliphatic group, a substituted or unsubstituted alicyclic group, a substituted or unsubstituted carbocyclic aromatic ring group, or a substituted or unsubstituted heterocyclic group, and $X^1$ and $X^2$ each independently represent an oxygen atom, a sulfur atom, or a dicyanomethylene group.)

In addition to the foregoing, the following compound (see JP 2000-173774 A) is also suitably used.

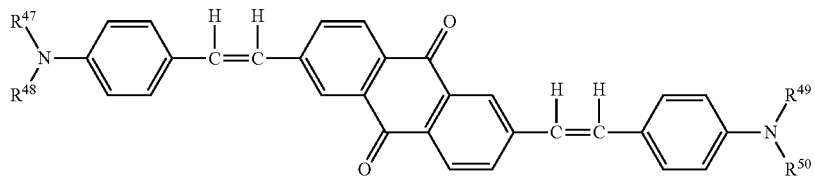

$Ar^b$ is selected from, for example, the following arylanthranil group.

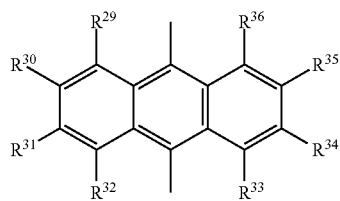

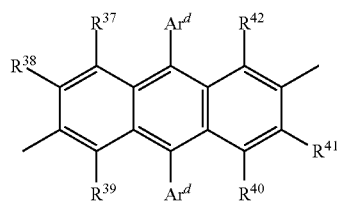

(In the formulae, $R^{29}$ to $R^{42}$ each independently represent a hydrogen atom, a halogen atom, an alkyl group having 1 to 20 carbon atoms, an alkoxy group having 1 to 20 carbon atoms, an aryloxy group having 6 to 40 carbon atoms, an aryl group which has 6 to 40 carbon atoms and which may have a substituent, or a heteroaryl group having 3 to 40 carbon atoms, and $Ar^d$ represents an aryl group which has 6 to 40 carbon atoms and which may have a substituent, or a heteroaryl group having 3 to 40 carbon atoms.)

In addition, a nitrogen-containing heterocyclic derivative in which $R^{29}$ to $R^{36}$ in $Ar^b$ represented by the above formula each represent a hydrogen atom is preferable.

In addition to the foregoing, the following compound (see JP 09-3448 A) is also suitably used.

In the formula, $R^{47}$, $R^{48}$, $R^{49}$, and $R^{50}$ represent groups identical to or different from one another, and each represent an aryl group represented by the following formula.

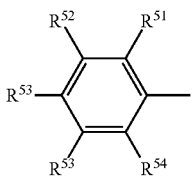

(In the formula, $R^{51}$, $R^{52}$, $R^{53}$, $R^{54}$, and $R^{55}$ represent groups identical to or different from one another, and each may represent a hydrogen atom, or at least one of them may represent a saturated or unsaturated alkoxyl, alkyl, amino, or alkylamino group.)

Further, a polymer compound containing the nitrogen-containing heterocyclic group or nitrogen-containing heterocyclic derivative is also permitted.

In addition, the electron transporting layer preferably contains at least one of the nitrogen-containing heterocyclic derivatives represented by the following general formulae (201) to (203).

(201)

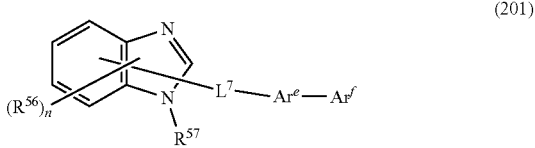

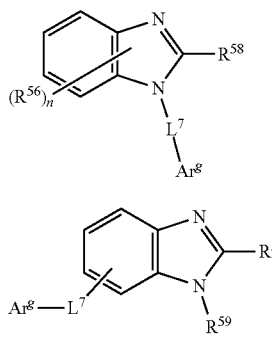

(202)

(203)

In the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, n represents an integer of 0 to 4, $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms, $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, $L^7$ represents a single bond, an arylene group which has 6 to 60 carbon atoms and which may have a substituent, a pyridinylene group which may have a substituent, a quinolihylene group which may have a substituent, or a fluorenylene group which may have a substituent, $Ar^g$ represents an arylene group which has 6 to 60 carbon atoms and which may have a substituent, a pyridinylene group which may have a substituent, or a quinolinylene group which may have a substituent, and $Ar^f$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

In the formulae, $Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$—$Ar^f$ ($Ar^e$ and $Ar^f$ each have the same meaning as that described above).

It should be noted that, in the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

The aryl group which has 6 to 60 carbon atoms is preferably an aryl group having 6 to 40 carbon atoms, or more preferably an aryl group having 6 to 20 carbon atoms, and specific examples of such groups include a phenyl group, a naphthyl group, an anthryl group, a phenanthryl group, a naphthacenyl group, a chrysenyl group, a pyrenyl group, a biphenyl group, a terphenyl group, a tolyl group, a t-butylphenyl group, a (2-phenylpropyl)phenyl group, a fluoranthenyl group, a fluorenyl group, a monovalent group composed of spirobifluorene, a perfluorophenyl group, a perfluoronaphthyl group, a perfluoroanthryl group, a perfluorobiphenyl group, a monovalent group composed of 9-phenylanthracene, a monovalent group composed of 9-(1'-naphthyl) anthracene, a monovalent group composed of 9-(2'-naphthyl)anthracene, a monovalent group composed of 6-phenylchrysene, and a monovalent group composed of 9-[4-(diphenylamino)phenyl]anthracene; a phenyl group, a naphthyl group, a biphenyl group, a terphenyl group, a 9-(10-phenyl)anthryl group, a 9-[10-(1'-naphthyl)]anthryl group, a 9-[10-(2'-naphthyl)]anthryl group, or the like is preferable.

The alkyl group which has 1 to 20 carbon atoms is preferably an alkyl group having 1 to 6 carbon atoms, and specific examples of such group include a methyl group, an ethyl group, a propyl group, a butyl group, a pentyl group, a hexyl group, and a haloalkyl group such as a trifluoromethyl group. An alkyl group having 3 or more carbon atoms may be linear, cyclic, or branched.

The alkoxy group which has 1 to 20 carbon atoms is preferably an alkoxy group having 1 to 6 carbon atoms, and specific examples of such group include a methoxy group, an ethoxy group, a propoxy group, a butoxy group, a pentyloxy group, and a hexyloxy group. An alkoxy group having 3 or more carbon atoms may be linear, cyclic, or branched.

Examples of the substituent of each group represented by $R^{56}$ include a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent.

Examples of the halogen atom include fluorine, chlorine, bromine, and iodine.

Examples of the alkyl group which has 1 to 20 carbon atoms, the alkoxy group which has 1 to 20 carbon atoms, and the aryl group which has 6 to 40 carbon atoms include the same examples as those described above.

Examples of the aryloxy group which has 6 to 40 carbon atoms include a phenoxy group and a biphenyloxy group.

Examples of the heteroaryl group which has 3 to 40 carbon atoms include a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, and a triazolyl group.

n represents an integer of 0 to 4, or preferably 0 to 2.

In the formula (201), $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms.

Specific examples of the respective groups, and preferable carbon numbers and preferable substituents of those groups are the same as those described for $R^{56}$.

In the formulae (202) and (203), $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of the respective groups, and preferable carbon numbers and preferable substituents of those groups are the same as those described for $R^{56}$.

In the formulae (201) to (203), $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent.

The arylene group which has 6 to 60 carbon atoms is preferably an arylene group having 6 to 40 carbon atoms, or more preferably an arylene group having 6 to 20 carbon atoms, and specific examples of such groups include divalent groups each formed by removing one hydrogen atom from the aryl group described for R. Examples of the substituent of each group represented by $L^7$ include the same examples as those described for $R^{56}$.

In addition, $L^7$ preferably represents a group selected from the group consisting of the following groups.

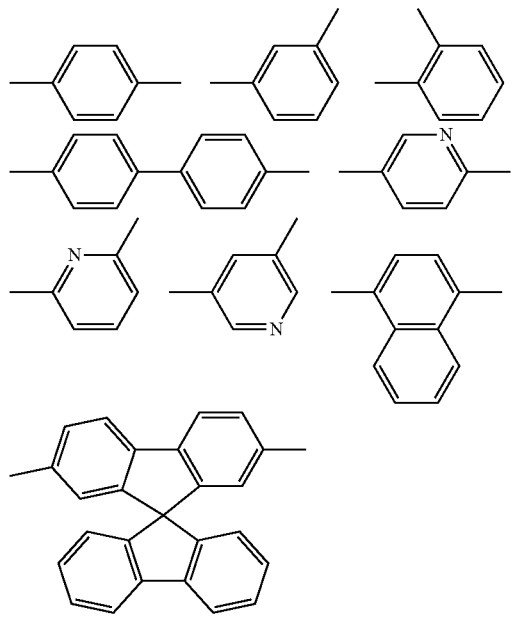

In the formula (201), $Ar^e$ represents an arylene group which has 6 to 60 carbon atoms and which may have a substituent, a pyridinylene group which may have a substituent, or a quinolinylene group which may have a substituent. Examples of the substituents of the respective groups represented by $Ar^e$ and $Ar^g$ include the same examples as those described for $R^{56}$.

In addition, $Ar^e$ preferably represents any one of the groups selected from fused ring groups represented by the following formulae

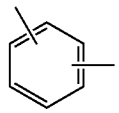
(101)

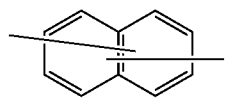
(102)

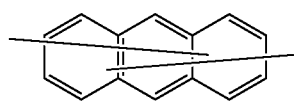
(103)

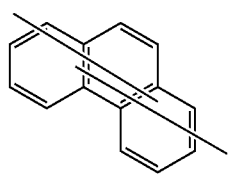
(104)

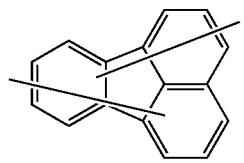
(105)

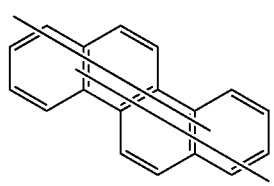
(106)

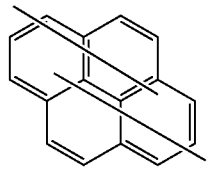
(107)

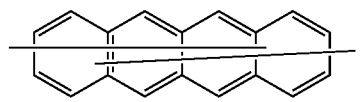
(108)

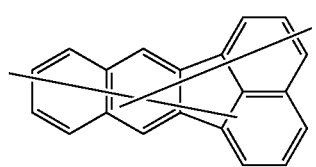
(109)

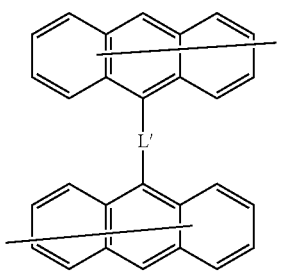 (110)

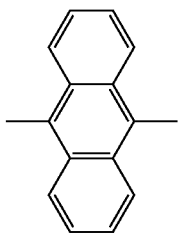 (111)

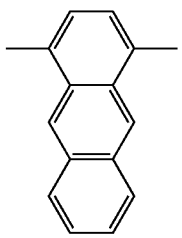 (112)

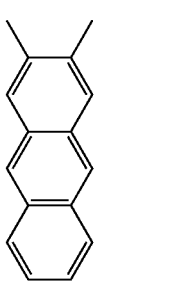 (113)

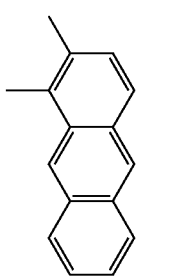 (114)

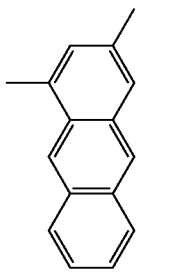 (115)

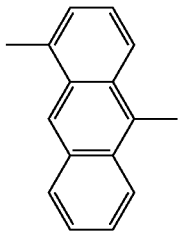 (116)

In the formulae (101) to (110), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (110), L' represents a single bond or a group selected from the group consisting of the following groups.

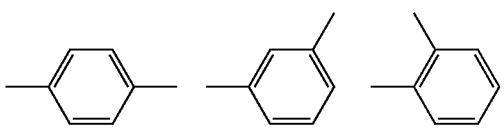

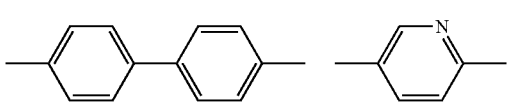

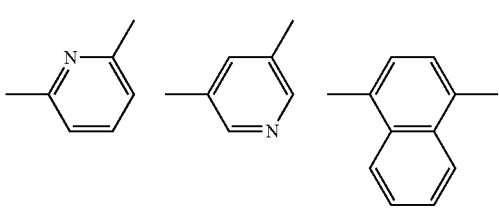

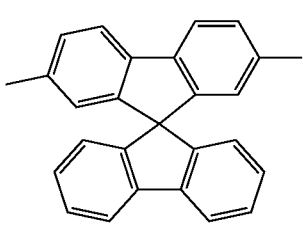

The formula (103) represented by $Ar^e$ is preferably a fused ring group represented by the following formulae (111) to (125).

-continued (117) 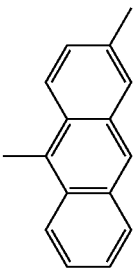

(118) 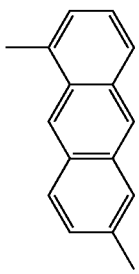

(119) 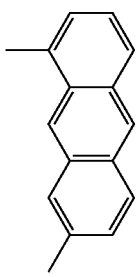

(120)

(121) 

(122) 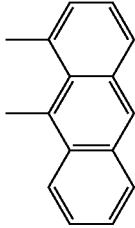

-continued

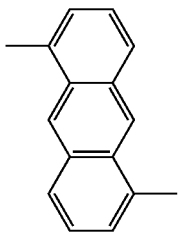

(123)

(124) 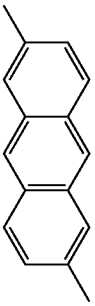

(125) 

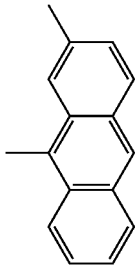

In the formulae (111) to (125), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (201), $Ar^f$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of the respective groups, and preferable carbon numbers and preferable substituents of those groups are the same as those described for $R^{56}$.

In the formulae (202) and (203), $Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which have a substituent, an alkoxy group which has 1 to 20 carbon atoms and which may have a substituent, or a group represented by —Ar$^e$—Ar$^f$ (Ar$^e$ and Ar$^e$ each have the same meaning as that described above).

Specific examples of the respective groups, and preferable carbon numbers and preferable substituents of those groups are the same as those described for R$^{56}$.

In addition, Ar$^g$ preferably represents any one of the groups selected from fused ring groups represented by the following formulae (126) to (135).

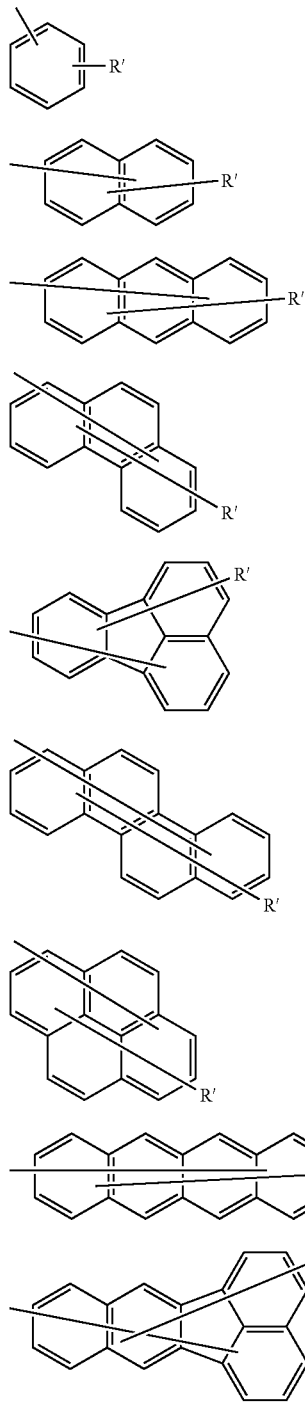

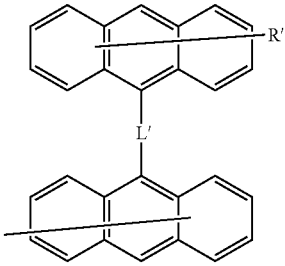

In the formulae (126) to (135), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above.

In the formula (135), L' is the same as that described above.

In the formulae (126) to (135), R' represents a hydrogen atom, an alkyl group which has 1 to 20 carbon atoms and which may have a substituent, an aryl group which has 6 to 40 carbon atoms and which may have a substituent, or a heteroaryl group which has 3 to 40 carbon atoms and which may have a substituent. Specific examples of the respective groups include the same examples as those described above.

The general formula (128) represented by Ar$^g$ is preferably a fused ring group represented by the following formulae (136) to (158).

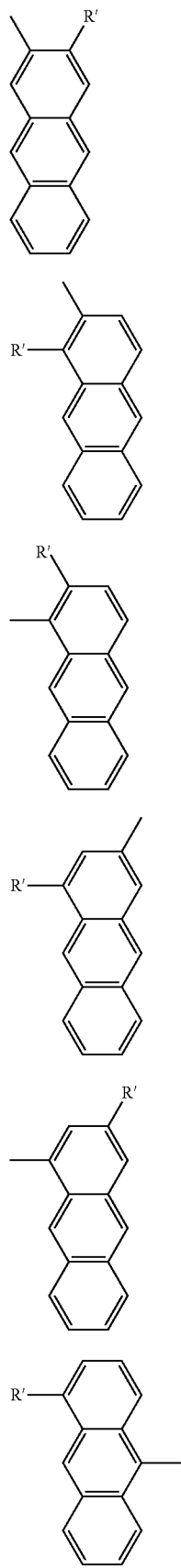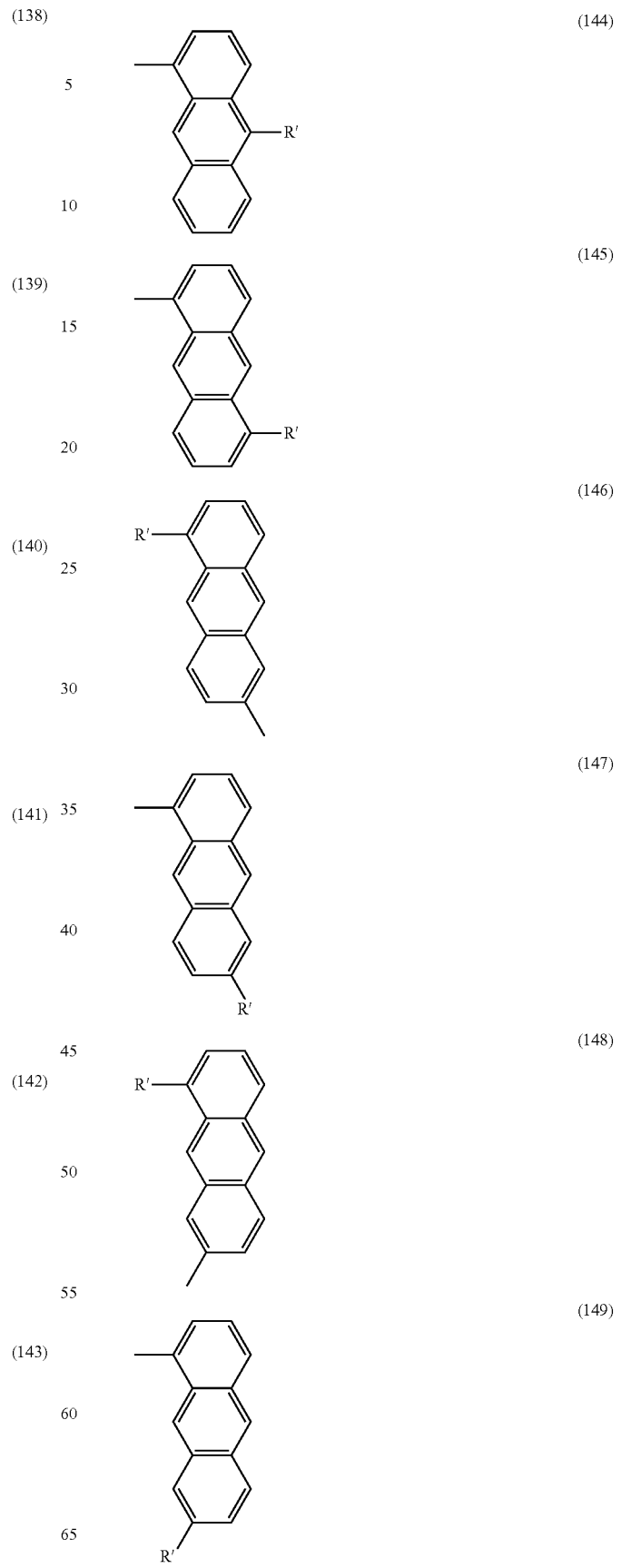

(150) 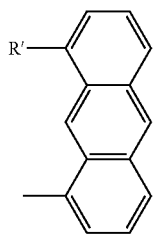

(151) 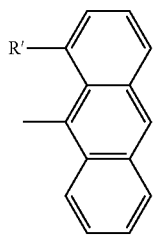

(152) 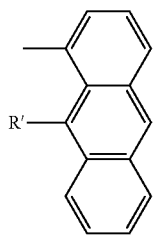

(153) 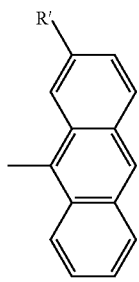

(154) 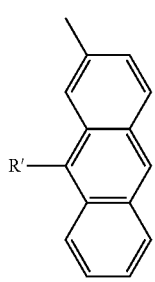

(155) 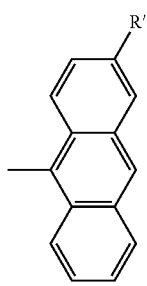

(156) 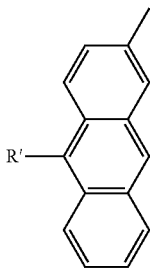

(157) 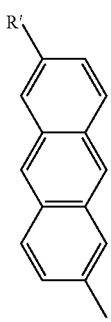

(158) 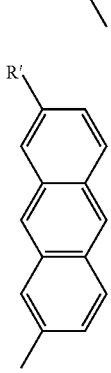

In the formulae (136) to (158), each fused ring may be bonded with a bonding group composed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent, and, when multiple bonding groups of this kind are present, the bonding groups may be identical to or different from each other. Specific examples of the respective groups include the same examples as those described above. R' is the same as that described above.

In addition, it is preferred that $Ar^f$ and $Ar^g$ each independently represent a group selected from the group consisting of the following groups.

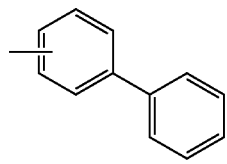

-continued

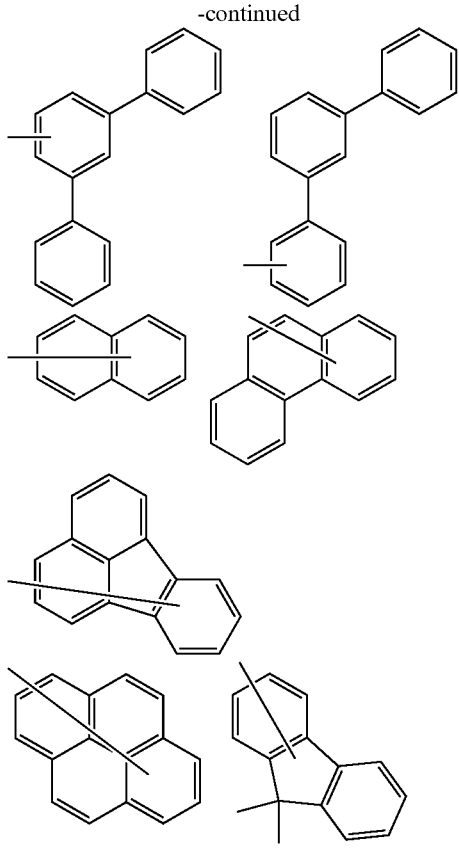

Specific examples of the nitrogen-containing heterocyclic derivatives represented by the formulae (201) to (203) of the present invention are shown below. However, the present invention is not limited to these exemplified compounds.

It should be noted that HAr in the following tables represent any one of the following parts in the formulae (201) to (203).

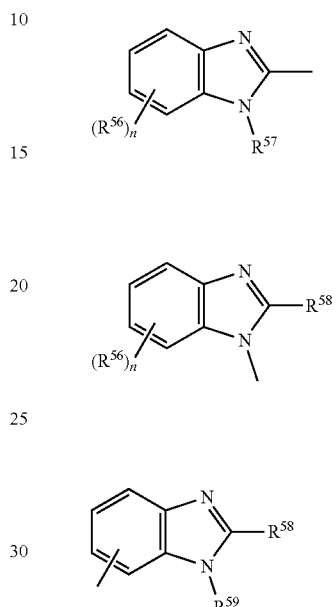

| | HAr—L$^7$—Ar$^e$—Ar$^f$ | | |
|---|---|---|---|
| HAr | L$^7$ | Ar$^e$ | Ar$^f$ |
| 1-1 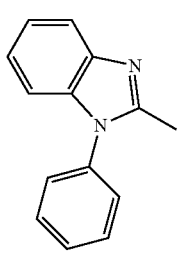 | 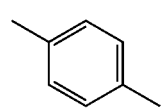 | 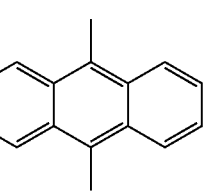 | 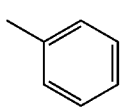 |
| 2 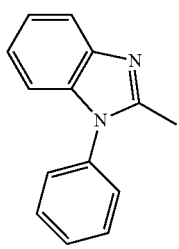 | 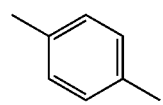 | 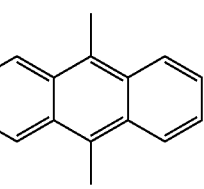 | 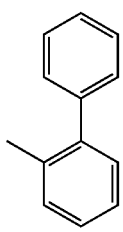 |

-continued
| | HAr—L⁷—Arᵉ—Arᶠ | | | |
|---|---|---|---|---|
| | HAr | L⁷ | Arᵉ | Arᶠ |
| 3 | 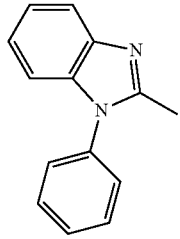 |  | 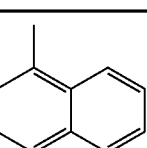 | 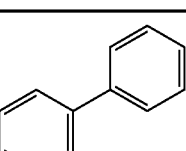 |
| 4 | 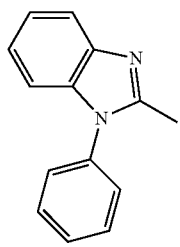 | 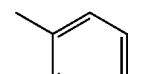 | 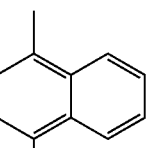 | 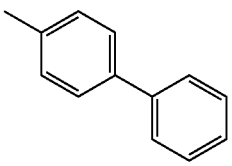 |
| 5 | 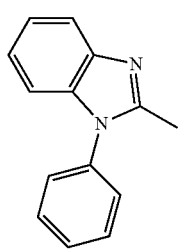 | 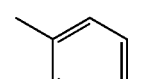 | 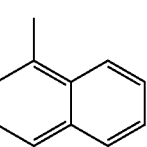 | 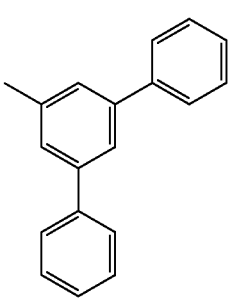 |
| 6 | 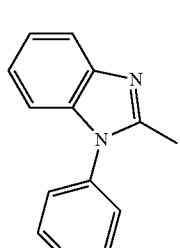 | 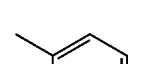 | 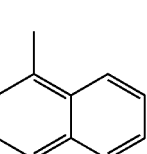 | 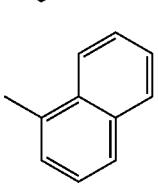 |
| 7 | 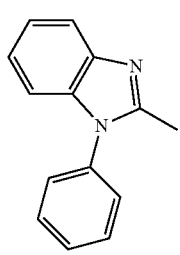 | 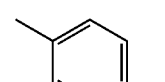 | 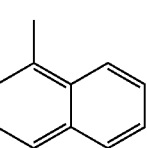 | 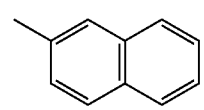 |
| 8 | 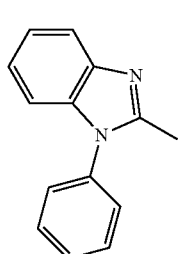 | 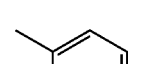 | 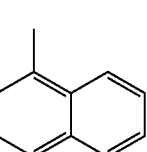 | 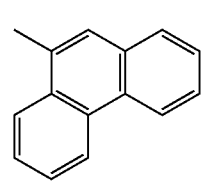 |

HAr—L⁷—Arᵉ—Ar_f
| | HAr | L⁷ | Arᵉ | Ar_f |
|---|---|---|---|---|
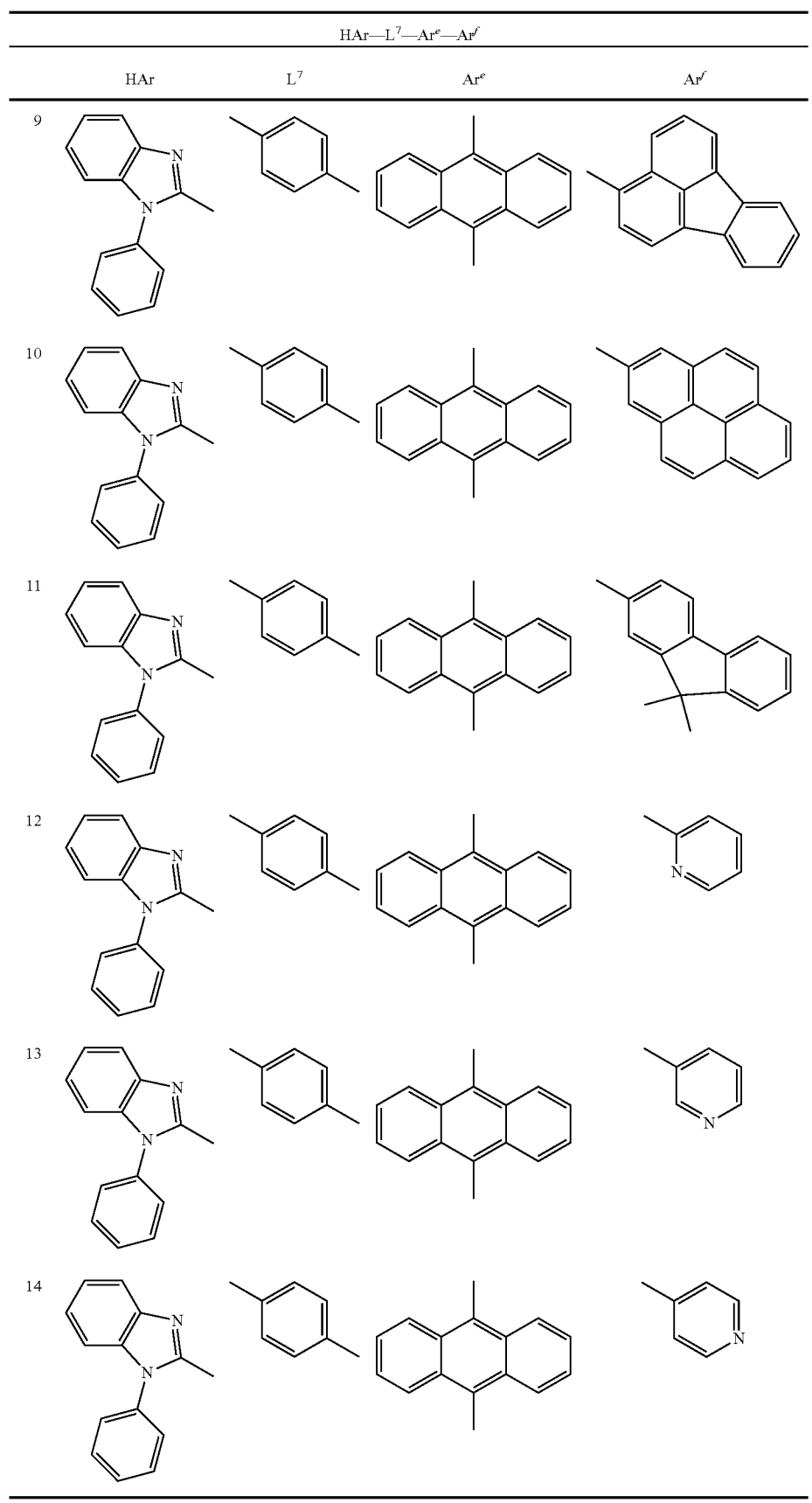

| | HAr | L⁷ | Arᵉ | Arᶠ |
|---|---|---|---|---|
| 2-1 | 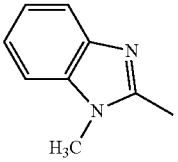 | 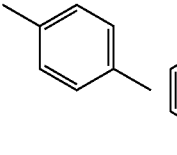 | 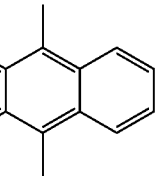 | 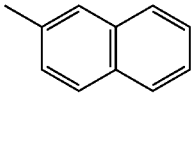 |
| 2 | 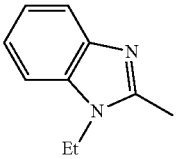 | 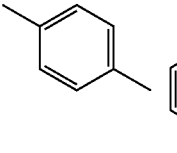 | 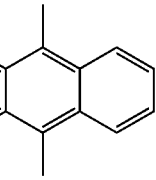 | 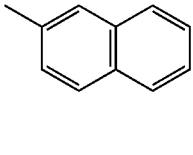 |
| 3 | 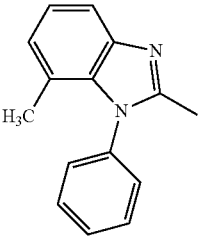 | 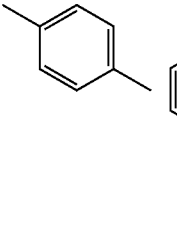 | 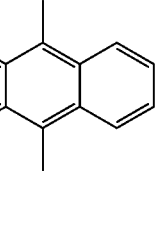 | 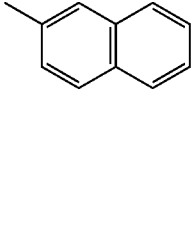 |
| 4 | 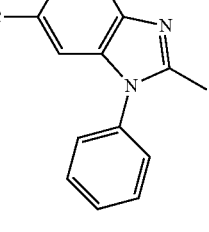 | 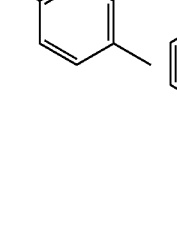 | 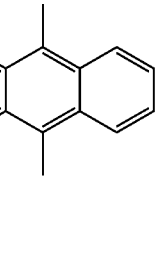 | 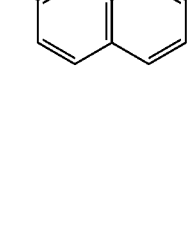 |
| 5 | 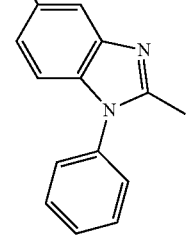 | 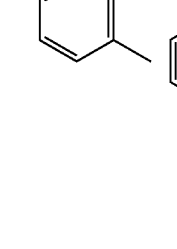 | 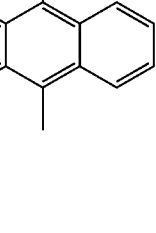 | 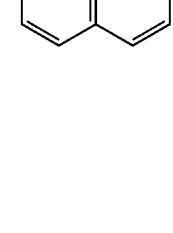 |
| 6 | 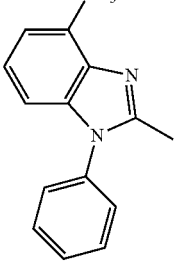 | 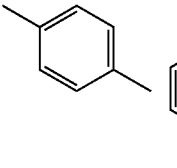 | 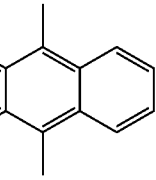 | 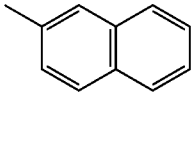 |

-continued
| HAr | L⁷ | Arᵉ | Arᶠ |
|---|---|---|---|
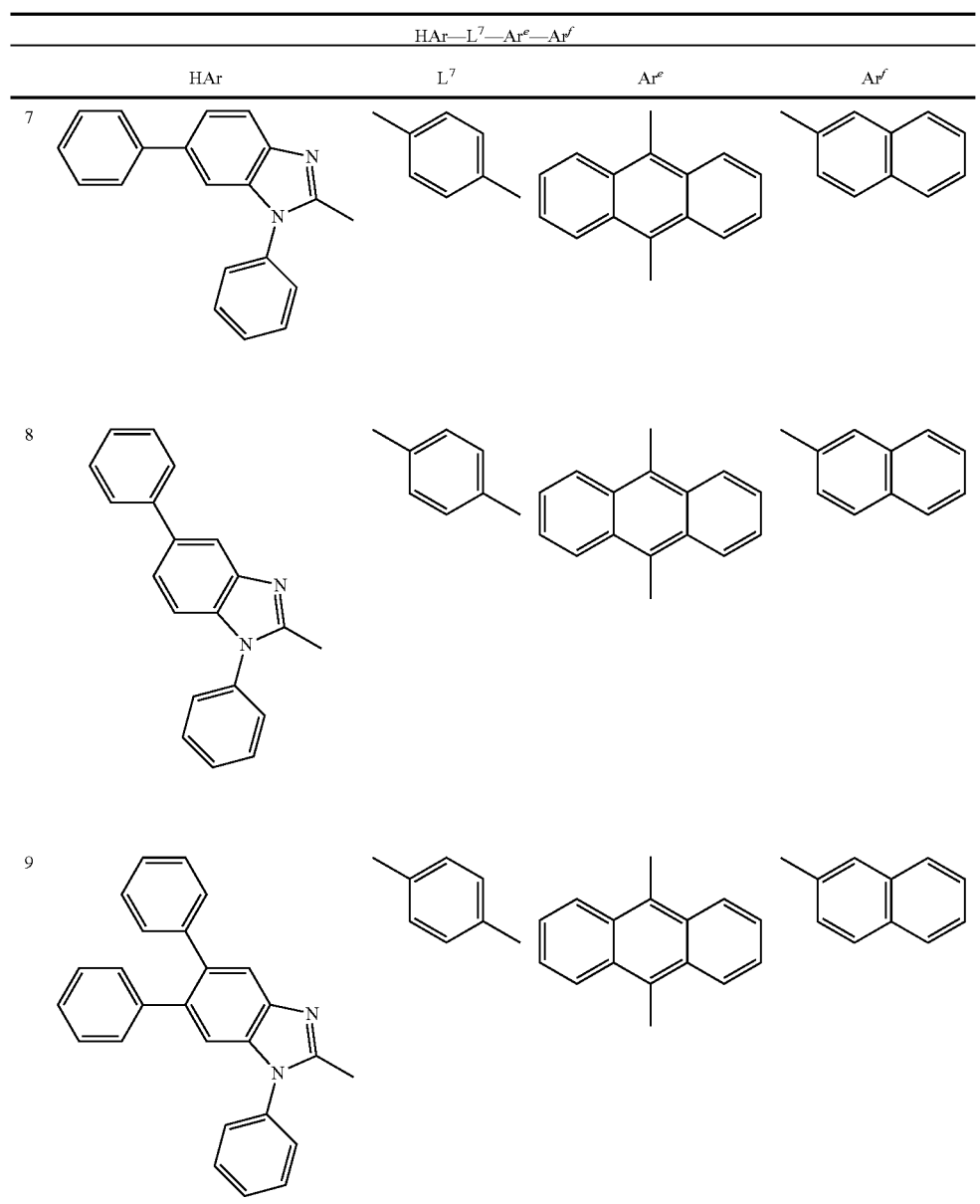
| HAr | L⁷ | Arᵉ | Arᶠ |
|---|---|---|---|
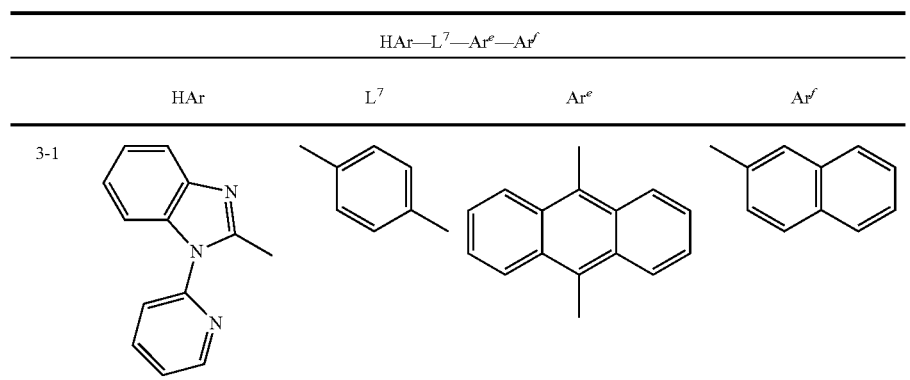

-continued
| | HAr | L⁷ | Arᵉ | Arᶠ |
|---|---|---|---|---|
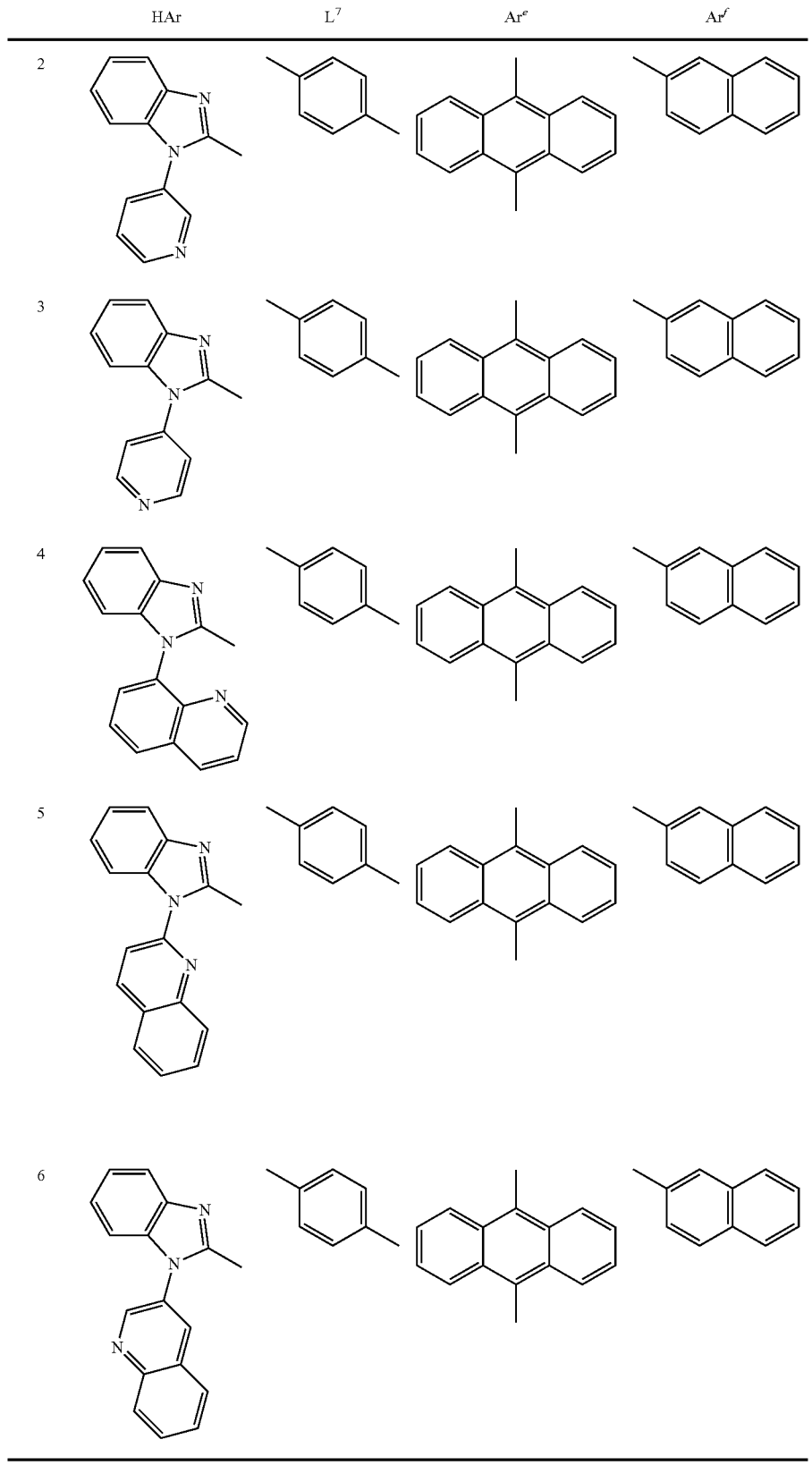

| | HAr—L⁷—Arᵉ—Arᶠ | | | |
|---|---|---|---|---|
| | HAr | L⁷ | Arᵉ | Arᶠ |
| 4-1 | 1-phenyl-2-methylbenzimidazole | — | 9,10-dimethylanthracene | 2-methylnaphthalene |
| 2 | 1-phenyl-2-methylbenzimidazole | 1,3-dimethylbenzene | 9,10-dimethylanthracene | 2-methylnaphthalene |
| 3 | 1-phenyl-2-methylbenzimidazole | 1,2-dimethylbenzene | 9,10-dimethylanthracene | 2-methylnaphthalene |
| 4 | 1-phenyl-2-methylbenzimidazole | 2,5-dimethylpyridine | 9,10-dimethylanthracene | 2-methylnaphthalene |
| 5 | 1-phenyl-2-methylbenzimidazole | 2,6-dimethylpyridine | 9,10-dimethylanthracene | 2-methylnaphthalene |
| 6 | 1-phenyl-2-methylbenzimidazole | 3,5-dimethylpyridine | 9,10-dimethylanthracene | 2-methylnaphthalene |

-continued
| | HAr | L[7] | Ar[e] | Ar[f] |
|---|---|---|---|---|
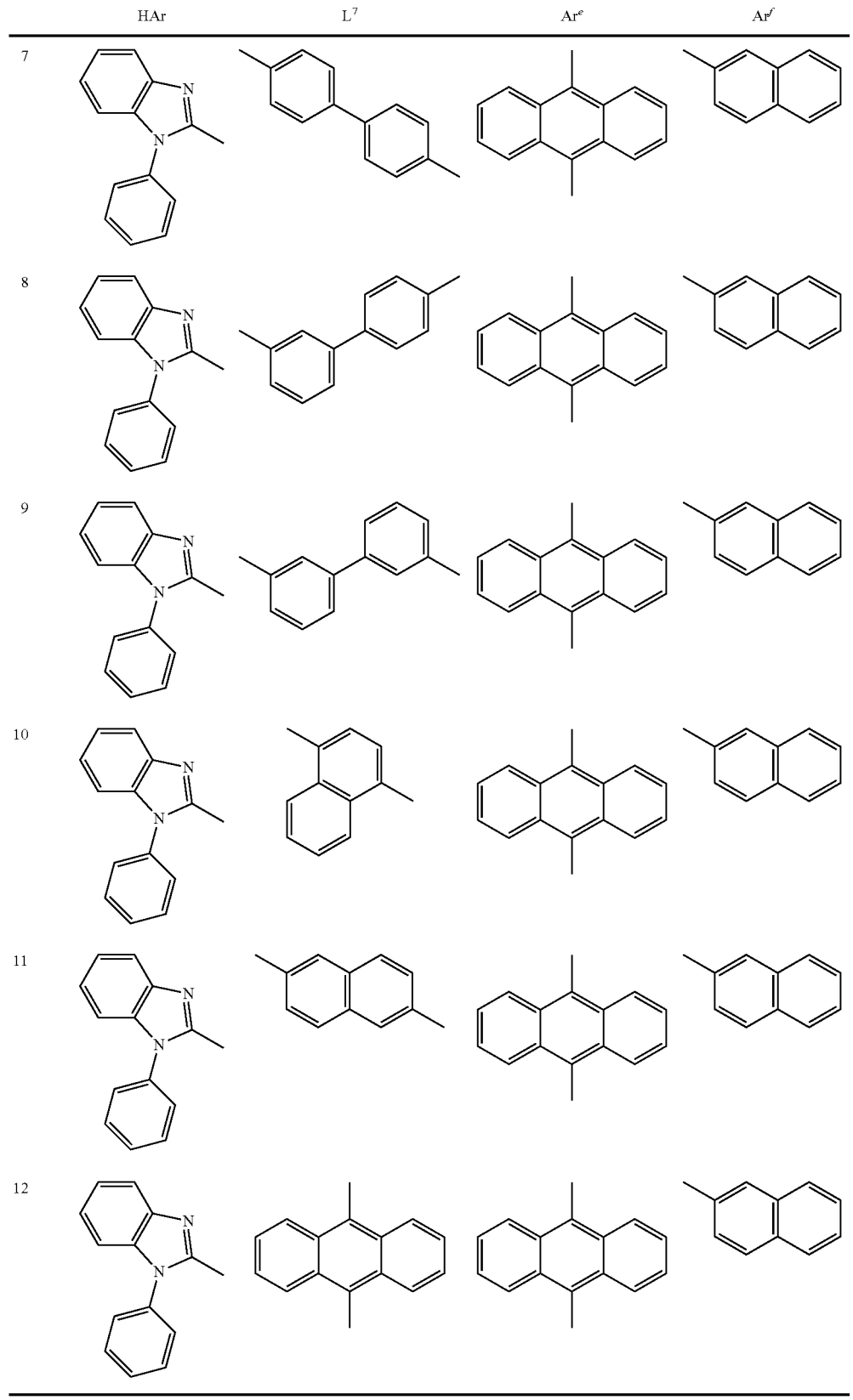

| | HAr | L⁷ | Arᵉ | Arᶠ |
|---|---|---|---|---|
| | | HAr—L⁷—Arᵉ—Arᶠ | | |
| 5-1 | 1-phenyl-2-methylbenzimidazole | 1,4-phenylene | 9,10-dimethyl-2-methylanthracene | 2-naphthyl |
| 2 | 1-phenyl-2-methylbenzimidazole | 1,4-phenylene | 9,10-dimethyl-2-tert-butylanthracene | 2-naphthyl |
| 3 | 1-phenyl-2-methylbenzimidazole | 1,4-phenylene | 9,10-dimethyl-2-phenylanthracene | 2-naphthyl |
| 4 | 1-phenyl-2-methylbenzimidazole | 1,4-phenylene | 9,10-dimethyl-2,6-dimethylanthracene | 2-naphthyl |
| 5 | 1-phenyl-2-methylbenzimidazole | 1,4-phenylene | 9,10-dimethyl-2,6-di-tert-butylanthracene | 2-naphthyl |
| 6 | 1-phenyl-2-methylbenzimidazole | 1,4-phenylene | 9,10-dimethyl-2,6-diphenylanthracene | 2-naphthyl |

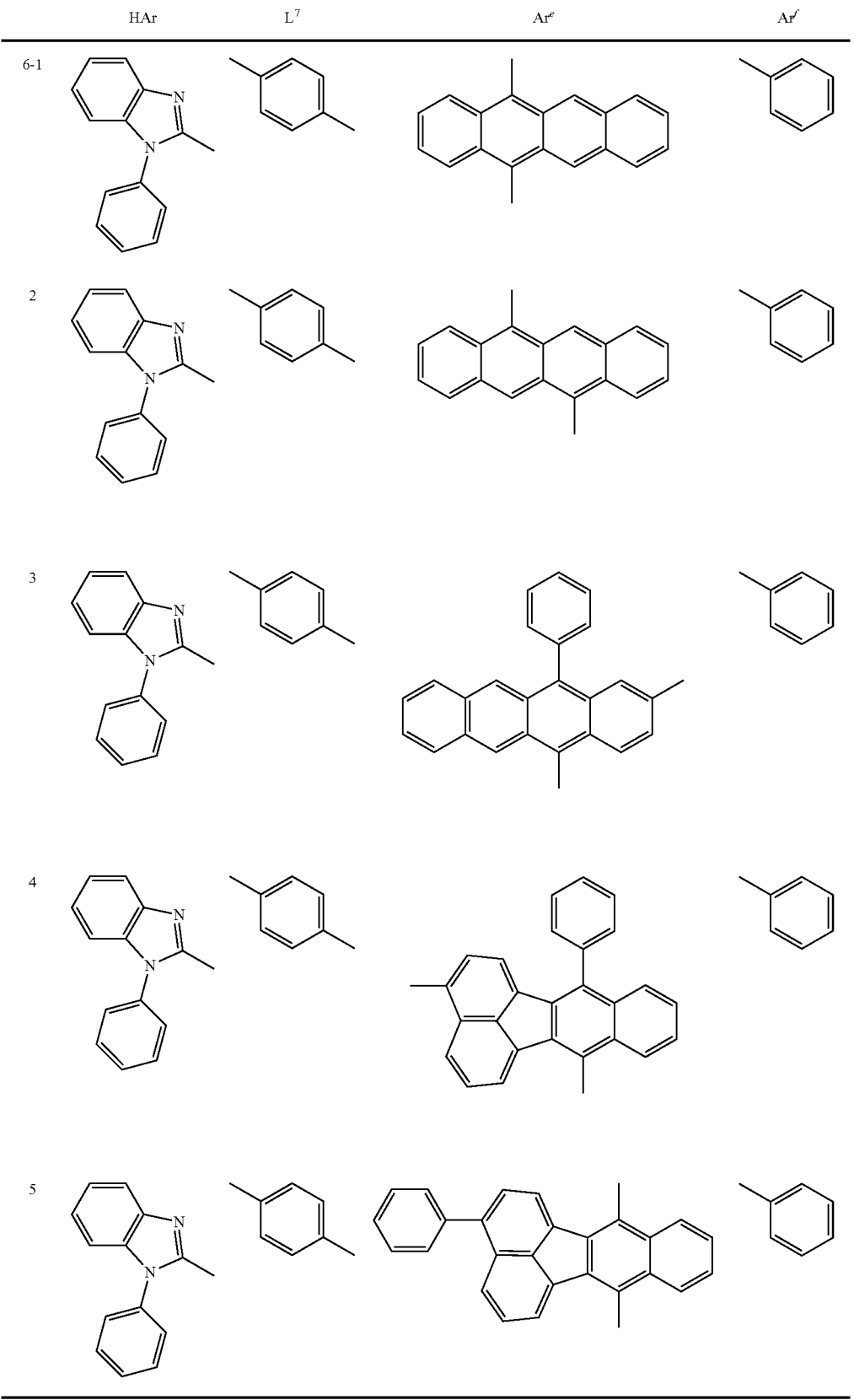

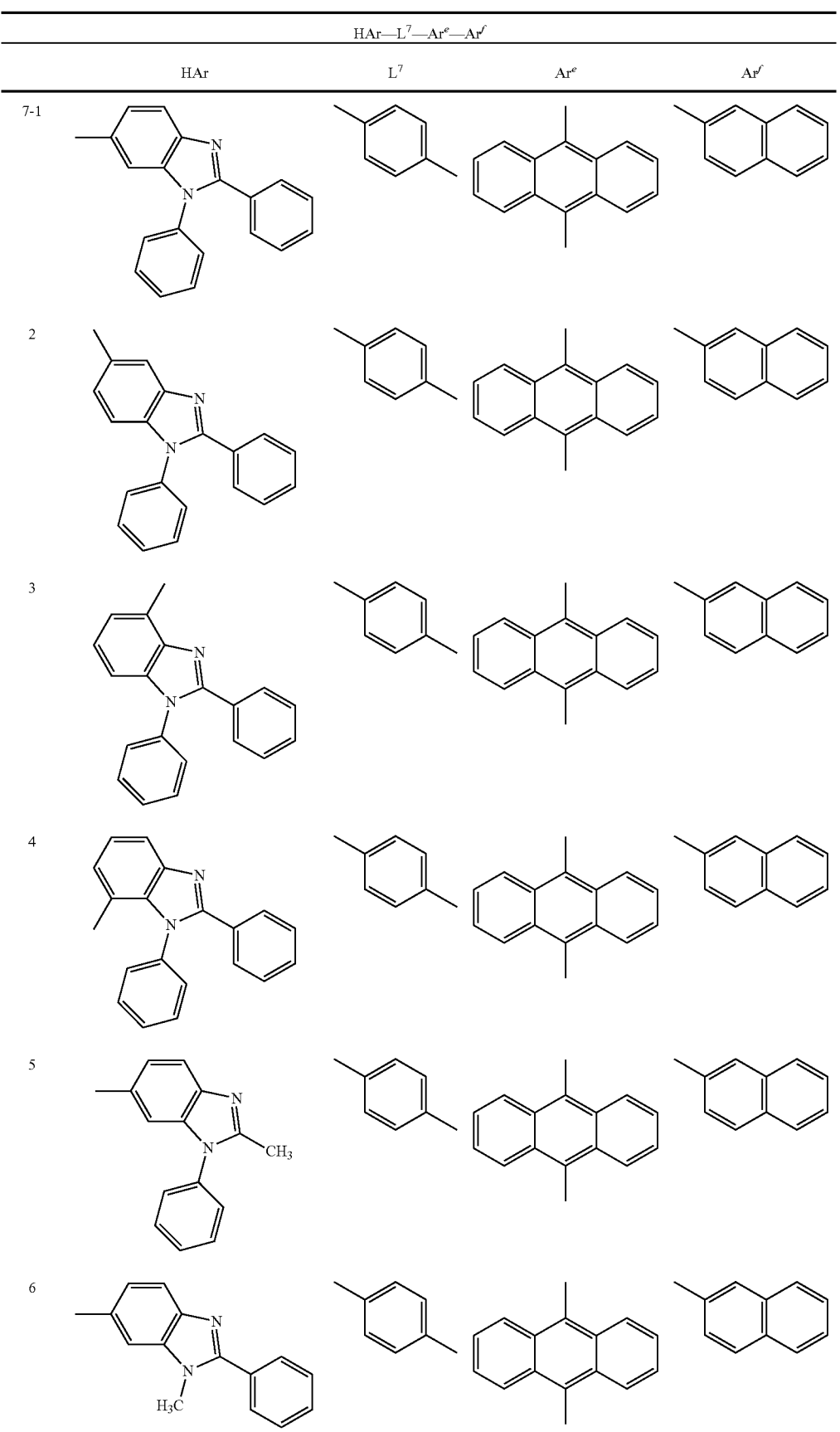

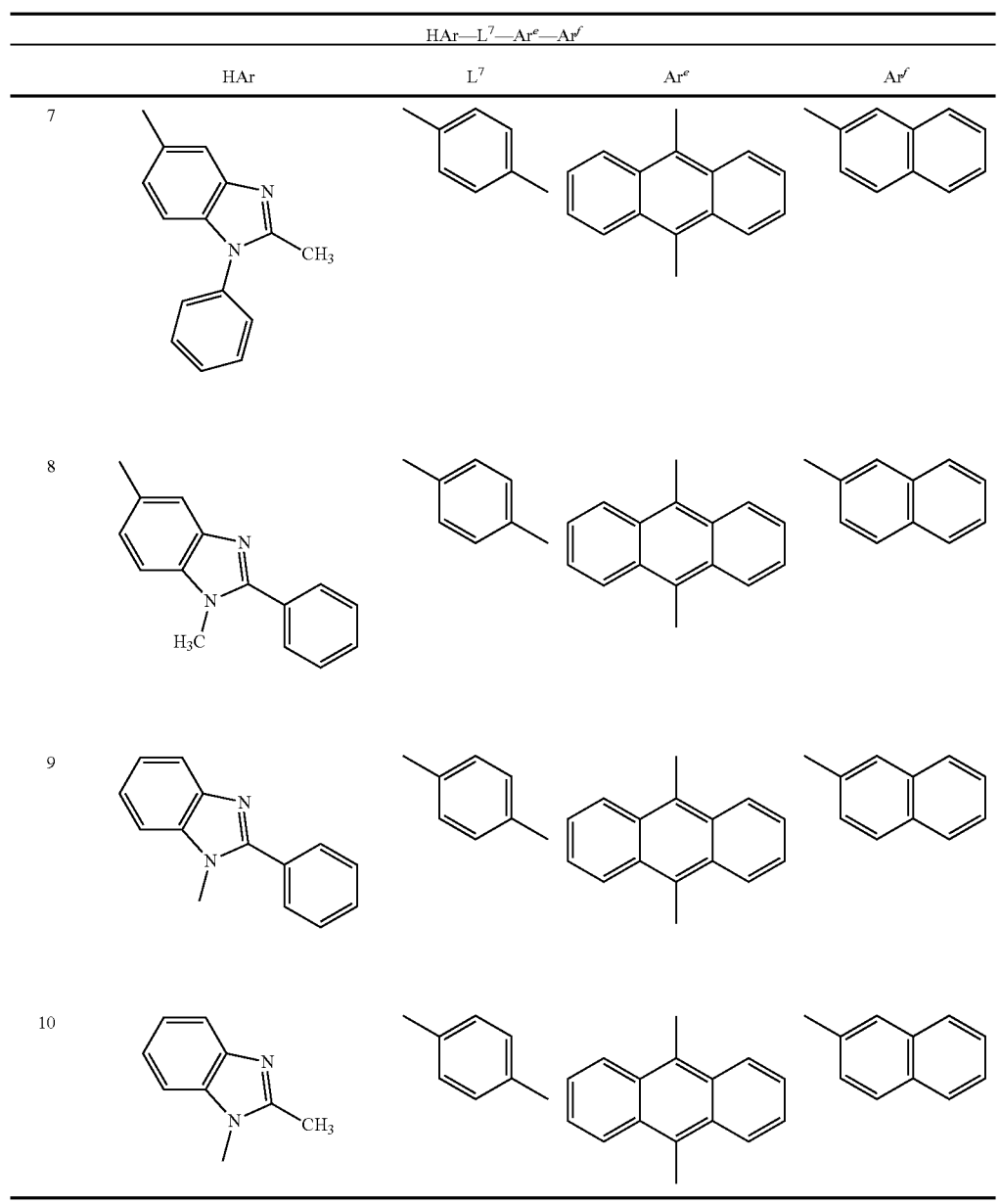
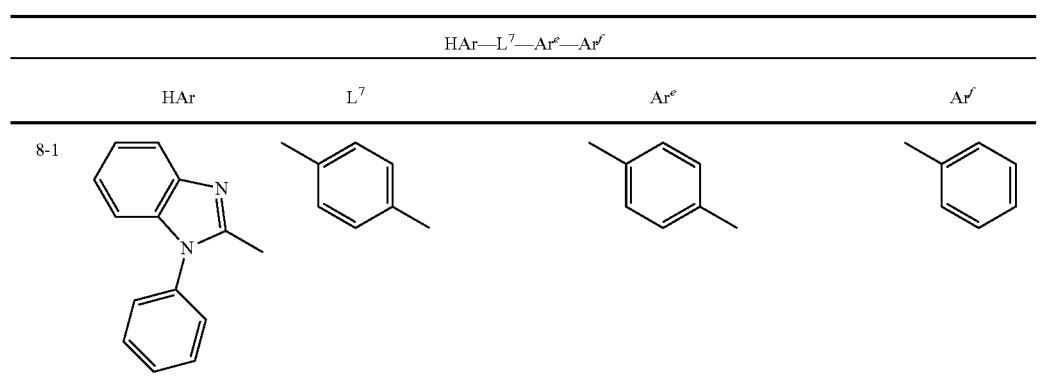

-continued

| | HAr | L⁷ | Arᵉ | Arᶠ |
|---|---|---|---|---|
| 2 | 1-phenyl-2-methylbenzimidazole | 1,4-phenylene | 1,3-phenylene (dimethyl) | phenyl |
| 3 | 1-phenyl-2-methylbenzimidazole | 1,4-phenylene | 1,4-naphthylene | phenyl |
| 4 | 1-phenyl-2-methylbenzimidazole | 1,4-phenylene | 2,6-naphthylene | phenyl |
| 5 | 1-phenyl-2-methylbenzimidazole | 1,4-phenylene | 9,10-phenanthrylene | phenyl |
| 6 | 1-phenyl-2-methylbenzimidazole | 1,4-phenylene | 2,7-phenanthrylene | phenyl |
| 7 | 1-phenyl-2-methylbenzimidazole | 1,4-phenylene | 9-phenanthryl | H |

| HAr—L⁷—Arᵉ—Arᶠ | | | |
|---|---|---|---|
| HAr | L⁷ | Arᵉ | Arᶠ |
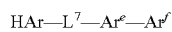

| | HAr—L⁷—Arᵉ—Ar^f | | | |
|---|---|---|---|---|
| | HAr | L⁷ | Arᵉ | Ar^f |
| 9-1 | 1-methyl-2-phenyl-benzimidazole | 1,4-phenylene | 9,10-anthracenediyl | phenyl |
| 2 | 1-methyl-2-phenyl-benzimidazole | 1,4-phenylene | 9,10-anthracenediyl | 2-biphenyl |
| 3 | 1-methyl-2-phenyl-benzimidazole | 1,4-phenylene | 9,10-anthracenediyl | 3-biphenyl |
| 4 | 1-methyl-2-phenyl-benzimidazole | 1,4-phenylene | 9,10-anthracenediyl | 4-biphenyl |
| 5 | 1-methyl-2-phenyl-benzimidazole | 1,4-phenylene | 9,10-anthracenediyl | 3,5-diphenylphenyl |
| 6 | 1-methyl-2-phenyl-benzimidazole | 1,4-phenylene | 9,10-anthracenediyl | 1-naphthyl |
| 7 | 1-methyl-2-phenyl-benzimidazole | 1,4-phenylene | 9,10-anthracenediyl | 2-naphthyl |

US 11,895,917 B2

-continued

| | HAr | L⁷ | Arᵉ | Ar^f |
|---|---|---|---|---|
| 8 | | | | |
| 9 | | | | |
| 10 | | | | |
| 11 | | | | |
| 12 | | | | |
| 13 | | | | |
| 14 | | | | |

| | HAr | L⁷ | Arᵉ | Arᶠ |
|---|---|---|---|---|
| 10-1 | 1-methyl-2-methylbenzimidazole | 1,4-phenylene | 9,10-anthracenediyl | 2-naphthyl |
| 2 | 1-methyl-2-ethylbenzimidazole | 1,4-phenylene | 9,10-anthracenediyl | 2-naphthyl |
| 3 | 1,7-dimethyl-2-phenylbenzimidazole | 1,4-phenylene | 9,10-anthracenediyl | 2-naphthyl |
| 4 | 1,6-dimethyl-2-phenylbenzimidazole | 1,4-phenylene | 9,10-anthracenediyl | 2-naphthyl |
| 5 | 1,5-dimethyl-2-phenylbenzimidazole | 1,4-phenylene | 9,10-anthracenediyl | 2-naphthyl |
| 6 | 1,4-dimethyl-2-phenylbenzimidazole | 1,4-phenylene | 9,10-anthracenediyl | 2-naphthyl |
| 7 | 1-methyl-2-phenyl-6-phenylbenzimidazole | 1,4-phenylene | 9,10-anthracenediyl | 2-naphthyl |

-continued
| | HAr | L⁷ | Arᵉ | Arᶠ |
|---|---|---|---|---|
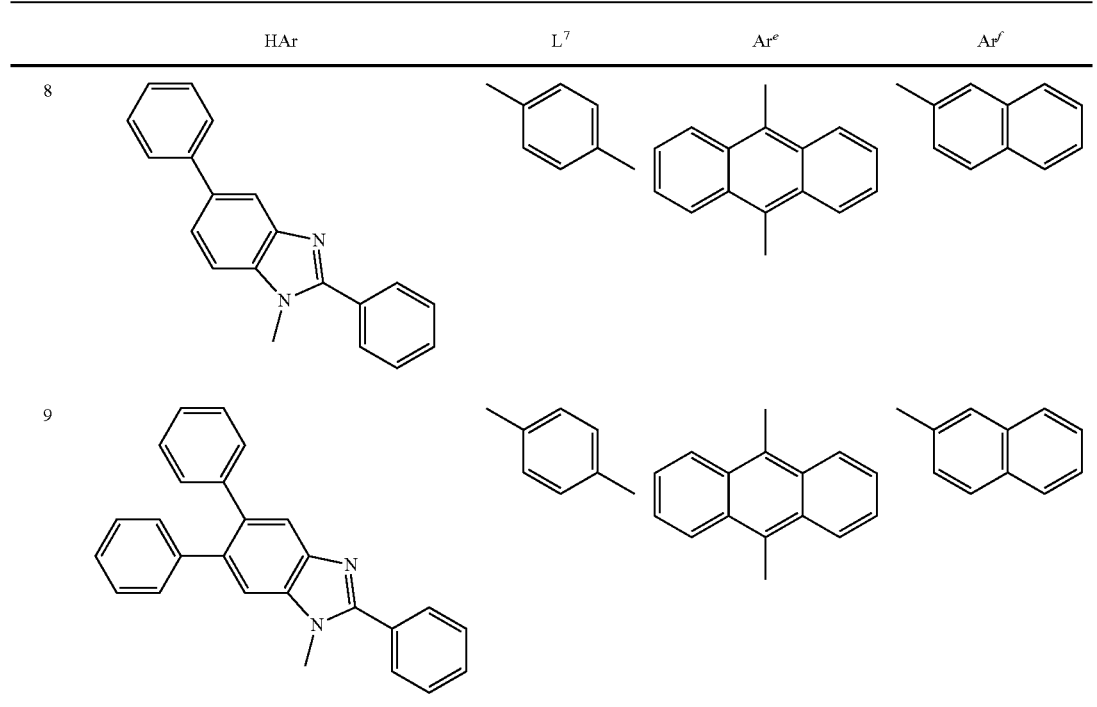
| | HAr | L⁷ | Arᵉ | Arᶠ |
|---|---|---|---|---|
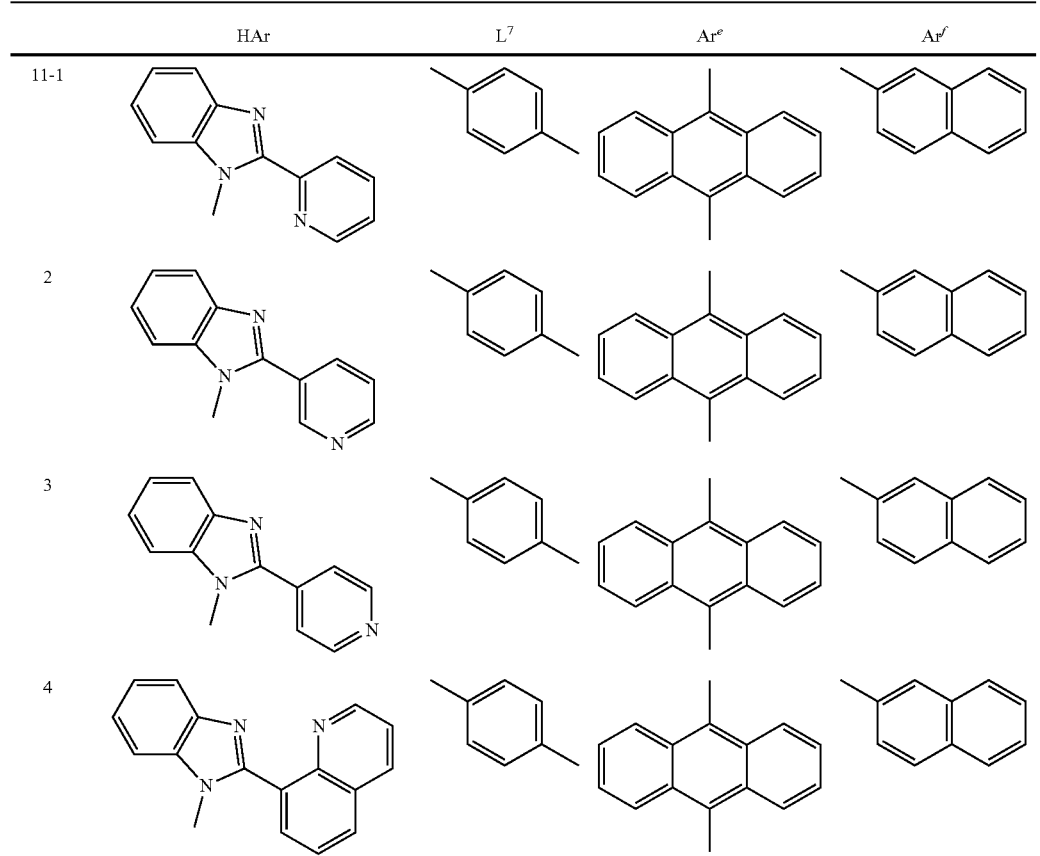

-continued
| | HAr | L⁷ | Arᵉ | Arᶠ |
|---|---|---|---|---|
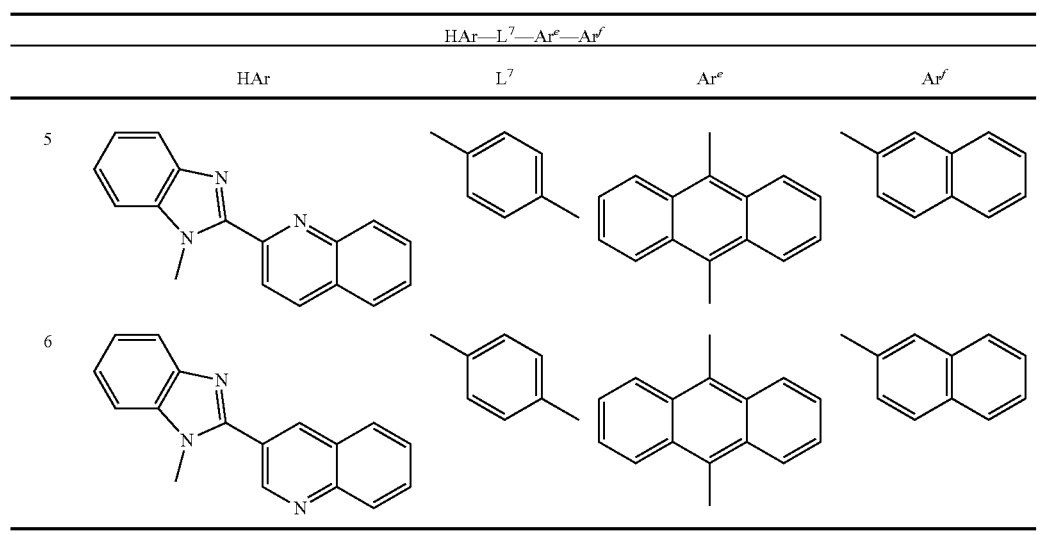
| | HAr | L⁷ | Arᵉ | Arᶠ |
|---|---|---|---|---|
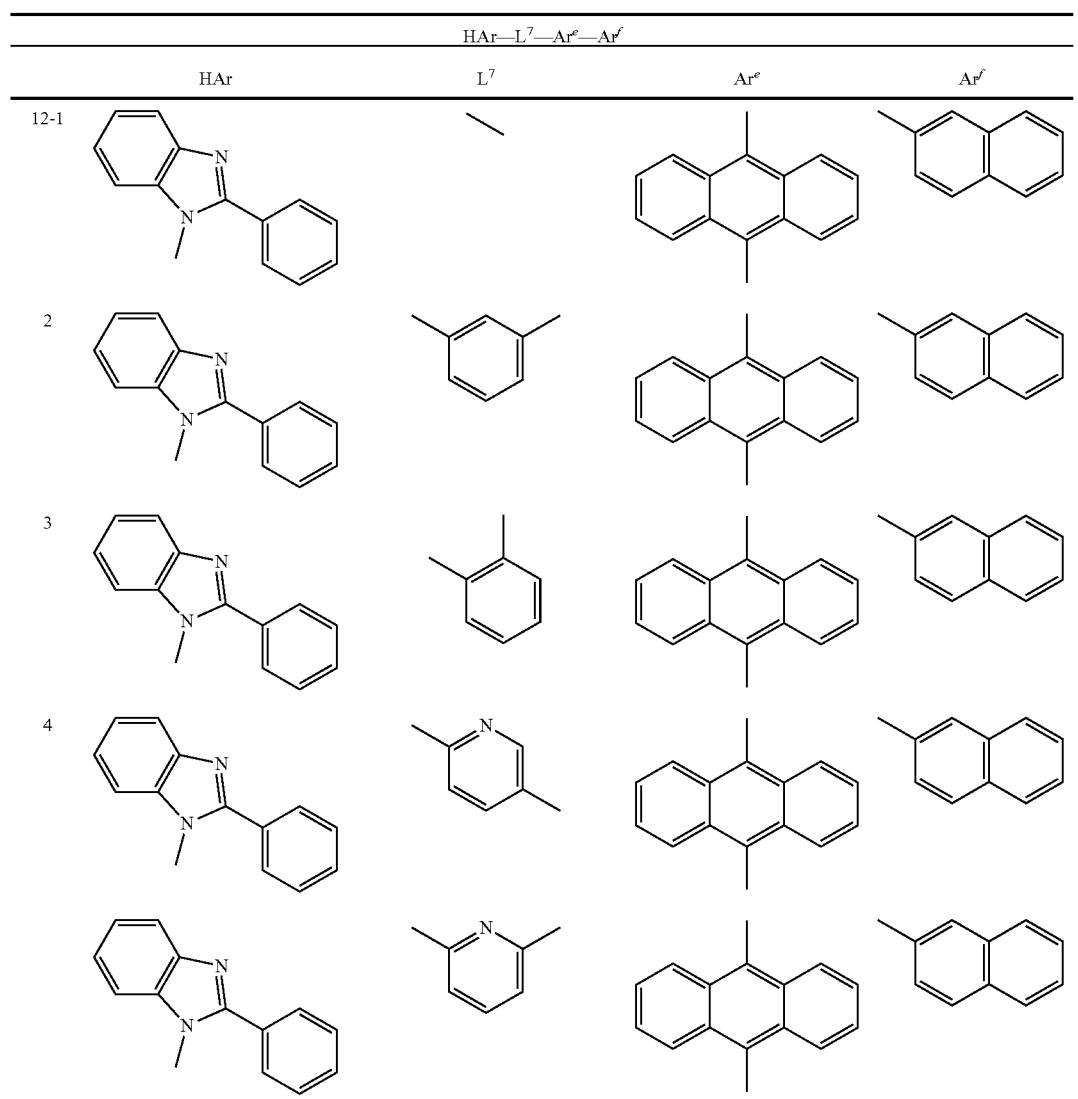

-continued
| | HAr | L[7] | Ar[e] | Ar[f] |
|---|---|---|---|---|
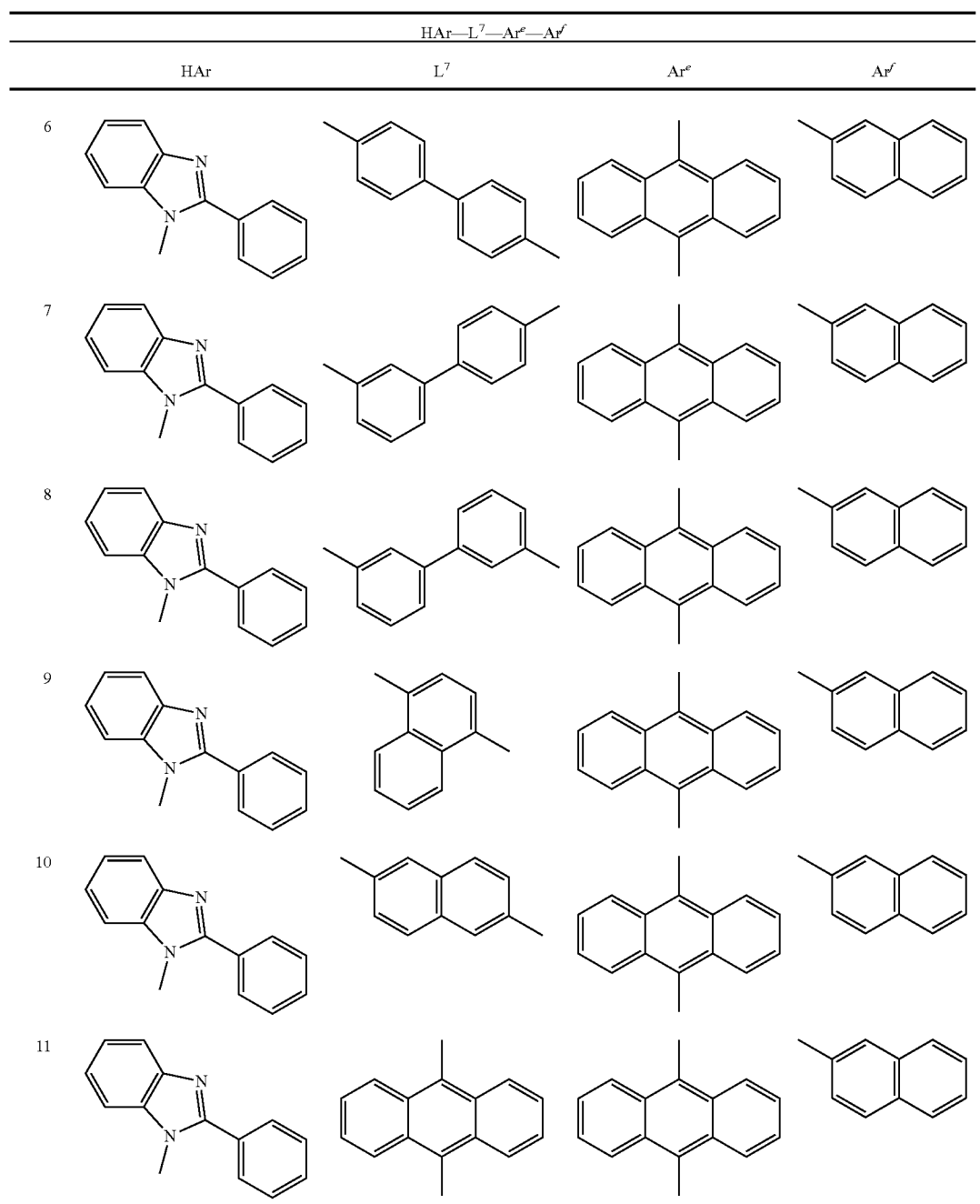
| | HAr | L[7] | Ar[e] | Ar[f] |
|---|---|---|---|---|
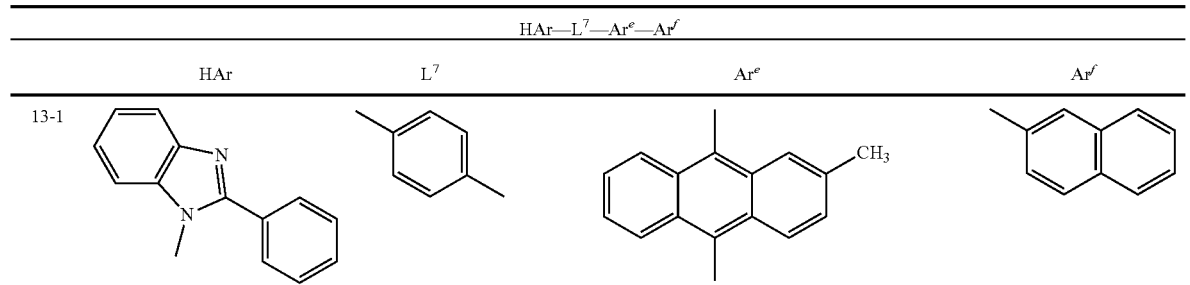

-continued
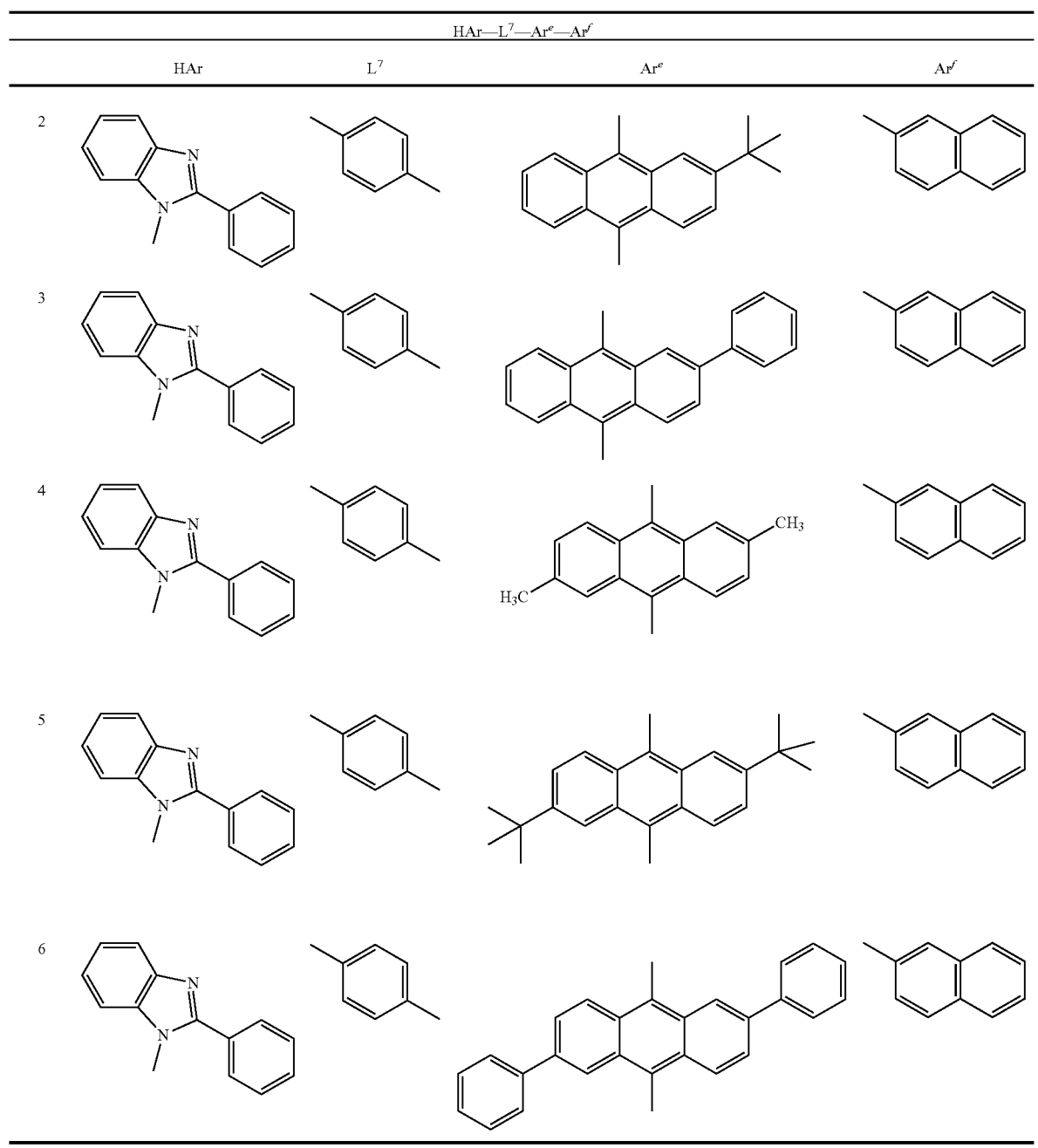
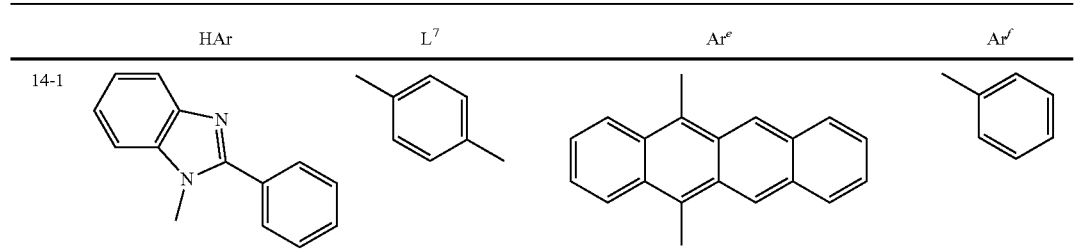

-continued
| HAr—L⁷—Arᵉ—Arᶠ | | | |
|---|---|---|---|
| HAr | L⁷ | Arᵉ | Arᶠ |
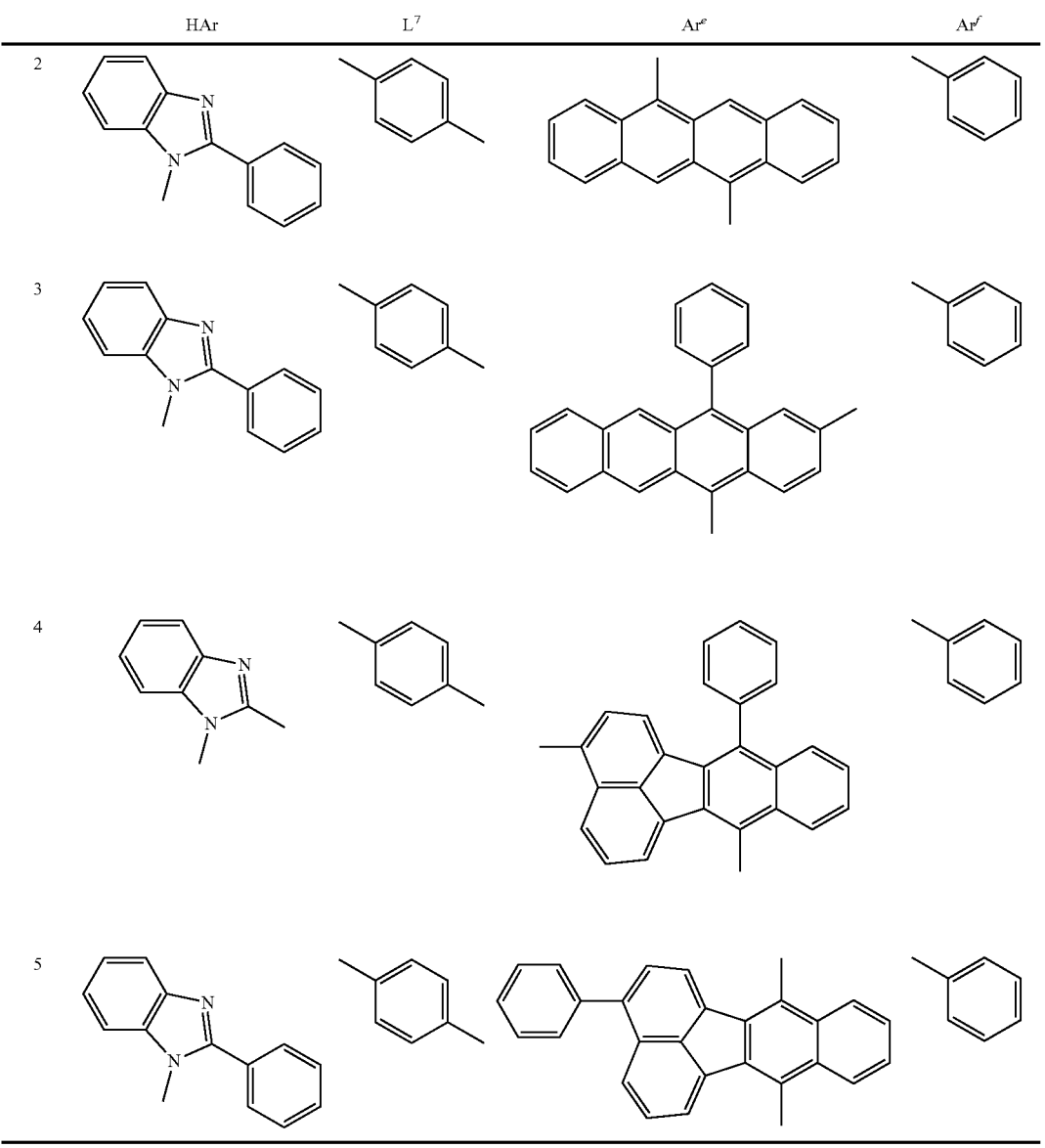
| HAr—L⁷—Arᵉ—Arᶠ | | | |
|---|---|---|---|
| HAr | L⁷ | Arᵉ | Arᶠ |
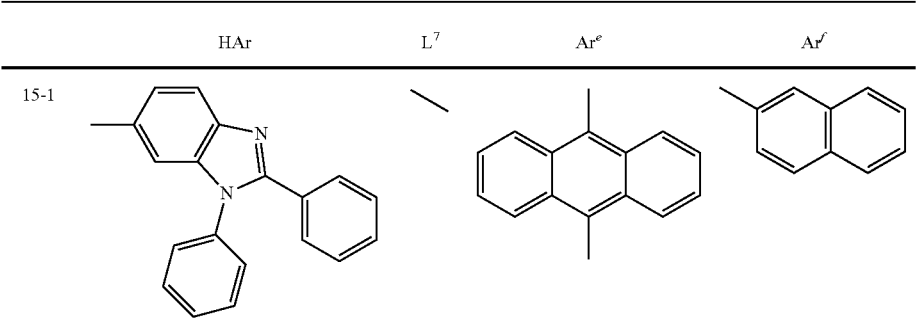

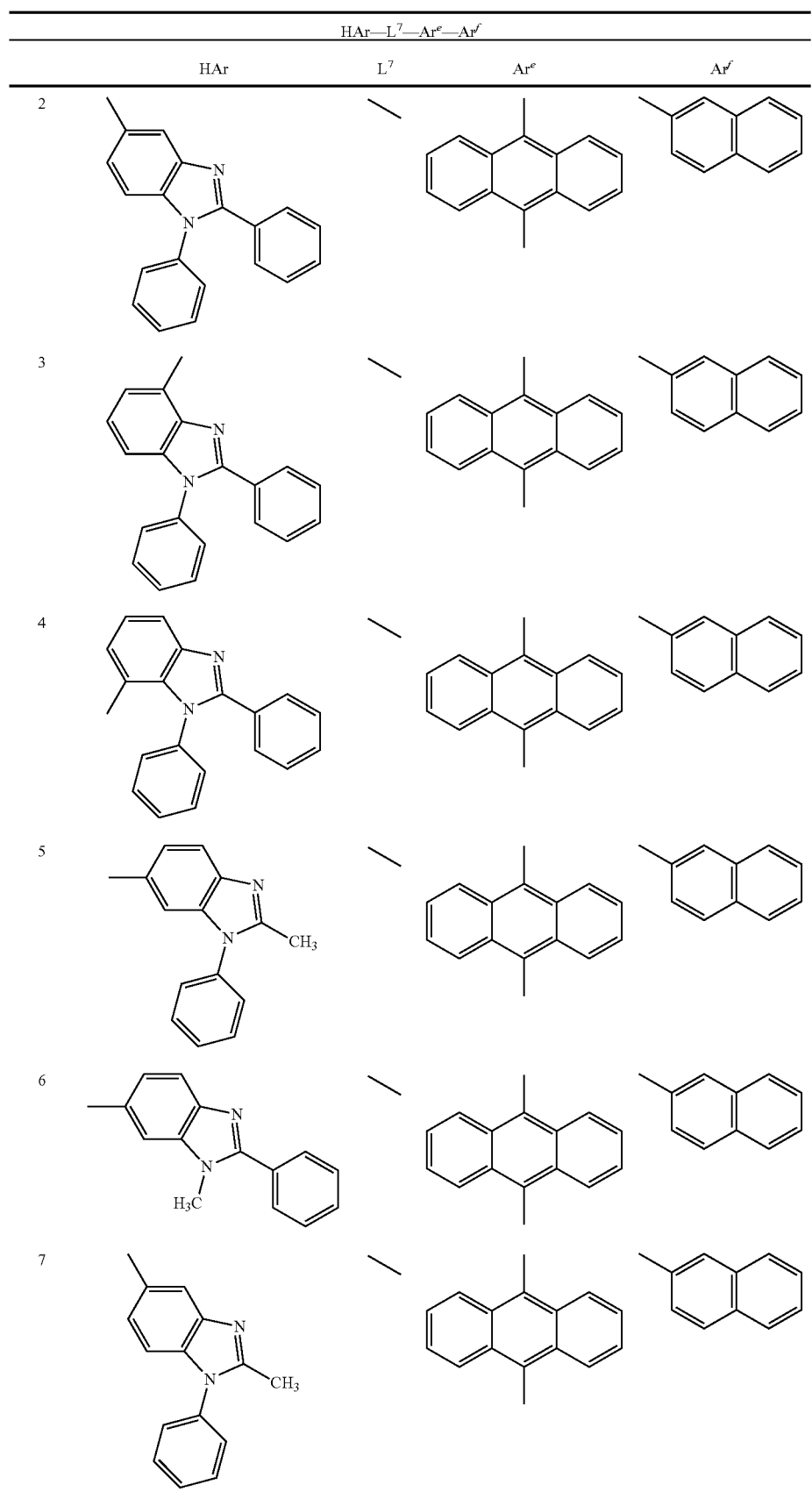

-continued
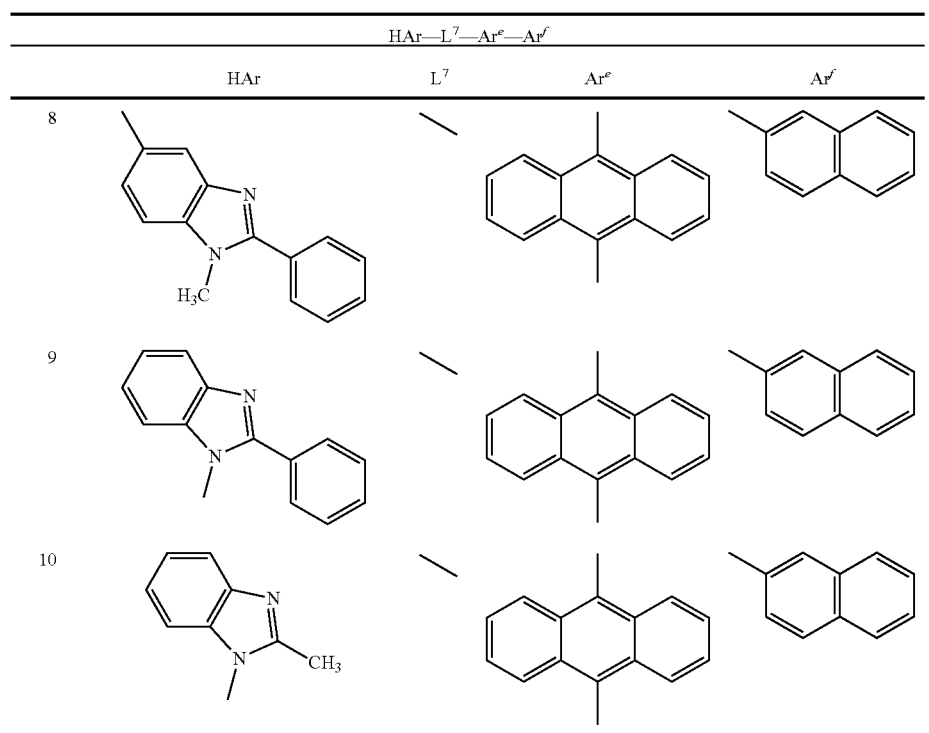
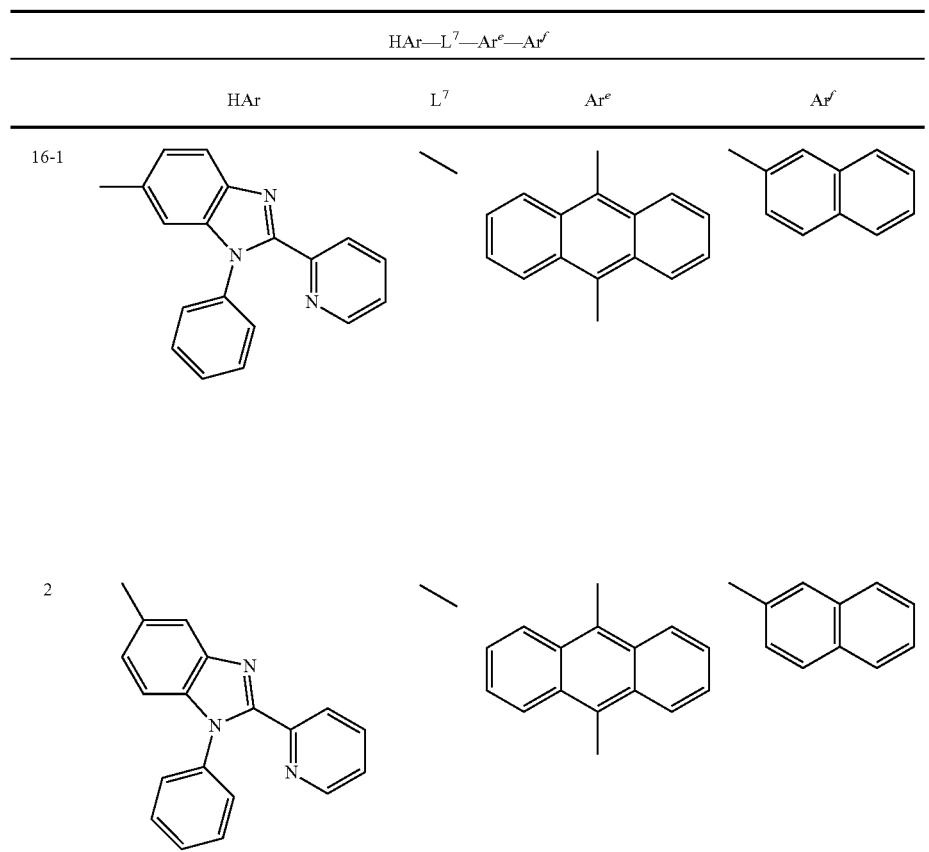

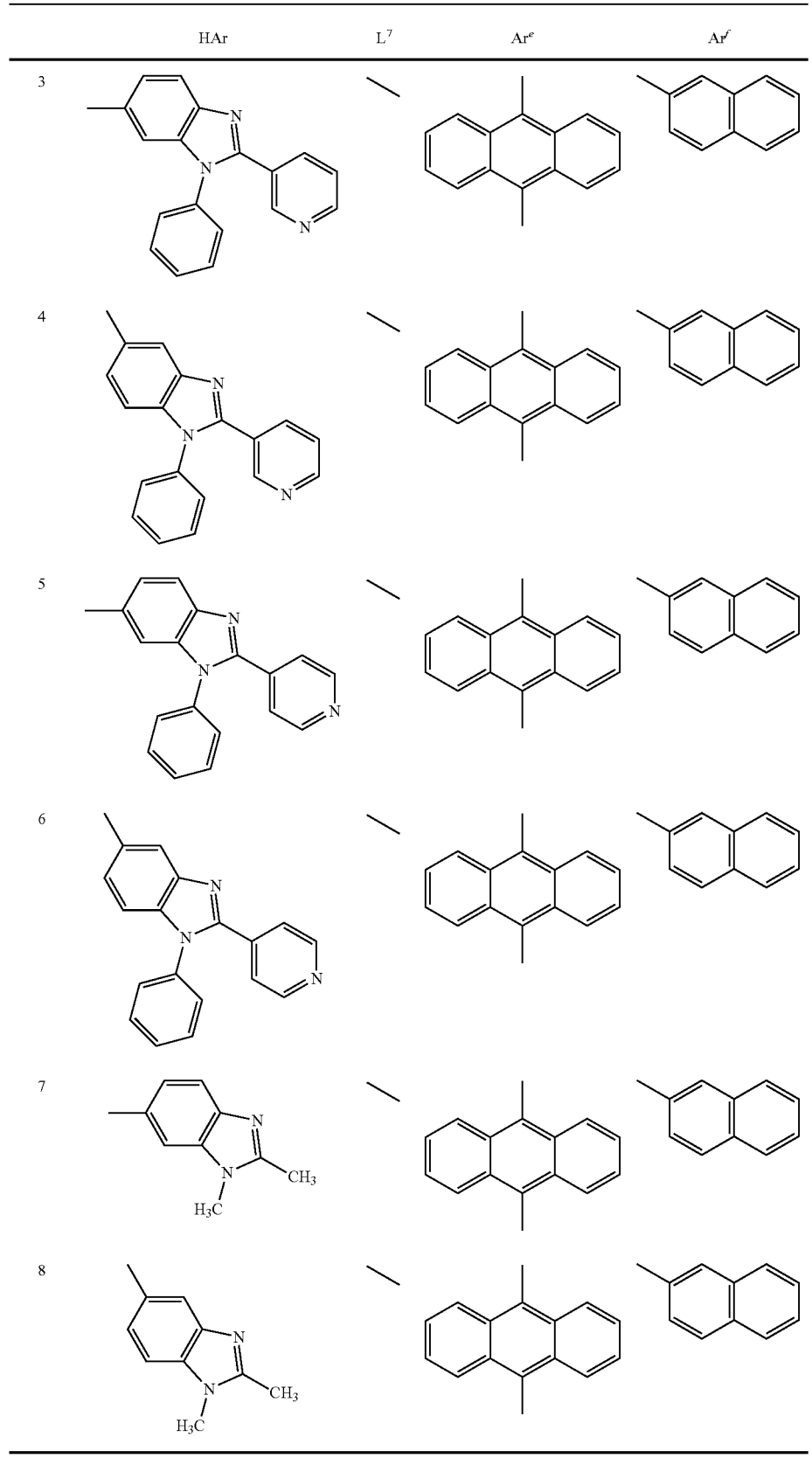

| | HAr—L⁷—Arᵉ—Arᶠ | | | |
|---|---|---|---|---|
| | HAr | L⁷ | Arᵉ | Arᶠ |
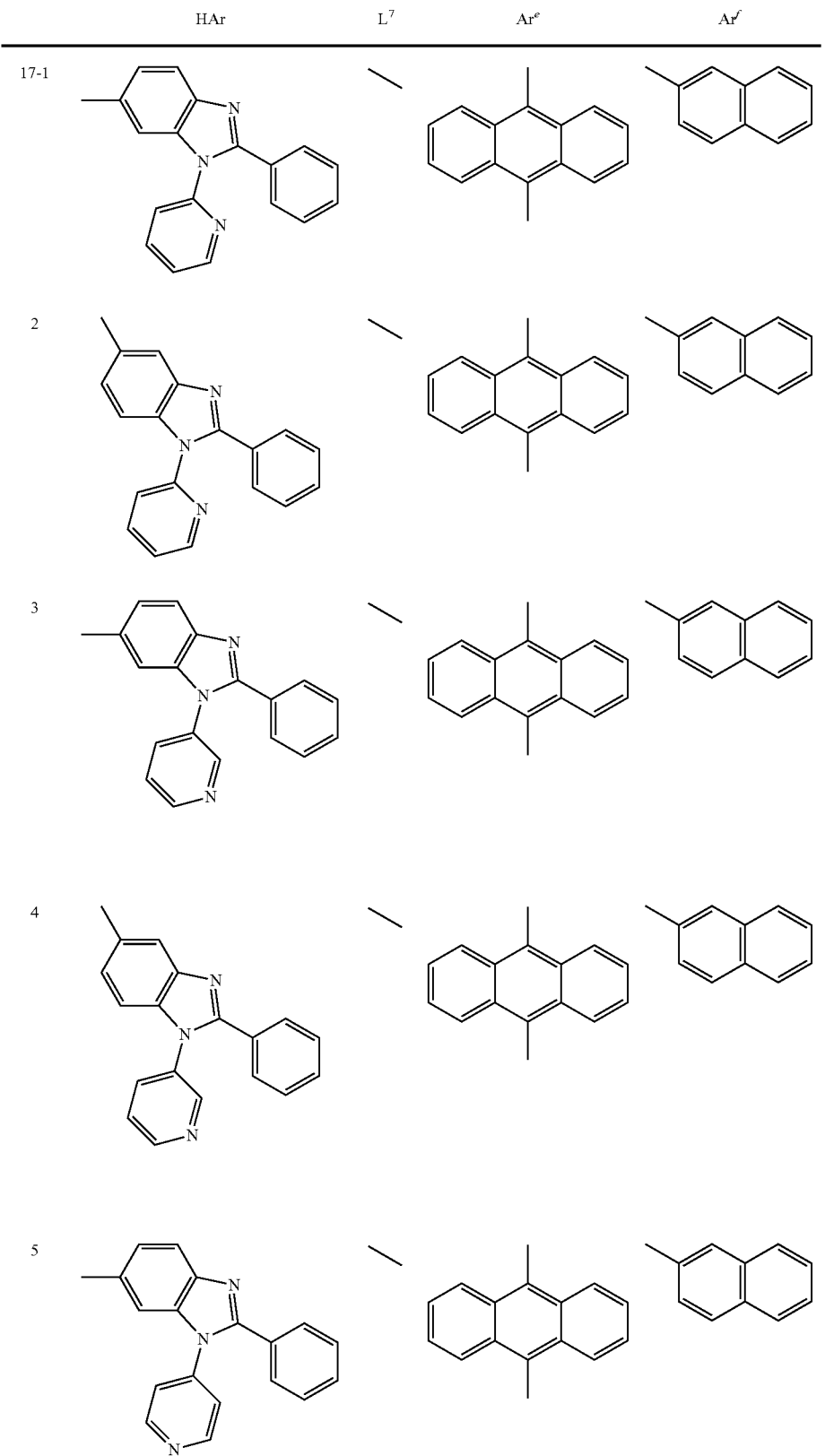

-continued

| | HAr—L⁷—Arᵉ—Ar^f | | | |
|---|---|---|---|---|
| | HAr | L⁷ | Arᵉ | Ar^f |

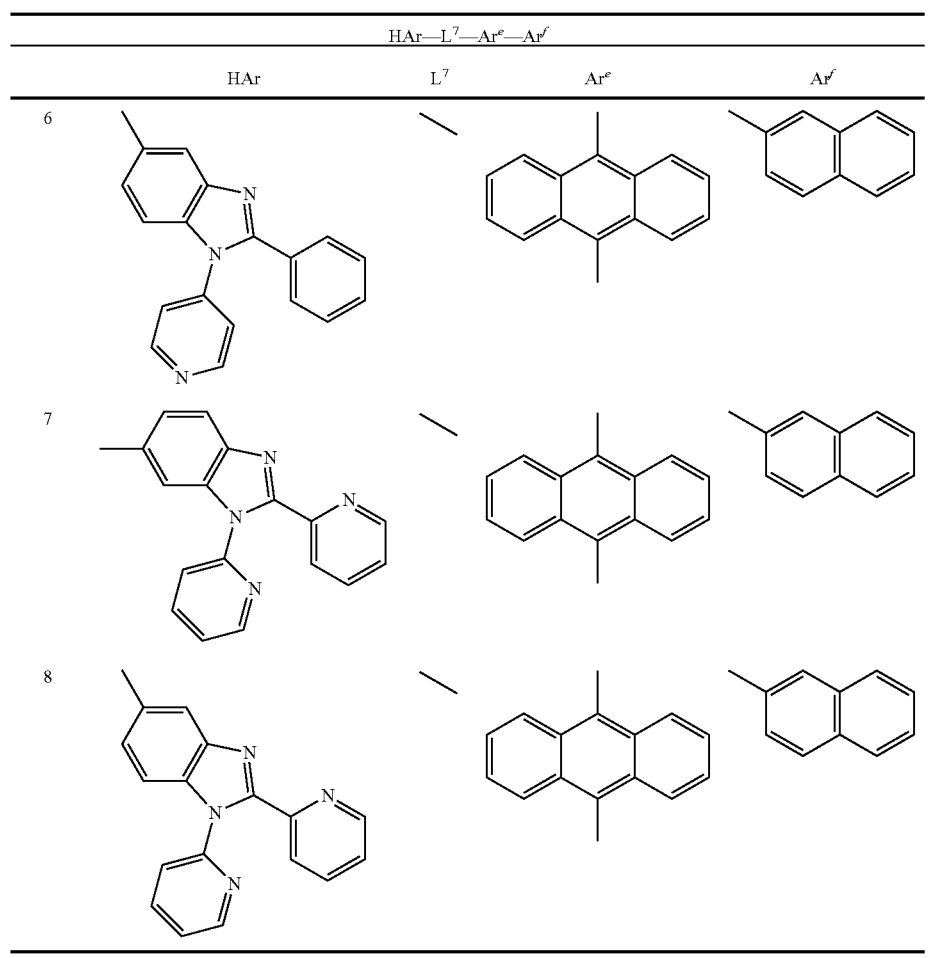

Of those specific examples, (1-1), (1-5), (1-7), (2-1), (3-1), (4-2), (4-6), (7-2), (7-7), (7-8), (7-9), (9-1), and (9-7) are particularly preferred.

In addition, as the nitrogen-containing ring derivative, nitrogen-containing five-membered ring derivative are also preferably exemplified. Examples of the nitrogen-containing five-membered ring include an imidazole ring, a triazole ring, a tetrazole ring, an oxadiazole ring, a thiadiazole ring, an oxatriazole ring, and a thiatriazole ring. Examples of the nitrogen-containing five-membered ring derivative include a benzoimidazole ring, a benzotriazole ring, a pyridinoimidazole ring, a pyrimidinoimidazole ring, and a pyridazinoimidazole ring. Particularly preferred is the compound represented by the following general formula (B).

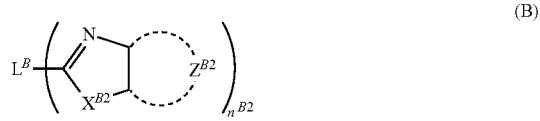

(B)

In the general formula (B), $L^B$ represents a divalent or more bonding group. Examples thereof include a carbon atom, a silicon atom, a nitrogen atom, a boron atom, an oxygen atom, a sulfur atom, metal atoms (for example, a barium atom, a beryllium atom), aromatic hydrocarbon rings, and aromatic heterocycles. Of those, preferred are a carbon atom, a nitrogen atom, a silicon atom, a boron atom, an oxygen atom, a sulfur atom, aromatic hydrocarbon rings, and aromatic heterocyclic groups, and more preferred are a carbon atom, a silicon atom, aromatic hydrocarbon rings, and aromatic heterocyclic groups.

The aromatic hydrocarbon rings and aromatic heterocyclic groups represented by $L^B$ may have a substituent. Examples of the substituent include alkyl groups, alkenyl groups, aryl groups, amino groups, alkoxy groups, aryloxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, sulfonyl groups, halogen atoms, cyano groups, and aromatic heterocyclic groups. Preferred are alkyl groups, aryl groups, alkoxy groups, aryloxy groups, halogen atoms, cyano groups, and aromatic heterocyclic groups, more preferred are alkyl groups, aryl groups, alkoxy groups, aryloxy groups, and aromatic heterocyclic groups, and particularly preferred are alkyl groups, aryl groups, alkoxy groups, and aromatic heterocyclic groups.

Specific examples of $L^B$ include compounds represented below.

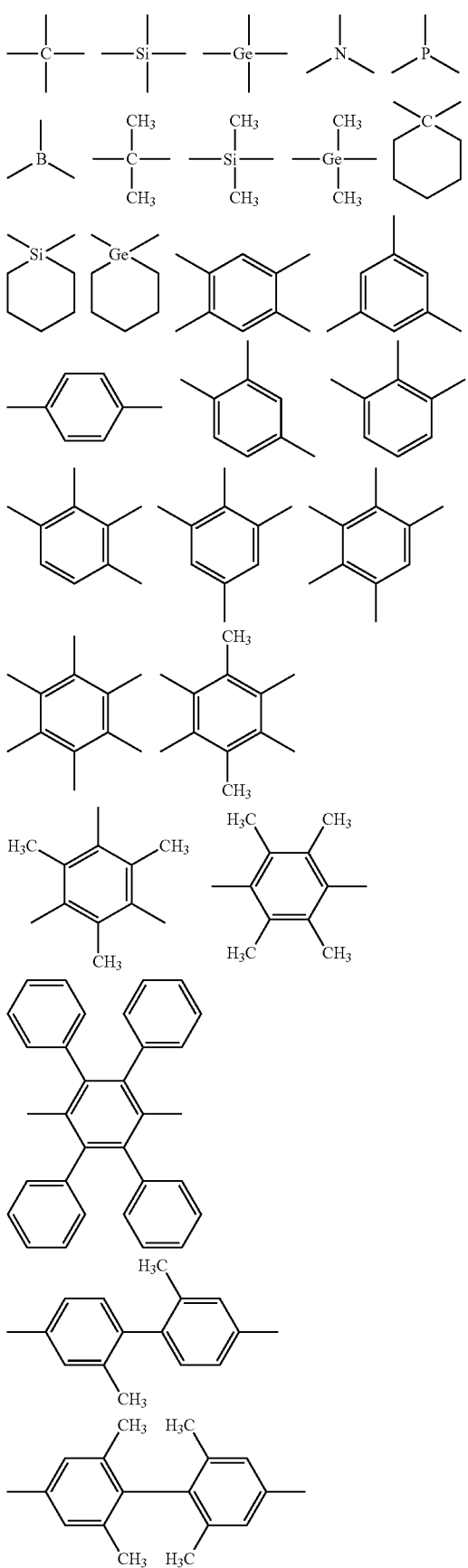

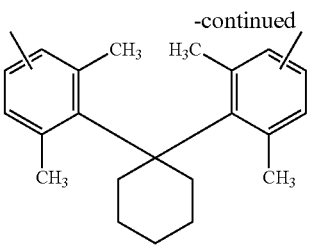

$X^{B2}$ in the general formula (B) represents —O—, —S—, or —N($R^{B2}$)—. $R^{B2}$ represents a hydrogen atom, an aliphatic hydrocarbon group, an aryl group, or a heterocyclic group.

The aliphatic hydrocarbon group represented by $R^{B2}$ is a linear or branched alkyl group (having preferably 1 to 20, more preferably 1 to 12, or particularly preferably 1 to 8 carbon atoms such as a methyl group, an ethyl group, an isopropyl group, a t-butyl group, an n-octyl group, an n-decyl group, or an n-hexadecyl group), a cycloalkyl group (having a ring formed of preferably 3 to 10 carbon atoms such as a cyclopropyl group, a cyclopentyl group, or a cyclohexyl group), an alkenyl group (having preferably 2 to 20, more preferably 2 to 12, or particularly preferably 2 to 8 carbon atoms such as a vinyl group, an aryl group, a 2-butenyl group, or a 3-pentenyl group), or an alkynyl group (having preferably 2 to 20, more preferably 2 to 12, or particularly preferably 2 to 8 carbon atoms such as a propargyl group or a 3-pentynyl group), or is preferably an alkyl group.

The aryl group represented by $R^{B2}$ is a monocycle or a fused ring, and is an aryl group having a ring formed of preferably 6 to 30, more preferably 6 to 20, or still more preferably 6 to 12 carbon atoms. Examples of such groups include a phenyl group, a 2-methylphenyl group, a 3-methylphenyl group, a 4-methylphenyl group, a 2-methoxyphenyl group, a 3-trifluoromethylphenyl group, a pentafluorophenyl group, a 1-naphthyl group, and a 2-naphthyl group. Of those, a phenyl group or a 2-methylphenyl group is preferable.

The heterocyclic group represented by $R^{B2}$ is a monocycle or a fused ring, and is a heterocyclic group having a ring formed of preferably 1 to 20, more preferably 1 to 12, or still more preferably 2 to 10 carbon atoms. The heterocyclic group is an aromatic heterocyclic group containing at least one heteroatom selected from a nitrogen atom, an oxygen atom, a sulfur atom, and a selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phanazine, tetrazole, benzoimidazole, benzoxazole, benzothiazole, benzotriazole, tetrazaindene, carbazole, azepine, and the like. Preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

The aliphatic hydrocarbon group, the aryl group, and the heterocyclic group each represented by $R^{B2}$ may each have a substituent, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or an aromatic heterocyclic group, more preferably an alkyl group, an aryl group, an alkoxy group, an aryloxy group, a halogen atom, a cyano group, or an aromatic heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$R^{B2}$ preferably represents an aliphatic hydrocarbon group, an aryl group, or a heterocyclic group, more preferably represents an aliphatic hydrocarbon group (having preferably € to 30, more preferably 6 to 20, or still more preferably 6 to 12 carbon atoms) or an aryl group, or still more preferably represents an aliphatic hydrocarbon group (having preferably 1 to 20, more preferably 1 to 12, or still more preferably 2 to 10 carbon atoms).

$X^{B2}$ preferably represents —O— or —N($R^{B2}$)—, or more preferably represents —N($R^{B2}$)—.

$Z^{B2}$ represents atoms necessary for forming an aromatic ring. The aromatic ring formed of $Z^{B2}$ is any one of aromatic hydrocarbon rings and aromatic heterocyclic rings. Specific examples thereof include a benzene ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellulazole ring, a thiadiazole ring, an oxadiazole ring, and a pyrazole ring. Preferred are a benzene ring, a pyridine ring, a pyrazine ring, a pyrimidine ring, and a pyridazine ring, more preferred are a benzene ring, a pyridine ring, and a pyrazine ring, still more preferred are a benzene ring and a pyridine ring, and particularly preferred is a pyridine ring.

The aromatic ring formed of $Z^{B2}$ may further form a fused ring with any other rings, or may have a substituent. Examples of the substituent include the same examples as those described for the substituent of the group represented by $L^B$, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or a heterocyclic group, more preferably an alkyl group, an aryl group, an alkoxy group, an aryloxy group, a halogen atom, a cyano group, or a heterocyclic group, still more preferably an alkyl group, an aryl group, an alkoxy group, an aryloxy group, or an aromatic heterocyclic group, or particularly preferably an alkyl group, an aryl group, an alkoxy group, or an aromatic heterocyclic group.

$n^{B2}$ represents an integer of 1 to 4, or preferably 2 or 3.

Of the nitrogen-containing five-membered ring derivatives each represented by the general formula (B), a derivative represented by the following general formula (B') is more preferable.

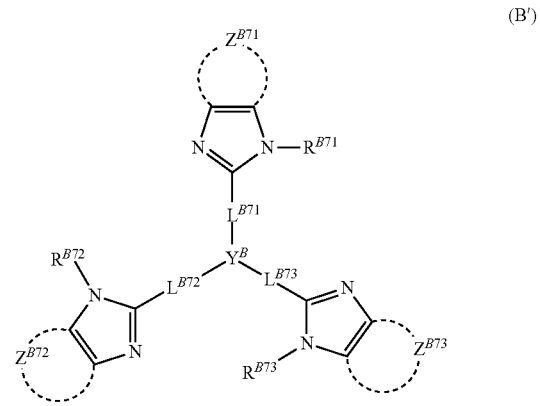

(B')

In the general formula (B'), $R^{B71}$, $R^{B72}$, and $R^{B73}$ each have the same meaning as that of $R^{B2}$ in the general formula (B), and the preferable ranges of $R^{B71}$, $R^{B72}$, and $R^{B73}$ are also the same as those of $R^{B2}$.

In the formula, $Z^{B71}$, $Z^{B72}$, and $Z^{B73}$ each have the same meaning as that of $Z^{B2}$ in the general formula (B), and the preferable ranges of $Z^{B71}$, $Z^{B72}$, and $Z^{B73}$ are also the same as those of $Z^{B2}$.

In the formula, $L^{B71}$, $L^{B72}$, and $L^{B73}$ each represent a linking group, and examples of the linking group include examples obtained by making the examples of $L^B$ in the general formula (B) divalent. The linking group is preferably a single bond, a divalent aromatic hydrocarbon ring group, a divalent aromatic heterocyclic group, or a linking group composed of a combination of two or more of them, or is more preferably a single bond. $L^{B71}$, $L^{B72}$, and $L^{B73}$ may each have a substituent. Examples of the substituent include the same examples as those described for the substituent of the group represented by $L^B$ in the general formula (B), and preferable examples of the substituent also include the same preferable examples as those described for the substituent of the group represented by $L^B$ in the general formula (B).

In the formula, $Y^B$ represents a nitrogen atom, a 1,3,5-benzenetriyl group, or a 2,4,6-triazinetriyl group. The 1,3,5-benzenetriyl group may have a substituent at any one of its 2-, 4-, and 6-positions, and examples of the substituent include an alkyl group, an aromatic hydrocarbon ring group, and a halogen atom.

Specific examples of the nitrogen-containing five-membered ring derivative represented by the general formula (B) or (B') are shown below. However, the present invention is not limited to these exemplified compounds.

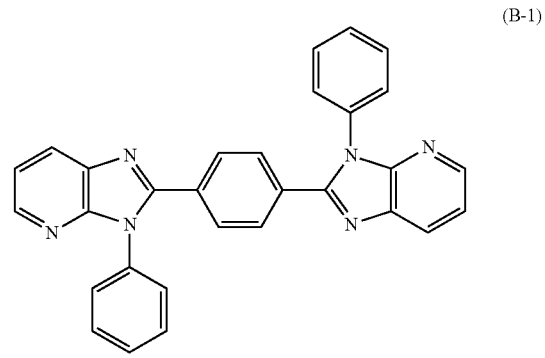

(B-1)

-continued
(B-2) 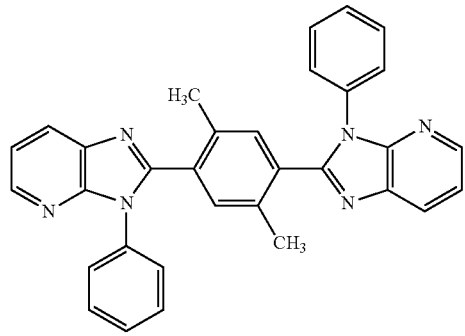
(B-3) 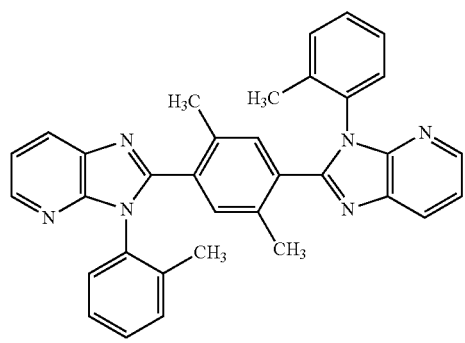
(B-4) 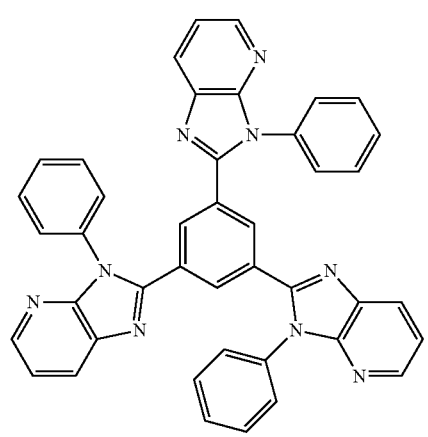
(B-5) 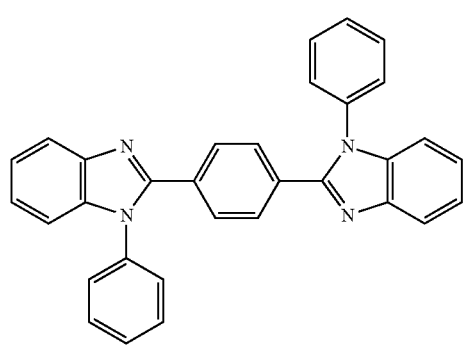
-continued
(B-6) 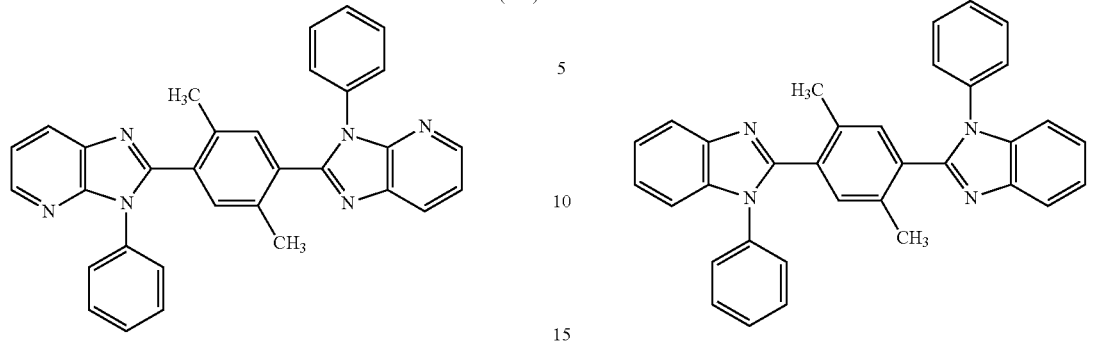
(B-7) 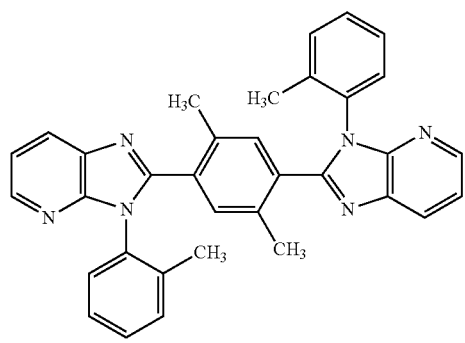
(B-8) 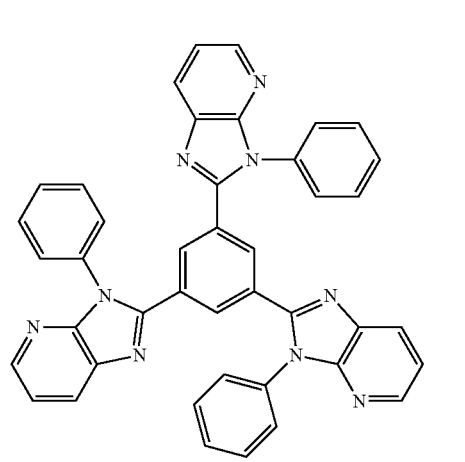
(B-9) 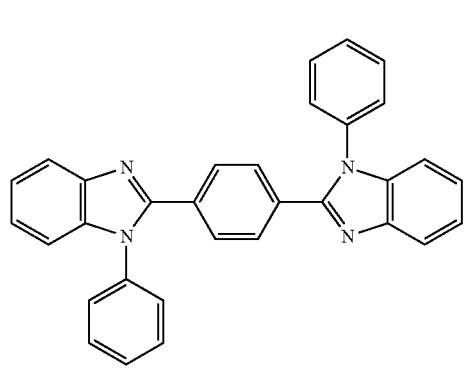

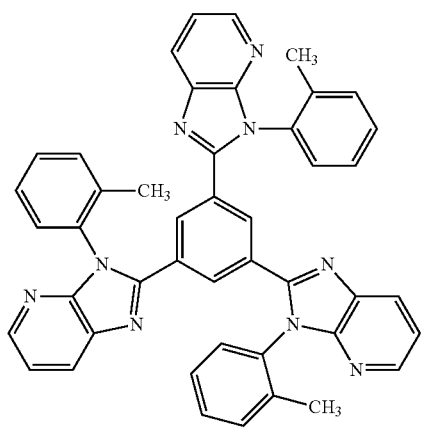
(B-10)
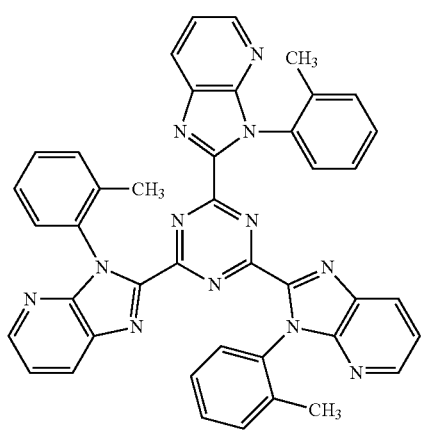
(B-11)
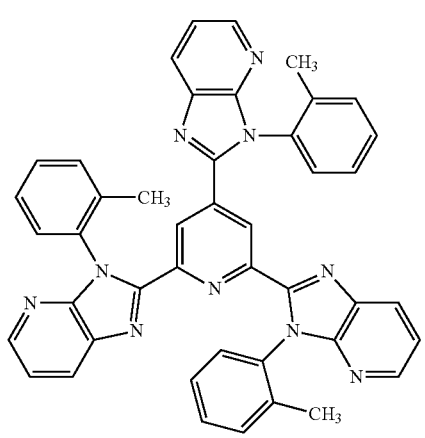
(B-12)
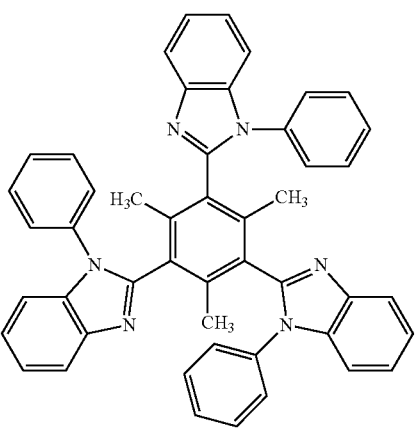
(B-13)
(B-14)
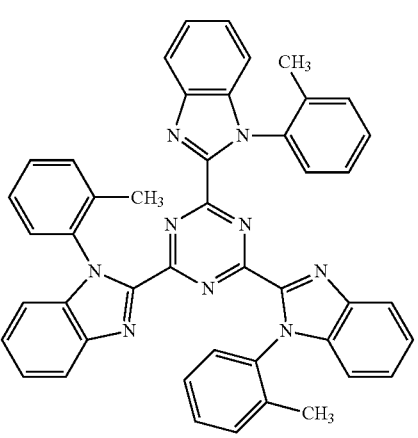
(B-15)

(B-16)

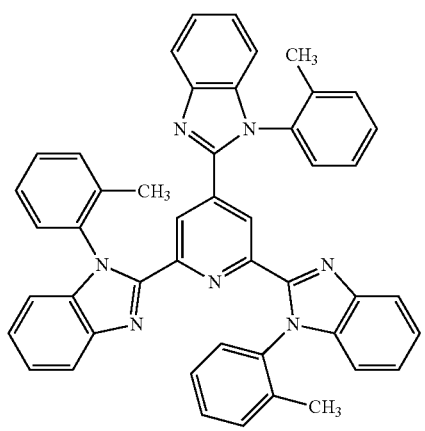

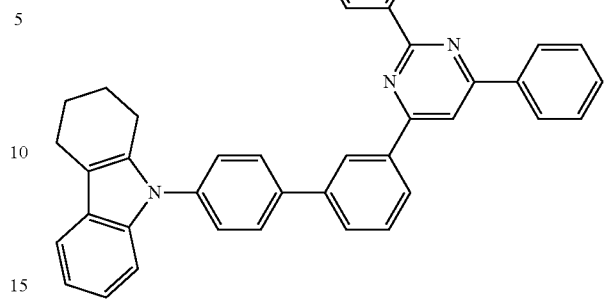

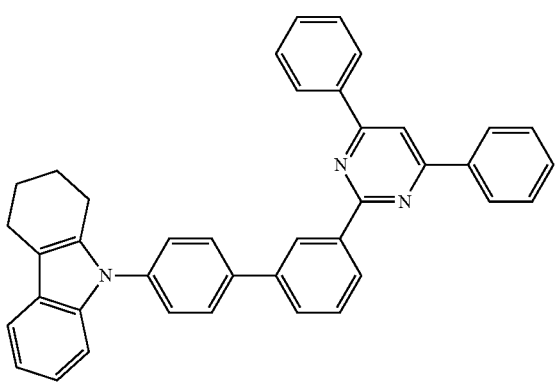

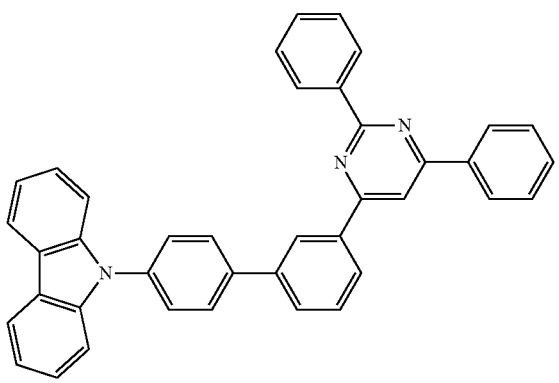

A compound of which each of the electron injecting layer and the electron transporting layer is constituted is, for example, a compound having a structure obtained by combining an electron-deficient, nitrogen-containing five-membered ring skeleton or electron-deficient, nitrogen-containing six-membered ring skeleton and a substituted or unsubstituted indole skeleton, substituted or unsubstituted carbazole skeleton, or substituted or unsubstituted azacarbazole skeleton as well as the material for an organic EL device of the present invention. In addition, a suitable electron-deficient, nitrogen-containing five-membered ring skeleton or electron-deficient, nitrogen-containing six-membered ring skeleton is a molecular skeleton such as a pyridine, pyrimidine, pyrazine, triazine, triazole, oxadiazole, pyrazole, imidazole, quinoxaline, or pyrrole skeleton, or benzimidazole or imidazopyridine obtained when two or more of them fuse with each other. Of those combinations, a preferable combination is, for example, a combination of a pyridine, pyrimidine, pyrazine, or triazine skeleton and a carbazole, indole, azacarbazole, or quinoxaline skeleton. The above-mentioned skeleton may be substituted or unsubstituted.

Specific examples of an electron transportable compound are shown below. However, the present invention is not particularly limited to these examples.

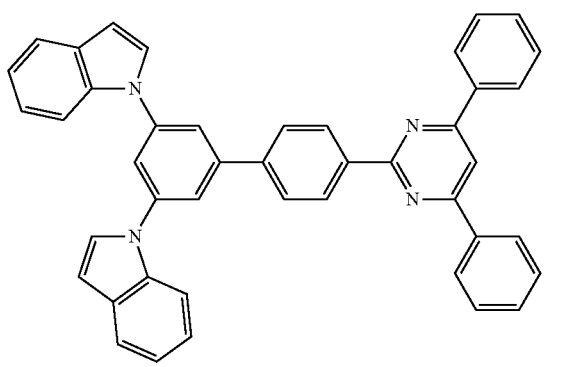

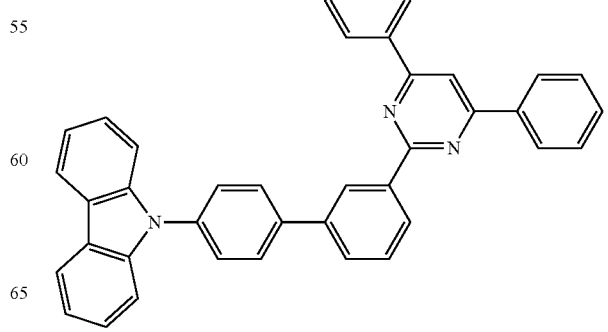

307
-continued
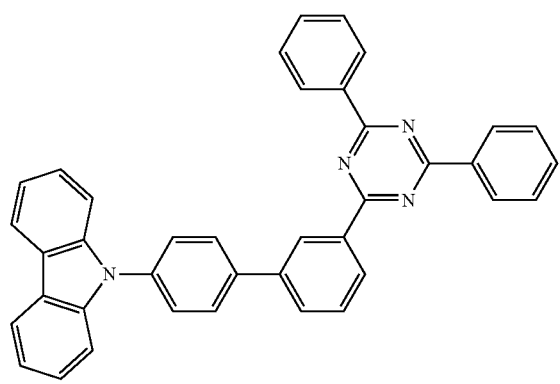
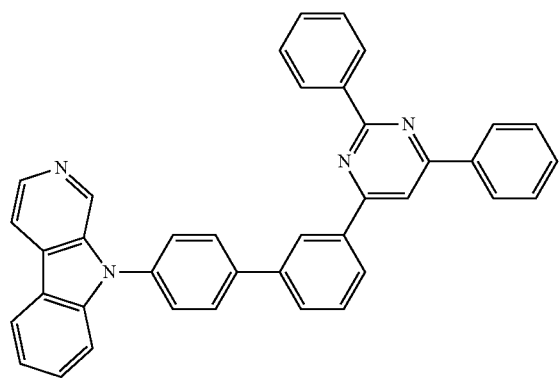
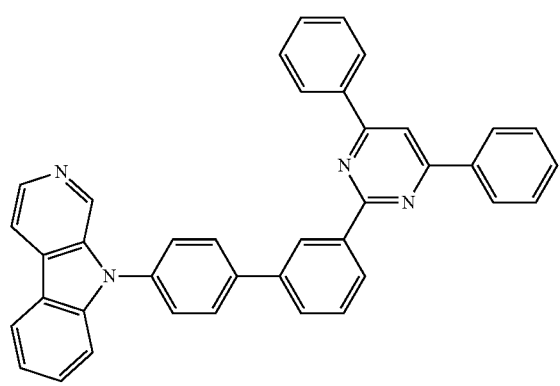
308
-continued
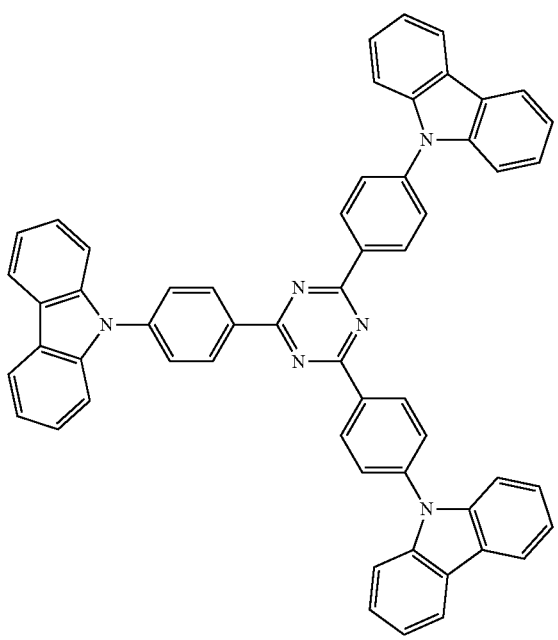
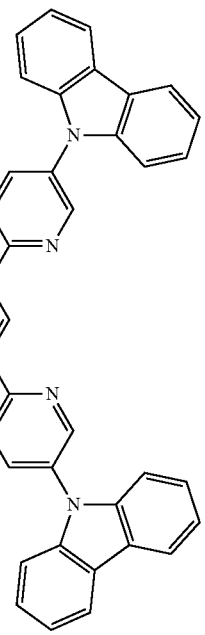

309
-continued
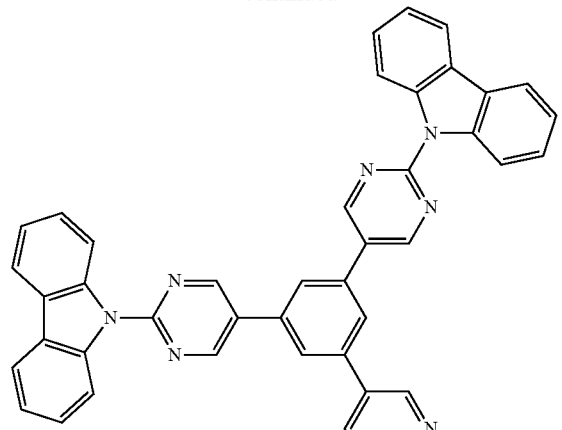
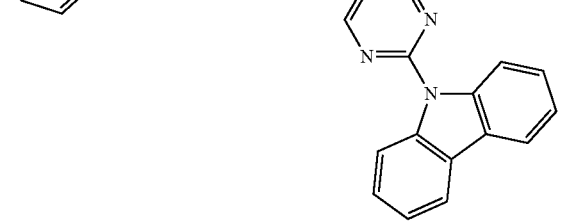

310
-continued
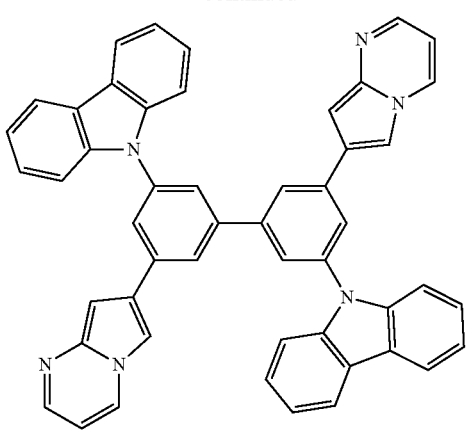

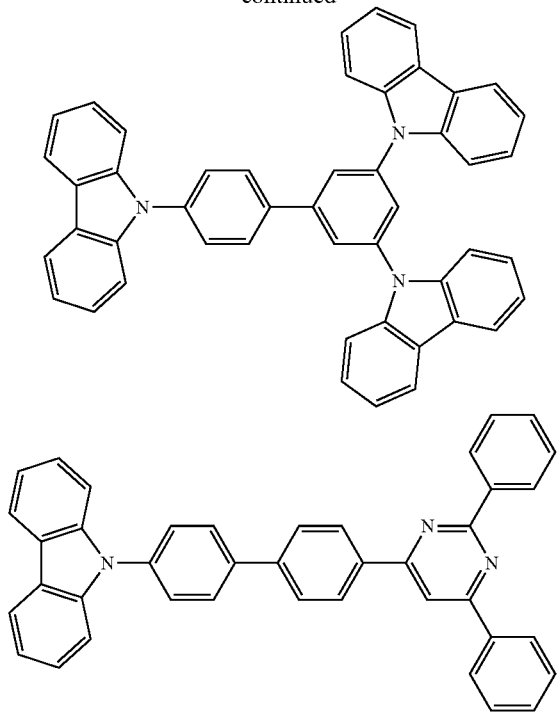

Each of the electron injecting layer and the electron transporting layer may be of a monolayer structure composed of one or two or more kinds of the above materials, or may be of a multi-layered structure composed of multiple layers identical to or different from each other in composition. Materials for those layers each preferably have a n-electron-deficient, nitrogen-containing heterocyclic group.

In addition, an insulator or semiconductor serving as an inorganic compound as well as the nitrogen-containing ring derivative is preferably used as a component of the electron injecting layer. When the electron injecting layer is constituted of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferable that the electron injecting layer be composed of the above-mentioned substance such as the alkali metal chalcogenide since the electron injecting property can be further improved. To be specific, preferable examples of the alkali metal chalcogenide include $Li_2O$, $K_2O$, $Na_2S$, $Na_2Se$, and $Na_2O$, and preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

In addition, examples of the semiconductor include oxides, nitrides, and oxide nitrides containing at least one element selected from the group consisting of Ba, Ca, Sr, Yb, Al, Ga, In, $L_1$, Na, Cd, Mg, Si, Ta, Sb, and Zn, and they may be used alone or in combination of two or more. It is preferable that the inorganic compound composing the electron injecting layer form a crystallite or amorphous insulating thin film. When the electron injecting layer is composed of the insulating thin film described above, a more uniform thin film can be formed, and defects of pixels such as dark spots can be decreased. Examples of the inorganic compound include alkali metal chalcogenides, alkaline earth metal chalcogenides, alkali metal halides, and alkaline earth metal halides.

In addition, the above-mentioned reducing dopant can be preferably incorporated into the electron injecting layer in the present invention.

It should be noted that the thickness of each of the electron injecting layer and the electron transporting layer, which is not particularly limited, is preferably 1 to 100 nm.

An aromatic amine compound such as an aromatic amine derivative represented by a general formula (I) is suitably used in the hole injecting layer or hole transporting layer (a hole injecting/transporting layer is also included in this category).

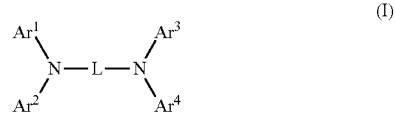

(I)

In the general formula (I), $Ar^1$ to $Ar^4$ each represent a substituted or unsubstituted aryl group having a ring formed of 6 to 50 carbon atoms, or a substituted or unsubstituted heteroaryl group having a ring formed of 5 to 50 atoms.

Examples of the substituted or unsubstituted aryl group having a ring formed of 6 to 50 carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having a ring formed of 5 to 50 atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group. Preferred are a phenyl group, a naphthyl group, a biphenyl group, an anthranyl group, a phenanthryl group, a pyrenyl group, a chrycenyl group, a fluoranthenyl group, and a fluorenyl group.

L represents a linking group, and specifically, a substituted or unsubstituted arylene group having a ring formed of 6 to 50 carbon atoms, a substituted or unsubstituted heteroarylene group having a ring formed of 5 to 50 atoms, or a divalent group in which two or more arylene groups or heteroarylene groups are bonded by a single bond, an ether bond, a thioether bond, with an alkylene group having 1 to 20 carbon atoms, an alkenylene group having 2 to 20 carbon atoms, and an amino group. Examples of the arylene group having a ring formed of 6 to 50 carbon atoms include a 1,4-phenylene group, a 1,2-phenylene group, a 1,3-phenylene group, a 1,4-naphthylene group, a 2,6-naphthylene group, a 1,5-naphthylene group, a 9,10-anthranylene group, a 9,10-phenanthrenylene group, a 3,6-phenanthrenylene group, 1,6-pyrenylene group, a 2,7-pyrenylene group, a 6,12-chrycenylene group, a 4,4'-biphenylene group, a 3,3'-biphenylene group, a 2,2'-biphenylene group, and a 2,7-fluorenylene group. Examples of the arylene group having a ring formed of 5 to 50 atoms include a 2,5-thiophenylene group, a 2,5-silolylene group, and a 2,5-oxadiazolylene group. Preferred are a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenlene group, a 2,2'-biphenylene group, and a 2,7-fluorenylene group.

In the case where L represents a linking group formed of two or more arylene groups or heteroarylene groups, adjacent arylene groups or heteroarylene groups may be bonded to each other through a divalent group to form a ring. Examples of the divalent group forming a ring include a tetramethylene group, a pentamethylene group, a hexamethylene group, a diphenylmethane-2,2'-diyl group, a diphenyl ethane-3,3'-diyl group, and a diphenylpropane-4,4'-diyl group.

The substituent of each of $Ar^1$ to $Ar^4$ and L is, for example, a substituted or unsubstituted aryl group having a ring formed of 6 to 50 carbon atoms, a substituted or unsubstituted heteroaryl group having a ring formed of 5 to 50 atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having a ring formed of 6 to 50 carbon atoms, a substituted or unsubstituted heteroaryloxy group having a ring formed of 5 to 50 atoms, a substituted or unsubstituted arylthio group having a ring formed of 6 to 50 carbon atoms, a substituted or unsubstituted heteroaryl thio group having a ring formed of 5 to 50 atoms, a substituted or unsubstituted alkoxycarbonyl group having 2 to 50 carbon atoms, an amino group substituted by a substituted or unsubstituted aryl group having a ring formed of 6 to 50 carbon atoms or by a substituted or unsubstituted heteroaryl group having a ring formed of 5 to 50 atoms, a halogen group, a cyano group, a nitro group, or a hydroxyl group.

Examples of the substituted or unsubstituted aryl group having a ring formed of 6 to 50 carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heteroaryl group having a ring formed of 5 to 50 atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Examples of the substituted or unsubstituted alkyl group having 1 to 50 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of Y include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3- tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

Examples of the substituted or unsubstituted aralkyl group having 7 to 50 carbon atoms include a benzyl group, a 1-phenylethyl group, a 2~phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group; a 1-α-naphthylisopropyl group, a 2-α-naphthyl isopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Examples of the substituted or unsubstituted aryloxy group having a ring formed of 6 to 50 carbon atoms is represented by —OY'. Examples of Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

Examples of the substituted or unsubstituted heteroaryloxy group having a ring formed of 5 to 50 atoms is represented by —OZ'. Examples of Z' include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxadinyl group, a 2-phenoxadinyl group, a 3-phenoxadinyl group, a 4-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

The substituted or unsubstituted arylthio group having a ring formed of 6 to 50 carbon atoms is represented by —SY". Examples of Y" include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

The substituted or unsubstituted heteroarylthio group having a ring formed of 5 to 50 atoms is represented by —SZ". Examples of Z" include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

The substituted or unsubstituted alkoxycarbonyl group having 2 to 50 carbon atoms is represented by —COOZ. Examples of Z include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and 1,2,3-trinitropropyl group.

The substituted or unsubstituted aryl group having a ring formed of 6 to 50 carbon atoms or an amino group substituted with a substituted or unsubstituted heteroaryl group having a ring formed of 5 to 50 atoms is represented by —NPQ. Examples of P and Q include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group, a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Specific examples of the compound represented by the general formula (I) are shown below. However, the present invention is not limited to these examples.

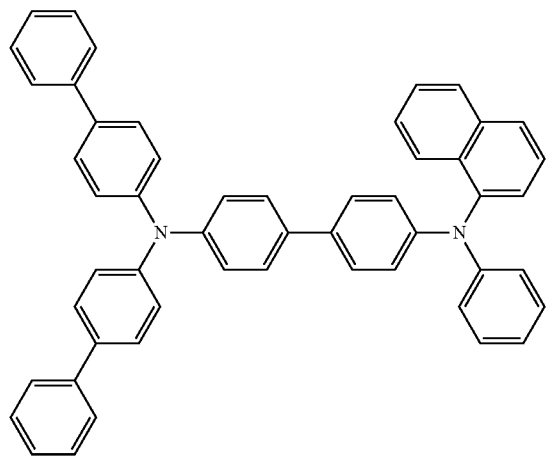

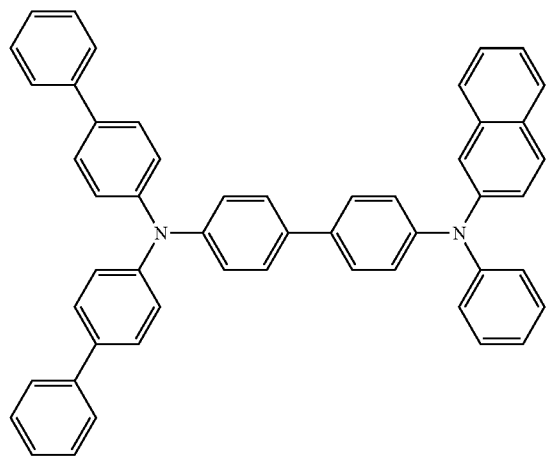

323
-continued
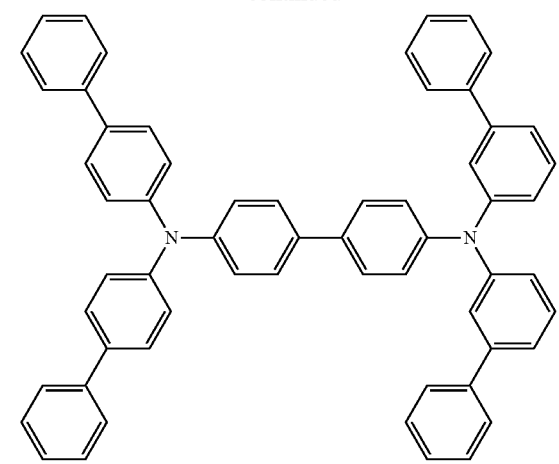
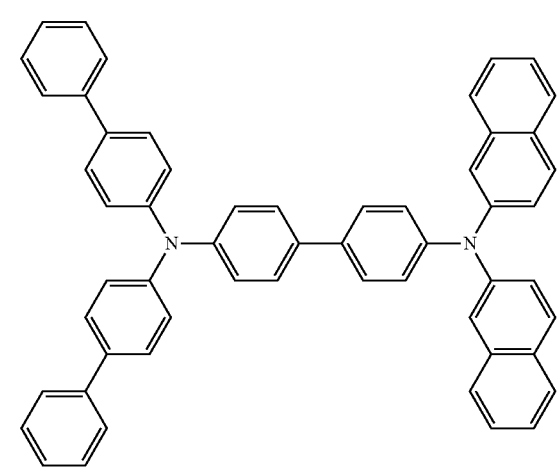
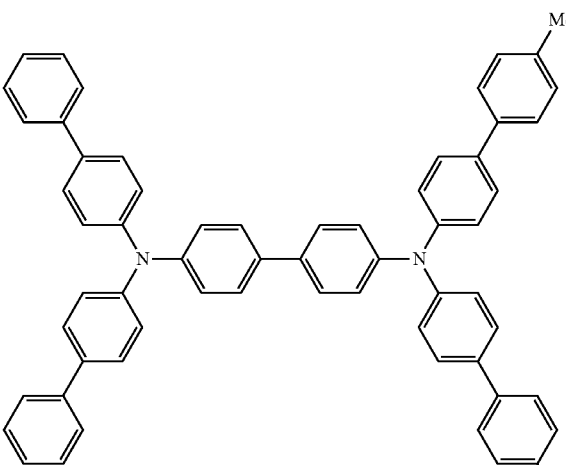
324
-continued
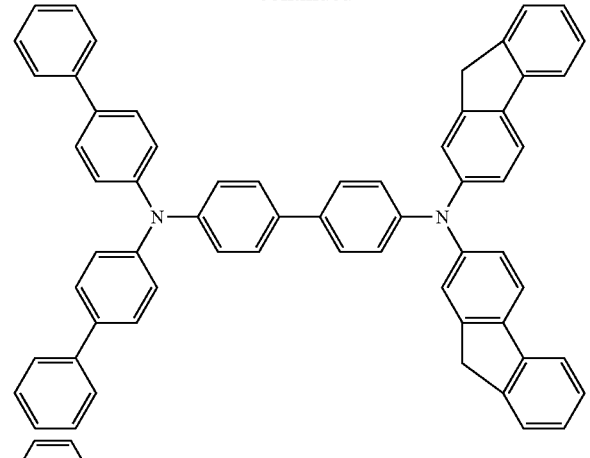
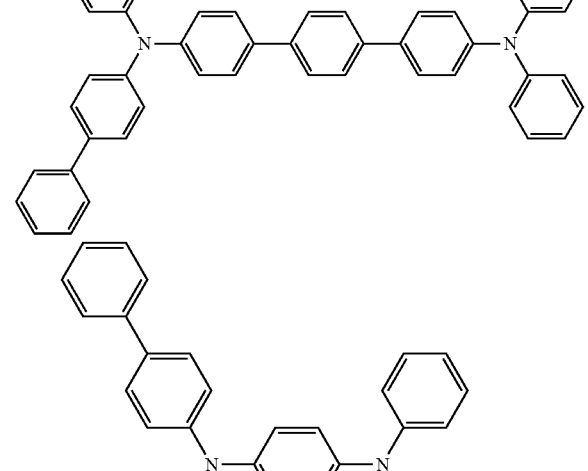
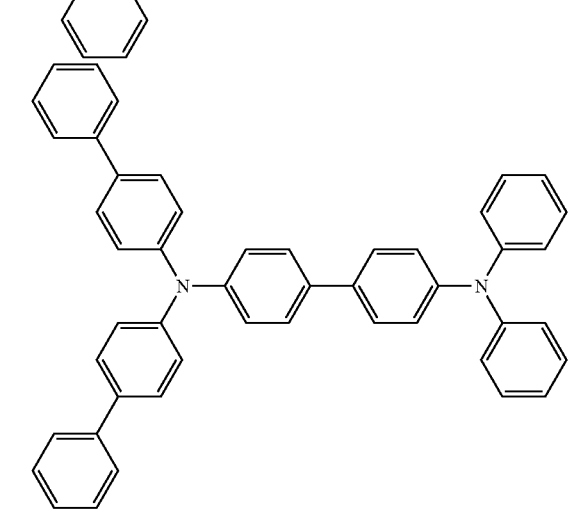

325
-continued
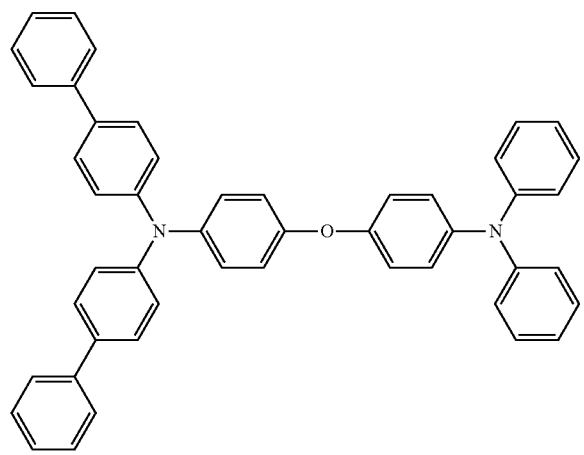
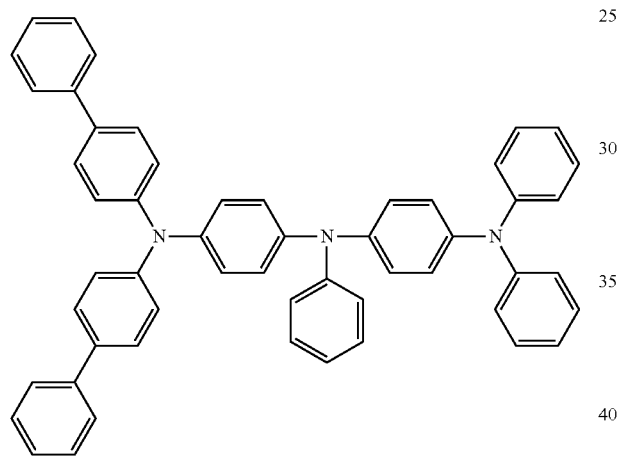
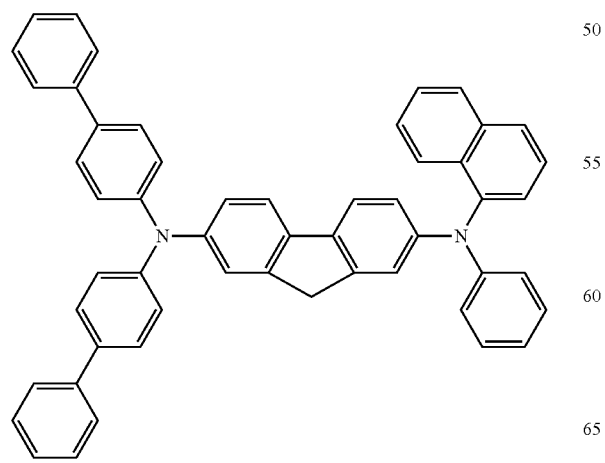
326
-continued
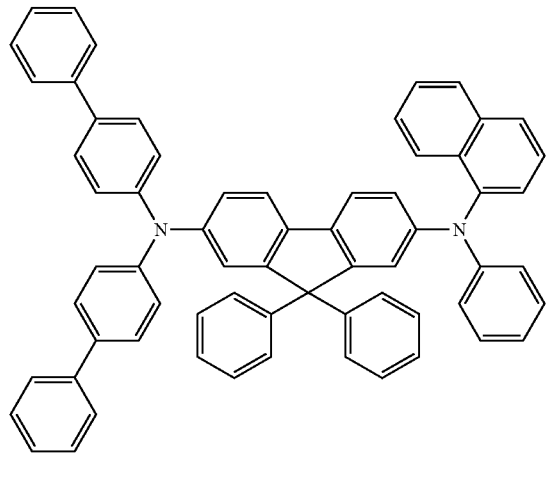
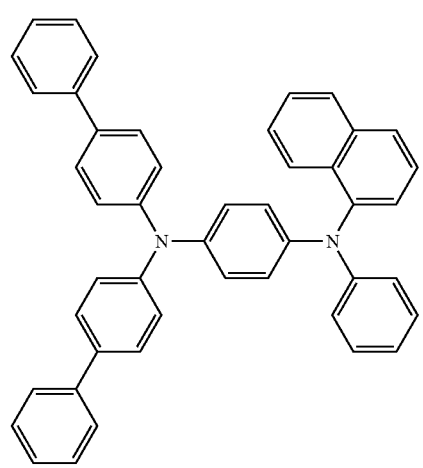
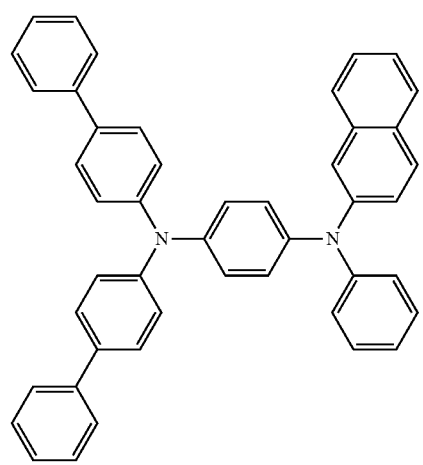

327
-continued
328
-continued
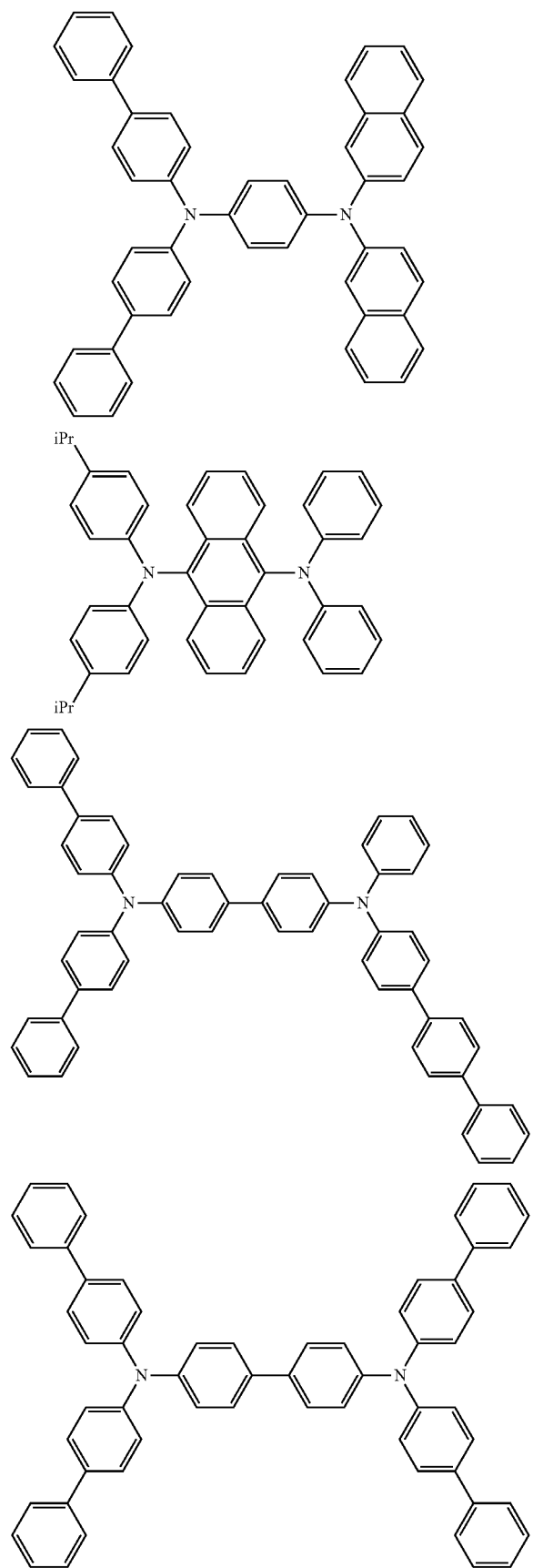
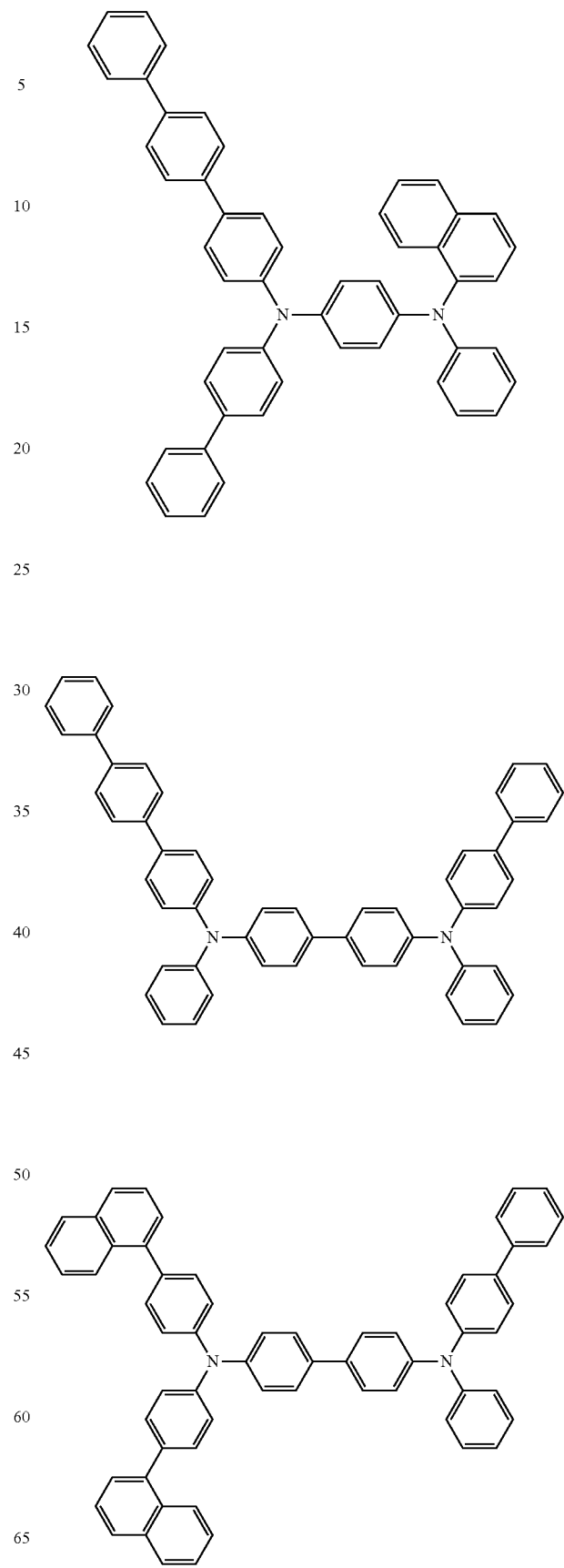

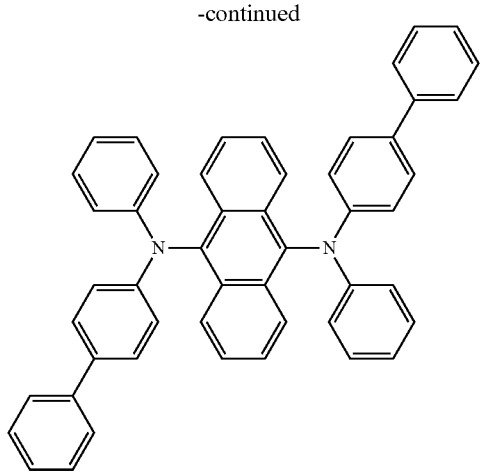

In addition, an aromatic amine represented by the following general formula (II) is also suitably used in the formation of the hole injecting layer or hole transporting layer.

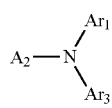 (II)

In the general formula (II), the definition of $Ar_1$ to $Ar_3$ is the same as that of $Ar_1$ to $Ar_4$ in the general formula (I). Specific examples of the compound represented by the general formula (II) are shown below. However, the present invention is not limited to these examples.

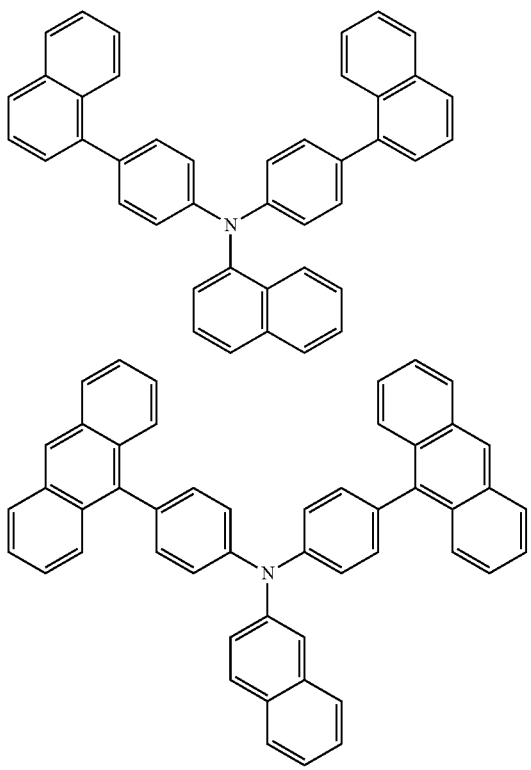

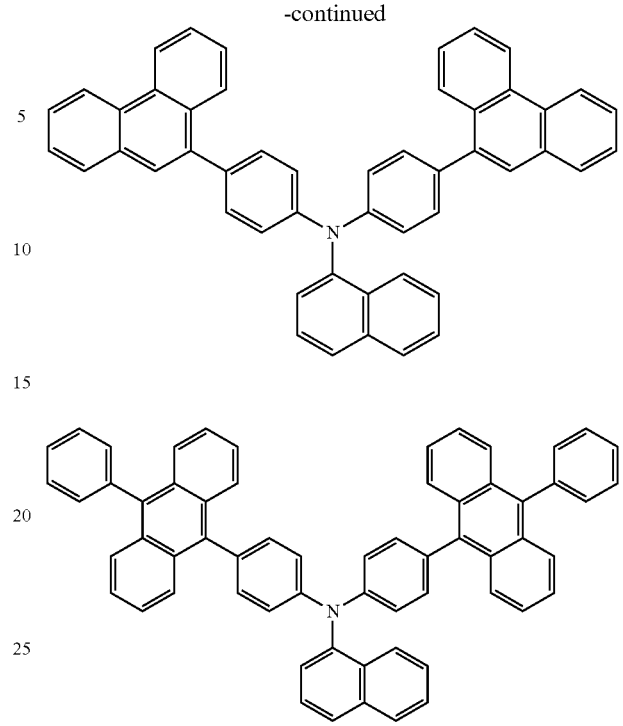

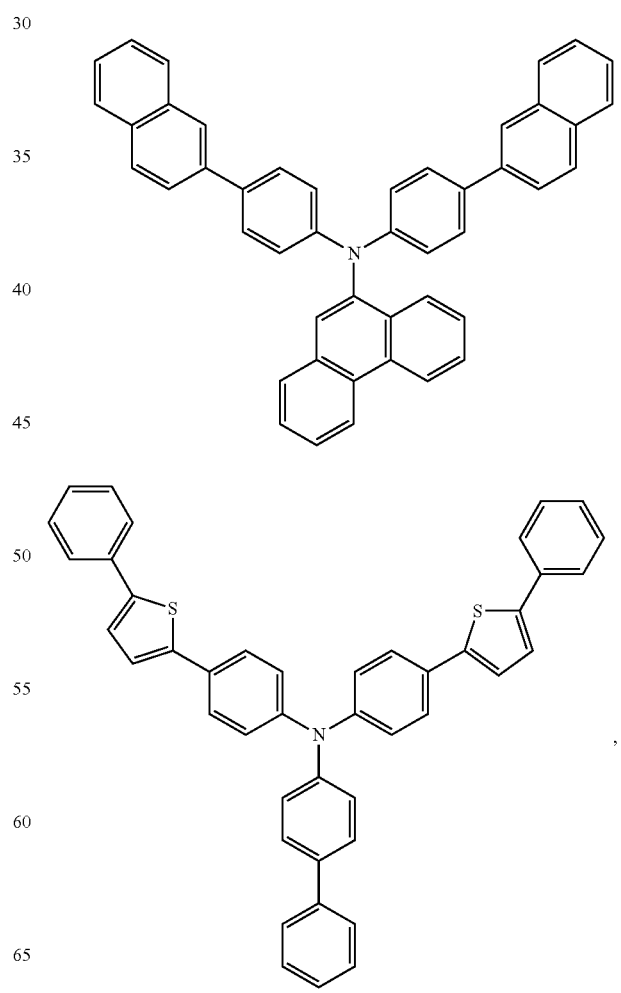

331
-continued
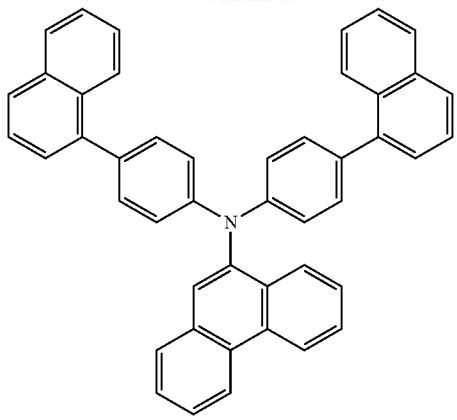
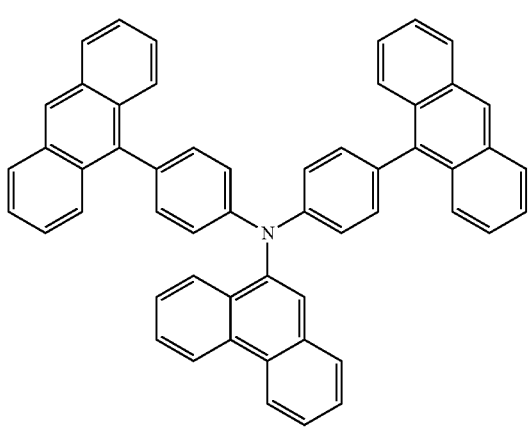
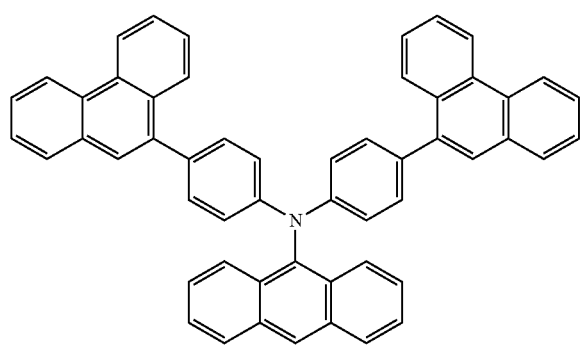
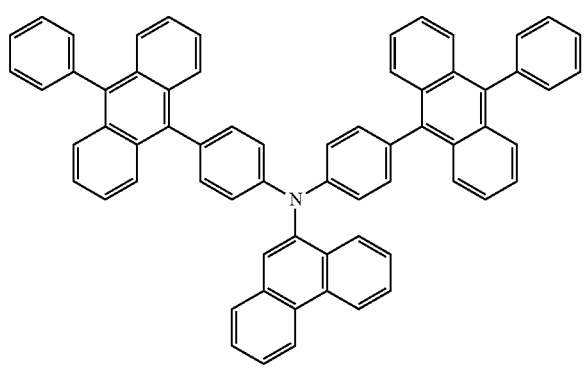
332
-continued
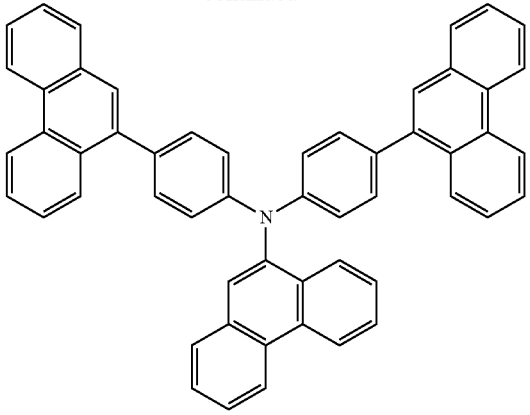
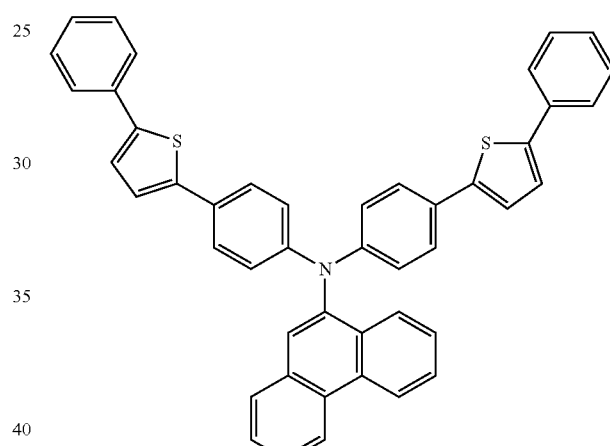
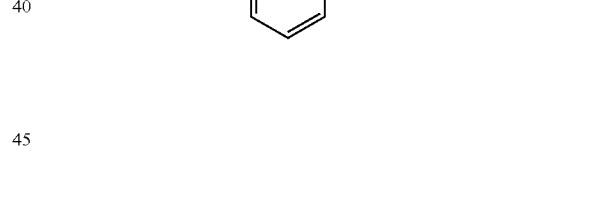
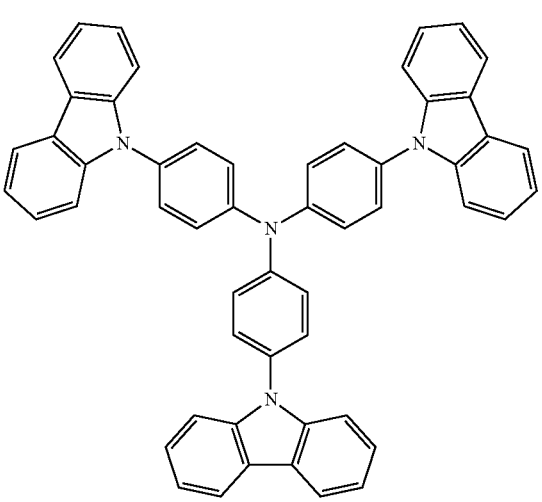

-continued

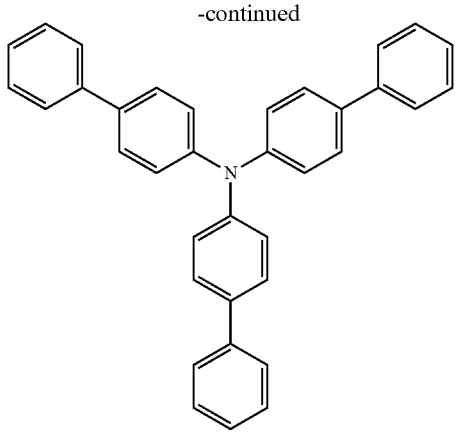

The compound of the present invention can be used in each of the hole injecting layer, the hole transporting layer, the electron injecting layer, and the electron transporting layer because the compound can transport both a hole and an electron.

In the present invention, the anode in the organic EL device has the function of injecting holes into the hole transporting layer or the light emitting layer. It is effective that the anode has a work function of 4.5 eV or greater. Specific examples of the material for the anode used in the present invention include indium tin oxide alloys (ITO), tin oxide (NESA), gold, silver, platinum, and copper. In addition, as the cathode, a material having a small work function is preferred in view to inject an electron into an electron injecting layer or a light emitting layer. Examples of the cathode material are not particularly limited, and specifically, indium, aluminum, magnesium, an magnesium-indium alloy, a magnesium-aluminum alloy, an aluminum-lithium alloy, an aluminum-scandium-lithium alloy, and a magnesium-silver alloy may be used.

The method of forming the layers in the organic EL device of the present invention is not particularly limited. A conventionally known process such as the vacuum vapor deposition process or the spin coating process can be used. The organic thin film layer which is used in the organic EL device of the present invention and includes the compound represented by general formula (1) described above can be formed in accordance with a known process such as the vacuum vapor deposition process or the molecular beam epitaxy process (MBE process) or, using a solution prepared by dissolving the compounds into a solvent, in accordance with a coating process such as the dipping process, the spin coating process, the casting process, the bar coating process, or the roll coating process.

The thickness of each organic layer in the organic EL device of the present invention is not particularly limited. In general, an excessively thin layer tends to have defects such as pin holes, whereas an excessively thick layer requires a high applied voltage to decrease the efficiency. Therefore, a thickness in the range of several nanometers to 1 μm is preferable.

EXAMPLES

Next, the present invention is described in detail by way of examples, but the present invention is not limited to the following examples. Note that, in the synthesis examples below, DMF refers to dimethylformamide, THF refers to tetrahydrofuran, DME refers to dimethoxyethane, NBS refers to N-bromosuccine imide, Ph refers to a phenyl group, AcOEt refers to ethyl acetate, and NMP refers to N-methyl pyrrolidone.

Synthesis Example 1 (Synthesis of Compound No. 11)

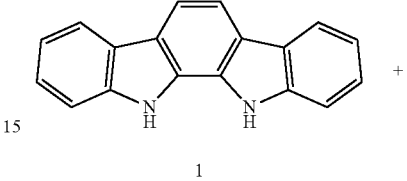

1

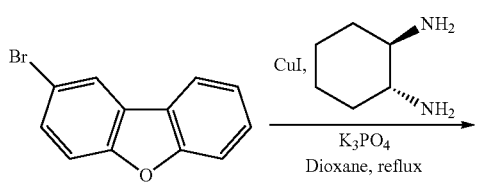

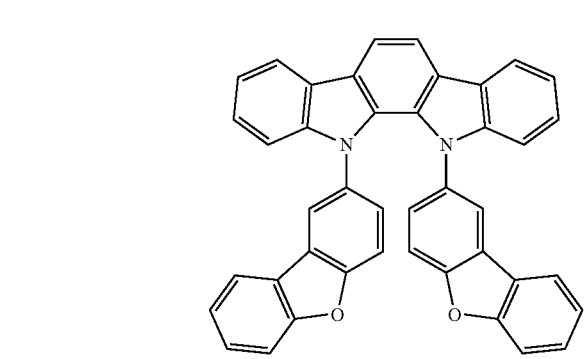

No. 11

Compound 1 (2.6 g, 10 mmol), 2-bromobenzofuran (5.0 g, 20 mmol), CuI (1.9 g, 10 mmol), transcyclohexane 1,2-diamine (3.4 g, 30 mmol), $K_3PO_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated and exsiccated, and was then recrystallized twice, whereby a white powder (Compound No. 11) was obtained. The powder was purified by sublimation, whereby a white solid was obtained in an amount of 0.7 g in 12% yield.

FD-MS $C_{42}H_{24}N_2O_2$: theoretical value 588, observed value 588

Synthesis Example 2 (Synthesis of Compound No. 40)

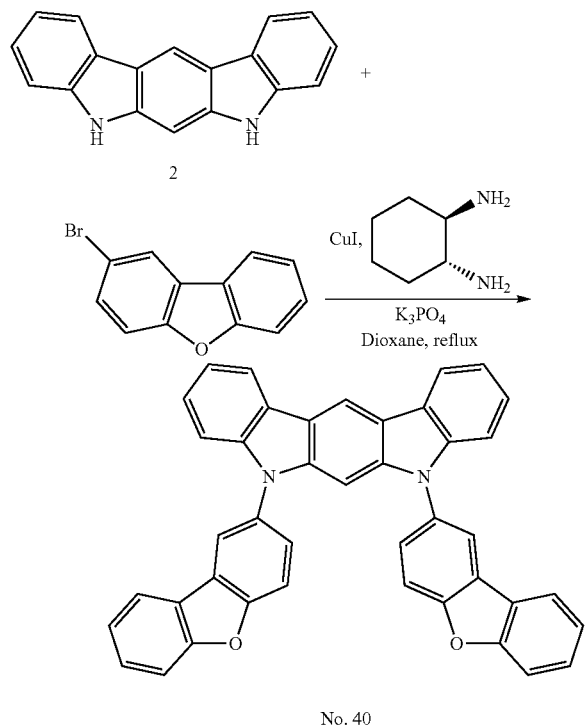

No. 40

Compound 2 (2.6 g, 10 mmol), 2-bromobenzofuran (5.0 g, 20 mmol), CuI (1.9 g, 10 mmol), transcyclohexane 1,2-diamine (3.4 g, 30 mmol), $K_3PO_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated and exsiccated, and was then recrystallized twice, whereby a white powder (Compound No. 40) was obtained. The powder was purified by sublimation, whereby a white solid was obtained in an amount of 1.9 g in 33% yield.

FD-MS $C_{42}H_{24}N_2O_2$: theoretical value 588, observed value 588

Synthesis Example 3 (Synthesis of Compound No. 47)

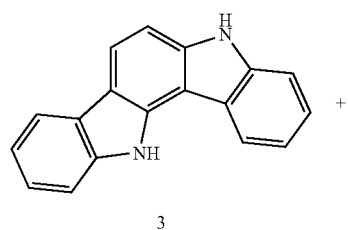

3

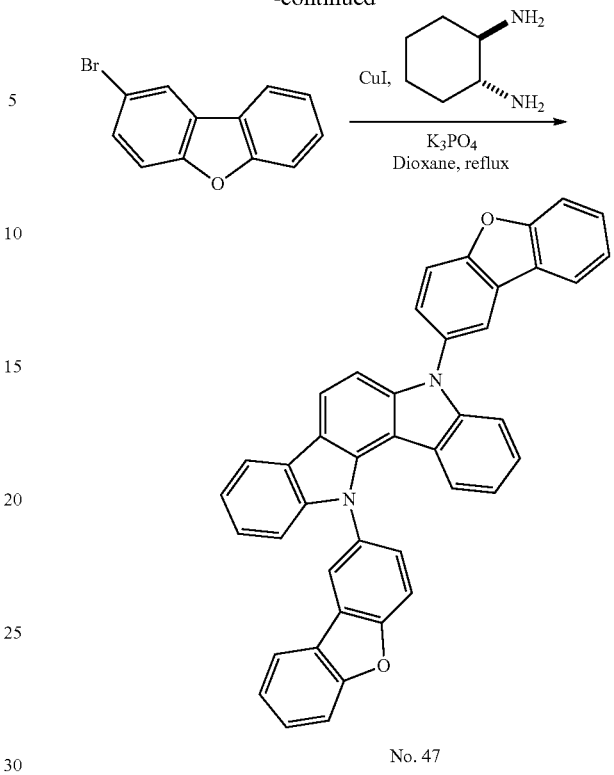

No. 47

Compound 3 (2.6 g, 10 mmol), 2-bromobenzofuran (5.0 g, 20 mmol), CuI (1.9 g, 10 mmol), transcyclohexane 1,2-diamine (3.4 g, 30 mmol), $K_3PO_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with $CH_2Cl_2$. The resultant sample was purified by silica gel column chromatography. The purified product was concentrated and exsiccated, and was then recrystallized twice, whereby a white powder (Compound No. 47) was obtained. The powder was purified by sublimation, whereby a white solid was obtained in an amount of 1.5 g in 25% yield.

FD-MS $C_{42}H_{24}N_2O_2$: theoretical value 588, observed value 588

Synthesis Example 4 (Synthesis of Compound No. 66)

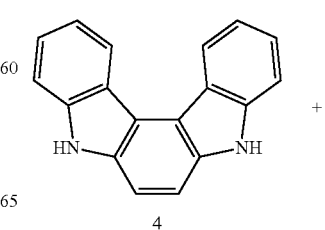

4

-continued

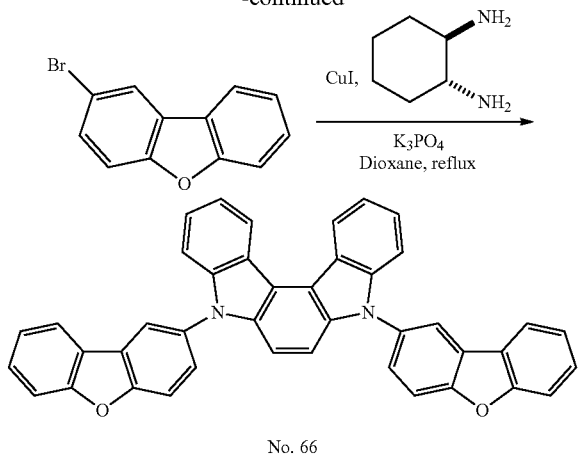

No. 66

Compound 4 (2.6 g, 10 mmol), 2-bromobenzofuran (5.0 g, 20 mmol), CuI (1.9 g, 10 mmol), transcyclohexane 1,2-diamine (3.4 g, 30 mmol), K$_3$PO$_4$ (8.5 g, 40 mmol), and 1,4-dioxane (10 mL) were loaded into a three-necked flask, and the mixture was refluxed under an argon atmosphere for 10 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The resultant sample was purified by silica gel column chromatography. The purified product was concentrated and exsiccated, and was then recrystallized twice, whereby a white powder (Compound No. 66) was obtained. The powder was purified by sublimation, whereby a white solid was obtained in an amount of 2.4 g in 40% yield. FD-MS C$_{42}$H$_{24}$N$_2$O$_2$: theoretical value 588, observed value 588

Synthesis Example 5 (Synthesis of Compound No. 100)

(1) Synthesis of Compound 5

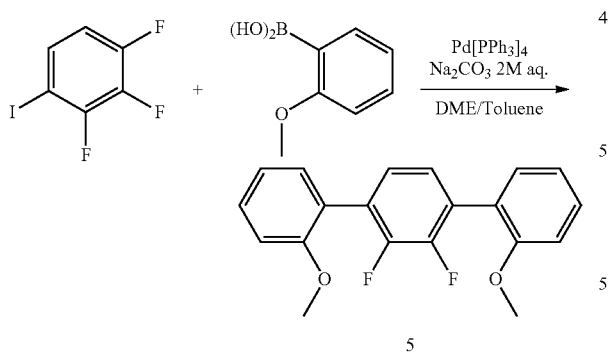

1,2-difluoro-3,6-diiodobenzene (65.9 g, 180.0 mmol), 2-methoxyphenylboronic acid (65.6 g, 432.0 mmol), a 2 M aqueous solution of Na$_2$CO$_3$ (360 mL, 720 mmol), DME (360 mL), toluene (360 mL), and Pd[PPh$_3$]$_4$ (20.8 g, 18.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with CH$_2$Cl$_2$. The extract was dried with MgSO$_4$, and was then filtrated and concentrated. The resultant sample was purified by silica gel column chromatography, whereby a white solid was obtained in an amount of 38.2 g in 65% yield. FD-MS C$_{20}$H$_{16}$F$_2$O$_2$: theoretical value 326, observed value 326

(2) Synthesis of Compound 6

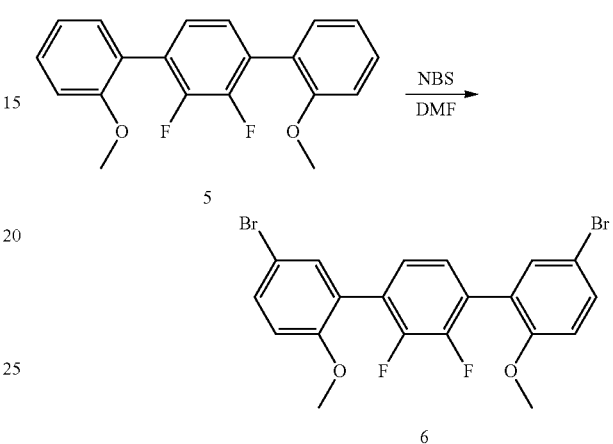

Compound 5 (38.0 g, 116.4 mmol), NBS (41.5 g, 232.9 mmol), and DMF (1,000 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 45.1 g in 80% yield. FD-MS C$_{20}$H$_{14}$Br$_2$F$_2$O$_2$: theoretical value 484, observed value 484

(3) Synthesis of Compound 7

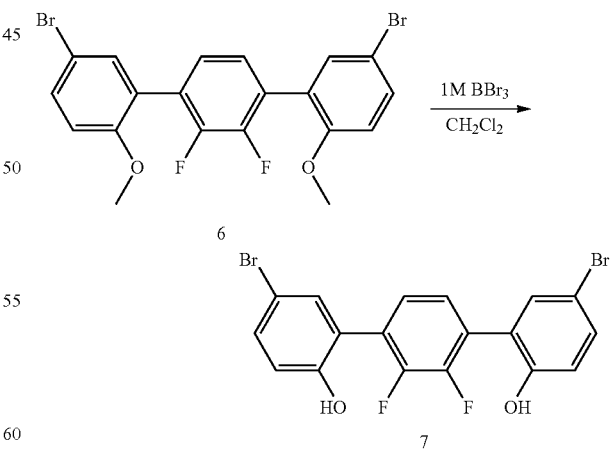

Compound 6 (45.0 g, 93.0 mmol), a 1 M solution of BBr$_3$ in CH$_2$Cl$_2$ (218 mL, 218 mmol), and CH$_2$Cl$_2$ (560 mL) were loaded into a three-necked flask, and the mixture was stirred under an Ar atmosphere at 0° C. for 8 hours. After that, the mixture was left to stand at room temperature overnight.

After the completion of the reaction, the resultant was neutralized with a saturated aqueous solution of NaHCO$_3$. The resultant sample was transferred to a separating funnel, and was extracted with CH$_2$Cl$_2$. The resultant sample was purified by column chromatography, whereby a white solid was obtained in an amount of 35.2 g in 83% yield.

FD-MS C$_{18}$H$_{10}$Br$_2$F$_2$O$_2$: theoretical value 456, observed value 456

(4) Synthesis of Compound 8

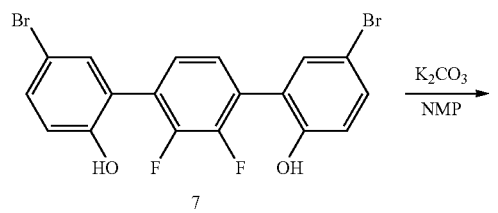

Compound 7 (35.0 g, 76.7 mmol), K$_2$CO$_3$ (23.3 g, 168.8 mmol), and NMP (320 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 27.1 g in 85% yield.

FD-MS C$_{18}$H$_8$Br$_2$O$_2$: theoretical value 416, observed value 416

(5) Synthesis of Compound No. 100

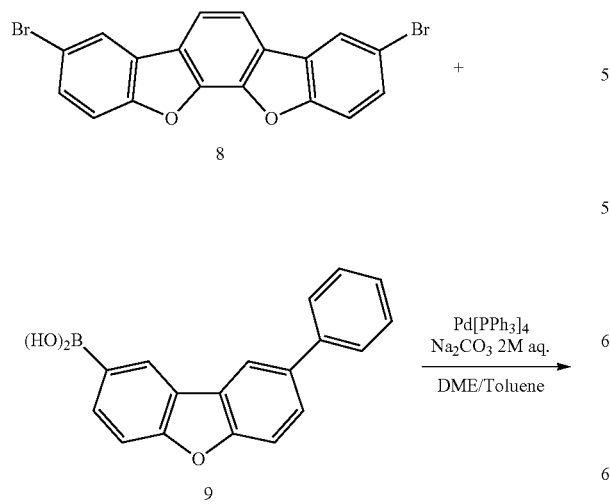

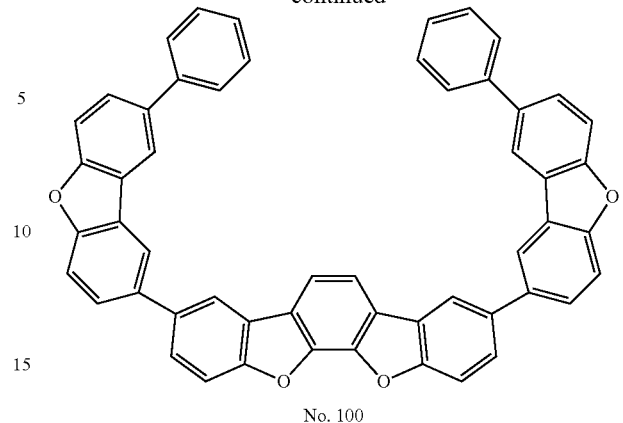

No. 100

Compound 8 (2.5 g, 6.0 mmol), Compound 9 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 100) was obtained. The powder was purified by sublimation, whereby a white solid was obtained in an amount of 2.0 g in 45% yield. FD-MS C$_{54}$H$_{30}$O$_4$: theoretical value 742, observed value 742

Synthesis Example 6 (Synthesis of Compound No. 103)

(1) Synthesis of Compound 10

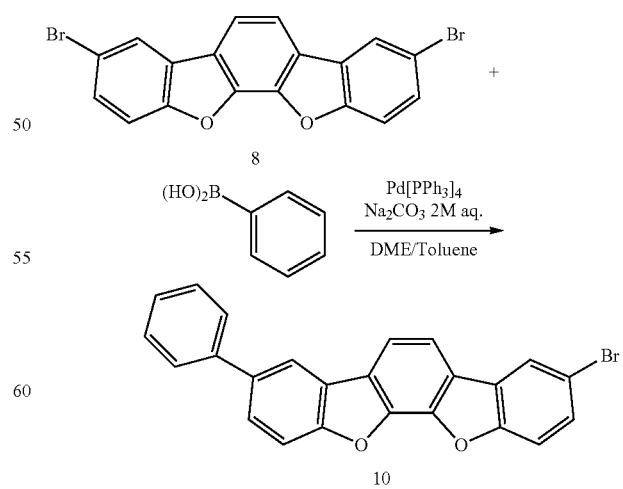

Compound 8 (16.8 g, 40 mmol), phenylboronic acid (4.8 g, 40 mmol), a 2 M aqueous solution of Na$_2$CO$_3$ (80 ml, 160 mmol), DME (80 mL), toluene (80 mL), and Pd[PPh₃]₄ (2.3 g, 2.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (150 mL) was with CH₂Cl₂. The extract was dried with MgSO₄, and was then filtrated and concentrated. The resultant sample was purified by recrystallization (toluene-hexane), whereby a white solid was obtained in an amount of 7.1 g in 65% yield.

(3) Synthesis of Compound No. 103

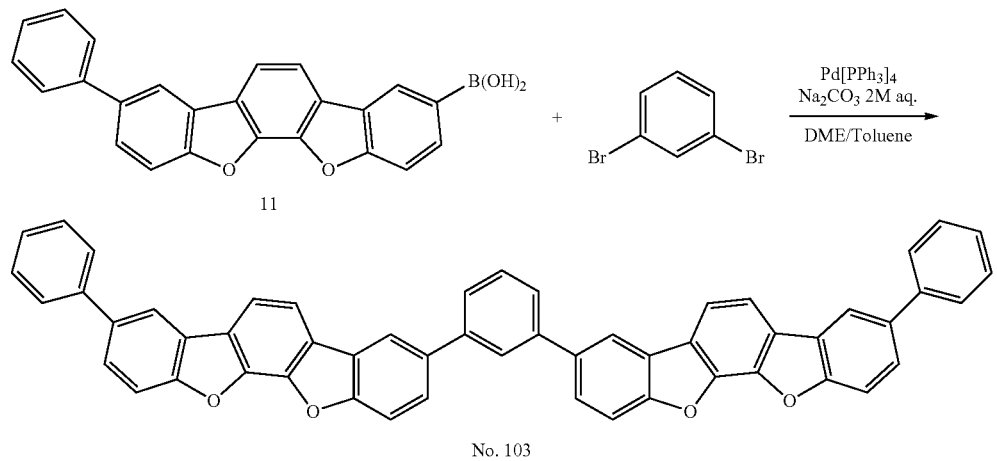

No. 103 charged into the funnel. Then, the mixture was extracted with CH₂Cl₂. The extract was dried with MgSO₄, and was then filtrated and concentrated. The resultant sample was purified by silica gel column chromatography, whereby a white solid was obtained in an amount of 12.4 g in 75% yield. FD-MS C₂₄H₁₃BrO₂: theoretical value 413, observed value 413

(2) Synthesis of Compound 11

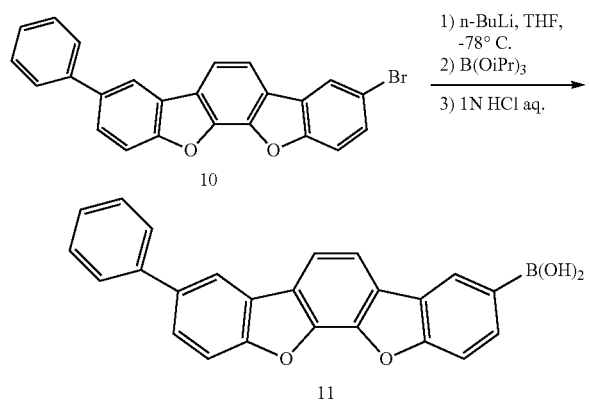

Compound 10 (12.0 g, 29.0 mmol) and THF (288 mL) were loaded into a three-necked flask, and the mixture was, cooled to −78° C. Then, n-BuLi (1.65 M solution in n-hexane, 19.4 mL, 31.9 mmol) was added dropwise to the flask, and the resultant mixture was stirred at −78° C. for 20 minutes. Triisopropyl borate (16.4 g, 87.0 mmol) was added to the resultant, and the mixture was stirred at −78° C. for 1 hour. After that, the resultant was left to stand overnight at room temperature. Then, 1N HCl (100 mL) was charged into the resultant, and the mixture was stirred at room temperature for 1 hour. The resultant sample was concentrated, and was then transferred to a separating funnel. Water (100 mL) was charged into the funnel, and the mixture was extracted Compound 11 (5.5 g, 14.5 mmol), 1,3-dibromobenzene (1-7 g, 7.3 mmol), a 2 M aqueous solution of Na₂CO₃ (15 mL, 30 mmol), DME (15 mL), toluene (15 mL), and Pd[PPh₃]₄ (0.42 g, 0.37 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH₂Cl₂. The extract was dried with MgSO₄, and was then filtrated and concentrated. The resultant sample was purified by silica gel column chromatography. The purified product was concentrated and exsiccated, and was then recrystallized twice, whereby a white powder (Compound No. 103) was obtained. The powder was purified by sublimation, whereby a white solid was obtained in an amount of 2.4 g in 45% yield. FD-MS C₅₄H₃₀O₄: theoretical value 742, observed value 742

Synthesis Example 7 (Synthesis of Compound No. 116)

(1) Synthesis of Compound 12

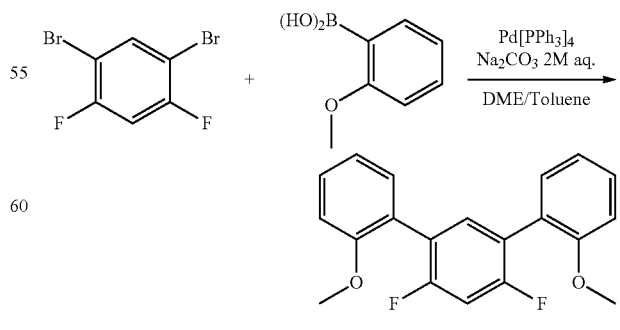

1,3-dibromo-4,6-difluorobenzene (50.0 g, 183.9 mmol), 2-methoxyphenylboronic acid (67.1 g, 441.1 mmol), and a 2 M aqueous solution of Na$_2$CO$_3$ (368 mL, 736 mmol), DME (370 mL), toluene (370 mL), and Pd[PPh$_3$]$_4$ (21 g, 18.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with CH$_2$Cl$_2$. The extract was dried with MgSO$_4$, and was then filtrated and concentrated. The resultant sample was purified by silica gel column chromatography, whereby a white solid was obtained in an amount of 40.2 g in 67% yield. FD-MS C$_{20}$H$_{16}$F$_2$O$_2$: theoretical value 326, observed value 326

(2) Synthesis of Compound 13

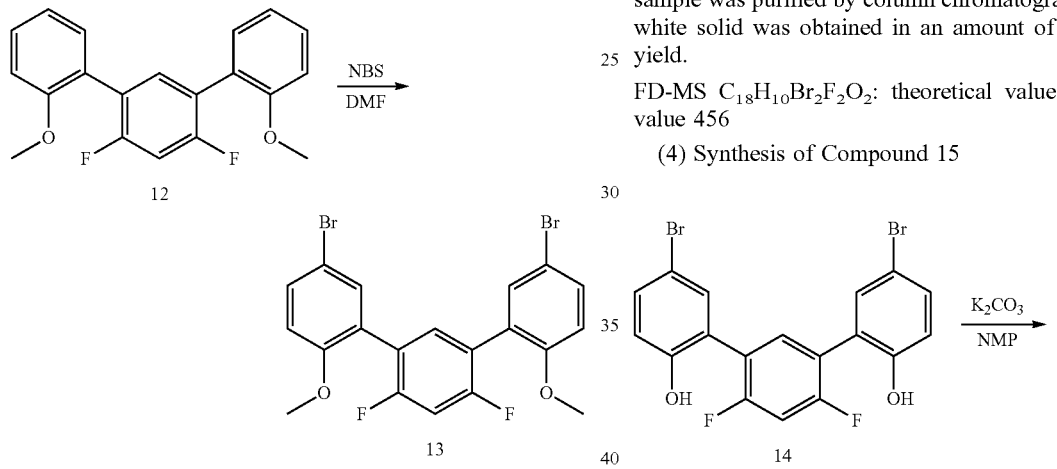

Compound 12 (40.0 g, 122.6 mmol), NBS (43.6 g, 245 mmol), and DMF (1,000 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 42.1 g in 71% yield. FD-MS C$_{20}$H$_{14}$Br$_2$F$_2$O$_2$: theoretical value 484, observed value 484

(3) Synthesis of Compound 14

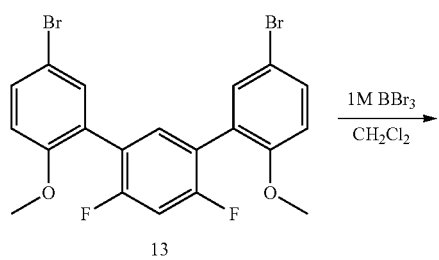

Compound 13 (40.0 g, 82.6 mmol), a 1 M solution of BBr$_2$ in CH$_2$Cl$_2$ (194 mL, 194 mmol), and CH$_2$Cl$_2$ (500 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of NaHCO$_3$. The resultant sample was transferred to a separating funnel, and was extracted with CH$_2$Cl$_2$. The resultant sample was purified by column chromatography, whereby a white solid was obtained in an amount of 30.2 g in 80% yield.

FD-MS C$_{18}$H$_{10}$Br$_2$F$_2$O$_2$: theoretical value 456, observed value 456

(4) Synthesis of Compound 15

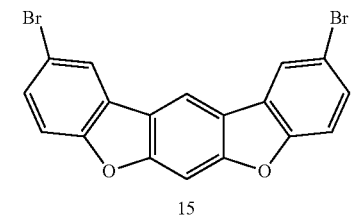

Compound 14 (30.0 g, 65.7 mmol), K$_2$CO$_3$ (19.9 g, 144.5 mmol), and NMP (270 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 21.9 g in 80% yield.

FD-MS C$_{18}$H$_8$Br$_2$O$_2$: theoretical value 416, observed value 416

Synthesis Example 8 (Synthesis of Compound No. 119)

(1) Synthesis of Compound 16

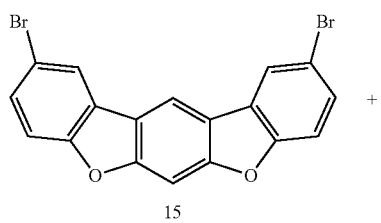

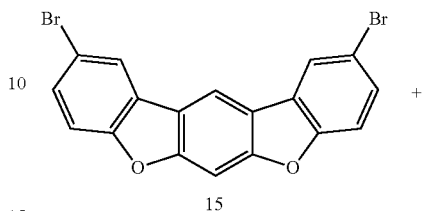

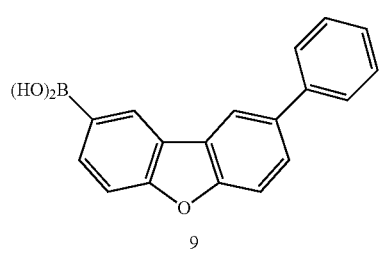

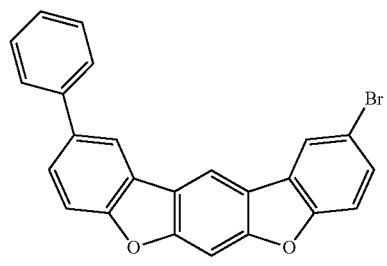

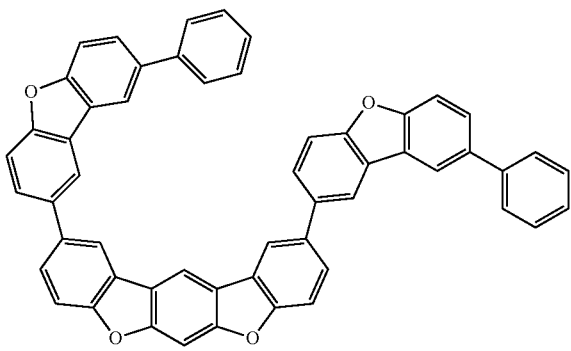

Compound 15 (2.5 g, 6.0 mmol), Compound 9 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 116) was obtained. The powder was purified by sublimation, whereby a white solid was obtained in an amount of 2.7 g in 60% yield. FD-MS C$_{54}$H$_{30}$O$_4$: theoretical value 742, observed value 742

Confound 15 (16.8 g, 40 mmol), phenylboronic acid (4.8 g, 40 mmol), a 2 M aqueous solution of Na$_2$CO$_3$ (80 mL, 160 mmol), DME (80 mL), toluene (80 mL), and Pd[PPh$_3$]$_4$ (2.3 g, 2.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (150 mL) was charged into the funnel. Then, the mixture was extracted with CH$_2$Cl$_2$. The extract was dried with MgSO$_4$, and was then filtrated and concentrated. The resultant sample was purified by silica gel column chromatography, whereby a white solid was obtained in an amount of 11.6 g in 70% yield. FD-MS C$_{24}$H$_{13}$BrO$_2$: theoretical value 413, observed value 413

(2) Synthesis of Compound 17

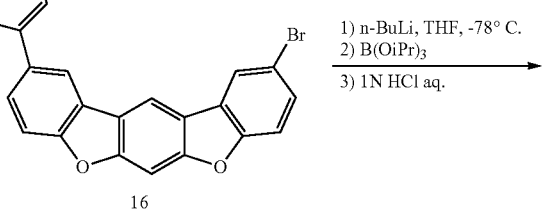

-continued

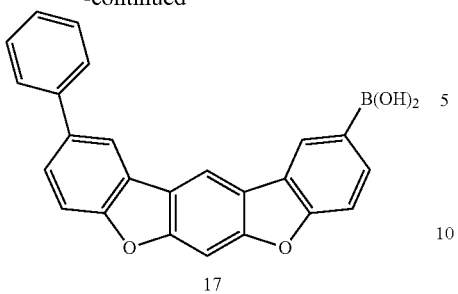

17

Compound 16 (11.0 g, 26.6 mmol) and THF (264 mL) were loaded into a three-necked flask, and the mixture was cooled to −78° C. Then, n-BuLi (1.65 M solution in n-hexane, 17.7 mL, 29.3 mmol) was added dropwise to the flask, and the resultant mixture was stirred at −78° C. for 20 minutes. Triisopropyl borate (15.1 g, 80 mmol) was added to the resultant, and the mixture was stirred at −78° C. for 1 hour. After that, the resultant was left to stand overnight at room temperature. Then, 1N HCl (100 mL) was charged into the resultant, and the mixture was stirred at room temperature for 1 hour. The resultant sample was concentrated, and was then transferred to a separating funnel. Water (100 mL) was charged into the funnel, and the mixture was extracted with $CH_2Cl_2$. The extract was dried with $MgSO_4$, and was then filtered and concentrated. The resultant sample was purified by recrystallization (toluene-hexane), whereby a white solid was obtained in an amount of 6.1 g in 61% yield.

(3) Synthesis of Compound No. 119

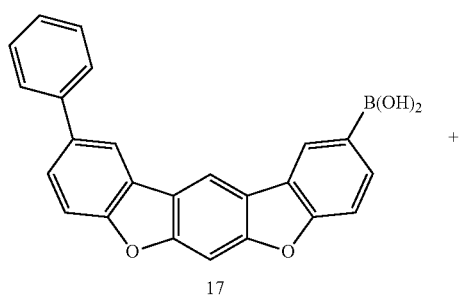

17

-continued

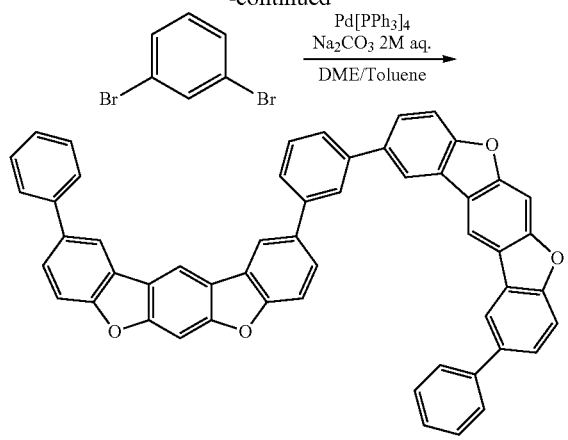

No. 119

Compound 17 (5.5 g, 14.5 mmol), 1,3-dibromobenzene (1.7 g, 7.3 mmol), a 2 M aqueous solution of $Na_2CO_3$ (15 mL, 30 mmol), DME (15 mL), toluene (15 mL), and $Pd[PPh_3]_4$ (0.42 g, 0.37 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtered and concentrated. The resultant sample was purified by silica gel column chromatography. The purified product was concentrated and exsiccated, and was then recrystallized twice, whereby a white powder (Compound No. 119) was obtained. The powder was purified by sublimation, whereby a white solid was obtained in an amount of 1.9 g in 35% yield. FD-MS $C_{54}H_{30}O_4$: theoretical value 742, observed value 742

Synthesis Example 9 (Synthesis of Compound No. 134)

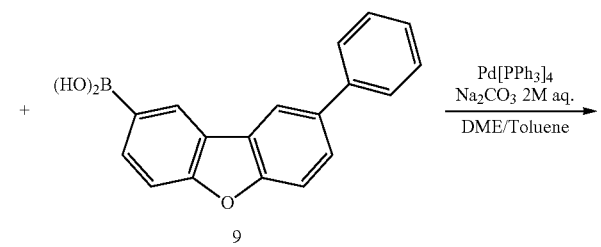

18 + 9

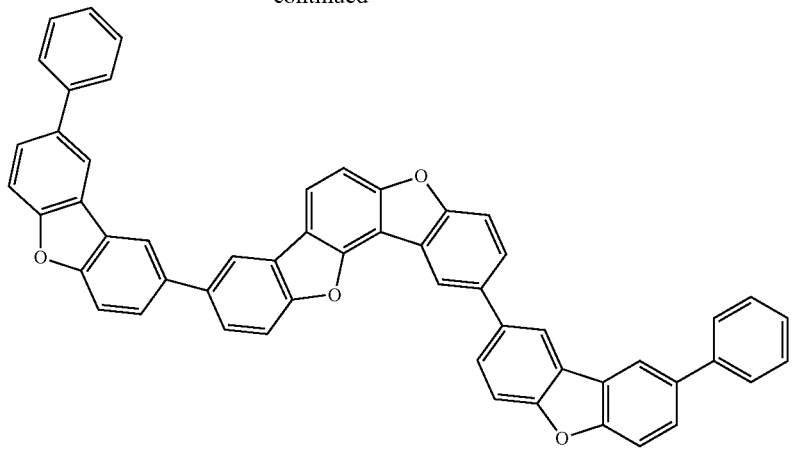

No. 134

Compound 18 (2.5 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 134) was obtained. The powder was purified by sublimation, whereby a white solid was obtained in an amount of 1.8 g in 41% yield. FD-MS $C_{54}H_{30}O_4$: theoretical value 742, observed value 742

Synthesis Example 10 (Synthesis of Compound No. 139)

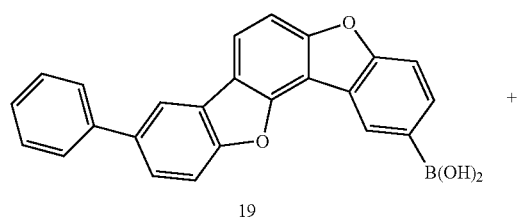

19

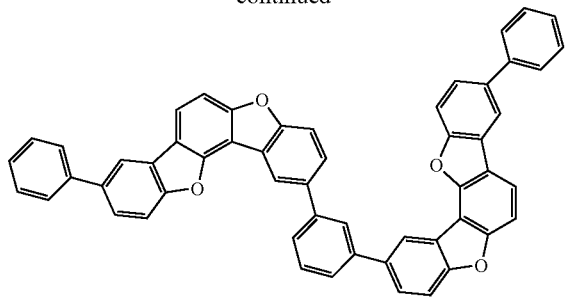

No. 139

Confound 19 (5.0 g, 13.2 mmol), 1,3-dibromobenzene (1.5 g, 6.6 mmol), a 2 M aqueous solution of $Na_2CO_3$ (14 mL, 28 mmol), DME (14 mL), toluene (14 mL), and $Pd[PPh_3]_4$ (0.38 g, 0.34 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 139) was obtained. The powder was purified by sublimation, whereby a white solid was obtained in an amount of 1.9 g in 39% yield. FD-MS $C_{54}H_{30}O_4$: theoretical value 742, observed value 742

Synthesis Example 11 (Synthesis of Compound No. 154)

(1) Synthesis of Compound 20

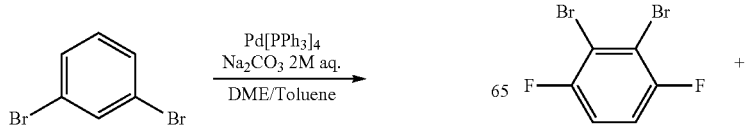

-continued

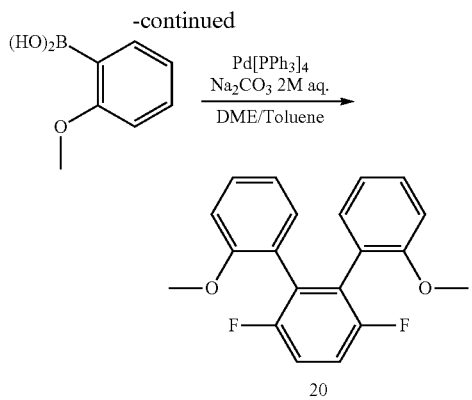

(3) Synthesis of Compound 22

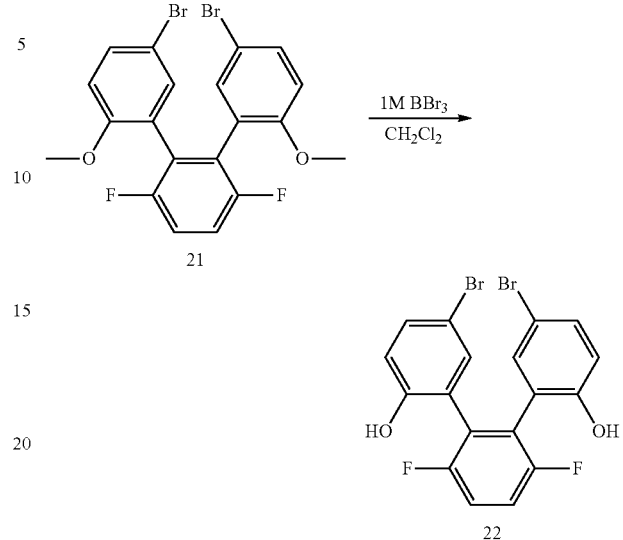

1,2-dibromo-3,6-difluorobenzene (50.0 g, 183.9 mmol), 2-methoxyphenylboronic acid (67.1 g, 441.4 mmol), and a 2 M aqueous solution of $Na_2CO_3$ (368 mL, 736 mmol), DME (370 mL), toluene (370 mL), and $Pd[PPh_3]_4$ (21.3 g, 18.4 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (500 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 30.6 g in 51% yield. FD-MS $C_{20}H_{16}F_2O_2$: theoretical value 326, observed value 326

(2) Synthesis of Compound 21

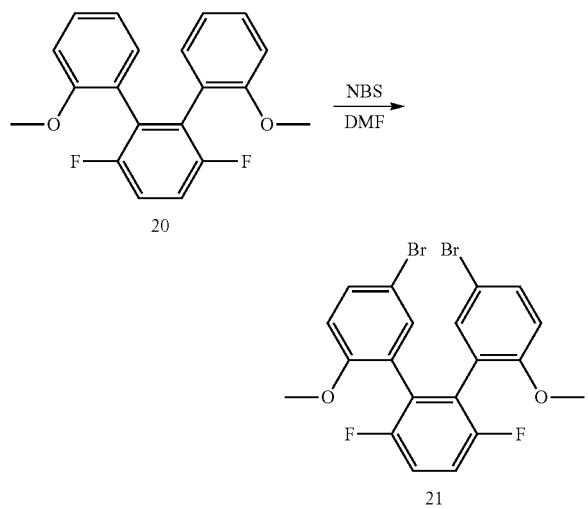

Compound 21 (32.0 g, 66.1 mmol), a 1 M solution of $BBr_3$ in $CH_2Cl_2$ (155 mL, 155 mmol), and $CH_2Cl_2$ (430 mL) were loaded into a three-necked flask, and the mixture was stirred under an Ar atmosphere at 0° C. for 8 hours. After that, the mixture was left to stand at room temperature overnight. After the completion of the reaction, the resultant was neutralized with a saturated aqueous solution of $NaHCO_3$. The resultant sample was transferred to a separating funnel, and was extracted with $CH_2Cl_2$. The resultant sample was purified by column chromatography, whereby a white solid was obtained in an amount of 24.1 g in 80% yield.

FD-MS $C_{18}H_{10}Br_2F_2O_2$: theoretical value 456, observed value 456

(4) Synthesis of Compound 23

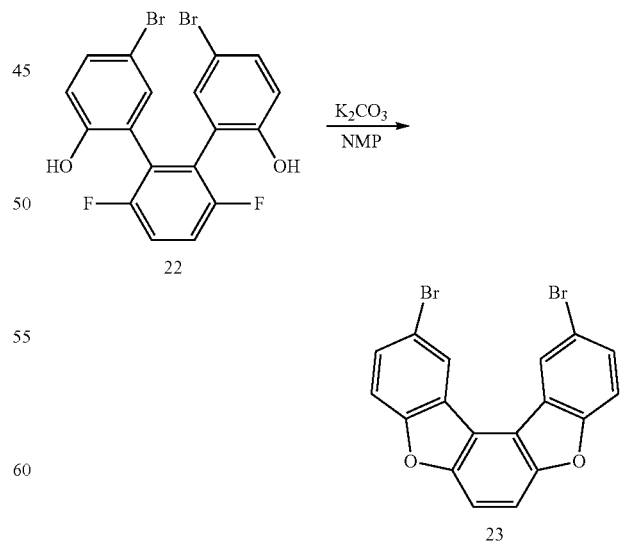

Compound 20 (30.0 g, 91.9 mmol), NBS (32.8 g, 184 mmol), and DMF (820 mL) were loaded into a three-necked flask, and the mixture was stirred under an Ar atmosphere at room temperature for 8 hours. After the completion of the reaction, the resultant sample was transferred to a separating funnel, and water (1,000 mL) was charged into the funnel. Then, the mixture was extracted with AcOEt. The resultant sample was purified by column chromatography, whereby a white solid was obtained in an amount of 32 g in 72% yield. FD-MS $C_{20}H_{14}Br_2F_2O_2$: theoretical value 484, observed value 484

Compound 22 (24.1 g, 52.8 mmol), $K_2CO_3$ (16.0 g, 116 mmol), and NMP (220 mL) were loaded into a three-necked flask, and the mixture was stirred under an Ar atmosphere at 150° C. for 8 hours. After the completion of the reaction, the resultant was cooled to room temperature. The resultant sample was transferred to a separating funnel, and water (500 mL) was charged into the funnel. Then, the mixture was extracted with AcOEt. The resultant sample was purified by column chromatography, whereby a white solid was obtained in an amount of 18.7 g in 85% yield.

FD-MS $C_{18}H_8Br_2O_2$: theoretical value 416, observed value 416

(5) Synthesis of Compound No. 154

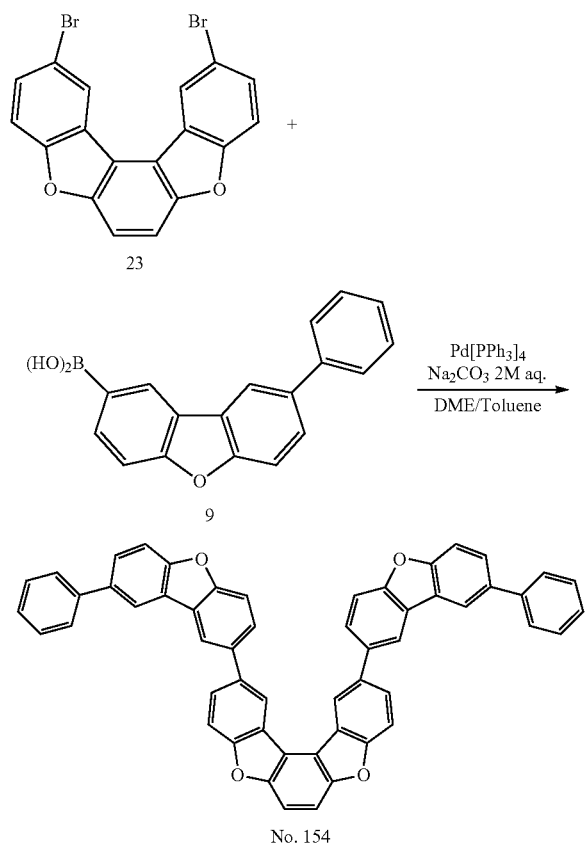

No. 154

Compound 23 (2.5 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 154) was obtained. The powder was purified by sublimation, whereby a white solid was obtained in an amount of 0.9 g in 20% yield. FD-MS $C_{54}H_{30}O_4$: theoretical value 742, observed value 742

Synthesis Example 12 (Synthesis of Compound No. 157)

(1) Synthesis of Compound 24

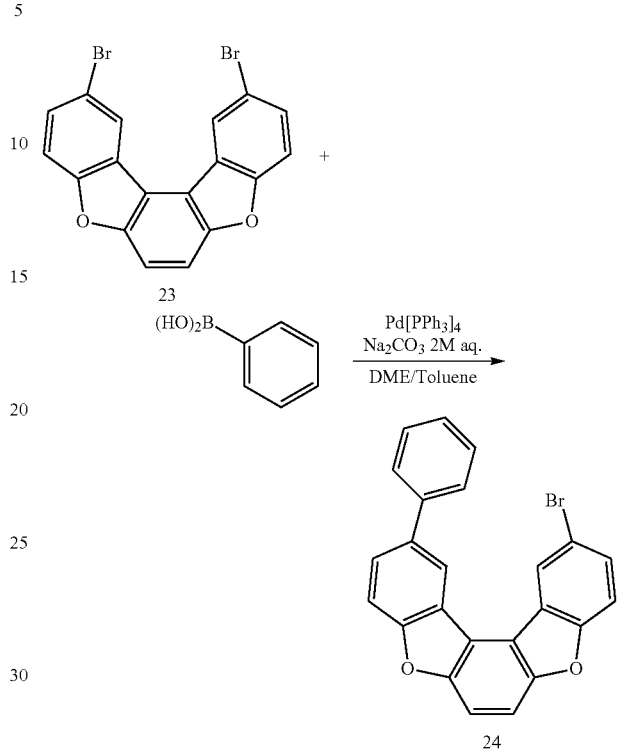

Compound 23 (16.8 g, 40.0 mmol), phenylboronic acid (4.8 g, 40 mmol), a 2 M aqueous solution of $Na_2CO_3$ (80 mL, 160 mmol), DME (80 mL), toluene (80 mL), and $Pd[PPh_3]_4$ (2.3 g, 2.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (150 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 9.1 g in 55% yield.

FD-MS $C_{24}H_{13}BrO_2$: theoretical value 413, observed value 413

(2) Synthesis of Compound 25

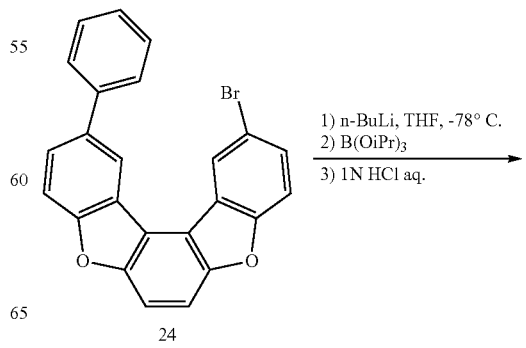

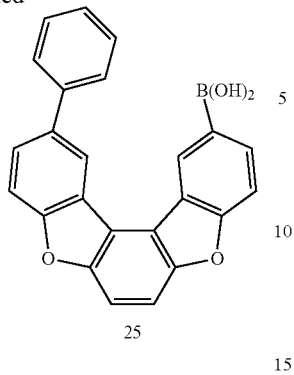

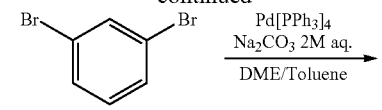

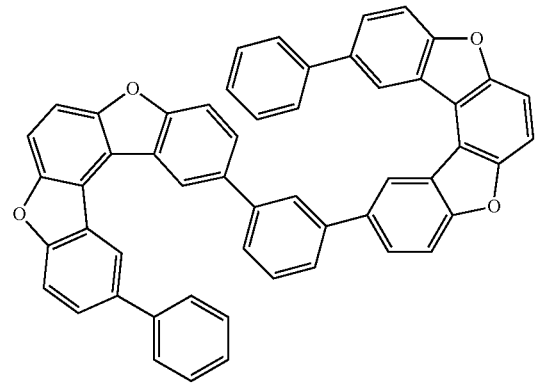

No. 157

Compound 24 (9.0 g, 21.8 mmol) and THF (220 mL) were loaded into a three-necked flask, and the mixture was cooled to −78° C. Then, n-BuLi (1.65 M solution in n-hexane, 14.5 mL, 23.9 mmol) was added dropwise to the flask, and the resultant mixture was stirred at −78° C. for 20 minutes. Triisopropyl borate (12.3 g, 65.3 mmol) was added to the resultant, and the mixture was stirred at −78° C. for 1 hour. After that, the resultant was left to stand overnight at room temperature. Then, 1N HCl (100 mL) was charged into the resultant, and the mixture was stirred at room temperature for 1 hour. The resultant sample was concentrated, and was then transferred to a separating funnel. Water (100 mL) was charged into the funnel, and the mixture was extracted with $CH_2Cl_2$. The extract was dried with $MgSO_4$, and was then filtrated and concentrated. The resultant sample was purified by recrystallization (toluene-hexane), whereby a white solid was obtained in an amount of 4.1 g in 50% yield.

(3) Synthesis of Compound No. 157

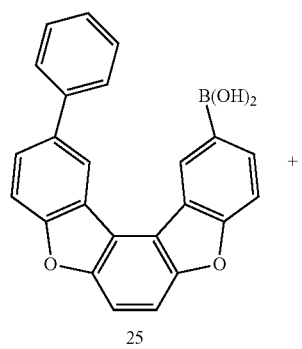

Compound 25 (4.0 g, 10.6 mmol), 1,3-dibromobenzene (1.2 g, 5.3 mmol), a 2 M aqueous solution of $Na_2CO_3$ (11 mL, 22 mmol), DME (11 mL), toluene (11 mL), and $Pd[PPh_3]_4$ (0.31 g, 0.27 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 157) was obtained. The powder was purified by sublimation, whereby a white solid was obtained in an amount of 0.63 g in 16% yield. FD-MS $C_{54}H_{30}O_4$: theoretical value 742, observed value 742

Synthesis Example 13 (Synthesis of Compound No. 239)

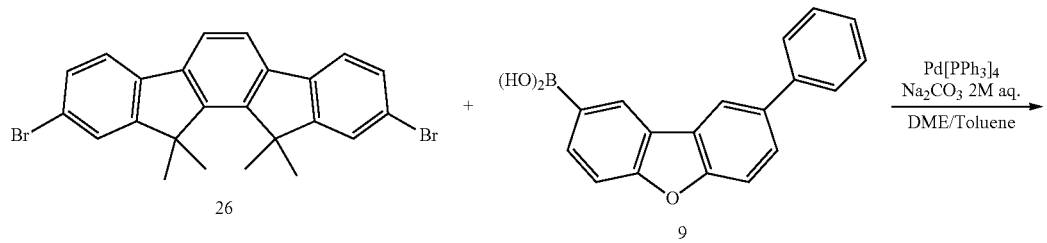

-continued

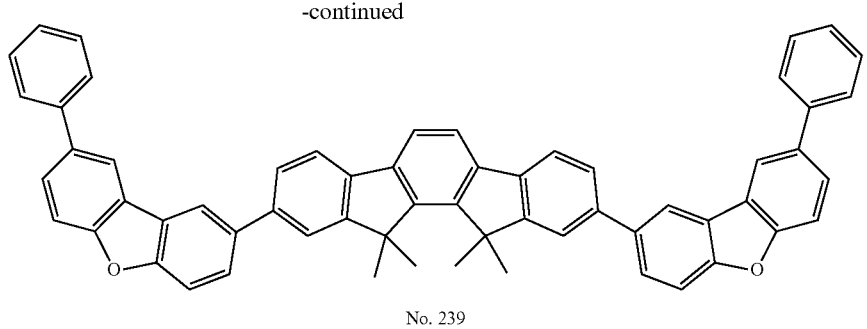

No. 239

Compound 26 (2.8 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 239) was obtained. The powder was purified by sublimation, whereby a white solid was obtained in an amount of 2.1 g in 45% yield. FD-MS $C_{60}H_{42}O_2$: theoretical value 794, observed value 794

Synthesis Example 14 (Synthesis of Compound No. 249)

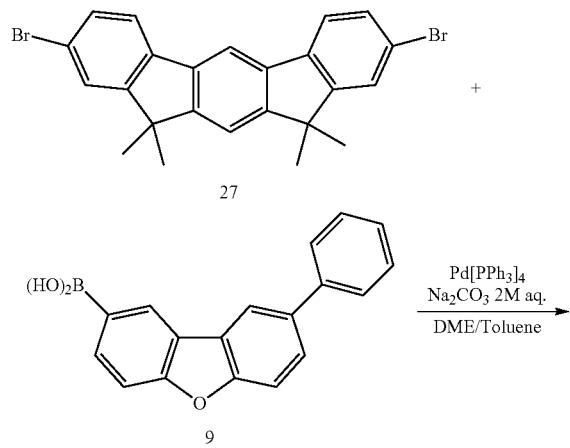

-continued

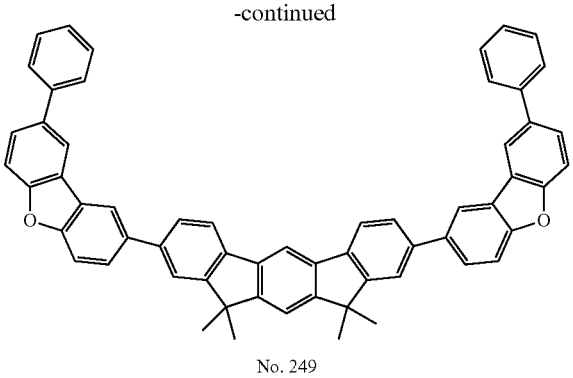

No. 249

Compound 27 (2.8 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 249) was obtained. The powder was purified by sublimation, whereby a white solid was obtained in an amount of 2.5 g in 52% yield. FD-MS $C_{60}H_{42}O_2$: theoretical value 794, observed value 794

Synthesis Example 15 (Synthesis of Compound No. 259)

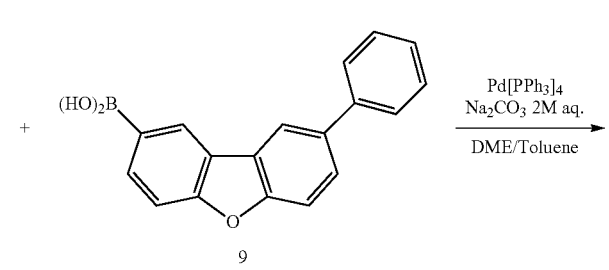

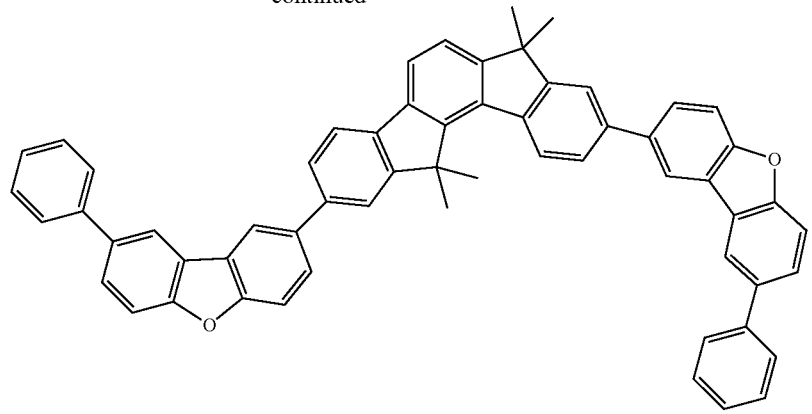

No. 259

Compound 28 (2.8 g, 6.0 mmol), Compound 9 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 259) was obtained. The powder was purified by sublimation, whereby a white solid was obtained in an amount of 1.9 g in 40% yield. FD-MS C$_{60}$H$_{42}$O$_2$: theoretical value 794, observed value 794

Synthesis Example 16 (Synthesis of Compound No. 269)

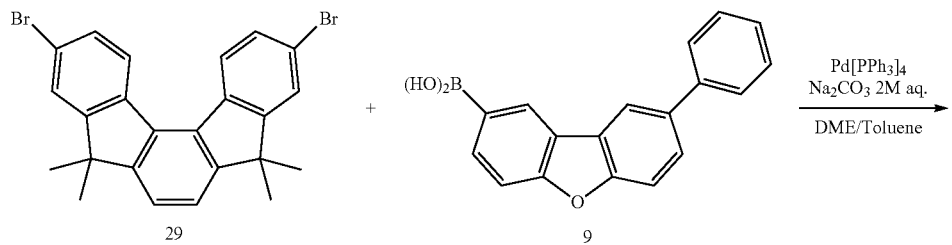

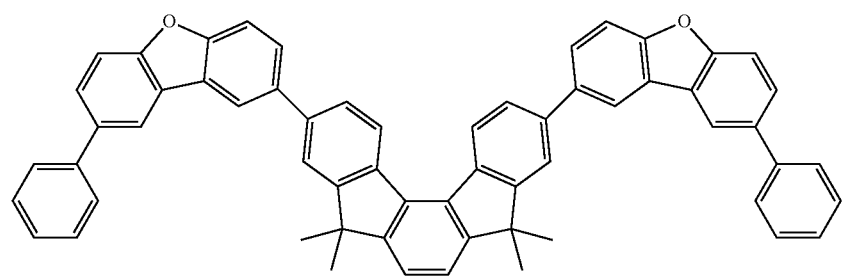

No. 269

Compound 29 (2.8 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 269) was obtained. The powder was purified by sublimation, whereby a white solid was obtained in an amount of 1.0 g in 21% yield. FD-MS $C_{60}H_{42}O_2$: theoretical value 794, observed value 794

Synthesis Example 17 (Synthesis of Compound No. 233)

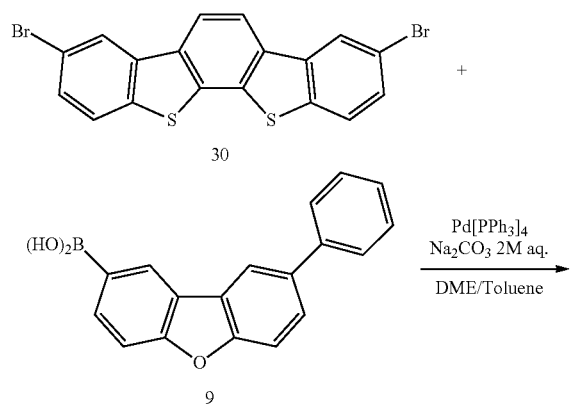

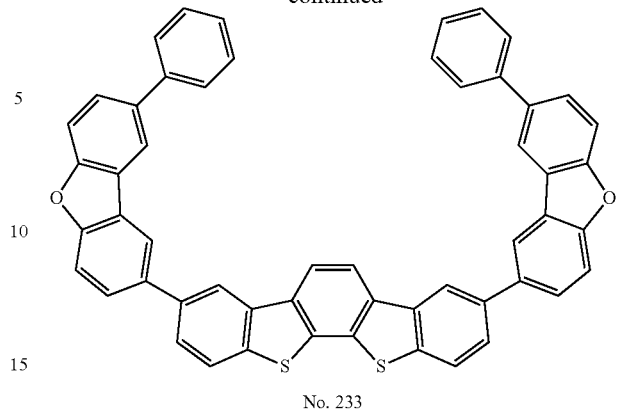

No. 233

Compound 30 (2.7 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 233) was obtained. The powder was purified by sublimation, whereby a white solid was obtained in an amount of 1.9 g in 40% yield. FD-MS $C_{54}H_{30}O_2S_2$: theoretical value 774, observed value 774

Synthesis Example 18 (Synthesis of Compound No. 243)

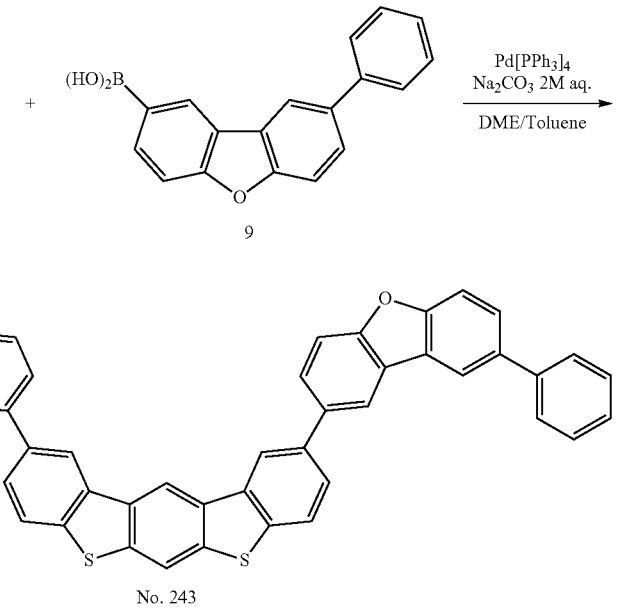

No. 243

Compound 31 (2.7 g, 6.0 mmol), Compound 9 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 243) was obtained. The powder was purified by sublimation, whereby a white solid was obtained in an amount of 2.1 g in 45% yield. FD-MS C$_{54}$H$_{30}$O$_2$S$_2$: theoretical value 774, observed value 774

Synthesis Example 19 (Synthesis of Compound No. 253)

Compound 32 (2.7 g, 6.0 mmol), Compound 9 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 253) was obtained. The powder was purified by sublimation, whereby a white solid was obtained in an amount of 1.8 g in 38% yield. FD-MS C$_{54}$H$_{30}$O$_2$S$_2$: theoretical value 774, observed value 774

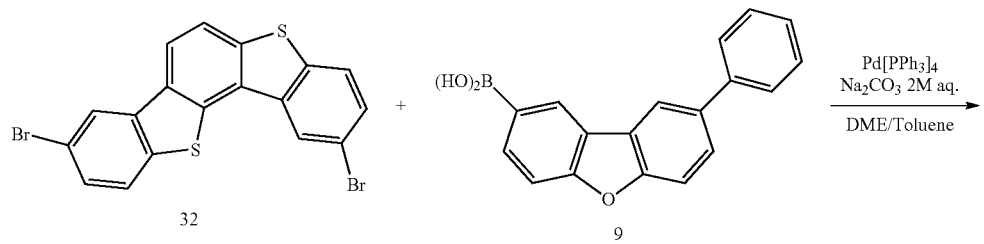

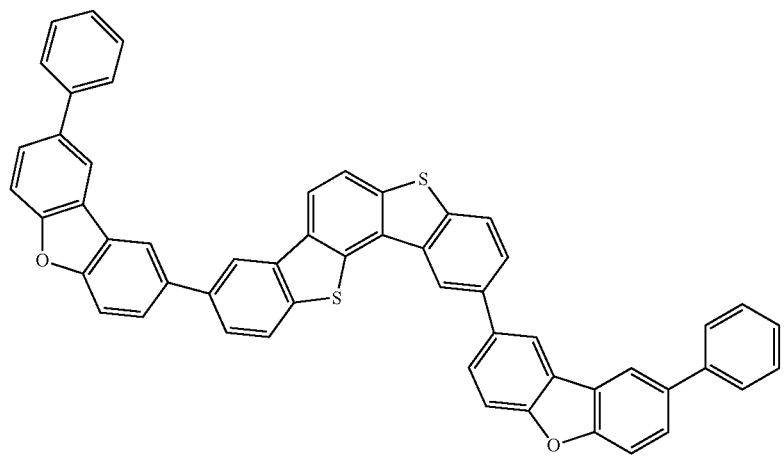

No. 253

Synthesis Example 20 (Synthesis of Compound No. 263)

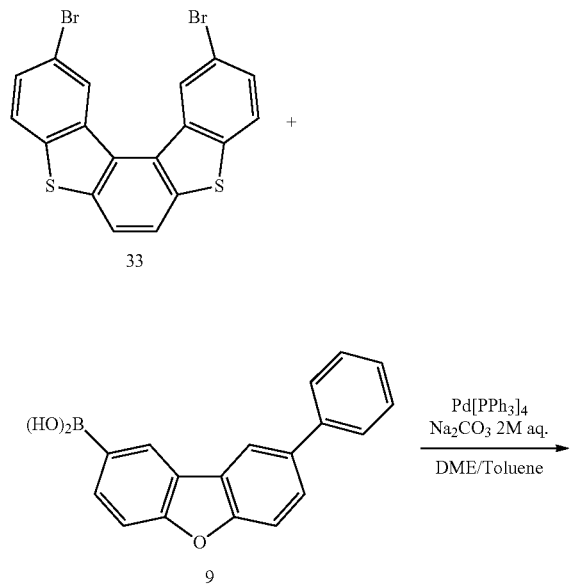

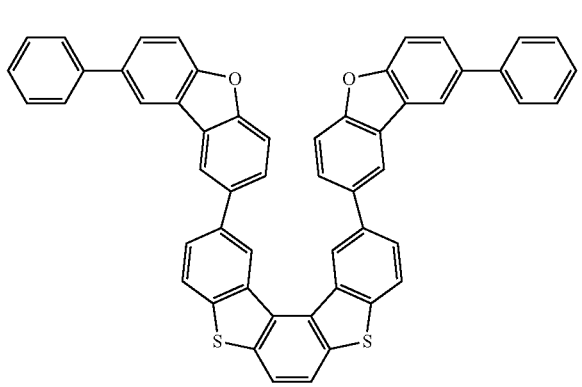

Synthesis Example 21 (Synthesis of Compound No. 272)

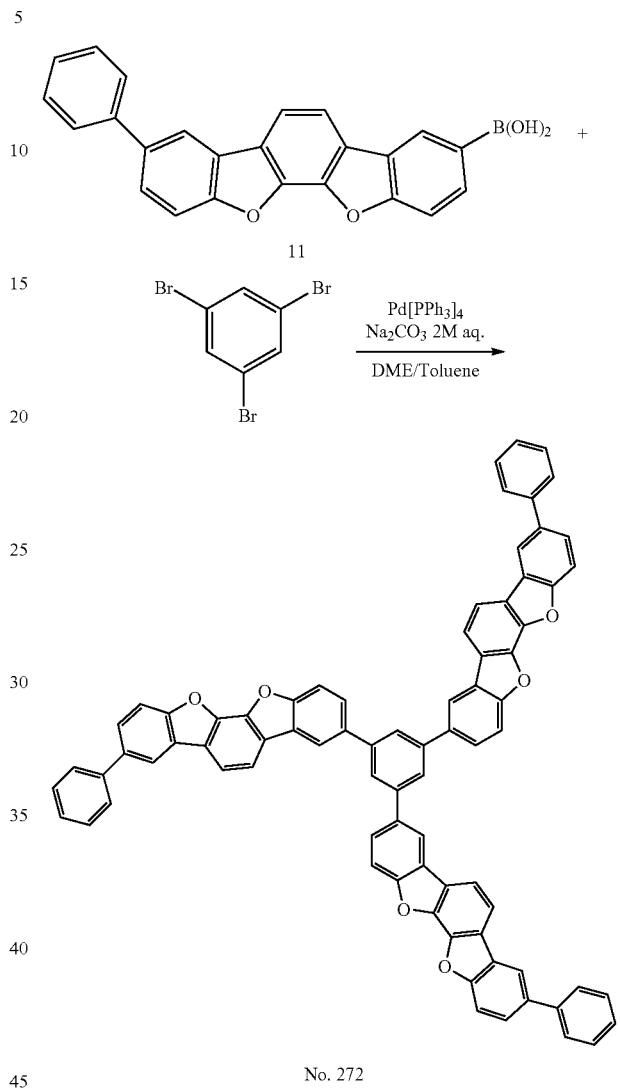

Compound 33 (2.7 g, 6.0 mmol), Compound 9 (3.8 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 263) was obtained. The powder was purified by sublimation, whereby a white solid was obtained in an amount of 0.6 g in 13% yield. FD-MS $C_{54}H_{30}O_2S_2$: theoretical value 774, observed value 774

Compound 11 (8.3 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 272) was obtained. The powder was purified by sublimation, whereby a white solid was obtained in an amount of 1.0 g in 13% yield. FD-MS $C_{78}H_{42}O_6$: theoretical value 1,075, observed value 1,075

Synthesis Example 22 (Synthesis of Compound No. 273)

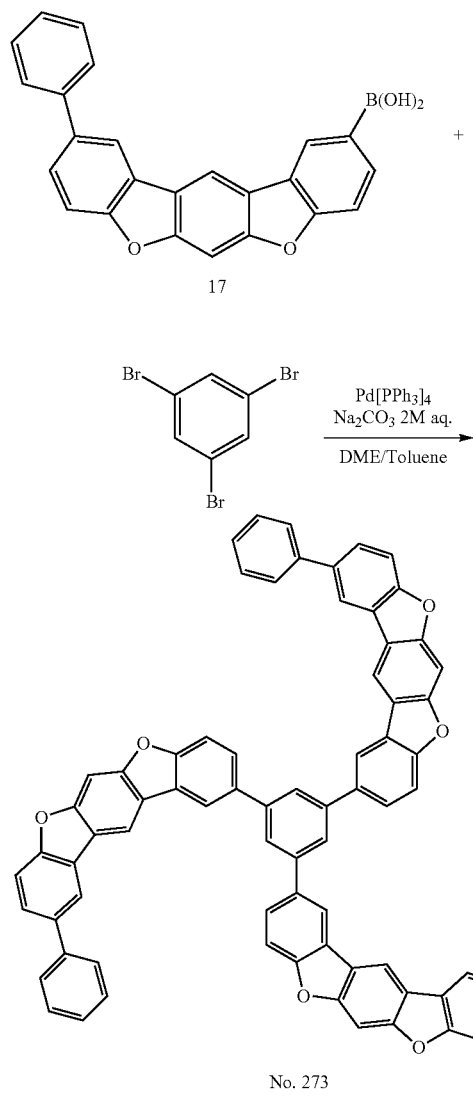

No. 273

Synthesis Example 23 (Synthesis of Compound No. 274)

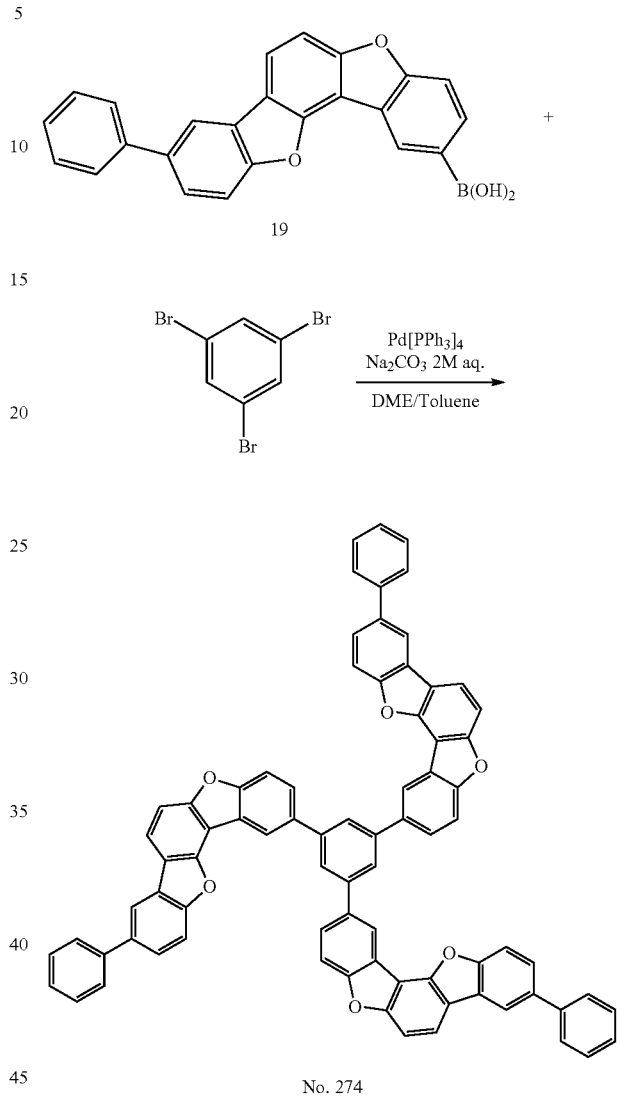

No. 274

Compound 17 (8.3 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 273) was obtained. The powder was purified by sublimation, whereby a white solid was obtained in an amount of 1.2 g in 15% yield. FD-MS $C_{78}H_{42}O_6$: theoretical value 1,075, observed value 1,075

Compound 19 (8.3 g, 21.9 mmol), 1,3,5-tribromobenzene (2.3 g, 7.3 mmol), a 2 M aqueous solution of $Na_2CO_3$ (22.5 mL, 45 mmol), DME (15 mL), toluene (15 mL), and $Pd[PPh_3]_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 274) was obtained. The powder was purified by sublimation, whereby a white solid was obtained in an amount of 0.94 g in 12% yield. FD-MS $C_{78}H_{42}O_6$: theoretical value 1,075, observed value 1,075

Synthesis Example 24 (Synthesis of Compound No. 276)

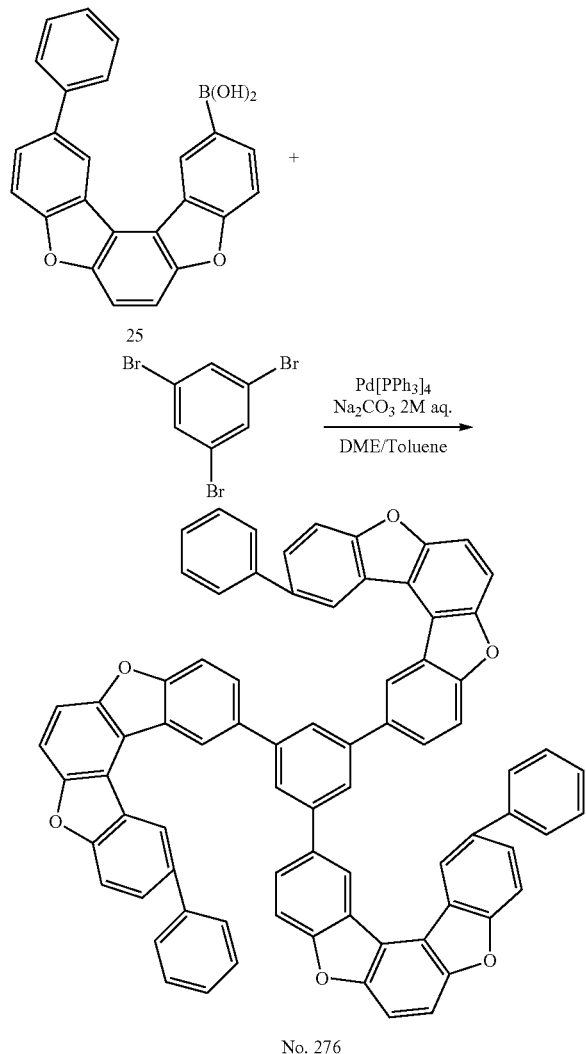

No. 276

Compound 25 (8.3 g, 21.9 mmol), 1,3,5-tribromobenzene (2.3 g, 7.3 mmol), a 2 M aqueous solution of Na$_2$CO$_3$ (22.5 mL, 45 mmol), DME (15 mL), toluene (15 mL), and Pd[PPh$_3$]$_4$ (0.63 g, 0.56 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 276) was obtained. The powder was purified by sublimation, whereby a white solid was obtained in an amount of 0.55 g in 7% yield. FD-MS C$_{78}$H$_{42}$O$_6$: theoretical value 1,075, observed value 1,075

Synthesis Example 25 (Synthesis of Compound No. 1)

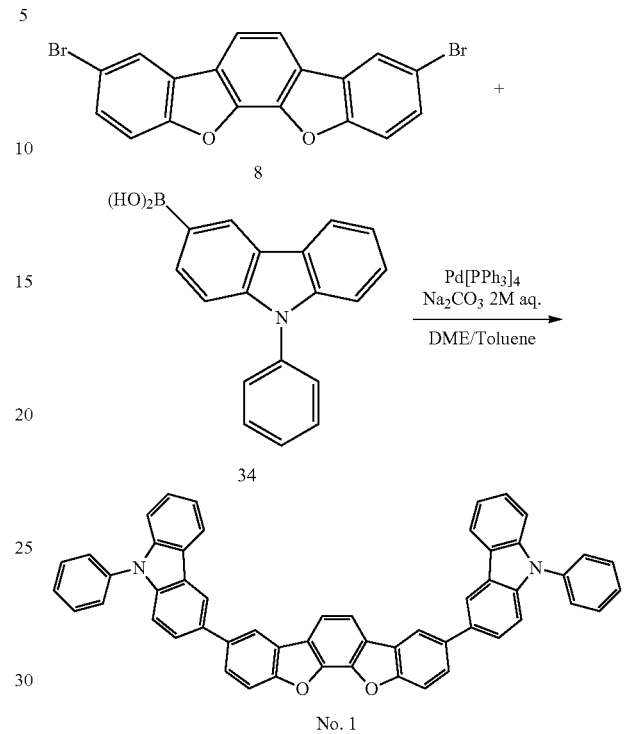

No. 1

Compound 8 (2.5 g, 6.0 mmol), compound 34 (3.8 g, 13.2 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 1) was obtained. The powder was purified by sublimation, whereby a white solid was obtained in an amount of 1.2 g in 27% yield.

FD-MS C$_{54}$H$_{32}$N$_2$O$_2$: theoretical value 740, observed value 740

Synthesis Example 26 (Synthesis of Compound No. 92)

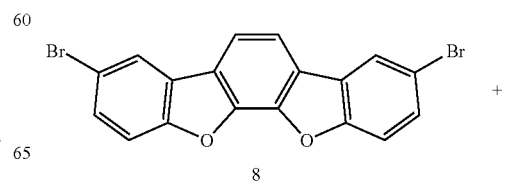

8

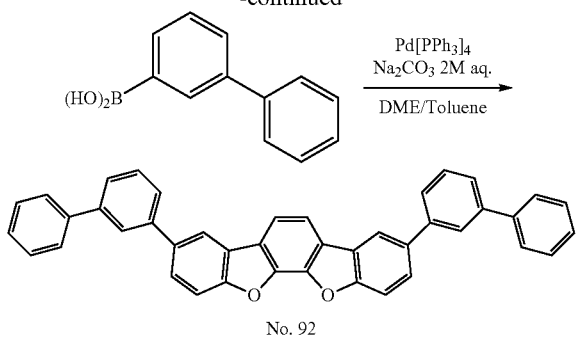

No. 92

Compound 8 (2.5 g, 6.0 mmol), 3-biphenylboronic acid (2.6 g, 13.2 mmol), a 2 M aqueous solution of $Na_2CO_3$ (12 mL, 24 mmol), DME (12 mL), toluene (12 mL), and $Pd[PPh_3]_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 92) was obtained. The powder was purified by sublimation, whereby a white solid was obtained in an amount of 1.1 g in 32% yield.

FD-MS $C_{42}H_{26}O_2$: theoretical value 562, observed value 562

Synthesis Example 27 (Synthesis of Compound No. 108)

(1) Synthesis of Compound 35

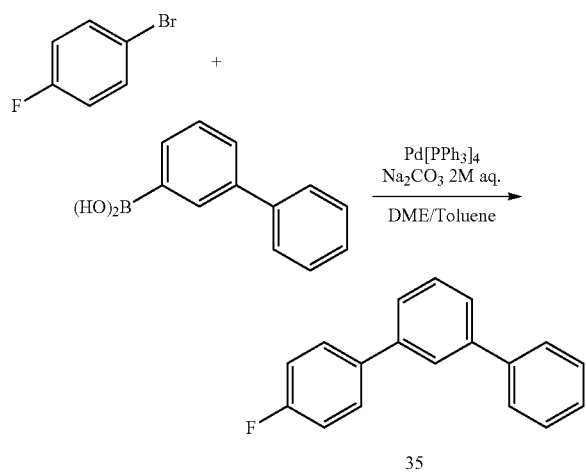

4-bromofluorobenzene (81.55 g, 466 mmol), 3-biphenyl-boronic acid (92.33 g, 466 mmol), a 2 M aqueous solution of $Na_2CO_3$ (530 mL), $Pd[PPh_3]_4$ (14.7 g, 12.7 mmol), EWE (500 mL), and toluene (500 mL) were loaded into a three-necked flask, and the mixture was refluxed under an Ar atmosphere for 6 hours.

After the completion of the reaction, the resultant was cooled to room temperature. The resultant sample was transferred to a separating funnel, and water (350 mL) was charged into the funnel. Then, the mixture was extracted with toluene. The extract was dried with $MgSO_4$, and was then filtrated and concentrated. The resultant sample was purified by silica gel column chromatography. The purified product was concentrated and exsiccated, and was then recrystallized, whereby a white solid was obtained in an amount of 31.7 g in 27% yield.

FD-MS $C_{18}H_{13}F$: theoretical value 248, observed value 248

(2) Synthesis of Compound 36

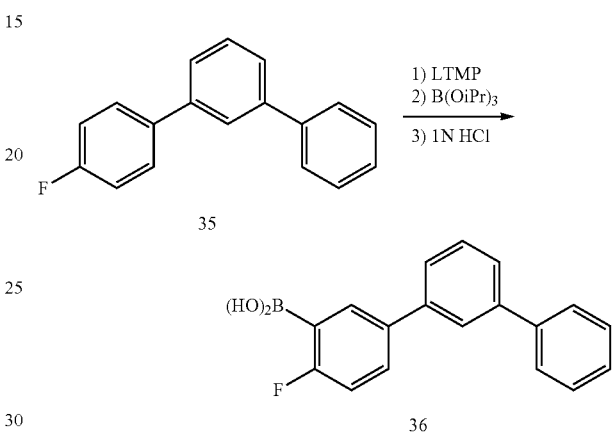

Compound 35 (31.7 g, 127 mmol) and THF (200 mL) were loaded into a three-necked flask, and the mixture was cooled to −78° C. Then, lithium 2,2,6,6-tetramethyl piperidine solution preliminarily prepared from n-BuLi (1.55 M solution in hexane, 82 mL, 127 mmol), 2,2,6,6-tetramethyl piperidine (17.9 g, 127 mmol), and THF (50 mL) were added to the flask, and the resultant mixture was stirred at −78° C. under an Ar atmosphere for 2 hours. After that, triisopropyl borate (71.6 g, 381 mmol) was added to the mixture, followed by stirring at −78° C. for 2 hours. Then, the temperature of the obtained mixture was returned to room temperature slowly and the mixture was left to stand overnight.

After the completion of the reaction, methanol (50 mL) was added to inactivate the resultant, and the resultant was concentrated to about the half volume. $CH_2Cl_2$ (200 mL) and 2N HCl (120 mL) were added, followed by stirring at room temperature for 2 hours. The resultant sample was transferred to a separating funnel, and extracted with $CH_2Cl_2$. The extract was dried with $MgSO_4$, and was then purified by silica gel column chromatography. The purified product was concentrated and exsiccated, and was then subjected to dispersion washing with toluene, whereby a white solid was obtained in an amount of 27.5 g in 74% yield.

(3) Synthesis of Compound 37

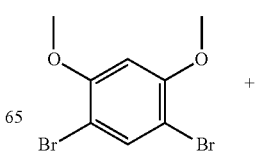

373

-continued

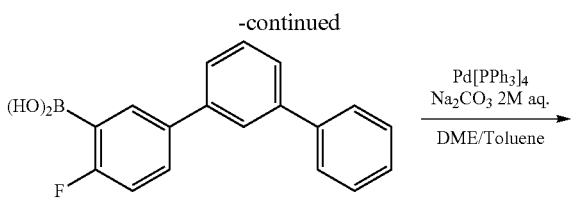

374

1,3-dibromo-4,6-dimethoxybenzene (5.92 g, 20 mmol), Compound 36 (14.02 g, 48 mmol), a 2 M aqueous solution of $Na_2CO_3$ (40 mL), $Pd[PPh_3]_4$ (1.15 g, 1 mmol), DME (20 mL), and toluene (20 mL) were loaded into a three-necked flask, and the mixture was refluxed under an Ar atmosphere for 36 hours.

After the completion of the reaction, the resultant was cooled to room temperature. The resultant sample was transferred to a separating funnel, and water (100 mL) was charged into the funnel. Then, the mixture was extracted with toluene. The extract was dried with $MgSO_4$, and was then filtrated and concentrated. The resultant sample was purified by silica gel column chromatography. The purified product was concentrated and exsiccated, and was then recrystallized, whereby a white solid was obtained in an amount of 9.49 g in 75% yield.

FD-MS $C_{44}H_{32}F_2O_2$: theoretical value 630, observed value 630

(4) Synthesis of Compound 38

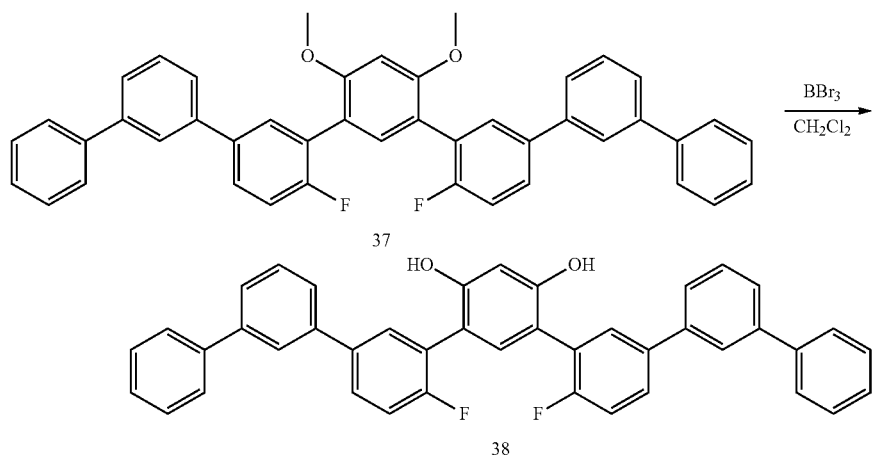

Compound 37 (9.49 g, 5 mmol) and $CH_2Cl_2$ (75 mL) were loaded into a three-necked flask, and the mixture was cooled to 0° C. Then, $BBr_3$ (15.03 g, 60 mmol) was added to the flask, and the resultant mixture was stirred under an Ar atmosphere at room temperature for 24 hours.

After the completion of the reaction, the obtained solution was cooled to −78° C., and inactivated using methanol (50 mL) and water (100 mL). The sample was transferred to a separating funnel, and water (100 mL) was charged into the funnel. Then, the mixture was extracted with $CH_2Cl_2$. The extract was dried with $MgSO_4$, and was then filtered and concentrated. The obtained sample was purified by silica gel column chromatography. The purified product was concentrated and exsiccated, whereby a white solid was obtained in an amount of 9.04 g in 100% yield.

FD-MS $C_{42}H_{28}F_2O_2$: theoretical value 602, observed value 602

(5) Synthesis of Compound No. 108

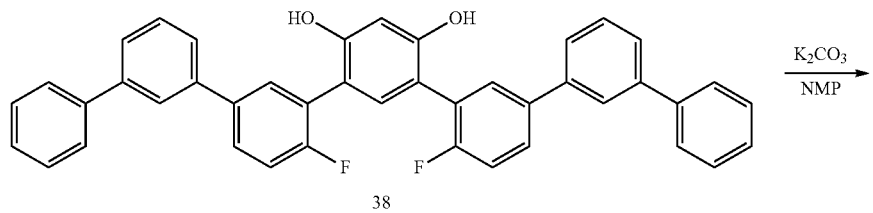

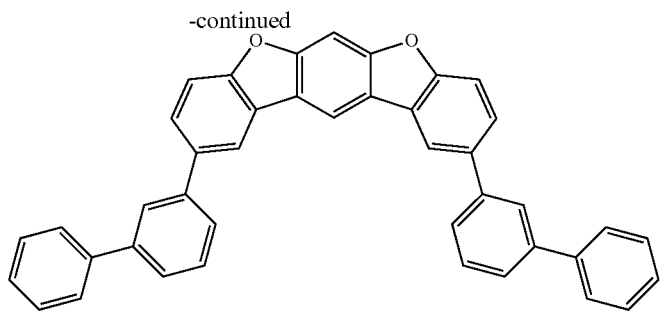

No. 108

Compound 38 (9.04 g, 15 mmol) and NMP (150 mL) were loaded into a three-necked flask, and Compound 38 was dissolved completely. $K_2CO_3$ (8.30 g, 60 mmol) was added to the flask, followed by stirring at 200° C. for 2 hours.

After the completion of the reaction, the obtained solution was cooled to room temperature. Toluene (1.5 L) was added to the resultant sample, and the sample was transferred to a separating funnel and washed with water. The resultant was dried with $MgSO_4$ and then filtered and concentrated. The resultant sample was purified by silica gel column chromatography. The purified product was concentrated and exsiccated, and was then recrystallized, whereby a white powder (Compound No. 108) was obtained. The powder was purified by sublimation, whereby a white solid was obtained in an amount of 3.37 g in 40% yield.

FD-MS $C_{42}H_{26}O_2$: theoretical value 562, observed value 562

Synthesis Example 28 (Synthesis of Compound No. 281)

(1) Synthesis of Compound 39

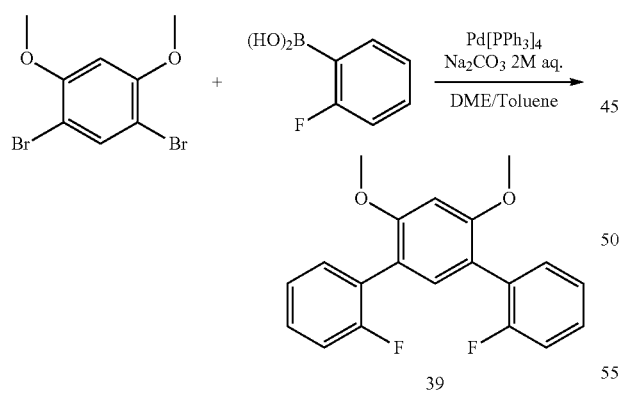

1,3-dibromo-4,6-dimethoxybenzene (88.8 g, 300 mmol), 2-fluorophenyl boric acid (100.7 g, 720 mmol), 2 M aqueous solution of $Na_2CO_3$ (600 mL), $Pd[PPh_3]_4$ (6.73 g, 6 mmol), DME (150 mL), and toluene (150 mL) were loaded into a three-necked flask, and the mixture was refluxed under an Ar atmosphere for 36 hours.

After the completion of the reaction, the obtained solution was cooled to room temperature. The resultant sample was transferred to a separating funnel, and water (500 mL) was charged into the funnel. Then, the mixture was extracted with toluene. After being dried with $MgSO_4$, the extract was filtered and concentrated. The resultant sample was purified by silica gel column chromatography. The purified product was concentrated and exsiccated, and was then recrystallized, whereby a white solid was obtained in an amount of 86.5 g in 88% yield.

FD-MS $C_{20}H_{16}F_2O_2$: theoretical value 326, observed value 326

(2) Synthesis of Compound 40

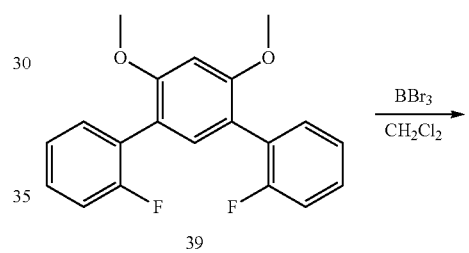

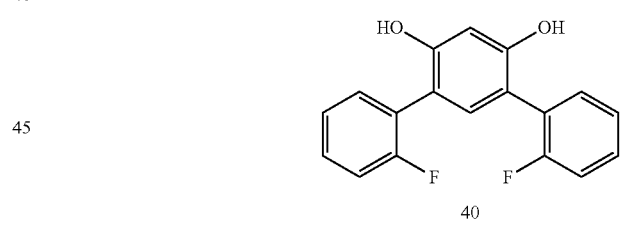

Compound 39 (48.3 g, 148 mmol) and $CH_2Cl_2$ (740 mL) were loaded into a three-necked flask, and the mixture was cooled to 0° C. Then, $BBr_3$ (89.0 g, 355 mmol) was added to the flask, and the resultant mixture was stirred at room temperature for 24 hours.

After the completion of the reaction, the obtained solution was cooled to −78° C., and inactivated using methanol (50 mL) and water (100 mL). The sample was transferred to a separating funnel. Then, the mixture was extracted with $CH_2Cl_2$. The extract was dried with $MgSO_4$, and was then filtered and concentrated. The obtained sample was purified by silica gel column chromatography. The purified product was concentrated and exsiccated, whereby a white solid was obtained in an amount of 44.14 g in 100% yield.

FD-MS $C_{18}H_{12}F_2O_2$: theoretical value 298, observed value 298

(3) Synthesis of Compound 41

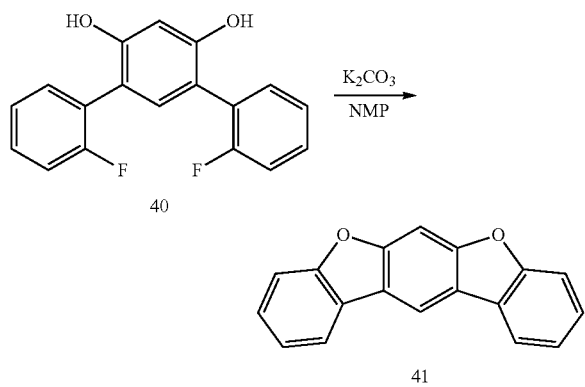

Compound 40 (44.14 g, 148 mmol) and NMP (888 mL) were loaded into a three-necked flask, and Compound 40 was dissolved completely. K$_2$CO$_3$ (81.8 g, 592 mmol) was added to the flask, followed by stirring at 200° C. for 2 hours.

After the completion of the reaction, the obtained solution was cooled to room temperature. The sample was transferred to a separating funnel, toluene (2 L) was added, and the resultant was a washed with water. The resultant was dried with MgSO$_4$ and then filtered and concentrated. The resultant sample was purified by silica gel column chromatography. The purified product was concentrated and exsiccated, and was then recrystallized, whereby a white solid was obtained in an amount of 27.9 g in 73% yield. FD-MS C$_{18}$H$_{10}$O$_2$: theoretical value 258, observed value 258

(4) Synthesis of Compound 42

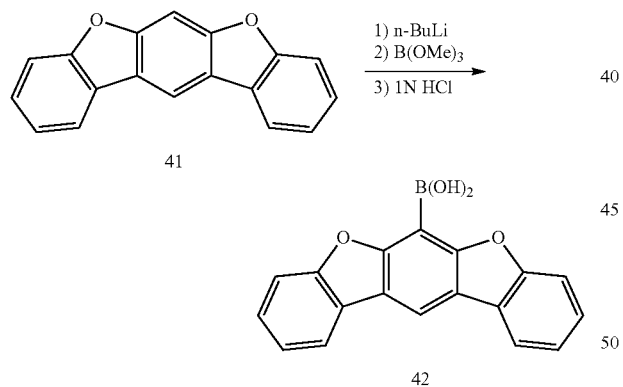

Compound 41 (12.9 g, 50 mmol) and THF (300 mL) were loaded into a three-necked flask, and the mixture was cooled to −78° C. Then, n-BuLi (2.63 M solution in hexane, 20.0 mL, 52.5 mmol) was added to the flask, and the resultant mixture was stirred at room temperature under an Ar atmosphere for 1 hour. Next, the resultant was cooled to −78° C. again, trimethyl borate (10.4 g, 100 mmol) was added to the resultant. After being stirred at −78° C. for 10 minutes, the mixture was stirred at room temperature for 1 hour.

After the completion of the reaction, the resultant was concentrated to about the half volume. 1N HCl (200 mL) was added to the concentrated resultant, followed by stirring at room temperature for 1 hour. The resultant sample was transferred to a separating funnel, and the mixture was extracted with ethyl acetate. After being dried with MgSO$_4$, the extract was concentrated. The concentrated product was subjected to dispersion washing with a toluene/hexane mixed solvent, whereby a white solid was obtained in an amount of 13.7 g in 91% yield.

(5) Synthesis of Compound No. 281

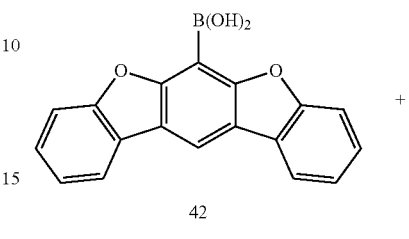

+

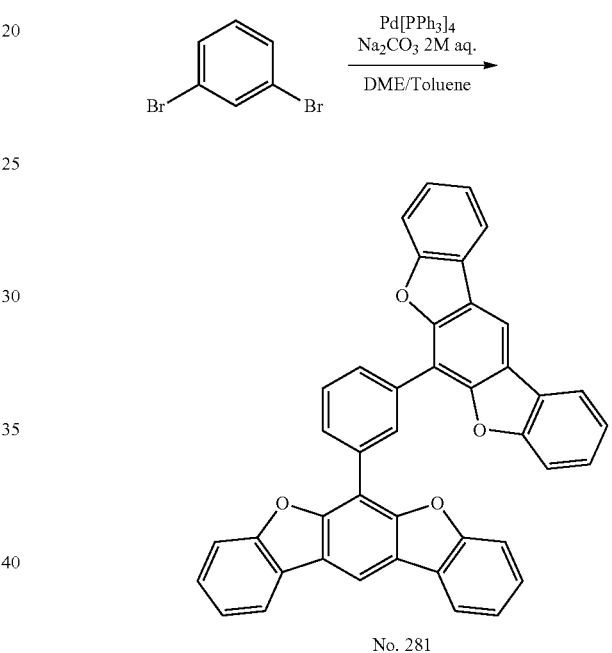

Compound 42 (3.8 g, 12.6 mmol), 1,3-dibromobenzene (1.4 g, 6.0 mmol), a 2 M aqueous solution of Na$_2$CO$_3$ (12 mL, 24 mmol), DME (12 mL), toluene (12 mL), and Pd[PPh$_3$]$_4$ (0.35 g, 0.3 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with CH$_2$Cl$_2$. The extract was dried with MgSO$_4$, and was then filtrated and concentrated. The resultant sample was purified by silica gel column chromatography. The purified product was concentrated and exsiccated, and was then recrystallized twice, whereby a white powder (Compound No. 281) was obtained. The powder was purified by sublimation, whereby a white solid was obtained in an amount of 1.3 g in 37% yield. FD-MS C$_{42}$H$_{22}$O$_4$: theoretical value 590, observed value 590

Synthesis Example 29 (Synthesis of Compound No. 284)

(1) Synthesis of Compound 43

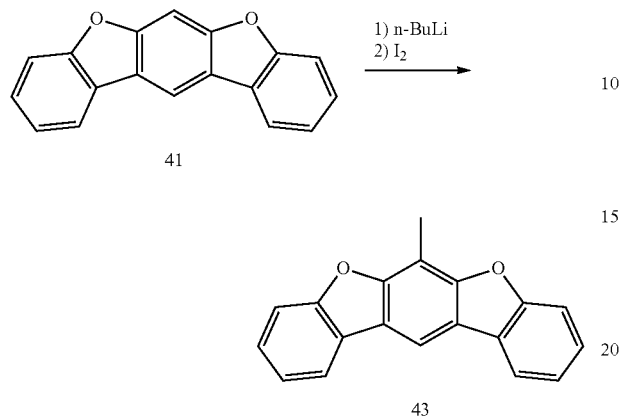

Compound 41 (2.69 g, 10.4 mmol) and THF (62 mL) were loaded into a three-necked flask, and the mixture was cooled to −78° C. Then, n-BuLi (1.66 M solution in hexane, 6.6 mL, 10.9 mmol) was added to the flask, and the resultant mixture was stirred at room temperature for 30 minutes. Next, the resultant was cooled to −78° C. again, $I_2$ (2.69 g, 10.6 mmol) was added to the resultant. After being stirred at −78° C. for 10 minutes, the mixture was stirred at room temperature for 1 hour.

After the completion of the reaction, water (30 mL) was added to inactivate the obtained solution, followed by concentration. After being subjected to dispersion washing with water, the sample was collected by filtration and then dissolved in toluene. After being dried with $MgSo_4$, the resultant was filtered and concentrated. The obtained sample was purified by silica gel column chromatography. The purified product was concentrated and exsiccated, and was then recrystallized, whereby a white solid was obtained in an amount of 3.77 g in 94% yield.

FD-MS $C_{18}H_9IO_2$: theoretical value 384, observed value 384

(2) Synthesis of Compound No. 284

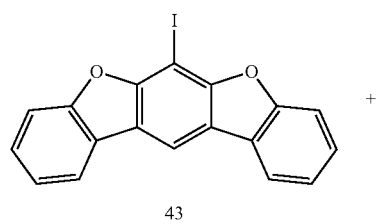

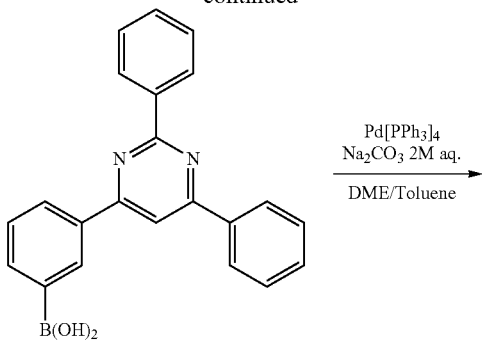

Compound 43 (2.3 g, 6.0 mmol), Compound 44 (2.2 g, 6.3 mmol), a 2 M aqueous solution of $Na_2CO_3$ (12 mL, 24 mmol), DME (12 mL), toluene (12 mL), and $Pd[PPh_3]_4$ (0.35 g, 0.30 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (50 mL) was charged into the funnel. Then, the mixture was extracted with $CH_2Cl_2$. The extract was dried with $MgSO_4$, and was then filtrated and concentrated. The resultant sample was purified by silica gel column chromatography. The purified product was concentrated and exsiccated, and was then recrystallized twice, whereby a white powder (Compound No. 284) was obtained. The powder was purified by sublimation, whereby a white solid was obtained in an amount of 1.0 g in 30% yield. FD-MS $C_{40}H_{24}N_2O_2$: theoretical value 564, observed value 564

Synthesis Example 30 (Synthesis of Compound No. 306)

(1) Synthesis of Compound 46

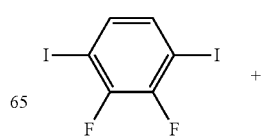

-continued

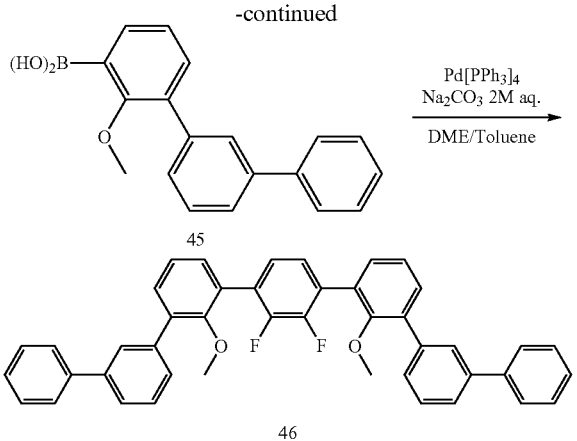

1,2-difluoro-3,6-diiodobenzene (7.3 g, 20.0 mmol), Compound 45 (12.8 g, 42.0 mmol), a 2 M aqueous solution of Na₂CO₃ (40 mL, 80.0 mmol), DME (40 mL), toluene (40 mL), and Pd[PPh₃]₄ (1.2 g, 1.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with CH₂Cl₂. The extract was dried with MgSO₄, and was then filtrated and concentrated. The resultant sample was purified by silica gel column chromatography, whereby a white solid was obtained in an amount of 8.2 g in 65% yield. FD-MS C₄₄H₃₂F₂O₂: theoretical value 630, observed value 630

(2) Synthesis of Compound 47

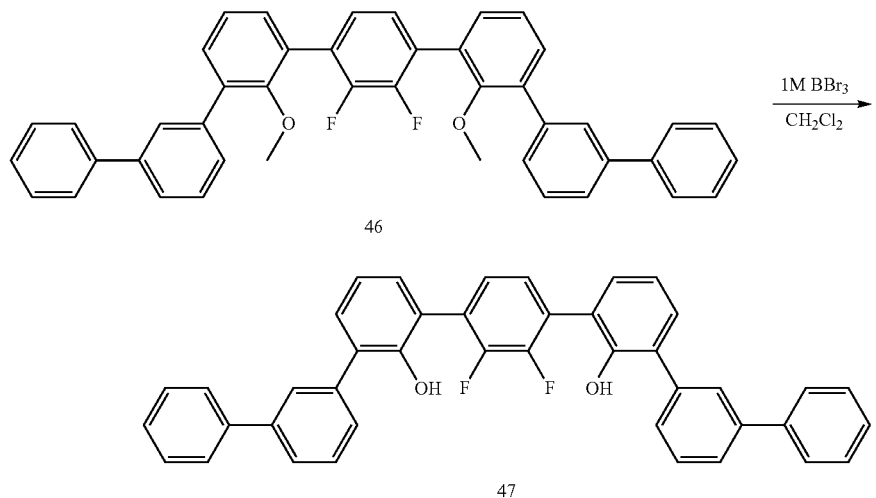

Compound 46 (8.2 g, 13.0 mmol), a 1 M solution of BBr₃ in CH₂Cl₂ (32 mL, 32.0 mmol), and CH₂Cl₂ (100 mL) were loaded into a three-necked flask, and the mixture was stirred under an Ar atmosphere at 0° C. for 8 hours. After that, the mixture was left to stand at room temperature overnight.

After the completion of the reaction, the resultant was neutralized with a saturated aqueous solution of NaHCO₃. The resultant sample was transferred to a separating funnel, and was extracted with CH₂Cl₂. The resultant sample was purified by silica gel column chromatography, whereby a white solid was obtained in an amount of 7.6 g in 97% yield. FD-MS C₄₂H₂₈F₂O₂: theoretical value 602, observed value 602

(3) Synthesis of Compound No. 306

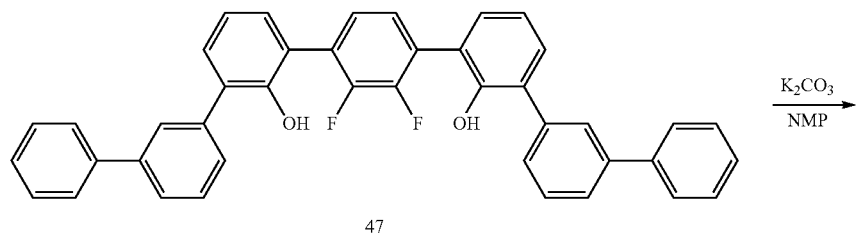

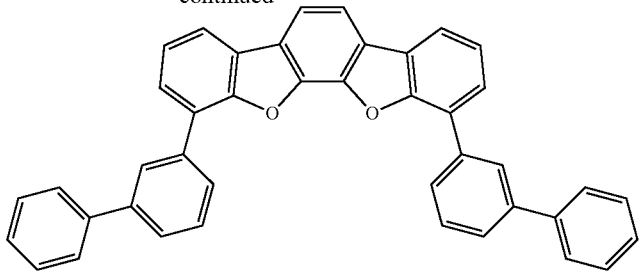

No. 306

Compound 47 (7.6 g, 12.6 mmol), $K_2CO_3$ (7.0 g, 50.4 mmol), and NMP (50 mL) were loaded into a three-necked flask, and the mixture was stirred under an Ar atmosphere at 200° C. for 3 hours. After the completion of the reaction, the resultant was cooled to room temperature. Toluene (500 mL) was charged into the resultant sample. The mixture was transferred to a separating funnel, and was washed with water. The washed product was dried with $MgSO_4$, and was then filtrated and concentrated. The resultant sample was purified by silica gel column chromatography. The purified product was concentrated and exsiccated, and was then recrystallized twice, whereby a white powder (Compound No. 306) was obtained. The powder was purified by sublimation, whereby a white solid was obtained in an amount of 2.9 g in 41% yield.

FD-MS $C_{42}H_{26}O_2$: theoretical value 562, observed value 562

Synthesis Example 31 (Synthesis of Compound No. 329)

(1) Synthesis of Compound 48

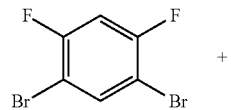

+

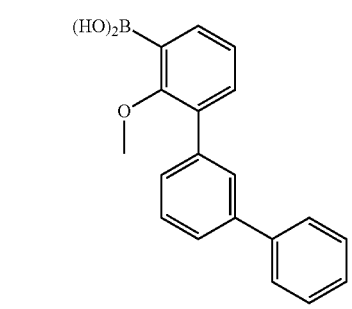

45

Pd[PPh$_3$]$_4$
Na$_2$CO$_3$ 2M aq.
―――――→
DME/Toluene

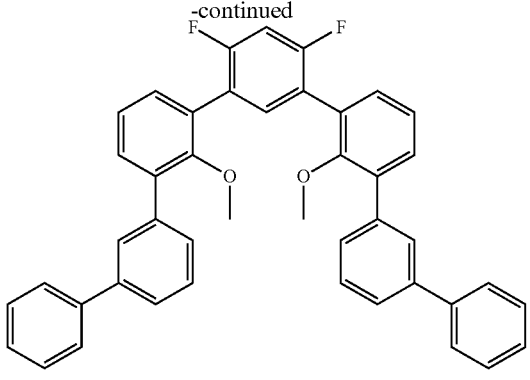

48

1,3-dibromo-4,6-difluorobenzene (5.4 g, 20.0 mmol), Compound 45 (12.8 g, 42.0 mmol), a 2 M aqueous solution of $Na_2CO_3$ (40 mL, 80.0 mmol), DME (40 mL), toluene (40 mL), and Pd[PPh$_3$]$_4$ (1.2 g, 1.0 mmol) were loaded into a three-necked flask, and the mixture was refluxed under an Ar atmosphere for 8 hours.

After the completion of the reaction, the resultant was cooled to room temperature. The resultant sample was transferred to a separating funnel, and water (100 mL) was charged into the funnel. Then, the mixture was extracted with $CH_2Cl_2$. The extract was dried with $MgSO_4$, and was then filtrated and concentrated. The resultant sample was purified by silica gel column chromatography, whereby a white solid was obtained in an amount of 7.2 g in 57% yield.

FD-MS $C_{44}H_{32}F_2O_2$: theoretical value 630, observed value 630

(2) Synthesis of Compound 49

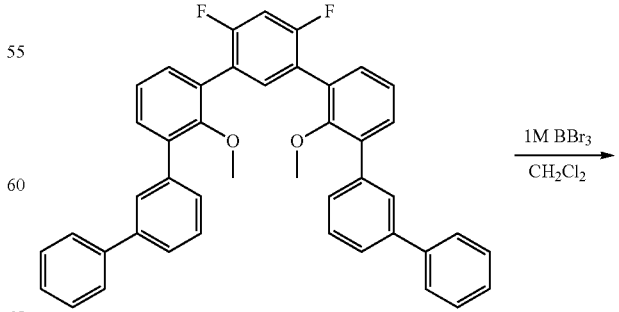

48

1M BBr$_3$
―――――→
CH$_2$Cl$_2$

-continued

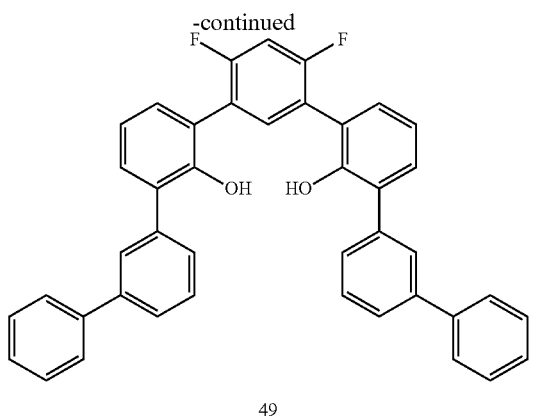

49

Compound 46 (7.2 g, 11.4 mmol), a 1 M solution of BBr$_3$ in CH$_2$Cl$_2$ (28 mL, 28.0 mmol), and CH$_2$Cl$_2$ (85 mL) were loaded into a three-necked flask, and the mixture was stirred under an Ar atmosphere at 0° C. for 8 hours. After that, the mixture was left to stand at room temperature overnight.

After the completion of the reaction, the resultant was neutralized with a saturated aqueous solution of NaHCO$_3$. The resultant sample was transferred to a separating funnel, and was extracted with CH$_2$Cl$_2$. The resultant sample was purified by silica gel column chromatography, whereby a white solid was obtained in an amount of 6.9 g in 100% yield.

FD-MS C$_{42}$H$_{28}$F$_2$O$_2$: theoretical value 602, observed value 602

(3) Synthesis of Compound No. 329

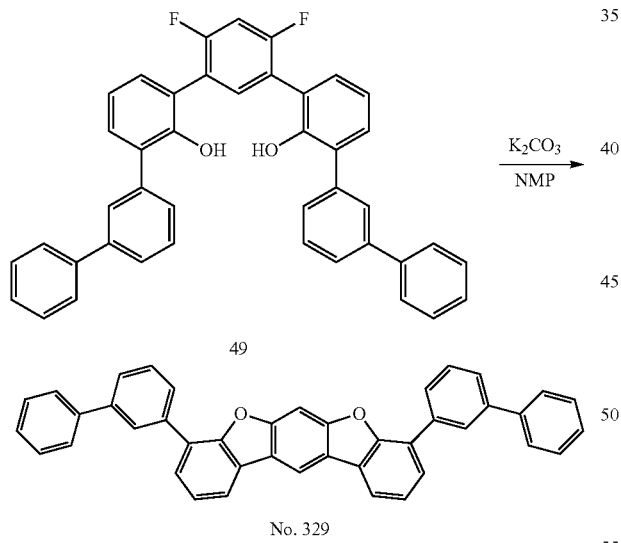

Compound 47 (6.9 g, 11.4 mmol), K$_2$CO$_3$ (6.3 g, 45.6 mmol), and NMP (50 mL) were loaded into a three-necked flask, and the mixture was stirred under an Ar atmosphere at 200° C. for 3 hours.

After the completion of the reaction, the resultant was cooled to room temperature. Toluene (500 mL) was charged into the resultant sample. The mixture was transferred to a separating funnel, and was washed with water. The washed product was dried with MgSO$_4$, and was then filtrated and concentrated. The resultant sample was purified by silica gel column chromatography. The purified product was concentrated and exsiccated, and was then recrystallized twice, whereby a white powder (Compound No. 329) was obtained. The powder was purified by sublimation, whereby a white solid was obtained in an amount of 2.3 g in 36% yield.

FD-MS C$_{42}$H$_{26}$O$_2$: theoretical value 562, observed value 562

An apparatus and measurement conditions adopted for field desorption mass spectrometry (FD-MS) in each of Synthesis Examples 1 to 31 are shown below.

Apparatus: HX110 (manufactured by JEOL Ltd.)
Conditions: accelerating voltage 8 kV
scan range m/z=50 to 1,500
emitter kind: carbon
emitter current: 0 mA→2 mA/min→40 mA (held for 10 minutes)

Example 1

(Production of Organic EL Device)

A glass substrate provided with an ITO transparent electrode measuring 25 mm by 75 mm by 1.1 mm (manufactured by GEOMATEC Co., Ltd.) was subjected to ultrasonic cleaning in isopropyl alcohol for 5 minutes. Further, the substrate was subjected to ultraviolet (UV)-ozone cleaning for 30 minutes.

The glass substrate provided with a transparent electrode thus cleaned was mounted on a substrate holder of a vacuum deposition apparatus. First, Compound A was deposited from the vapor onto the surface of the glass substrate on the side where a transparent electrode line was formed so as to cover the transparent electrode, whereby a hole transporting layer having a thickness of 30 nm was obtained.

Compound No. 11 as a host for phosphorescence and Ir(Ph-ppy)3 as a dopant for phosphorescence were co-deposited from the vapor onto the hole transporting layer, whereby a phosphorescent layer having a thickness of 30 nm was obtained. The concentration of Ir(Ph-ppy)$_3$ was 5 mass %.

Subsequently, Compound B having a thickness of 10 nm, Compound C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

Compound

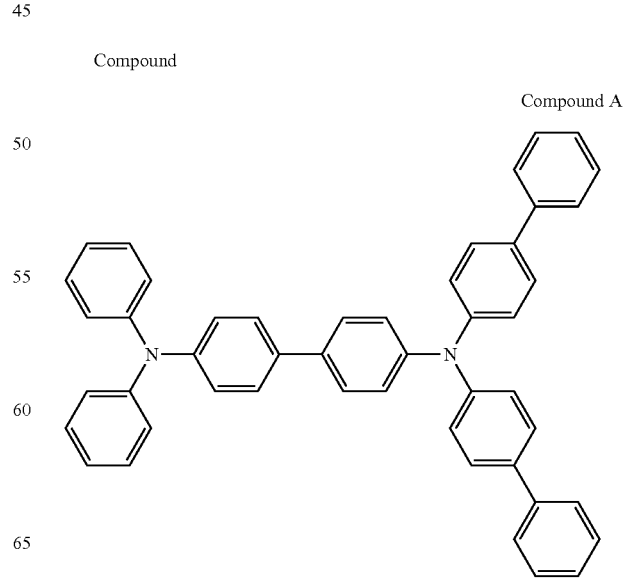

Compound A

-continued

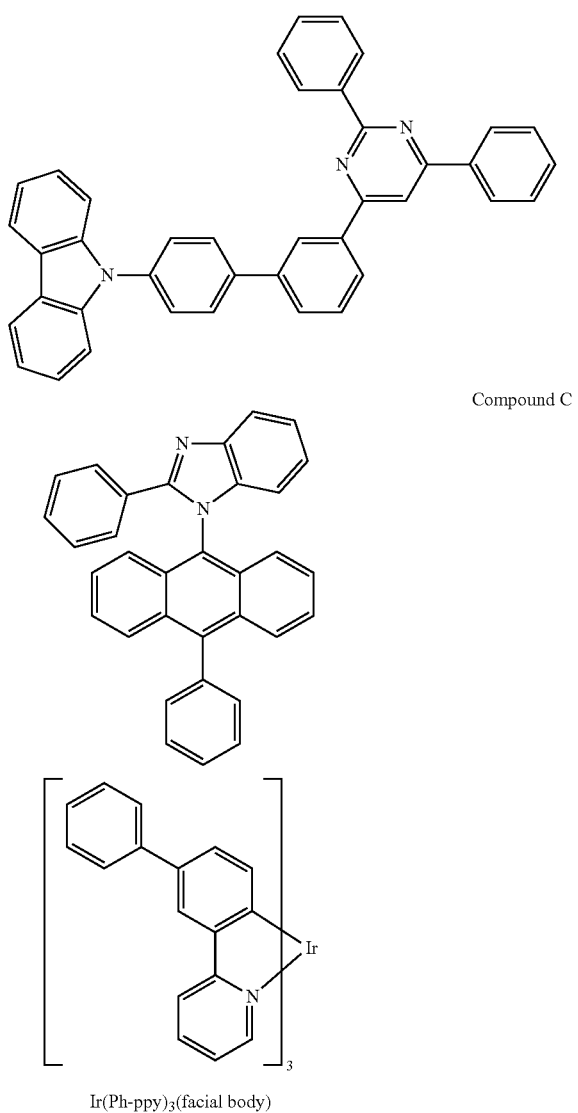

Compound B

Compound C

Ir(Ph-ppy)₃(facial body)

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m² was determined. Further, the lifetime of the device at a luminance of 20,000 cd/m² was determined. Table 1 shows the results.

Examples 2 to 26

Organic EL devices were each produced in the same manner as in Example 1 except that a host material listed in Table 1 was used instead of Host Compound No. 11 in Example 1, and the devices were each evaluated in the same manner as in Example 1. Table 1 shows the results of the evaluation for light emitting performance.

Comparative Examples 1 to 7

Organic EL devices were each produced in the same manner as in Example 1 except that the following compounds (a) to (g) described in EP 0908787 A was used as a host material instead of Host Compound No. 11 in Example 1, and the devices were each evaluated in the same manner as in Example 1. Table 1 shows the results of the evaluation for light emitting performance.

Comparative Examples 8 to 11

Organic EL devices were each produced in the same manner as in Example 1 except that the following compounds (h) to (k) described in WO 2006-122630 was used as a host material instead of Host Compound No. 11 in Example 1, and the devices were each evaluated in the same manner as in Example 1. Table 1 shows the results of the evaluation for light emitting performance.

Comparative Examples 12 and 13

An organic EL device was produced in the same manner as in Example 1 except that the following compound (1) or (m) described in WO 2007-063754 was used as a host material instead of Host Compound No. 11 in Example 1, and the device was evaluated in the same manner as in Example 1. Table 1 shows the results of the evaluation for light emitting performance.

Comparative Example 14

An organic EL device was produced in the same manner as in Example 1 except that the following compound (n) described in US 2002-0132134 A and US 2003-0044646 A was used as a host material instead of Host Compound No. 11 in Example 1, and the device was evaluated in the same manner as in Example 1. Table 1 shows the results of the evaluation for light emitting performance.

Comparative Example 15

An organic EL device was produced in the same manner as in Example 1 except that the following compound (o) described in JP 2008-81494 A was used as a host material instead of Host Compound No. 11 in Example 1, and the device was evaluated in the same manner as in Example 1. Table 1 shows the results of the evaluation for light emitting performance.

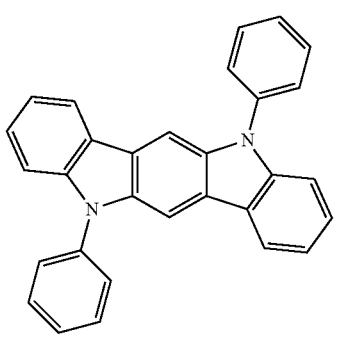

(a)

389
-continued
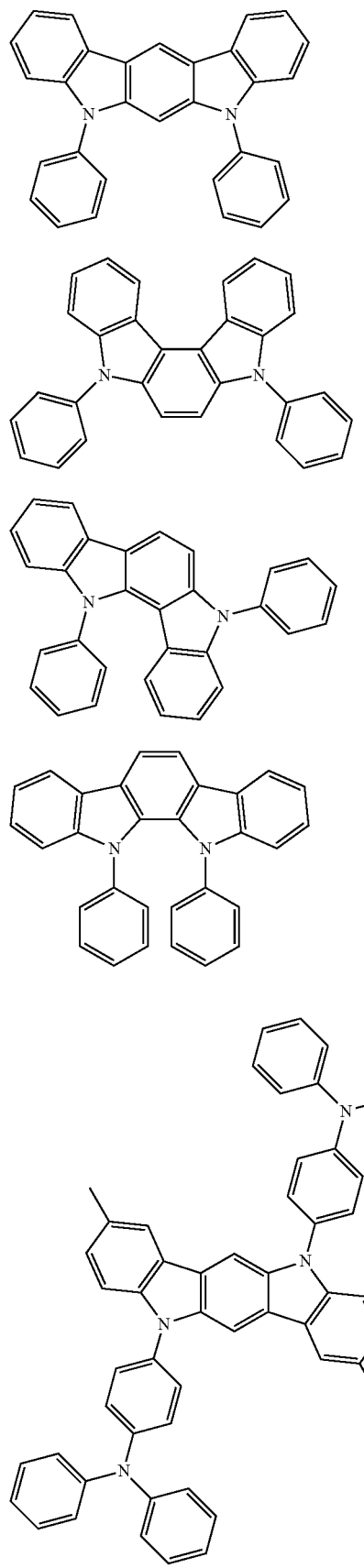
390
-continued
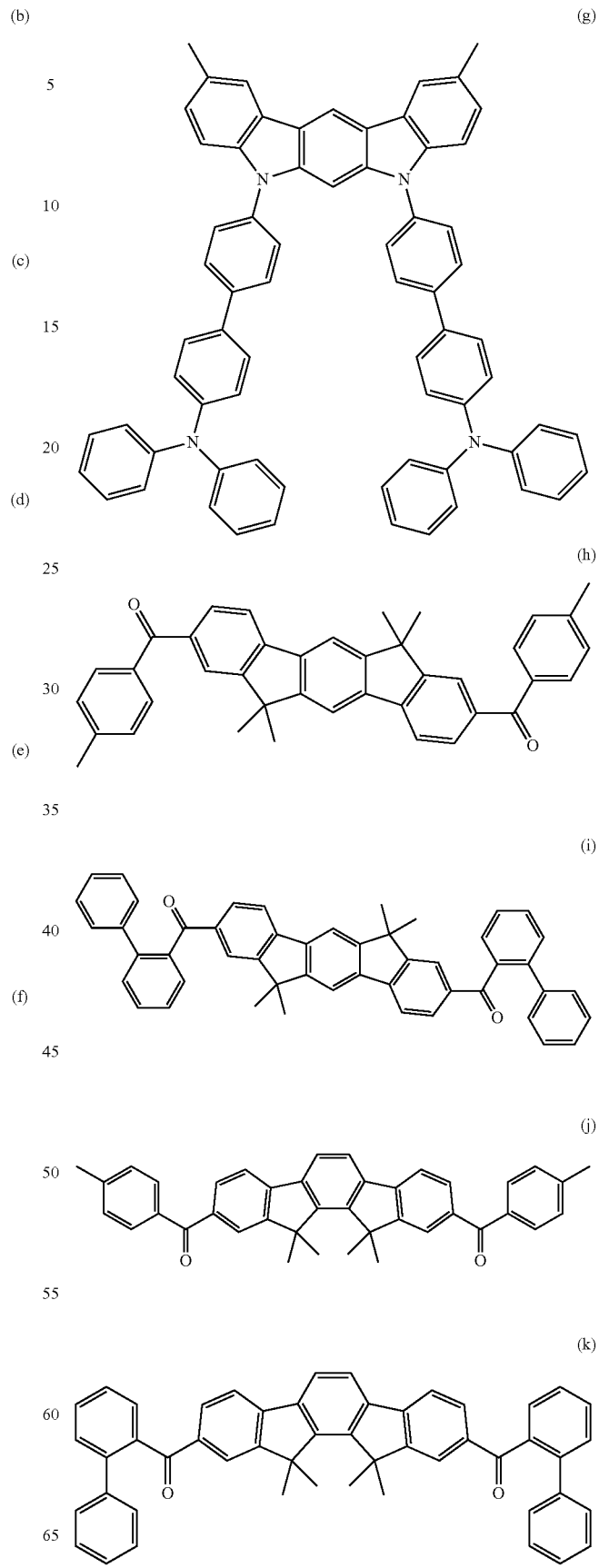

(l)

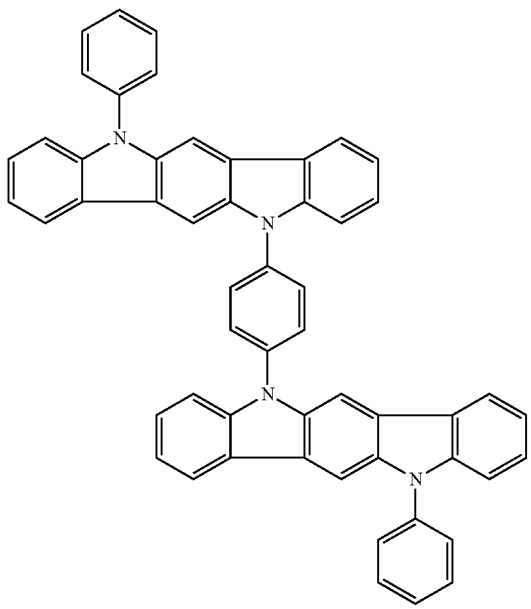

(m)

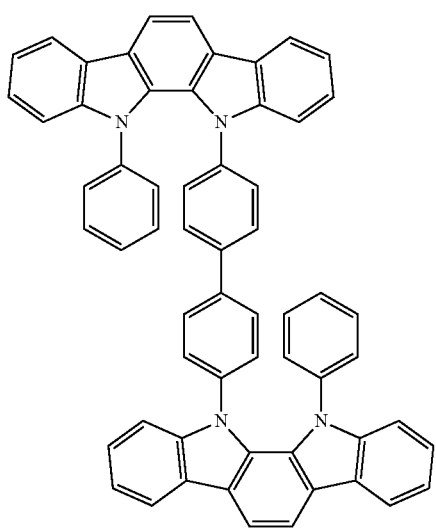

(n)

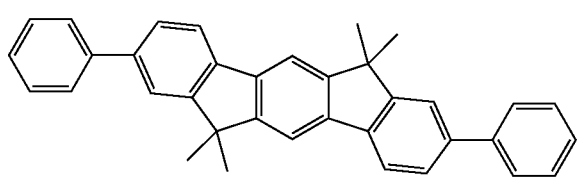

(o)

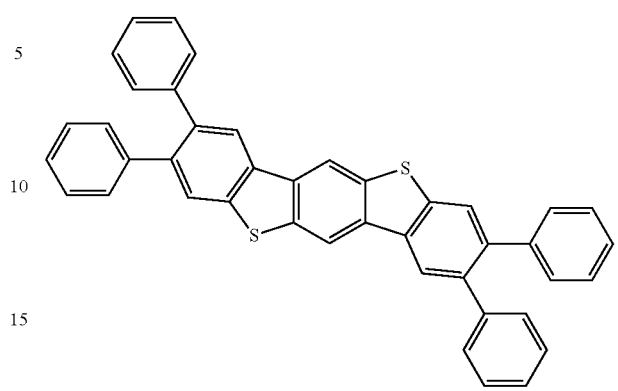

TABLE 1

| | Host compound | Voltage (V) @20 mA/cm² | Efficiency (cd/A) @1,000 cd/m² | Life time (hr) @20,000 cd/m² |
|---|---|---|---|---|
| Example 1 | (11) | 5.3 | 47.6 | 190 |
| Example 2 | (40) | 5.2 | 46.2 | 200 |
| Example 3 | (47) | 5.3 | 47.1 | 200 |
| Example 4 | (66) | 5.4 | 49.1 | 160 |
| Example 5 | (100) | 5.5 | 58.2 | 250 |
| Example 6 | (103) | 5.6 | 59.1 | 230 |
| Example 7 | (116) | 5.5 | 58.3 | 300 |
| Example 8 | (119) | 5.5 | 57.1 | 320 |
| Example 9 | (134) | 5.2 | 54.9 | 290 |
| Example 10 | (139) | 5.3 | 55.3 | 280 |
| Example 11 | (154) | 5.5 | 59.3 | 200 |
| Example 12 | (157) | 5.6 | 60.1 | 180 |
| Example 13 | (233) | 5.3 | 54.3 | 150 |
| Example 14 | (239) | 5.5 | 58.5 | 420 |
| Example 15 | (243) | 5.5 | 55.9 | 90 |
| Example 16 | (249) | 5.6 | 58.3 | 440 |
| Example 17 | (253) | 5.6 | 56.6 | 80 |
| Example 18 | (259) | 5.8 | 59.7 | 400 |
| Example 19 | (263) | 5.7 | 57.2 | 70 |
| Example 20 | (269) | 5.9 | 59.8 | 360 |
| Example 21 | (272) | 5.5 | 55.7 | 420 |
| Example 22 | (273) | 5.4 | 55.8 | 470 |
| Example 23 | (274) | 5.4 | 59.7 | 410 |
| Example 24 | (276) | 5.6 | 59.9 | 250 |
| Example 25 | (1) | 5.4 | 54.3 | 510 |
| Example 26 | (108) | 6.1 | 58.7 | 530 |
| Comparative Example 1 | (a) | 4.6 | 26.5 | 50 |
| Comparative Example 2 | (b) | 4.7 | 28.9 | 60 |
| Comparative Example 3 | (c) | 4.5 | 23.1 | 50 |
| Comparative Example 4 | (d) | 4.7 | 28.1 | 60 |
| Comparative Example 5 | (e) | 4.7 | 26.1 | 30 |
| Comparative Example 6 | (f) | 4.2 | 17.6 | 30 |
| Comparative Example 7 | (g) | 4.3 | 18.5 | 30 |
| Comparative Example 8 | (h) | 4.9 | 37.5 | 50 |
| Comparative Example 9 | (i) | 4.7 | 35.9 | 60 |
| Comparative Example 10 | (j) | 4.7 | 35.5 | 50 |
| Comparative Example 11 | (k) | 4.5 | 35.7 | 50 |
| Comparative Example 12 | (l) | 4.3 | 17.3 | 30 |

TABLE 1-continued

| | Host compound | Voltage (V) @20 mA/cm$^2$ | Efficiency (cd/A) @1,000 cd/m$^2$ | Life time (hr) @20,000 cd/m$^2$ |
|---|---|---|---|---|
| Comparative Example 13 | (m) | 4.5 | 17.7 | 20 |
| Comparative Example 14 | (n) | 5.4 | 28.7 | 60 |
| Comparative Example 15 | (o) | 5.5 | 38.2 | 50 |

Example 27

(Production of Organic EL Device)

The glass substrate provided with a transparent electrode cleaned in the same manner as described above was mounted on a substrate holder of a vacuum deposition apparatus. First, Compound A was deposited from the vapor onto the surface of the glass substrate on the side where a transparent electrode line was formed so as to cover the transparent electrode, whereby a hole transporting layer having a thickness of 30 nm was obtained.

Compound No. 108 as a host for phosphorescence and Ir(Ph-ppy) 3 as a dopant for phosphorescence were co-deposited from the vapor onto the hole transporting layer, whereby a phosphorescent layer having a thickness of 30 nm was obtained. The concentration of Ir(Ph-ppy)$_3$ was 10 mass %.

Subsequently, Compound No. 92 having a thickness of 10 nm, Compound C having a thickness of 20 nm, LiF having a thickness of 1 nm, and metal Al having a thickness of 80 nm were sequentially laminated on the phosphorescent layer, whereby a cathode was obtained. It should be noted that LiF as an electron injectable electrode was formed at a rate of 1 Å/min.

(Evaluation of Organic EL Device for Light Emitting Performance)

The organic EL device thus produced was caused to emit light by being driven with a direct current. The luminance (L) of the emitted light and the current density at which the device started to emit the light were measured. Then, the current efficiency (L/J) of the device at a luminance of 1,000 cd/m$^2$ was determined. Further, the lifetime of the device at a luminance of 20,000 cd/m$^2$ was determined. Table 2 shows the results.

Examples 28 to 37

Organic EL devices were each produced in the same manner as in Example 27 except that a host compound and an electron transportable compound listed in Table 2 were used instead of Host Compound No. 108 and Electron Transportable Compound No. 92 in Example 27, and the devices were each evaluated in the same manner as in Example 27. Table 2 shows the results of the evaluation for light emitting performance.

Comparative Example 16

An organic EL device was produced in the same manner as in Example 27 except that: CBP was used instead of Host Compound No. 108 in Example 27; and BAlq was used instead of Electron Transportable Compound No. 92 in Example 27. Then, the device was evaluated in the same manner as in Example 27. Table 2 shows the results of the evaluation for light emitting performance.

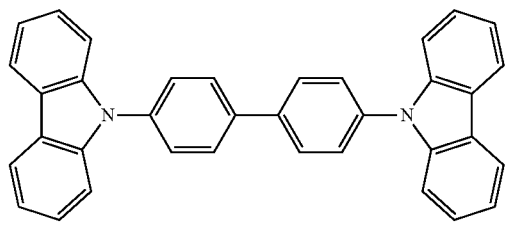

CBP

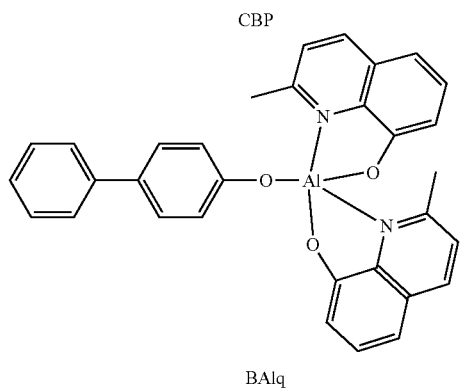

BAlq

TABLE 2

| | Host compound | Electron transportable compound | Voltage (V) @20 mA/cm$^2$ | Efficiency (cd/A) @1,000 cd/m$^2$ | Life time (hr) @20,000 cd/m$^2$ |
|---|---|---|---|---|---|
| Example 27 | (108) | (92) | 5.8 | 60.2 | 580 |
| Example 28 | (108) | (306) | 5.7 | 62.1 | 560 |
| Example 29 | (108) | (108) | 6.0 | 63.7 | 600 |
| Example 30 | (108) | (329) | 5.9 | 62.3 | 550 |
| Example 31 | (1) | (92) | 4.8 | 55.6 | 550 |
| Example 32 | (103) | (92) | 5.5 | 66.1 | 590 |
| Example 33 | (119) | (92) | 5.7 | 68.9 | 570 |
| Example 34 | CBP | (92) | 5.7 | 48.5 | 100 |
| Example 35 | CBP | (306) | 5.6 | 49.6 | 120 |
| Example 36 | CBP | (108) | 5.9 | 48.2 | 100 |
| Example 37 | CBP | (329) | 5.8 | 49.3 | 120 |
| Comparative Example 16 | CBP | BAlq | 6.5 | 45.1 | 30 |

Each of the organic EL devices of the comparative examples showed a lower current efficiency, was driven at a higher voltage, and had a shorter lifetime than those of each of the organic EL devices of the examples.

INDUSTRIAL APPLICABILITY

As described above in detail, the utilization of the material for an organic EL device of the present invention can provide an organic EL device which shows high luminous efficiency, is free of any pixel defect, and has a long lifetime. Accordingly, the organic EL device of the present invention is extremely useful as, for example, a light source for various electronic instruments. In addition, the material can be effectively used also as a material for an organic electron device, and is extremely useful in an organic solar cell, organic semiconductor laser, a sensor using organic matter, or an organic TFT.

The invention claimed is:

1. A material for an organic electroluminescence device represented by any one of formulas (5) to (14):

(5)
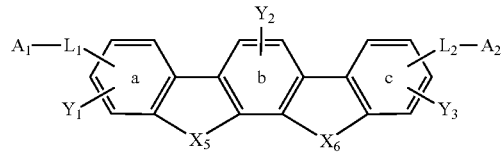

(6)
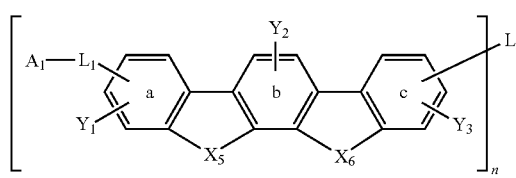

(7)
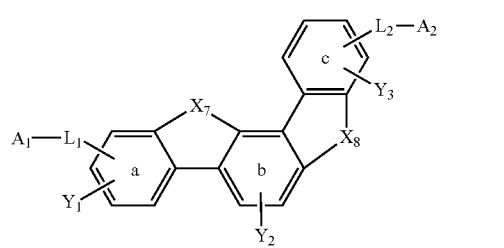

(8)

(9)
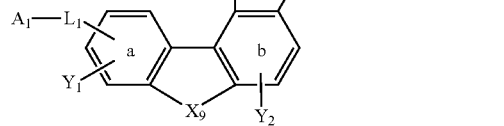

(10)
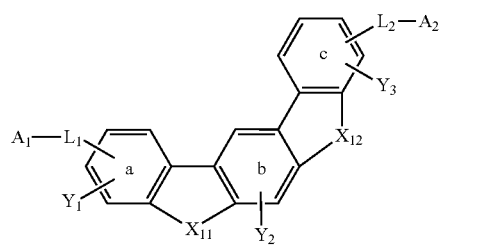

(11)
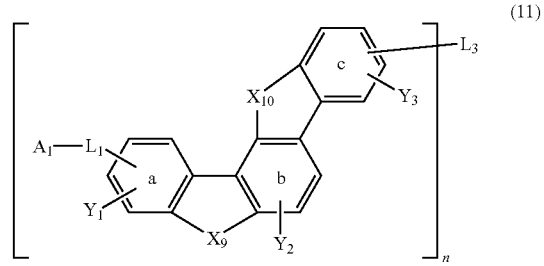

(12)
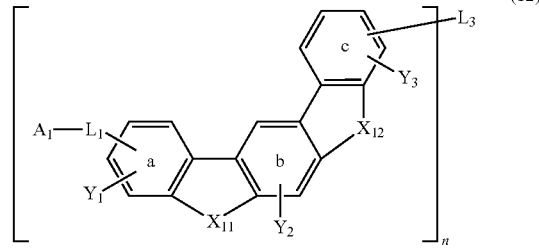

(13)
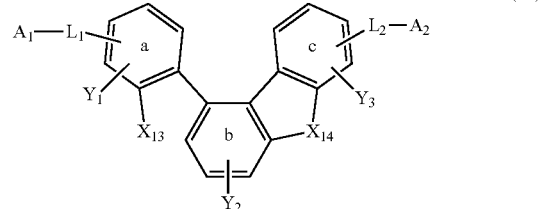

(14)
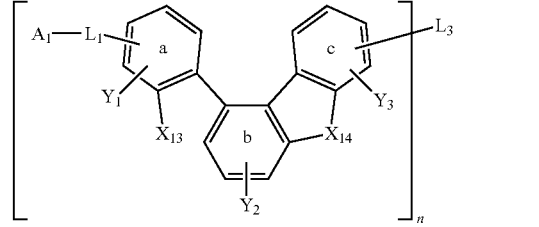

wherein formulas (5) and (6):
one of $X_5$ and $X_6$ is S and the other of $X_5$ and $X_6$ is O, S, or $CR_2R_3$; $R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms;
n represents 2, 3, or 4, and the material represented by the formula (6) comprises a dimer using $L_3$ as a linking group for n=2, a trimer using $L_3$ as a linking group for n=3, or a tetramer using $L_3$ as a linking group for n=4;
$L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond;

$L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond;

when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, $L_3$ represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond;

$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded;

$A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case where $A_2$ represents a hydrogen atom is excluded;

$Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, be or c through a carbon-carbon bond, a number of each of $Y_1$, $Y_2$, and $Y_3$ is 0, 1, 2, or 3, and a number of $Y_2$ is 0, 1, or 2; and $A_2$, $L_1$, $L_2$, and $L_3$ are each free of any carbonyl group; wherein formulas (7) to (12): one of $X_7$ and $X_8$ is S and the other of $X_7$ and $X_8$ is O, S, or $CR_2R_3$, one of $X_9$ and $X_{10}$ is S and the other of X, and $X_{10}$ is O, S, or $CR_2R_3$, and one of $X_{11}$ and $X_{12}$ is S and the other of $X_{11}$ and $X_{12}$ is O, S, or $CR_2R_3$;

$R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group having a ring formed of 3 to 24 atoms;

n represents 2, 3, or 4, and the material represented by any one of the formulae (10) to (12) comprises a dimer using $L_3$ as a linking group for n=2, a trimer using $L_3$ as a linking group for n=3, or a tetramer using $L_3$ as a linking group for n=4;

$L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond;

$L_2$ represents a single bond, an alkyl or alkylene group having 1 to 2.0 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond;

when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, $L_3$ represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic; hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond;

$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom s excluded;

$A_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_2$ through a carbon-carbon bond, provided that, when $L_2$ represents an alkyl or alkylene group having 1 to 20 carbon atoms, a case there $A_2$ represents a hydrogen atom is excluded;

$Y_1$, $Y_2$, and $Y_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, b, or c through a carbon-carbon bond, a number of each of $Y_1$, $Y_2$, and $Y_3$ is 0, 1, 2, or 3, and a number of $Y_2$ is 0, 1, or 2; and $A_1$, $A_2$, $L_1$, $L_2$, and $L_3$ are each free of any carbonyl group; wherein formulas (3) and (14) one of $X_{13}$ and $X_{14}$ is S and the other of $X_{13}$ and $X_{14}$ is O, S, or $CR_2R_3$;

$R_2$, and $R_3$ each independently represent an alkyl group having 1 to 20 carbon atoms, a substituted or unsubstituted cycloalkyl group having a ring formed of 3 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or substituted or unsubstituted aromatic heterocyclic group having a ring formed of 3 to 24 atoms;

n represents 2, 3, or 4, and the material represented by the formula (14) comprises a dimer using $L_3$ as a linking group for n=2, a trimer using $L_3$ as a linking group for n=3, or a tetramer using $L_3$ as a linking group for n=4;

$L_1$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring a through a carbon-carbon bond;

$L_2$ represents a single bond, an alkyl or alkylene group having 1 to 20 carbon atoms, a substituted or unsubstituted cycloalkyl or cycloalkylene group having a ring formed of 3 to 20 carbon atoms, a monovalent or divalent silyl group having 2 to 20 carbon atoms, a substituted or unsubstituted, monovalent or divalent aromatic hydrocarbon group having a ring formed of 6 to 24 carbon atoms, or a substituted or unsubstituted, monovalent or divalent aromatic heterocyclic group which has a ring formed of 3 to 24 atoms and which is linked with a benzene ring c through a carbon-carbon bond;

when n represents 2, $L_3$ represents a single bond, an alkylene group having 1 to 20 carbon atoms, a substituted or unsubstituted cycloalkylene group having a ring formed of 3 to 20 carbon atoms, a divalent silyl group having 2 to 20 carbon atoms, a substituted or unsubstituted, divalent aromatic hydrocarbon group having a ring formed of 6 to 24 carbon atoms, or a substituted or unsubstituted, divalent aromatic heterocyclic group which has a ring formed of 3 to 24 atoms and which is linked with the benzene ring c through a carbon-carbon bond, when n represents 3, represents a trivalent alkane having 1 to 20 carbon atoms, a substituted or unsubstituted, trivalent cycloalkane having a ring formed of 3 to 20 carbon atoms, a trivalent silyl group having 1 to 20 carbon atoms, a substituted or unsubstituted, trivalent aromatic hydrocarbon group having a ring formed of 6 to 24 carbon atoms, or a substituted or unsubstituted, trivalent aromatic heterocyclic group which has 3 to 24 atoms and which is linked with the benzene ring c through a carbon-carbon bond, or when n represents 4, represents a tetravalent alkane having 1 to 20 carbon atoms, a substituted or unsubstituted, tetravalent cycloalkane having a ring formed of 3 to 20 carbon atoms, a silicon atom, a substituted or unsubstituted, tetravalent aromatic hydrocarbon group having a ring formed of 6 to 24 carbon atoms, or a substituted or unsubstituted, tetravalent aromatic heterocyclic group which has a ring formed of 3 to 24 atoms and which is linked with the benzene ring c through a carbon-carbon bond;

$A_1$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with $L_1$ through a carbon-carbon bond, provided that, when $L_1$ represents an alkyl or alkylene group having 1 to 20 carbon atoms, a case where $A_1$ represents a hydrogen atom is excluded;

A$_2$ represents a hydrogen atom, a substituted or unsubstituted cycloalkyl group having a ring formed of 3 to 20 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with L$_2$ through a carbon-carbon bond, provided that, when L$_2$ represents an alkyl or alkylene group having 1 to 20 carbon atoms, a case where A$_2$ represents a hydrogen atom is excluded;

Y$_1$, Y$_2$, and Y$_3$ each represent an alkyl group having 1 to 20 carbon atoms, a substituted or unsubstituted cycloalkyl group having a ring formed of 3 to 20 carbon atoms, an alkoxy group having 1 to 20 carbon atoms, an aralkyl group having 7 to 24 carbon atoms, a silyl group having 3 to 20 carbon atoms, a substituted or unsubstituted aromatic hydrocarbon group having a ring formed of 6 to 24 carbon atoms, or a substituted or unsubstituted aromatic heterocyclic group which has a ring formed of 3 to 24 atoms and which is linked with the benzene ring a, or c through a carbon-carbon bond, a number of each of Y$_1$ and Y$_4$ is 0, 1, 2, or 3, and a number of Y$_2$ is 0, 1, or 2; and A$_1$, A$_2$, L$_1$, L$_2$, and L$_3$ are each free of any carbonyl group.

2. The material for an organic electroluminescence device according to claim 1, which is represented by one of formulae (5) and (6).

3. The material for an organic electroluminescence device according to claim 1, wherein the material for an organic electroluminescence device is represented by any one of the formulae (7) to (12).

4. The material for an organic electroluminescence device according to claim 1, wherein the material is represented by one of formulae (13) and (14).

5. The material for an organic electroluminescence device according to claim 1, wherein the material is represented by formula (6) wherein n represents 2.

6. The material for an organic electroluminescence device according to claim 1, wherein the material is represented by any one of formulas (10) to (12) wherein n represents 2.

7. The material for an organic electroluminescence device according to claim 1, wherein the material is represented by formula (14) wherein n represents 2.

8. The material for an organic electroluminescence device according to claim 2, wherein the material is represented by formulas (5) or (6) wherein a total number of substituents represented by Y$_1$, Y$_2$, and Y$_3$ in the general formula (5) is 3 or less, and a total number of the substituents represented by Y$_1$, Y$_2$, and Y$_3$ in the structure of the general formula (6) is 3 or less.

9. The material for an organic electroluminescence device according to claim 1, wherein the material is represented by any one of formulas (7) to (12) wherein a total number of substituents represented by Y$_1$, Y$_2$, and Y$_3$ in the general formulae (7) to (9) is 3 or less, and a total number of the substituents represented by Y$_1$, Y$_2$, and Y$_3$ in the structure of the general formulae (10) to (12) is 3 or less.

10. The material for an organic electroluminescence device according to claim 1, wherein the material is represented by formulas (13) or (14) wherein a total number of substituents represented by Y$_1$, Y$_2$, and Y$_3$ in the general formula (13) is 3 or less, and a total number of the substituents represented by Y$_1$, Y$_2$, and Y$_3$ in the structure of the general formula (14) is 3 or less.

11. An organic electroluminescence device comprising one or more organic thin film layers including a light emitting layer between a cathode and an anode, wherein at least one layer of the organic thin film layers contains the material for an organic electroluminescence device according to claim 1 as a compound having a n-conjugated heteroacene skeleton crosslinked with a carbon atom, oxygen atom, or sulfur atom.

12. The organic electroluminescence device according to claim 11, wherein the light emitting layer contains the material for an organic electroluminescence device as a host material.

13. The organic electroluminescence device according to claim 12, wherein the light emitting layer further contains a phosphorescent material.

14. The organic electroluminescence device according to claim 11, wherein the light emitting layer contains a host material and a phosphorescent material, and the phosphorescent material comprises an orthometalated complex of an iridium (Ir), osmium (Os), or platinum (Pt) metal.

15. The organic electroluminescence device according to claim 11, further comprising an electron injecting layer between the light emitting layer and the cathode, wherein the electron injecting layer contains a nitrogen-containing ring derivative.

16. The organic electroluminescence device according to claim 11, further comprising an electron transporting layer between the light emitting layer and the cathode, wherein the electron transporting layer contains the material for an organic electroluminescence device.

17. The organic electroluminescence device according to claim 16, wherein the light emitting layer contains the material for an organic electroluminescence device as a host material.

18. The organic electroluminescence device according to claim 11, further comprising a hole transporting layer between the light emitting layer and the anode, wherein the hole transporting layer contains the material for an organic electroluminescence device.

19. The organic electroluminescence device according to claim 11, further comprising a reducing dopant at an interfacial region between the cathode and the organic thin film layers.

20. An organic electroluminescence device comprising one or more organic thin film layers including a light emitting layer between a cathode and an anode, wherein at least one layer of the organic thin film layers contains the material for an organic electroluminescence device represented by any one of formulae (5) and (6) according to claim 1 as a compound having a n-conjugated heteroacene skeleton crosslinked with a carbon atom, oxygen atom, or sulfur atom, wherein the organic electroluminescence device further comprises an electron transporting layer between the light emitting layer and the cathode, and wherein the electron transporting layer contains the material for an organic electroluminescence device as a host material.

21. An organic electroluminescence device comprising one or more organic thin film layers including a light emitting layer between a cathode and an anode, wherein at least one layer of the organic thin film layers contains the material for an organic electroluminescence device represented by any one of formulae (9) and (12) according to claim 1 as a compound having a π-conjugated heteroacene skeleton crosslinked with a carbon atom, oxygen atom, or sulfur atom, wherein the organic electroluminescence device further comprises an electron transporting layer between the light emitting layer and the cathode, and wherein the electron transporting layer contains the material for an organic electroluminescence device as a host material.

22. An organic electroluminescence device comprising one or more organic thin film layers including a light emitting layer between a cathode and an anode, wherein at least one layer of the organic thin film layers contains the material for an organic electroluminescence device according to claim 1 as a compound having a π-conjugated heteroacene skeleton crosslinked with a carbon atom, oxygen atom, or sulfur atom.

23. The organic electroluminescence device according to claim 22, wherein the light emitting layer contains the material for an organic electroluminescence device as a host material.

24. The organic electroluminescence device according to claim 23, wherein the light emitting layer further contains a phosphorescent material.

\* \* \* \* \*

UNITED STATES PATENT AND TRADEMARK OFFICE
CERTIFICATE OF CORRECTION

PATENT NO. : 11,895,917 B2
APPLICATION NO. : 17/345838
DATED : February 6, 2024
INVENTOR(S) : Tomoki Kato et al.

Page 1 of 8

It is certified that error appears in the above-identified patent and that said Letters Patent is hereby corrected as shown below:

In the Claims

Claim 1, Column 395, Line 5, replace formula (5)

" 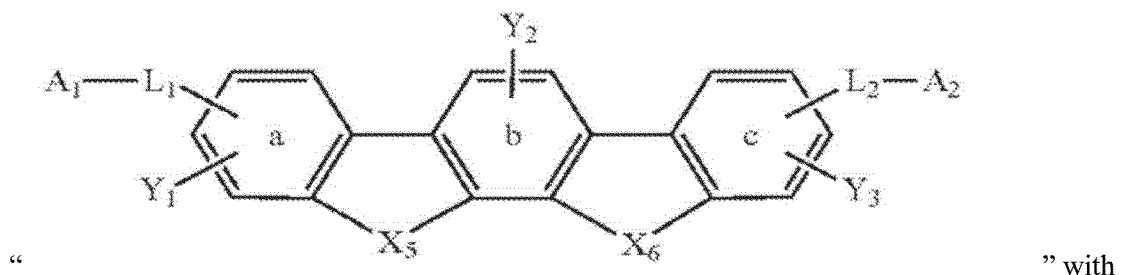 " with

-- 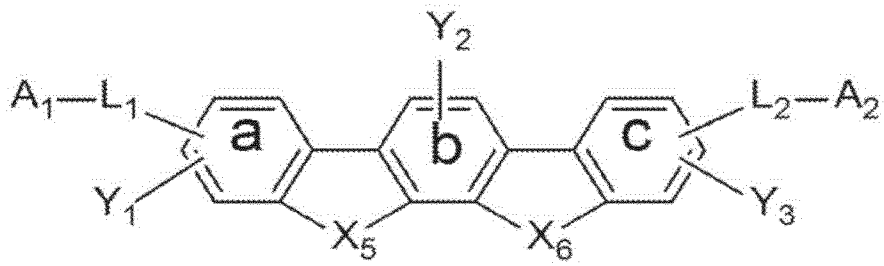 --;

Signed and Sealed this
Twentieth Day of August, 2024

Katherine Kelly Vidal
*Director of the United States Patent and Trademark Office*

CERTIFICATE OF CORRECTION (continued)
U.S. Pat. No. 11,895,917 B2

Claim 1, Column 395, Line 15, replace formula (6)

"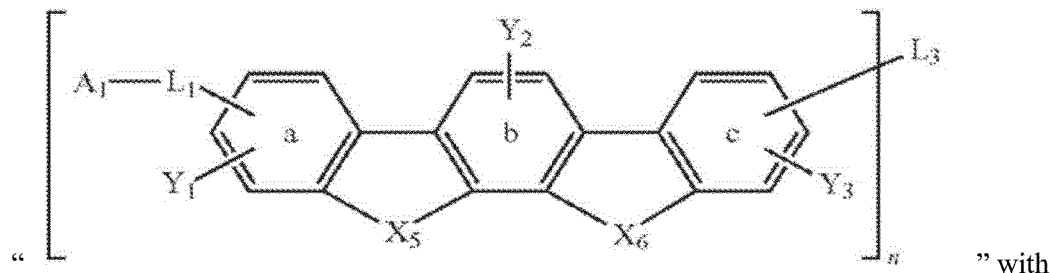" with

--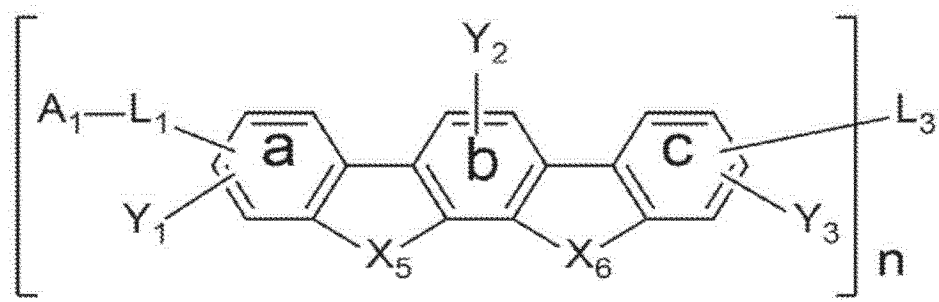--;

Claim 1, Column 395, Line 25, replace formula (7)

"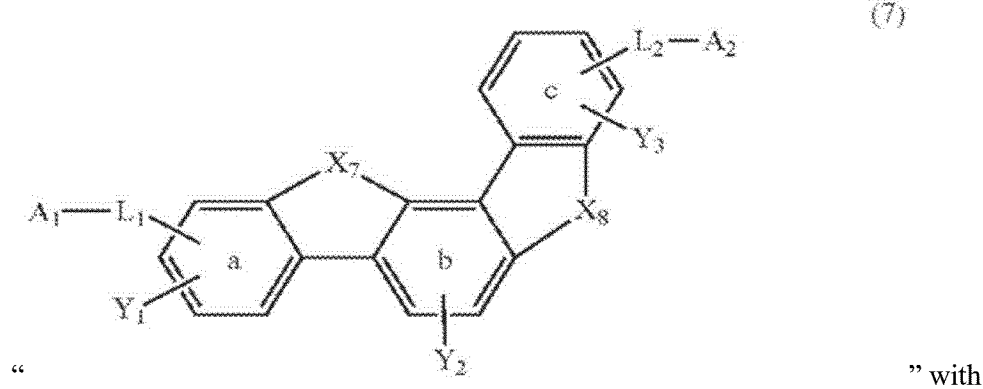" with

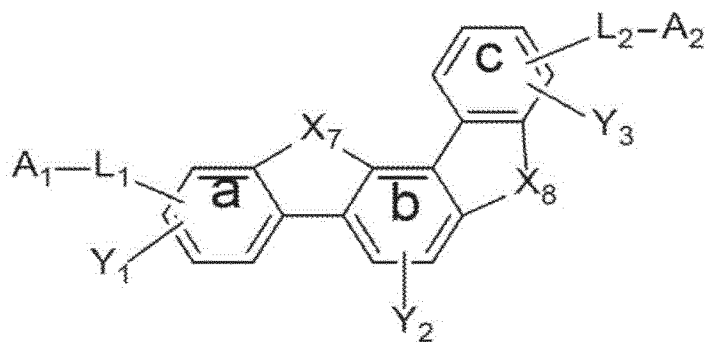
(7)
--                                                                    --;
Claim 1, Column 395, Line 35, replace formula (8)
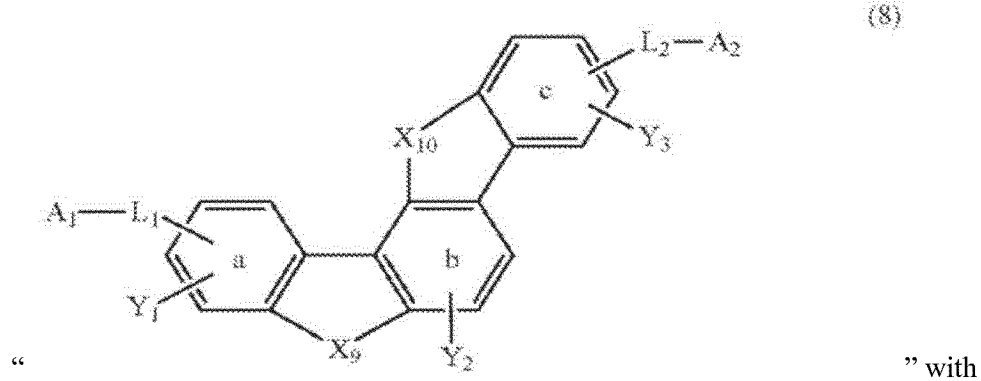
"                                                                    " with
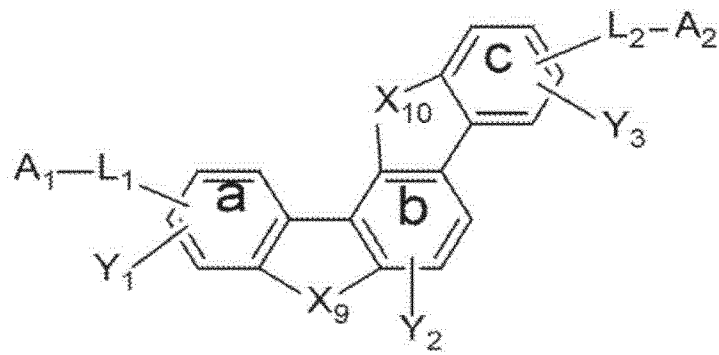
(8)
--                                                                    --;

CERTIFICATE OF CORRECTION (continued)
U.S. Pat. No. 11,895,917 B2

Claim 1, Column 395, Line 45, replace formula (9)

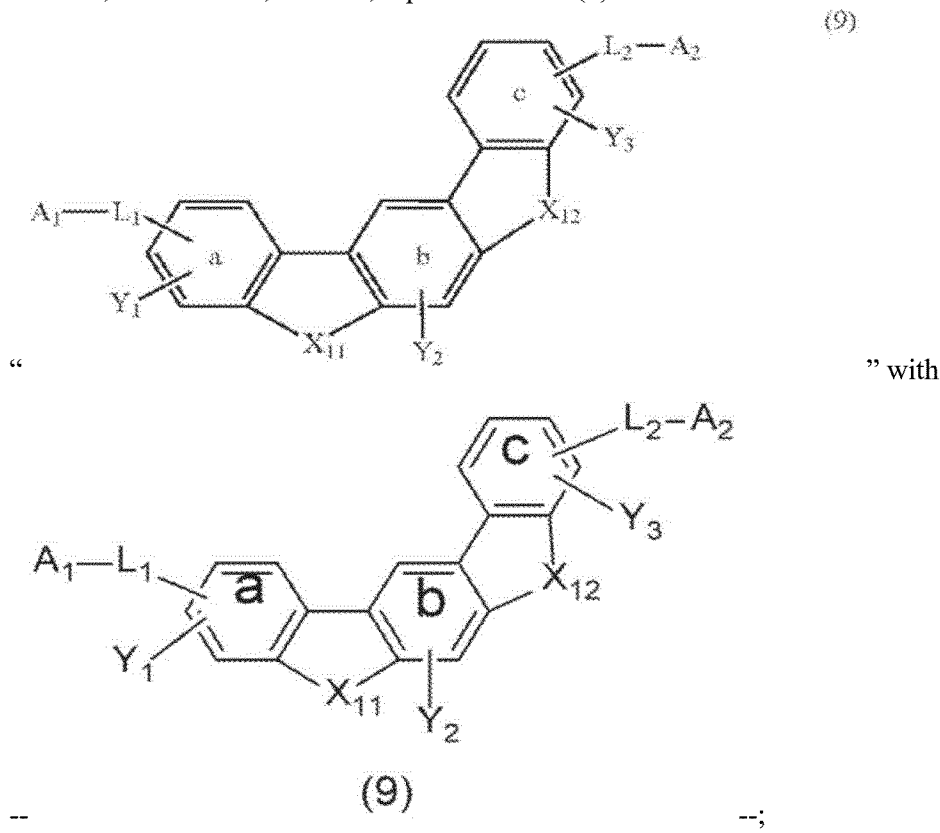

" with

" --;

Claim 1, Column 395, Line 55, replace formula (10)

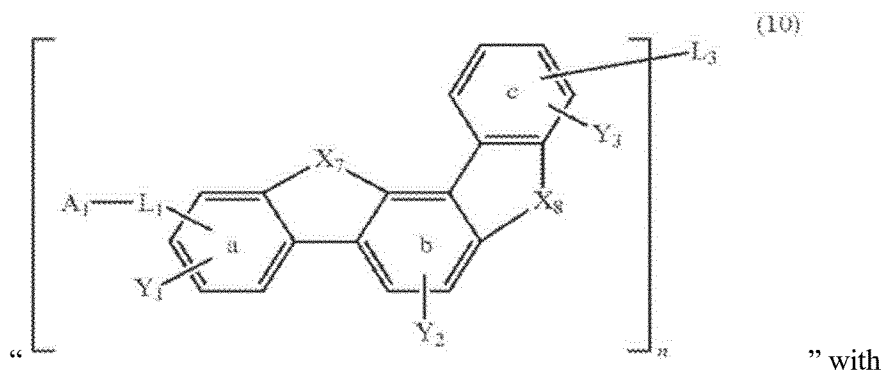

" with

CERTIFICATE OF CORRECTION (continued)
U.S. Pat. No. 11,895,917 B2

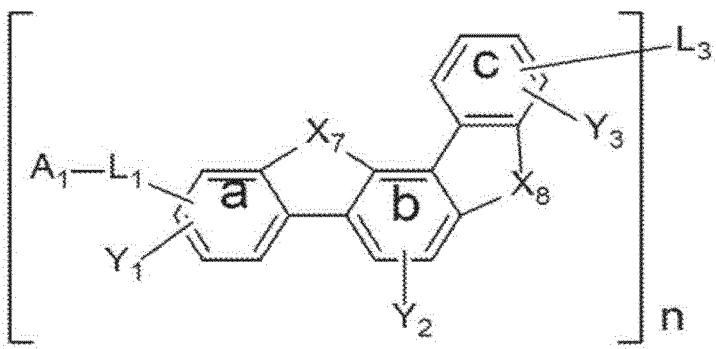

(10)

Claim 1, Column 396, Line 5, replace formula (11)

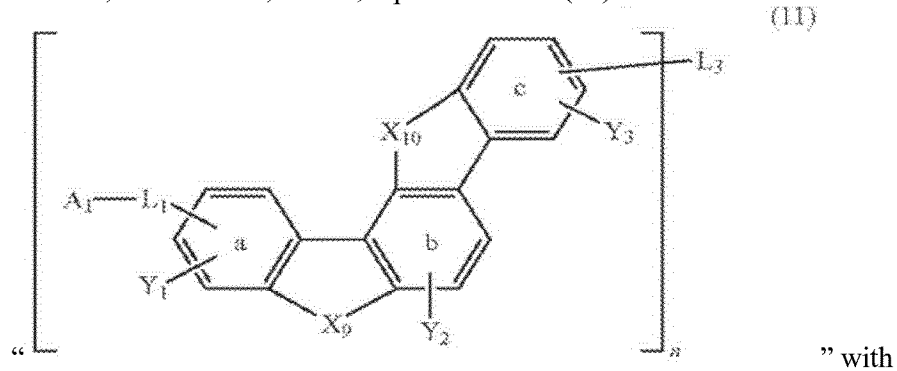

" with

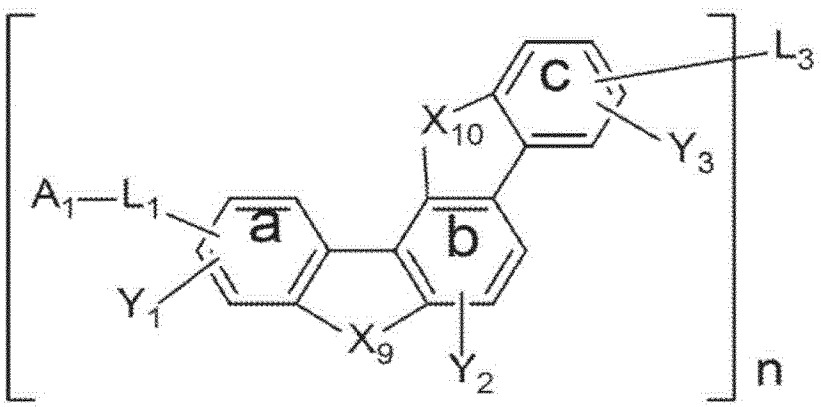

(11)

CERTIFICATE OF CORRECTION (continued)
U.S. Pat. No. 11,895,917 B2

Claim 1, Column 396, Line 15, replace formula (12)

"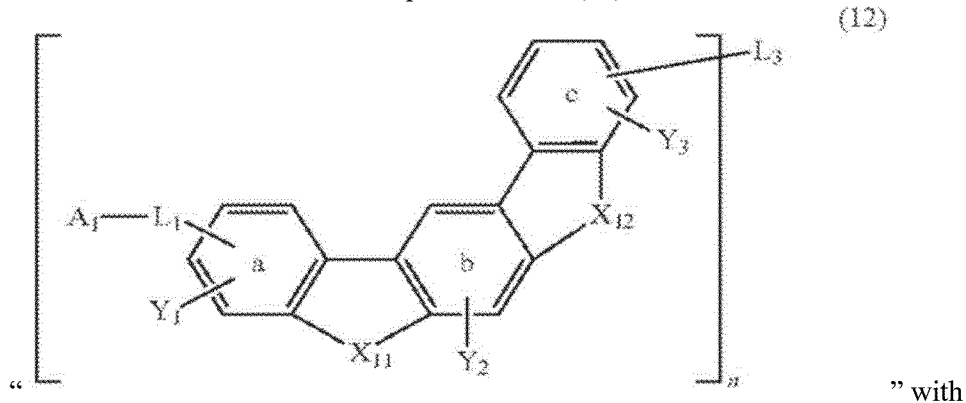" with

--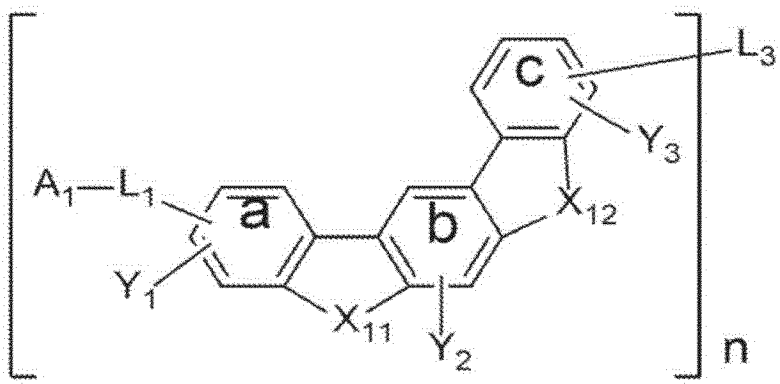--;

Claim 1, Column 396, Line 20, replace formula (13)

"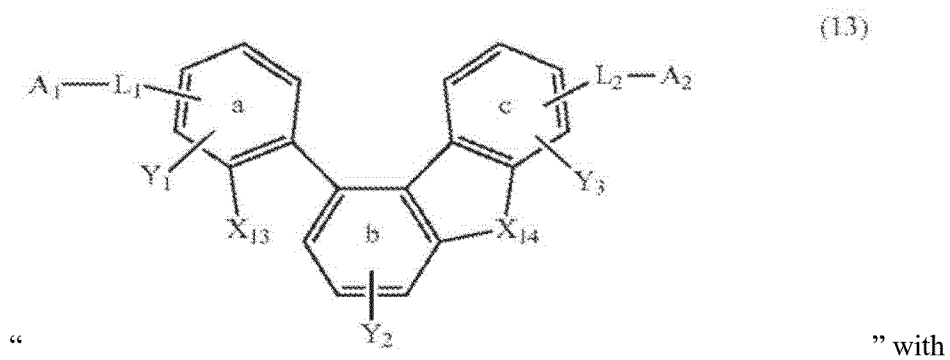" with

CERTIFICATE OF CORRECTION (continued)
U.S. Pat. No. 11,895,917 B2

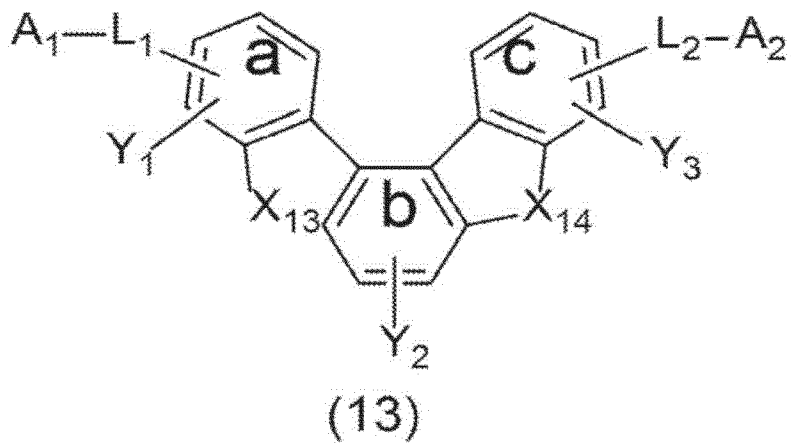

-- --;

Claim 1, Column 396, Line 30, replace formula (14)

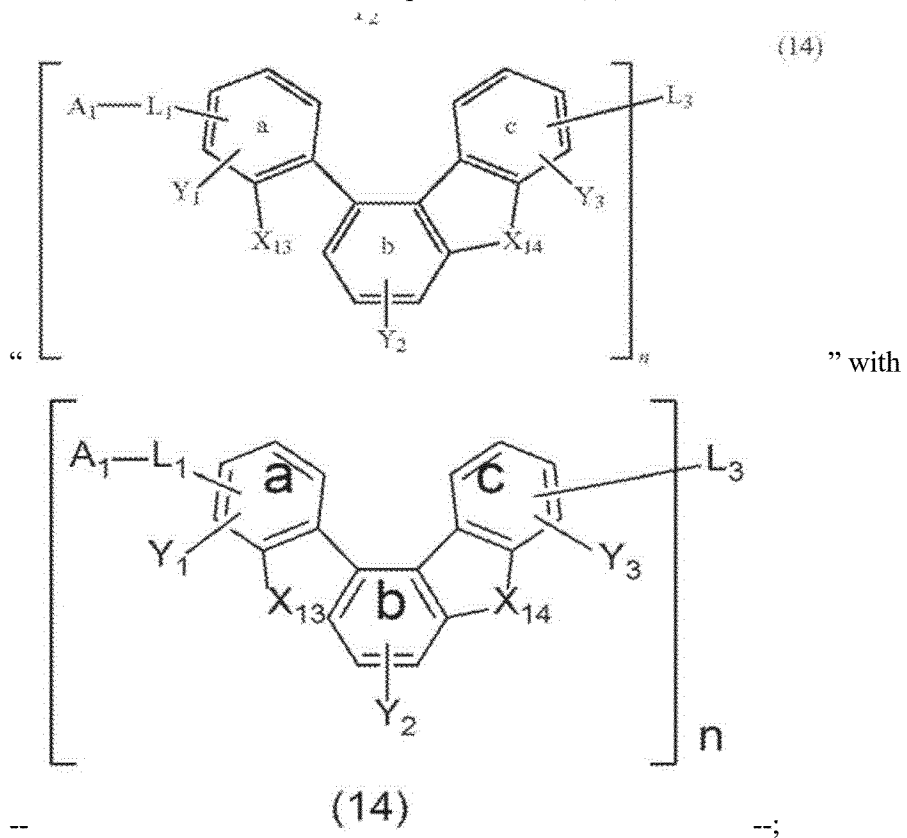

-- --;

Claim 1, Column 398, Line 8, "the benzene ring a, be, or c through a carbon-carbon" should read
-- "the benzene ring a, b, or c through a carbon-carbon --;

Claim 1, Column 398, Line 11, "$A_2$, $L_1$, $L_2$, and $L_3$ are each free of any carbonyl group;" should read
-- $A_1$, $A_2$, $L_1$, $L_2$, and $L_3$ are each free of any carbonyl group; --;

CERTIFICATE OF CORRECTION (continued)
U.S. Pat. No. 11,895,917 B2

Claim 1, Column 398, Line 14, "$X_{10}$ is S and the other of X and $X_{10}$ is O, S, or $CR_2R_3$," should read -- and $X_{10}$ is S and the other of $X_9$ and $X_{10}$ is O, S, or $CR_2R_3$, --;

Claim 1, Column 398, Line 44, "having 1 to 2.0 carbon atoms," should read -- having 1 to 20 carbon atoms, --;

Claim 1, Column 399, Line 3, "trivalent aromatic; hydrocarbon group" should read -- trivalent aromatic hydrocarbon group --;

Claim 1, Column 399, Line 8, "represents a tetravalent" should read -- $L_3$ represents a tetravelent --;

Claim 1, Column 399, Line 29, "a hydrogen atom s excluded;" should read -- a hydrogen atom is excluded; --;

Claim 1, Column 399, Line 40, "there A2 represents" should read -- where $A_2$ represents --;

Claim 1, Column 399, Line 55, "formulas (3) and (14)" should read -- formulas (13) and (14) --;

Claim 1, Column 400, Line 37, "represents a trivalent" should read -- $L_3$ represents a trivalent --;

Claim 1, Column 400, Line 47, "represents a tetravalent" should read -- $L_3$ represents a tetravelent --;

Claim 1, Column 401, Line 22, "the benzene ring a, or c through" should read -- the benzene ring a, b, or c through --;

Claim 1, Column 401, Line 23, "each of $Y_1$ and $Y_4$ is" should read -- each of $Y_1$ and $Y_3$ is --;

Claim 11, Column 402, Line 4, "having a n-conjugated" should read -- having a π-conjugated --;

Claim 20, Column 402, Line 48, "having a n-conjugated" should read -- having a π-conjugated --.